US007303917B2

(12) United States Patent
Robert et al.

(10) Patent No.: US 7,303,917 B2
(45) Date of Patent: Dec. 4, 2007

(54) MODIFICATION OF POLLEN COAT PROTEIN COMPOSITION

(75) Inventors: Laurian S. Robert, Gatineau (CA); Stephen Gleddie, Ottawa (CA); Elizabeth Foster, Nepean (CA)

(73) Assignee: Her Majesty the Queen in Right of Canada as Represented by the Minister of Agriculture and Agri-Food Eastern Cereal & Oilseed, Research Center, Ottawa (CA)

(*) Notice: Subject to any disclaimer, the term of this patent is extended or adjusted under 35 U.S.C. 154(b) by 351 days.

(21) Appl. No.: 10/322,656

(22) Filed: Dec. 19, 2002

(65) Prior Publication Data

US 2003/0182691 A1 Sep. 25, 2003

Related U.S. Application Data

(63) Continuation-in-part of application No. 09/272,204, filed on Mar. 19, 1999, now abandoned.

(60) Provisional application No. 60/078,728, filed on Mar. 20, 1998.

(51) Int. Cl.
*C12N 15/82* (2006.01)
*C12N 15/87* (2006.01)
*C12N 15/29* (2006.01)
*C07H 21/00* (2006.01)
*A01H 5/00* (2006.01)

(52) U.S. Cl. .................. 435/468; 435/320.1; 435/419; 536/23.4; 800/278; 800/306

(58) Field of Classification Search ................ 800/271, 800/278–280; 435/69.7, 320.1, 419, 468
See application file for complete search history.

(56) References Cited

U.S. PATENT DOCUMENTS

| | | | |
|---|---|---|---|
| 5,275,819 A | 1/1994 | Amer et al. | |
| 5,409,823 A | 4/1995 | Crossland et al. | |
| 5,412,085 A | 5/1995 | Allen et al. | |
| 5,477,002 A | 12/1995 | Tuttle et al. | |
| 5,484,905 A | 1/1996 | Nasrallah et al. | |
| 5,545,546 A | 8/1996 | Allen et al. | |
| 5,571,904 A | 11/1996 | Bridges et al. | |
| 5,585,543 A | 12/1996 | Kao | |
| 5,589,610 A | 12/1996 | De Beuckeleer et al. | |
| 5,633,438 A | 5/1997 | Baszczynski et al. | |
| 5,633,441 A | 5/1997 | De Greef et al. | |
| 5,652,354 A | 7/1997 | Mariani et al. | |
| 5,659,124 A | 8/1997 | Crossland et al. | |
| 5,723,754 A | 3/1998 | Scott et al. | |
| 5,955,653 A | 9/1999 | Scott et al. | |
| 6,265,566 B1 | 7/2001 | Singh et al. | |

FOREIGN PATENT DOCUMENTS

| | | |
|---|---|---|
| CA | 2099482 | 1/1994 |
| CA | 2106718 | 3/1994 |
| CA | 2165934 | 6/1997 |
| EP | 0 222 526 A2 | 5/1987 |
| EP | 0 270 248 A2 | 6/1988 |
| EP | 0 343 947 A2 | 11/1989 |
| EP | 0 388 593 A1 | 9/1990 |
| EP | 0 436 467 A2 | 7/1991 |
| WO | WO 90/08828 | 8/1990 |
| WO | WO 92/13957 | 8/1992 |
| WO | WO 92/18625 | 10/1992 |
| WO | WO 93/02197 | 2/1993 |
| WO | WO 93/18149 | 9/1993 |
| WO | WO 93/25695 | 12/1993 |
| WO | WO 94/09139 | 4/1994 |
| WO | WO 94/25613 | 11/1994 |
| WO | WO 95/21913 | 8/1995 |
| WO | WO 96/21029 | 7/1996 |

(Continued)

OTHER PUBLICATIONS

Piffanelli et al. (Trends in Plant Science, 3:250-253, 1998).*
Ross et al. (Plant Journal, 9(5):625-637, 1996).*
Doughty, J. et al., "Interaction between a coating-borne peptide of the *Brassica* pollen grain and stigmatic S (self-incompatibility)-locus-specific glycoproteins," Proc. Natl. Acad. Sci. USA, vol. 90, pp. 467-471, Jan. 1993.
Jefferson, Richard A., "Assaying Chimeric Genes in Plants: The GUS Gene Fusion System," Plant Molecular Biology Reporter, vol. 5, No. 4, pp. 387-405, 1987.

(Continued)

*Primary Examiner*—Ashwin Mehta
*Assistant Examiner*—Vinod Kumar
(74) *Attorney, Agent, or Firm*—Oliff & Berridge, PLC

(57) ABSTRACT

This invention is directed to a method for the expression of a gene of interest, or a chimeric or modified gene allowing the localization of a protein, protein fusion, peptide or fragment of interest within the extracellular domain of a floral cell. This method comprises preparing a construct comprising a promoter sequence capable of expressing a gene encoding the protein, protein fusion, peptide, or fragment of interest, within the floral cell; a translated sequence of the protein, protein fusion, peptide, or fragment of interest, which is localized within the extracellular domain of a floral cell; a gene that encodes the protein, protein fusion, peptide, or fragment of interest; and a terminator sequence, and transforming a plant. Plants transformed with such a construct are characterized as having a protein, fragment thereof, or peptide of interest on the surface of a floral cell. Such localized proteins or peptides may be used for the purposes of peptide display, mediating plant sterility, modifying pollen-pistil interactions, altering pollen for insect consumption etc.

25 Claims, 45 Drawing Sheets

FOREIGN PATENT DOCUMENTS

| WO | WO 97/13401 | 4/1997 |
| --- | --- | --- |
| WO | WO 97/30166 | 8/1997 |
| WO | WO 97/41240 | 11/1997 |

OTHER PUBLICATIONS van Kan, Jan. A. L. et al., "Cloning and Characterization of cDNA of Avirulence Gene avr9 of the Fungal Pathogen *Cladosporium fulvum*, Causal Agent of Tomato Leaf Mold," Molecular Plant-Microbe Interactions, vol. 4, No. 1, pp. 52-59, 1991.

Vanoosthuyse, Vincent, et al., "Two large *Arabidopsis thaliana* gene families are homologous to the *Brassica* gene superfamily that encodes pollen coat proteins and the male component of the self-incompatibility response," Plant Molecular Biology, vol. 16, pp. 17-34, 2001.

Gomez-Gomez, Lourdes et al., "Both the Extracellular Leucine-Rich Repeat Domain and the Kinase Activity of FLS2 Are Required for Flagellin Binding and Signaling in *Arabidopsis*," The Plant Cell, vol. 13, pp. 1155-1163, May 2001.

Foster, Elizabeth et al., "Modifying the pollen coat protein composition in *Brassica*," The Plant Journal, vol. 31, No. 4, pp. 477-486, Aug. 2002.

Bonnet, Philippe et al., "Acquired resistance triggered by elicitins in tobacco and other plants," European Journal of Plant Pathology, vol. 102, pp. 181-192, 1996.

Joosten, Matthieu H. A. J. et al., "Host resistance to a fungal tomato pathogen lost by a single base-pair change in an avirulence gene," Nature, vol. 367, pp. 384-386, Jan. 1994.

Datla, Raju S. S. et al., "Modified binary plant transformation vectors with the wild-type gene encoding NPTII," Gene, vol. 211, pp. 383-484, 1992.

Alexander, M. P., "A Versatile Stain For Pollen Fungi, Yeast and Bacteria," Stain Technology, vol. 55, No. 1, pp. 13-18, 1980.

Alexander, M. P., "Differential Staining of Aborted and Nonaborted Pollen," Stain Technology, vol. 44, No. 3, pp. 117-122, 1969.

Babic, Datla et al., "Development of an efficient *Agrobacterium*-mediated transformation system for *Brassica carinata*," Plant Cell Reports, vol. 17, No. 3, pp. 183-188, 1998.

Datla, Raju S. S., "A bifunctional fusion between β-glucuronidase and neomycin phosphotransferase: a broad-spectrum marker enzyme for plants," Gene, vol. 101, pp. 239-246, 1991.

Koltunow, Anna M. et al., "Different Temporal and Spatial Gene Expression Patterns Occur during Anther Development," The Plant Cell, vol. 2, pp. 1201-1224, Dec. 1990.

Clough, Steven J. and Bent, Andrew F., "Floral dip: a simplified method for *Agrobacterium*-mediated transformation of *Arabidopsis thaliana*," The Plant Journal, vol. 16, No. 6, pp. 735-743, 1998.

Timmermans, Maliga et al., "The pFF Plasmids: cassettes utilising CaMV sequences for expression of foreign genes in plants," Journal of Biotechnology, vol. 14, pp. 333-344, 1990.

Bih, Fong Yih et al., "The Predominant Protein on the Surface of Maize Pollen Is an Endoxylanase Synthesized by a Tapetum mRNA with a Long 5' Leader," The Journal of Biological Chemistry, vol. 274, No. 32, pp. 22884-22894, Aug. 6, 1999.

Abell, Ben M. et al., "Role of the Proline Knot Motif in Oleosin Endoplasmic Reticulum Topology and Oil Body Targeting," The Plant Cell, vol. 9, pp. 1481-1493, Aug. 1997.

Shiba, Hiroshi et al., "The Dominance of Alleles Controlling Self-Incompatibility in *Brassica* Pollen is Regulated at the RNA Level," The Plant Cell, vol. 14, pp. 491-504, Feb. 2002.

Shiba, Hiroshi et al., "A Pollen Coat Protein, SP11/SCR, Determines the Pollen S-Specificity in the Self-Incompatibility of *Brassica* Species," Plant Physiology, vol. 125, pp. 2095-2103, Apr. 2001.

Kachroo, Aardra et al., "Allele-Specific Receptor-Ligand Interactions in *Brassica* Self-Incompatibility," Science, vol. 293, pp. 1824-1826, Sep. 7, 2001.

Takayama, Seiji et al., "The pollen determinant of self-incompatibility in *Brassica campestris*," PNAS, vol. 97, No. 4, pp. 1920-1925, Feb. 15, 2000.

Robert, Laurian S. et al., "Molecular analysis of two *Brassica napus* genes expressed in the stigma," Plant Molecular Biology, vol. 26, pp. 1217-1222, 1994.

Robert, L. S. et al., "Analyses in transgenic tobacco of the promoter from a *Brassica napus* gene highly expressed in the stigma," Plant Cell Reports, vol. 18, pp. 357-362, 1999.

Schopfer, Christel R. et al., "The Male Determinant of Self-Incompatibility in *Brassica*," Science, vol. 286, pp. 1697-1700, Nov. 26, 1999.

Nasrallah, June and Nasrallah, Mikhall, "Pollen-Stigma Signaling in the Sporophytic Self-Incompatibility Response," The Plant Cell, vol. 5, pp. 1325-1335, Oct. 1993.

Murphy, Denis J., "Structure, Function and Biogenesis of Storage Lipid Bodies and Oleosins in Plants," Prog. Lipid Res., vol. 32, No. 3, pp. 247-280, 1993.

Staiger, Dorothy et al., "The proteins encoded by two tapetum-specific transcripts, *Sa*tap35 and *Sa*tap 44, from *Sinapis alba* L. are localized in the exine cell wall layer of developing microspores," Planta, vol. 192, pp. 221-231, 1994.

Hird, Diane L. et al., "The anther-specific protein encoded by the *Brassica napus* and *Arabidopsis thaliana* A6 gene displays similarity to β-1,3-glucanases," The Plant Journal, vol. 4, No. 6, pp. 1023-1033, 1993.

Bucciaglia, Paul A. and Smith, Alan G., "Cloning and characterization of *Tag 1*, a tobacco anther β-1,3-glucanase expressed during tetrad dissolution," Plant Molecular Biology, vol. 24, pp. 903-914, 1994.

Schrauwen, J. A. M. et al., "Tapetum-specific genes: what role do they play in male gametophyte development?," Acta Bot. Neerl., vol. 45, No. 1, pp. 1-15, Mar. 1996.

Stanchev, Borislav S. et al., "Cloning of *PCPI*, a member of a family of pollen coat protein (*PCP*) genes from *Brassica oleracea* encoding novel cysteine-rich proteins involved in pollen-stigma interactions," The Plant Journal, vol. 10, No. 2, pp. 303-313, 1996.

Robert, Laurian S. et al., "Isolation and characterization of a polygalacturonase gene highly expressed in *Brassica napus* pollen," Plant Molecular Biology, vol. 23, pp. 1273-1278, 1993.

De Oliveira, D. E. et al., "Inflorescence-specific genes from *Arabidopsis thaliana* encoding glycine-rich proteins," The Plant Journal, vol. 3, No. 4, pp. 495-507, 1993.

Roberts, M. R. et al., "A *Brassica napus* mRNA expressed specifically in developing microspores," Plant Molecular Biology, vol. 17, pp. 295-299, 1991.

Roberts, Michael R. et al., "*Brassica napus* pollen oleosins possess a characteristic C-terminal domain," Planta, vol. 195, pp. 469-470, 1995.

Hong, H. P. et al., "The promoter of a *Brassica napus* polygalacturonase gene directs pollen expression of β-glucuronidase in transgenic *Brassica* plants," Plant Cell Reports, vol. 16, pp. 373-378, 1997.

Hong, Hai Ping et al., "Promoter sequences from two different *Brassica napus* tapetal oleosin-like genes direct tapetal expression of β-glucuronidase in transgenic *Brassica* plants," Plant Molecular Biology, vol. 34, pp. 549-555, 1997.

Gerster, Jean et al., "Molecular Characterization of Two *Brassica napus* Pollen-Expressed Genes Encoding Putative Arabinogalactan Proteins," Plant Physiol., vol. 110, pp. 1231-1237, 1996.

Matsumoto, Ichiro et al., "Characterization of a Gene Family Encoding Cysteine Proteinases of *Sitophilus zeamais* (Maize Weevil), and Analysis of the Protein Distribution in Various Tissues Including Alimentary Tract and Germ Cells," J. Biochem., vol. 121, pp. 464-476, 1997.

Corey, David R. et al., "Trypsin display on the surface of bacteriophage," Gene, vol. 128, pp. 129-134, 1993.

Hodge, Rachel et al., "Cold-plaque screening: a simple technique for the isolation of low abundance, differentially expressed transcripts from conventional cDNA libraries," The Plant Journal, vol. 2, No. 2, pp. 257-260, 1992.

Mayfield, Jacob A. et al., "Gene Families from the *Arabidopsis thaliana* Pollen Coat Proteome," Science, vol. 292, pp. 2482-2485, Jun. 29, 2001.

Nasrallah, Mikhail E. et al., "Generation of Self-Incompatible *Arabidopsis thaliana* by Transfer of Two *S* Locus Genes from *A. lyrata*," Science, vol. 297, pp. 247-249, Jul. 12, 2002.

Bevan, Michael, "Binary *Agrobacterium* vectors for plant transformation," Nucleic Acids Research, vol. 12, No. 22, pp. 8711-8721, 1984.

Worrall, Dawn et al., "Premature Dissolution of the Microsporocyte Callose Wall Causes Male Sterility in Transgenic Tobacco," The Plant Cell, vol. 4, pp. 759-771.

De Block, Marc et al., "In-situ Enzyme Histochemistry on Plastic-Embedded Plant Material. The Development of an Artefact-Free β-Glucuronidase Assay," The Plant Journal, vol. 2, No. 2, pp. 261-266, 1992.

Robert, Laurian S. et al., "Molecular Characterization of Two *Brassica napus* Genes Related to Oleosins which are Highly Expressed in the Tapetum," The Plant Journal, vol. 6, No. 6, pp. 927-933, 1994.

Hiscock, Simon J. et al., "A 7-kDa Pollen Coating-Borne Peptide from *Brassica napus* Interacts with S-Locus Glycoprotein and S-Locus-Related Glycoprotein," Publication Unknown, pp. 367-374, Spring 1995.

Huang, Anthony H. C., "Oleosins and Oil Bodies in Seeds and Other Organs," Plant Physiol. vol. 110, pp. 1055-1061, 1996.

Ross, Joanne H.E. et al., "Characterization of Anther-Expressed Genes Encoding a Major Class of Extracellular Oleosin-Like Proteins in the Pollen Coat of *Brassicaceae*," The Plant Journal, vol. 9, No. 5, pp. 625-637, 1996.

Ruiter, Rene K. et al., "Characterization of Oleosins in the Pollen Coat of *Brassica oleracea*," The Plant Cell, vol. 9, pp. 1621-1631, 1997.

Wang, Tzann-Wei et al., "Identification, Subcellular Localization, and Developmental Studies of Oleosins in the Anther of *Brassica napus*," The Plant Journal, vol. 11, No. 3, pp. 475-487, 1997.

Sasaki, Yoko et al., "Localization of an SLG Protein Expressed under the Regulation of a Tapetum-Specific Promoter in Anthers of Transgenic *Brassica napus*," Sex. Plant Reprod., vol. 11, pp. 245-250, 1998.

Piffanelli, Pietro et al., "Novel Organelles and Targeting Mechanisms in the Anther Tapetum," Elsevier Science Ltd., vol. 3, No. 7, pp. 250-253 1998.

Murphy, Dennis J., "Biosynthesis, Targeting and Processing of Oleosin-Like Proteins, Which are Major Pollen Coat Components in *Brassica napus*," The Plant Journal, vol. 13, No. 1, pp. 1-16, 1998.

K. Toriyama et al; "Transformation of *Brassica oleracea* with an S-Locus Gene from B Campestris Changes The Self-Incompatibility Phenotype" Theoretical and Applied Genetics, vol. 81, No. 6, pp. 769-776, Jan. 1, 1991.

R. J. Stahl et al. "The Self-Incompatibility Phenotype in *Brassica* is Altered by the Transformation of A Mutant S Locus Receptor Kinase" Plant cell, vol. 10, pp. 209-218, Feb. 1, 1998.

D. J. Murphy et al. "Biosyntheses, targeting and processing of oleosin-like proteins, which are major pollen coat components in *Brassica napus*" The Plant Journal, vol. 13. No. 1, pp. 1-16, Jan. 1998.

Millra et al. "Plant Cell", vol. 10, pp. 1889-1902, 1998.

Boase et al. In Vitro Cellular and Developmental Biology, vol. 34, pp. 46-51, 1998.

Hadfield et al, Plant Physiol, 117:337-343, 1998.

Kandasamy et al., Dev. Biol. 134:462-472, 1989.

Kandasamy et al., Plant Cell, 5(3): 263-275, Mar. 1993.

Thorsness et al., Plant Cell, 5(3): 253-261, Mar. 1993.

Goldman et al., EMBO Journal, 13(13):2976-2985, 1994.

Pang et al., Gene 116:165-172, 1992.

Stein et al., Proc. Natl. Acad. Sci. USA, 88:8816-8820, Oct. 1991.

Toriyama et al., Dev. Biol. 143:427-431, 1991.

Nasrallah et al., Proc. Natl. Acad. Sci. USA, 85:5551-5555, Aug. 1988.

Turk et al., New Phytol. 136(1):29-38, 1997.

* cited by examiner

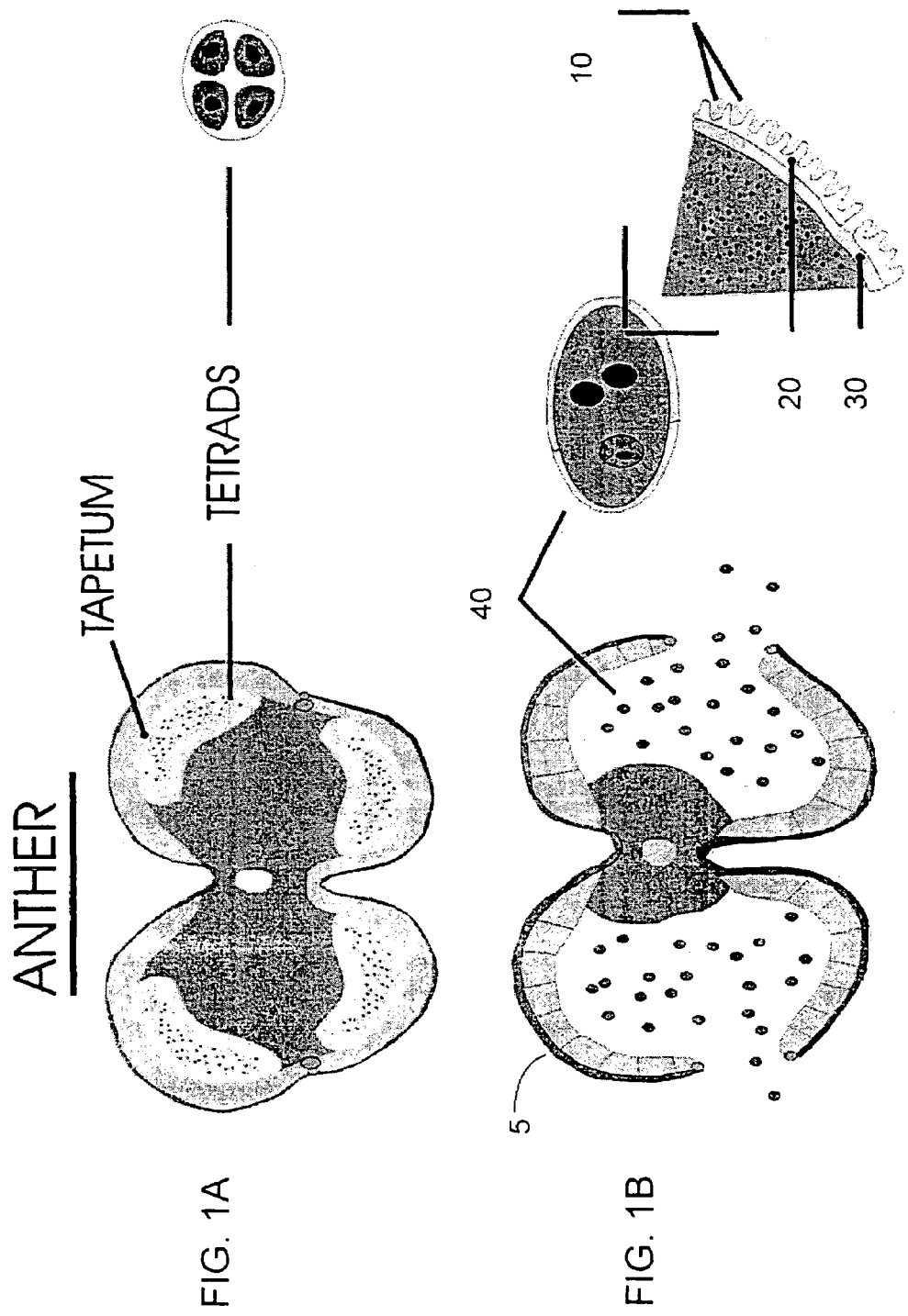

Fig. 3A C-terminal translational fusion with full length tapetal oleosin
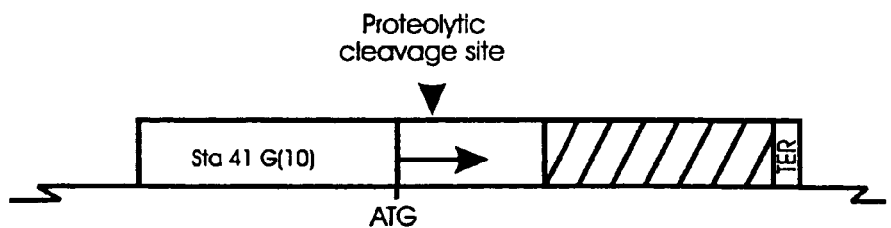
Fig. 3B C-terminal translational fusion at proteolytic cleavage site
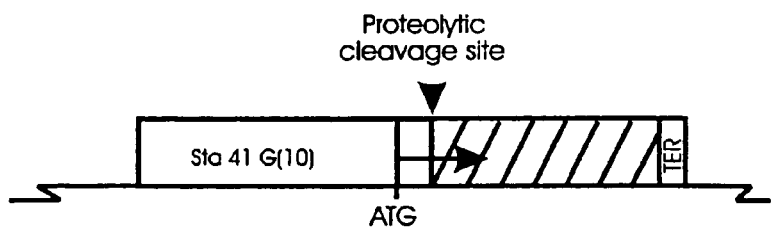
Fig. 3C Internal translational fusion at proteolytic cleavage site
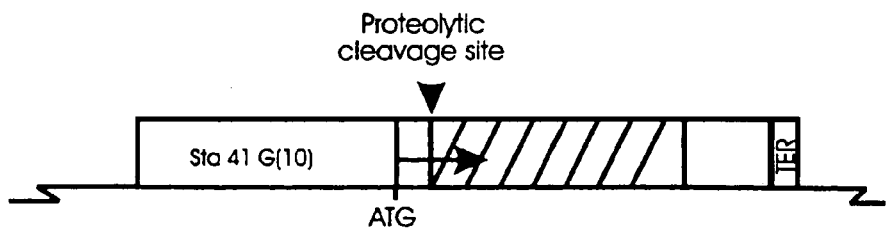

FIG. 27

SEQUENCE LISTING

<160> NUMBER OF SEQ ID NOS: 51

<210> SEQ ID NO 1
<211> LENGTH: 23
<212> TYPE: DNA
<213> ORGANISM: artificial
<220> FEATURE:
<223> OTHER INFORMATION: oligonucleotide sequence (KSB-3)

<400> SEQUENCE: 1

| taggtaccga gctcggggga tcc | 23 |

```
<210> SEQ ID NO 2
<211> LENGTH: 23
<212> TYPE: DNA
<213> ORGANISM: artificial
<220> FEATURE:
<223> OTHER INFORMATION: oligonucleotide sequence (KSB-4)

<400> SEQUENCE: 2
```

| taggatcccc cgagctcggt acc | 23 |

```
<210> SEQ ID NO 3
<211> LENGTH: 4936
<212> TYPE: DNA
<213> ORGANISM: artificial
<220> FEATURE:
<223> OTHER INFORMATION: nucleotide sequence of the translational fusion
      in plasmid TOG-1 (see Example 2; Figure 5A)

<400> SEQUENCE: 3
```

| gagctccacc cacagaagca gataaaccag ctgaaggaac aacagaaaaa ccaaaagata | 60 |
| attcgactgg aggagcagcc gataaaccag aagataaacc agttggagga gcagccgata | 120 |
| aaccagaagg taaaccggat ggaggagcaa caaataagcc agaaagtaaa ccagctggag | 180 |
| gaccatcaaa taaccaaaaa gataaacccg ctggaggacc aacggataaa ccagaaagta | 240 |
| agccagcaga taaaccgct ggaggaccaa cagataagcc aggaagtaaa ccggttgata | 300 |
| aacccgctgg aggaccaaca gataagacag aaagtaaact ggttggagag gcatcaaata | 360 |
| aaccaaaaga taaacccgct ggtggatcaa cagatatgcc agaagctgga gagacatcaa | 420 |
| ataaaccaaa agataaatcc gttggaggac caacaaataa gccagaaagt aaaccagctg | 480 |
| gagaaacatc acataaacca aaagataaac ccgctggtgg accaacagat aagccagaaa | 540 |
| gtaaaccggc tggagaaaca tcacataaac caaaagataa actcgctggt ggaccaacag | 600 |
| ataagccaga agtaaaccag ctggagagg catcaaataa accaaaagat aaacccgctg | 660 |
| gtggaccaac agataaacca gctggaggat cagtagataa accaaaagat aaacctgccg | 720 |
| gaggaccaac agataaacca acaaataaac cgactggagg ggctgcaaat aaaccggctg | 780 |
| gagaggcagc aaacaaaccg actggaaaac cgaaaaataa accggctgga gagaataaac | 840 |
| caccgggatg gtataggtga atggagtagt atgaaattaa agtattgggt tccacaaatt | 900 |
| attcctaatt tatcctacac tacatgtttc ataatcattt ctataaatgt acgacttgtt | 960 |
| acaaagaaat gataaacagt gtacagaatt ttctttgtaa atttattaaa ttgatgtgga | 1020 |
| tatcattata actgacgtta gcgtatatcg accaatgcga taaccaaatc atcggtatat | 1080 |
| acctaagact tcctttttaa aaatgaatct gatactaatt taatgtacga cttccaataa | 1140 |
| ccaatcttct tgcattttc attgccattt accttgaacg cctctctttc tagtatgaga | 1200 |
| cattaacatt gcgctcttgt cacaatgaag ccatggaaaa cttcggctct ttaatcacac | 1260 |
| atgtgacaat ccagttggtt taagggaaag tatttatat tttatatagc tcgttctcag | 1320 |
| aacaaaaaaa ccaaattctt tagcaaaaat ggtccttaag gcccattccg tttcttctta | 1380 |
| taatgttctg ggctagccca tttgaattta aacctttcct ttcaatttct gcattaatat | 1440 |
| aattcagttg ttcaaaaaaa aaatagcgct tattgaaata atagagagaa agataatgag | 1500 |
| aagggagaaa atgaaaagcg tatttcatat gagagattgt caacaaaaat tgagtgactt | 1560 |
| ttatgatatt tgttcaaaga atagtctaat aaccttctct atttaaattt taattatgtt | 1620 |

-continued

| | | | | | |
|---|---|---|---|---|---|
| atatatcaat | aatactaaaa | taattagtta | ctcacagttc | gtgacaaaaa | aaaaagcaaa | 1680 |
| tagatgaaat | gaaatgaaag | aaagatcttt | cttcacgcgt | tgatattcat | aaaacaatgg | 1740 |
| aatgaaagaa | aacagttaag | attctacaag | aaagaaaaga | aagtcccaaa | acatgacaa | 1800 |
| atagatgaag | aagcaaatgt | gacttgacgt | aacgtagaac | tccatatata | ctcccatcgt | 1860 |
| tttgcatgga | gcatgcatgt | gtaccgtgca | cgtcgtagac | cacacaactc | cttcataaaa | 1920 |
| agccctctct | cttcccatca | ccaaaccatc | agaaaatatg | agaaacgaaa | ttcaaaacga | 1980 |
| aacagctcag | actgatcaga | cccagggaag | tatgttttct | ttttcaatt | tgttcccttt | 2040 |
| cctcctccca | atgtttgagg | ttatcaagat | ggttgttgct | tccgttgcgt | ccgtagtata | 2100 |
| tttaggcttc | gccggtgtaa | cactcagtgg | ttcagccgtg | gcattagccg | tatccacccc | 2160 |
| tcttttcatc | atattcagtc | cgattctctt | acctgctatt | gcagccacta | ctgtcctagc | 2220 |
| cgccgggctc | ggaggtaaaa | aagtggcggc | ggctccggaa | gcttctccgg | cagcttcgcc | 2280 |
| atccctatct | ctgttgggca | taccggagag | cattaaacca | agtaatatta | taccggagag | 2340 |
| tattaaacca | agtaatatta | taccggaggg | tattaaacca | agtaatatta | aggacaaaat | 2400 |
| taaggatacg | ataggcaaag | ttaagaataa | gatcaaagct | aaaaggaag | aaaaatccaa | 2460 |
| aggtaaaagt | gaagattctt | ccaagggtaa | aggtaaatca | aagggtgaag | atacgactac | 2520 |
| ggatgacgat | acgactacgg | atgaagacaa | acacggaagt | ggagctaaac | acggaaaggg | 2580 |
| agagagtaaa | cacggaaaag | gtgagagtac | acacggaaag | ggaggtaaac | atggaagtga | 2640 |
| aggtaagcat | ggaagtggag | gttcgtctat | gggtggaggt | aaaacacgaa | gcggaggtaa | 2700 |
| acatgaaact | ggaggtaaac | acggaagcgg | aggtaaacat | gaaagtggag | gttcgcctat | 2760 |
| gggtggaggt | aaacatggaa | gtgaaggtaa | gcatggaagt | ggaggtgcgt | ctatgggtgg | 2820 |
| aggtaaacac | ggaagcggag | gtaaacatga | agtggaggt | tcggctatgg | gtggaggtaa | 2880 |
| gcacggaagt | ggaggcaaac | acggaagtga | aggtaaacac | ggggtgaag | gctcttctat | 2940 |
| gggtaaaaat | agtctatcca | agaagaaaaa | ggaattccat | tatagaggtc | aagctatgga | 3000 |
| tgcaagtagt | acaagtgaaa | gttcagatgg | aagttcagat | ggcagcagtt | cagatggaag | 3060 |
| ttcacatggg | agtggtggta | aacacatagg | taccgagctc | ggggatccc | cggtggtca | 3120 |
| gtcccttatg | ttacgtcctg | tagaaacccc | aacccgtgaa | atcaaaaaac | tcgacggcct | 3180 |
| gtgggcattc | agtctggatc | gcgaaaactg | tggaattgat | cagcgttggt | gggaaagcgc | 3240 |
| gttacaagaa | agccgggcaa | ttgctgtgcc | aggcagtttt | aacgatcagt | tcgccgatgc | 3300 |
| agatattcgt | aattatgcgg | gcaacgtctg | gtatcagcgc | gaagtcttta | taccgaaagg | 3360 |
| ttgggcaggc | cagcgtatcg | tgctgcgttt | cgatgcggtc | actcattacg | gcaaagtgtg | 3420 |
| ggtcaataat | caggaagtga | tggagcatca | gggcggctat | acgccatttg | aagccgatgt | 3480 |
| cacgccgtat | gttattgccg | ggaaaagtgt | acgtatcacc | gtttgtgtga | acaacgaact | 3540 |
| gaactggcag | actatcccgc | cgggaatggt | gattaccgac | gaaaacggca | agaaaaagca | 3600 |
| gtcttacttc | catgatttct | ttaactatgc | cgggatccat | cgcagcgtaa | tgctctacac | 3660 |
| cacgccgaac | acctgggtgg | acgatatcac | cgtggtgacg | catgtcgcgc | aagactgtaa | 3720 |
| ccacgcgtct | gttgactggc | aggtggtggc | caatggtgat | gtcagcgttg | aactgcgtga | 3780 |
| tgcggatcaa | caggtggttg | caactggaca | aggcactagc | gggactttgc | aagtggtgaa | 3840 |
| tccgcacctc | tggcaaccgg | gtgaaggtta | tctctatgaa | ctgtgcgtca | cagccaaaag | 3900 |
| ccagacagag | tgtgatatct | acccgcttcg | cgtcggcatc | cggtcagtgg | cagtgaaggg | 3960 |
| ccaacagttc | ctgattaacc | acaaaccgtt | ctactttact | ggctttggtc | gtcatgaaga | 4020 |

```
tgcggactta cgtggcaaag gattcgataa cgtgctgatg gtgcacgacc acgcattaat    4080
ggactggatt ggggccaact cctaccgtac ctcgcattac ccttacgctg aagagatgct    4140
cgactgggca gatgaacatg gcatcgtggt gattgatgaa actgctgctg tcggctttaa    4200
cctctcttta ggcattggtt tcgaagcggg caacaagccg aaagaactgt acagcgaaga    4260
ggcagtcaac ggggaaactc agcaagcgca cttacaggcg attaaagagc tgatagcgcg    4320
tgacaaaaac cacccaagcg tggtgatgtg gagtattgcc aacgaaccgg atacccgtcc    4380
gcaagtgcac gggaatattt cgccactggc ggaagcaacg cgtaaactcg acccgacgcg    4440
tccgatcacc tgcgtcaatg taatgttctg cgacgctcac accgatacca tcagcgatct    4500
ctttgatgtg ctgtgcctga accgttatta cggatggtat gtccaaagcg gcgatttgga    4560
aacggcagag aaggtactgg aaaaagaact tctggcctgg caggagaaac tgcatcagcc    4620
gattatcatc accgaatacg gcgtggatac gttagccggg ctgcactcaa tgtacaccga    4680
catgtggagt gaagagtatc agtgtgcatg gctggatatg tatcaccgcg tctttgatcg    4740
cgtcagcgcc gtcgtcggtg aacaggtatg gaatttcgcc gattttgcga cctcgcaagg    4800
catattgcgc gttggcggta acaagaaagg gatcttcact cgcgaccgca aaccgaagtc    4860
ggcggctttt ctgctgcaaa aacgctggac tggcatgaac ttcggtgaaa aaccgcagca    4920
gggaggcaaa caatga                                                   4936
```

<210> SEQ ID NO 4
<211> LENGTH: 3766
<212> TYPE: DNA
<213> ORGANISM: artificial
<220> FEATURE:
<223> OTHER INFORMATION: nucleotide sequence of the translational fusion
      in plasmid TOP-1 (see Example 3, Figure 6)

<400> SEQUENCE: 4

```
gagctccacc cacagaagca gataaaccag ctgaaggaac aacagaaaaa ccaaaagata      60
attcgactgg aggagcagcc gataaaccag aagataaacc agttggagga gcagccgata     120
aaccagaagg taaaccggat ggaggagcaa caaataagcc agaaagtaaa ccagctggag     180
gaccatcaaa taaccaaaaa gataaacccg ctggaggacc aacggataaa ccagaaagta     240
agccagcaga taaacccgct ggaggaccaa cagataagcc aggaagtaaa ccggttgata     300
aacccgctgg aggaccaaca gataagacag aaagtaaact ggttggagag gcatcaaata     360
aaccaaaaga taaacccgct ggtggatcaa cagatatgcc agaagctgga gagacatcaa     420
ataaaccaaa agataaatcc gttggaggac caacaaataa gccagaaagt aaaccagctg     480
gagaaacatc acataaacca aaagataaac ccgctggtgg accaacagat aagccagaaa     540
gtaaaccggc tggagaaaca tcacataaac caaagataa actcgctggt ggaccaacag     600
ataagccaga aagtaaacca gctggagagg catcaaataa ccaaaagat aaaccgctg      660 gtggaccaac agataaacca gctggaggat cagtagataa ccaaaagat aaacctgccg     720 gaggaccaac agataaacca acaaataaac gactggagg ggctgcaaat aaaccggctg     780
gagaggcagc aaacaaaccg actggaaaac cgaaaaataa accggctgga gagaataaac     840
caccgggatg gtataggtga atggagtagt atgaaattaa agtattgggt tccacaaatt     900
attcctaatt tatcctacac tacatgtttc ataatcattt ctataaatgt acgacttgtt     960
acaaagaaat gataaacagt gtacagaatt ttctttgtaa atttattaaa ttgatgtgga    1020
tatcattata actgacgtta gcgtatatcg accaatgcga taaccaaatc atcggtatat    1080
```

```
acctaagact tcctttttaa aaatgaatct gatactaatt taatgtacga cttccaataa   1140
ccaatcttct tgcatttttc attgccattt accttgaacg cctctctttc tagtatgaga   1200
cattaacatt gcgctcttgt cacaatgaag ccatggaaaa cttcggctct taatcacac    1260
atgtgacaat ccagttggtt taagggaaag tattttatat tttatatagc tcgttctcag   1320
aacaaaaaaa ccaaattctt tagcaaaaat ggtccttaag gcccattccg tttcttctta   1380
taatgttctg ggctagccca tttgaattta aacctttcct ttcaatttct gcattaatat   1440
aattcagttg ttcaaaaaaa aaatagcgct tattgaaata atagagagaa agataatgag   1500
aagggagaaa atgaaaagcg tatttcatat gagagattgt caacaaaaat tgagtgactt   1560
ttatgatatt tgttcaaaga atagtctaat aacctttctt atttaaattt taattatgtt   1620
atatatcaat aatactaaaa taattagtta ctcacagttc gtgacaaaaa aaaaagcaaa   1680
tagatgaaat gaaatgaaag aaagatcttt cttcacgcgt tgatattcat aaaacaatgg   1740
aatgaaagaa aacagttaag attctacaag aaagaaaaga agtcccaaa  aacatgacaa   1800
atagatgaag aagcaaatgt gacttgacgt aacgtagaac tccatatata ctcccatcgt   1860
tttgcatgga gcatgcatgt gtaccgtgca cgtcgtagac cacacaactc cttcataaaa   1920
agccctctct cttcccatca ccaaaccatc agaaaatatg agaaacgaaa ttcaaaacga   1980
aacagctcag actgatcaga cccagggaag tatgttttct tttttcaatt tgttcccttt   2040
cctcctccca atgtttgagg ttatcaagat ggttgttgct tccgttgcgt ccgtagtata   2100
tttaggcttc gccggtgtaa cactcagtgg ttcagccgtg gcattagccg tatccacccc   2160
tcttttcatc atattcagtc cgattctctt acctgctatt gcagccacta ctgtcctagc   2220
cgccgggctc ggaggtaaaa aagtggcggc ggctccggaa gcttctccgg cagcttcgcc   2280
atccctatct ctgttgggca taccggagag cattaaacca agtaatatta taccggagag   2340
tattaaacca agtaatatta taccggaggg tattaaacca agtaatatta aggacaaaat   2400
taaggatacg ataggcaaag ttaagaataa gatcaaagct aaaaaggaag aaaaatccaa   2460
aggtaaaagt gaagattctt ccaagggtaa aggtaaatca aagggtgaag atacgactac   2520
ggatgacgat acgactacgg atgaagacaa acacggaagt ggagctaaac acggaaaggg   2580
agagagtaaa cacggaaaag gtgagagtac acacggaaag ggaggtaaac atggaagtga   2640
aggtaagcat ggaagtggag gttcgtctat gggtggaggt aaacacggaa gcggaggtaa   2700
acatgaaact ggaggtaaac acggaagcgg aggtaaacat gaaagtggag gttcgcctat   2760
gggtggaggt aaacatggaa gtgaaggtaa gcatggaagt ggaggtgcgt ctatgggtgg   2820
aggtaaacac ggaagcggag gtaaacatga agtggaggt tcggctatgg gtggaggtaa    2880
gcacggaagt ggaggcaaac acggaagtga aggtaaacac ggggtgaag gctcttctat    2940
gggtaaaaat agtctatcca agaagaaaaa ggaattccat tatagaggtc aagctatgga   3000
tgcaagtagt acaagtgaaa gttcagatgg aagttcagat ggcagcagtt cagatggaag   3060
ttcacatggg agtggtggta acacatagg  taccgagctc gggggatcct tgcctgatac    3120
tgttgactgg agggacaaag gagctgtcac tgaagtcaaa gaccaaggtc actgcgggtc   3180
gtgttggagt ttcagtgcta ctggttcact cgaaggtcag cacttccgta aaaccggcaa   3240
actagtgtcc cttagcgaac aaaacttggt agattgttca ggaagatacg gcaacaacgg   3300
ctgcaacggc ggtctcatgg acaacgcctt ccgttacatc aaagacaacg gcggtatcga   3360
cacggaaaag tcctaccccct acctagccga ggacgagaaa tgccactaca aagcccagaa   3420
```

```
cagcggcgca accgacaagg gctttgtaga catcgaagaa gccaacgaag atgaccttaa    3480
ggctgcagtg gccaccgtag gccccgtttc tattgccatt gatgccagcc acgaaacctt    3540
ccaactgtac tcggatggag tctacagtga tcctgaatgt agctcacaag aactagacca    3600
tggggtgttg gtagtgggat acggtaccag cgacgatggt caggactact ggttggtgaa    3660
aaattcgtgg ggacccagct ggggattgaa cggatacatc aagatggcca ggaatcaaga    3720
taacatgtgc ggagttgcat ctcaggctag ttatcctttg gtttag                   3766
```

<210> SEQ ID NO 5
<211> LENGTH: 3496
<212> TYPE: DNA
<213> ORGANISM: artificial
<220> FEATURE:
<223> OTHER INFORMATION: nucleotide sequence of the translational fusion
      in plasmid TOPI-1 (see example 4; Figure 7)

<400> SEQUENCE: 5

```
gagctccacc cacagaagca gataaaccag ctgaaggaac aacagaaaaa ccaaaagata     60
attcgactgg aggagcagcc gataaaccag aagataaacc agttggagga gcagccgata    120
aaccagaagg taaaccggat ggaggagcaa caaataagcc agaaagtaaa ccagctggag    180
gaccatcaaa taaccaaaaa gataaacccg ctggaggacc aacggataaa ccagaaagta    240
agccagcaga taaacccgct ggaggaccaa cagataagcc aggaagtaaa ccggttgata    300
aacccgctgg aggaccaaca gataagacag aaagtaaact ggttggagag gcatcaaata    360
aaccaaaaga taaacccgct ggtggatcaa cagatatgcc agaagctgga gagacatcaa    420
ataaaccaaa agataaatcc gttggaggac caacaaataa gccagaaagt aaaccagctg    480
gagaaacatc acataaacca aagataaaac cgctggtgg accaacagat aagccagaaa    540
gtaaaccggc tggagaaaca tcacataaac caaagataaa actcgctggt ggaccaacag    600
ataagccaga aagtaaacca gctggagagg catcaaataa accaaaagat aaacccgctg    660
gtggaccaac agataaacca gctggaggat cagtagataa accaaaagat aaacctgccg    720
gaggaccaac agataaacca acaaataaac cgactggagg ggctgcaaat aaaccggctg    780
gagaggcagc aaacaaaccg actggaaaac cgaaaaataa accggctgga gagaataaac    840
caccgggatg gtataggtga atggagtagt atgaaattaa agtattgggt tccacaaatt    900
attcctaatt tatcctacac tacatgtttc ataatcattt ctataaatgt acgacttgtt    960
acaaagaaat gataaacagt gtacagaatt ttctttgtaa atttattaaa ttgatgtgga   1020
tatcattata actgacgtta gcgtatatcg accaatgcga taaccaaatc atcggtatat   1080
acctaagact tcctttttaa aaatgaatct gatactaatt taatgtacga cttccaataa   1140
ccaatcttct tgcattttc attgccattt accttgaacg cctctctttc tagtatgaga   1200
cattaacatt gcgctcttgt cacaatgaag ccatggaaaa cttcggctct ttaatcacac   1260
atgtgacaat ccagttggtt taagggaaag tattttatat tttatatagc tcgttctcag   1320
aacaaaaaaa ccaaattctt tagcaaaaat ggtccttaag gcccattccg tttcttctta   1380
taatgttctg ggctagccca tttgaattta aacctttcct ttcaatttct gcattaatat   1440
aattcagttg ttcaaaaaaa aaatagcgct tattgaaata atagagagaa agataatgag   1500
aagggagaaa atgaaaagcg tatttcatat gagagattgt caacaaaaat tgagtgactt   1560
ttatgatatt tgttcaaaga atagtctaat aacctttctt attttaaattt taattatgtt   1620 atatatcaat aatactaaaa taattagtta ctcacagttc gtgacaaaaa aaaaagcaaa   1680
```

```
tagatgaaat gaaatgaaag aaagatcttt cttcacgcgt tgatattcat aaaacaatgg   1740
aatgaaagaa aacagttaag attctacaag aaagaaaaga aagtcccaaa acatgacaa    1800 atagatgaag aagcaaatgt gacttgacgt aacgtagaac tccatatata ctcccatcgt   1860
tttgcatgga gcatgcatgt gtaccgtgca cgtcgtagac cacacaactc cttcataaaa   1920
agccctctct cttcccatca ccaaaccatc agaaaatatg agaaacgaaa ttcaaaacga   1980
aacagctcag actgatcaga cccagggaag tatgttttct tttttcaatt tgttcccttt   2040
cctcctccca atgtttgagg ttatcaagat ggttgttgct tccgttgcgt ccgtagtata   2100
tttaggcttc gccggtgtaa cactcagtgg ttcagccgtg cattagccg tatccacccc    2160 tcttttcatc atattcagtc cgattctctt acctgctatt gcagccacta ctgtcctagc   2220
cgccgggctc ggaggtaaaa aagtggcggc ggctccggaa gcttctccgg cagcttcgcc   2280
atccctatct ctgttgggca taccggagag cattaaacca agtaatatta taccggagag   2340
tattaaacca agtaatatta taccggaggg tattaaacca agtaatatta aggacaaaat   2400
taaggatacg ataggcaaag ttaagaataa gatcaaagct aaaaaggaag aaaaatccaa   2460
aggtaaaagt gaagattctt ccaagggtaa aggtaaatca aagggtgaag atacgactac   2520
ggatgacgat acgactacgg atgaagacaa acacggaagt ggagctaaac acggaaaggg   2580
agagagtaaa cacggaaaag gtgagagtac acacggaaag ggaggtaaac atggaagtga   2640
aggtaagcat ggaagtggag gttcgtctat gggtggaggt aaacacggaa gcggaggtaa   2700
acatgaaact ggaggtaaac acggaagcgg aggtaaacat gaaagtggag gttcgcctat   2760
gggtggaggt aaacatggaa gtgaaggtaa gcatggaagt ggaggtgcgt ctatgggtgg   2820
aggtaaacac ggaagcggag gtaaacatga agtggaggt tcggctatgg gtggaggtaa    2880
gcacggaagt ggaggcaaac acggaagtga aggtaaacac gggggtgaag gctcttctat   2940
gggtaaaaat agtctatcca agaagaaaaa ggaattccat tatagaggtc aagctatgga   3000
tgcaagtagt acaagtgaaa gttcagatgg aagttcagat ggcagcagtt cagatggaag   3060
ttcacatggg agtggtggta acacataggg tacccaattc cgcaaaaatc cgtcaaaaat   3120
ggagtccaaa acaggtgaaa atcaagatcg tcccgtttta ttgggaggtt gggaagatcg   3180
cgatccaaag gatgaagaaa tcctggaact attgccaagc atattgatga agtaaatga    3240 acaatcaaac gatgaatatc atttgatgcc gatcaaatta ctgaaggttt catctcaagt   3300
tgtcgctggt gtgaaataca agatggatgt gcaggttgct cgatcgcaat gtaaaaaaag   3360
ttcgaatgaa aaagttgatc taacaaagtg caaaaaatta gaaggacatc ctgaaaaggt   3420
tatgactttg gaagtttggg agaaaccatg ggagaatttt atgcgcgtcg aaattctggg   3480
aacaaaagaa gtatga                                                   3496
```

```
<210> SEQ ID NO 6
<211> LENGTH: 24
<212> TYPE: DNA
<213> ORGANISM: artificial
<220> FEATURE:
<223> OTHER INFORMATION: oligonucleotide sequence (BKX-1)

<400> SEQUENCE: 6
tcgaggggat ccggtacctc taga                                          24

<210> SEQ ID NO 7
<211> LENGTH: 24
<212> TYPE: DNA
<213> ORGANISM: artificial
```

<220> FEATURE:
<223> OTHER INFORMATION: oligonucleotide sequence (BKX-2)

<400> SEQUENCE: 7
tcgatctaga ggtaccggat cccc                                              24

<210> SEQ ID NO 8
<211> LENGTH: 3459
<212> TYPE: DNA
<213> ORGANISM: artificial
<220> FEATURE:
<223> OTHER INFORMATION: nucleotide sequence of the translational fusion
      in plasmid SPF-1 (see Example 5, Figure 8)

<400> SEQUENCE: 8

| | | | | | |
|---|---|---|---|---|---|
| gggatctat | cttagatatt | gtttgaaaag | agagtaccaa | ctctcccata | ctcaaagtca | 60 |
| cagaagtcaa | atgttgtttg | aaataattat | agcatttgtt | tgttttagtt | aaaagtttga | 120 |
| aaaactacga | acgattatg | gatcatcatt | catcacgcat | attgttaatg | tgagaaccag | 180 |
| accaatagtt | tcttaagtat | tgaatataca | aaaaacattt | gataaacaaa | tctttcgctt | 240 |
| tggaaaaata | tagggtgggt | aatattttgt | ataatctaag | cggcttgttc | atttgtaatc | 300 |
| atggatttta | atgttttga | tgactttgtt | tgtggatgtg | caactgcata | tttttagttt | 360 |
| ttttgtttg | ttaattgtgt | tgtgatcctt | aatcctaatt | atgaaacaca | caagtatgac | 420 |
| tgataagagt | tagtaagcat | tcggtggtca | agatatttag | tggctagcga | cctacccta | 480 |
| atttattat | ttattttaac | taatctttat | ttgatcgttc | attatgtcaa | caaactttct | 540 |
| tcttctctaa | agtacgtgaa | attactacta | catttaata | ctgcaattga | agtaagtagt | 600 |
| acggtttca | tctcttaaat | gcatggaaac | aaacactaat | acgtagcaaa | attgagagaa | 660 |
| catatactat | gcttcgcacc | ggattttatt | agagcatttg | acacactaaa | gtcccacatg | 720 |
| gttaccagca | gggcctgccc | tgagatttag | agggaggtgg | tttttaaaaa | aaattccgtt | 780 |
| aaaaatttt | tttggtaaat | tggaggtct | aaaaaaaaat | tttaaaagtt | ttttcctatg | 840 |
| taatttttc | caaaattttt | agaggtctaa | gcctaatatt | tcgttaggct | ttaagcagga | 900 |
| ccggccctgg | ttaccatatg | tataatacat | acacaaaaca | caattgtgtt | gtcgttttta | 960 |
| gtactttgtg | tccgtttcat | tgtatatgac | gtacgtaacc | attcaaaacc | taattaaata | 1020 |
| tggtgatccc | ctaattgatc | acattctaag | ctctggtaaa | cttctcatgg | catactcttt | 1080 |
| tgatttcgta | aacccttct | caaaaagcta | ttttcgtatt | aatttggtaa | gaattatttt | 1140 |
| cctggtccat | gtaggttttg | tatgttttt | tttttgataa | ctctggtatc | tgggcagcca | 1200 |
| cattcccaac | tatccattcg | aaagggtcc | agcgccccgg | gatgttaaat | cctgttgtgg | 1260 |
| ccaaggctcg | aacccgggta | gcggcagtac | aaccatacct | cctttaccac | caagttacga | 1320 |
| gtgtttggtt | aagttttgta | tgttgatgca | gcgtgtgagt | atcttagact | cttagtgtct | 1380 |
| ccagccccat | attcttttaa | aacatggagg | actgatcact | atccataact | cttttaacaa | 1440 |
| aactacacac | aagaaataca | cattttcat | ctcacacaca | gttttaggta | tactaatatt | 1500 |
| taatgtaatt | aaaggttttc | ttagttatca | tattttggga | tataataaaa | actgtatagg | 1560 |
| ttgaactttt | tatagtgact | gggctcactc | cgaagggtca | ccttgccaga | aatctccgta | 1620 |
| gggatttttt | agctaaccca | gtaccacccc | gctgtccctg | agtatcgaac | tggcgacctc | 1680 |
| gggtaatcgt | gtgtgagaaa | cgttcagtac | tgccgctagg | cacctgacgt | tctcaaaaaa | 1740 |
| actgtatagg | ttgaactttt | tttaataact | aggctcaccc | cggagatcac | ctcgccagaa | 1800 |
| atccccgtag | atataataac | catatagcct | ccaaaagtgg | agcaatttct | ttgaaacgca | 1860 |

-continued

```
tctcatccat atagagacca acattaacca ttatcaccaa ttcactcttt atttccacct    1920
aaccatttaa aagtctatat atatatatat atatatatat atatatgtta aaggagctaa    1980
attaatcaaa aatgataaac atctaatata tcctattctc ctatatatag acactcccac    2040
taactctcac agacccacaa cactcacacc atcatggctt tctccactag atcaagactc    2100
ttcctcttgt tcttaacact tcttcctttc tccactcaaa tcaatgcaag agagagctat    2160
tcctttggaa agttccagag agaatacccc aaagatcaaa accctaataa tctccaaacc    2220
aacgagacga gcgagcaaga cgaccagaac cctccctttta tgccccagtc cggaaacggg    2280
tacggcttgt atggtcaaga acaacctac aacaacaatg aagagcagtt gaataacaaa    2340
aaatacgacg agaacgttaa ctacgacgac tctttctcaa ccccaagcct aagccaaacc    2400
caagaatctt acaagacata tggagacagc tatcctaaga cgaccgagag ttacaacgag    2460
aacaacaagg acacaagcta ctacgaaaac tccaatggct acgggccaga aatagagag    2520 gaggatgcgt acaagggtta tggcaacaac gtggagagac aaaggatgag cgataagagc    2580
tactacgaaa actccaatgg ttacgagccg gagaagagag agaaggaggc gtacaagggc    2640
tacaggaaca atgtggagag acaagggatg agcgatacga ggttcatggc caatggtaag    2700
tactactatg accttgatga cgacagaaac cacggccgtt tctaccagaa gcattactac    2760
agctacaacc ccaccagtta caatgaggac tcgaggggat ccttgcctga tactgttgac    2820
tggagggaca aaggagctgt cactgaagtc aaagaccaag gtcactgcgg gtcgtgttgg    2880
agtttcagtg ctactggttc actcgaaggt cagcacttcc gtaaaaccgg caaactagtg    2940
tcccttagcg aacaaaactt ggtagattgt tcaggaagat acggcaacaa cggctgcaac    3000
ggcggtctca tggacaacgc cttccgttac atcaaagaca acggcggtat cgacacggaa    3060
aagtcctacc cctacctagc cgaggacgag aaatgccact acaaagccca gaacagcggc    3120
gcaaccgaca agggctttgt agacatcgaa gaagccaacg aagatgacct taaggctgca    3180
gtggccaccg taggccccgt ttctattgcc attgatgcca gccacgaaac cttccaactg    3240
tactcggatg gagtctacag tgatcctgaa tgtagctcac aagaactaga ccatggggtg    3300
ttggtagtgg gatacggtac cagcgacgat ggtcaggact actggttggt gaaaaattcg    3360
tggggaccca gctggggatt gaacggatac atcaagatgg ccaggaatca agataacatg    3420
tgcggagttg catctcaggc tagttatcct ttggtttag                          3459
```

<210> SEQ ID NO 9
<211> LENGTH: 3210
<212> TYPE: DNA
<213> ORGANISM: artificial
<220> FEATURE:
<223> OTHER INFORMATION: nucleotide sequence of the translational fusion in plasmid SPIF-1 (see Example 6, Figure 8)

<400> SEQUENCE: 9

```
ggggatctat cttagatatt gtttgaaaag agagtaccaa ctctcccata ctcaaagtca      60
cagaagtcaa atgttgtttg aaataattat agcatttgtt tgttttagtt aaaagtttga     120
aaaactacga acgatttatg gatcatcatt catcacgcat attgttaatg tgagaaccag     180
accaatagtt tcttaagtat tgaatataca aaaacatttt gataaacaaa tctttcgctt     240
tggaaaaata tagggtgggt aatatttttgt ataatctaag cggcttgttc atttgtaatc     300
atggatttta atgttttttga tgactttgtt tgtggatgtg caactgcata ttttttagttt     360 tttttgtttg ttaattgtgt tgtgatccctt aatcctaatt atgaaacaca caagtatgac     420
```

-continued

```
tgataagagt tagtaagcat tcggtggtca agatatttag tggctagcga cctaccccta      480
atttatttat ttattttaac taatctttat ttgatcgttc attatgtcaa caaactttct      540
tcttctctaa agtacgtgaa attactacta cattttaata ctgcaattga agtaagtagt      600
acggttttca tctcttaaat gcatggaaac aaacactaat acgtagcaaa attgagagaa      660
catatactat gcttcgcacc ggattttatt agagcatttg acacactaaa gtcccacatg      720
gttaccagca gggcctgccc tgagatttag agggaggtgg ttttttaaaaa aaattccgtt      780
aaaaattttt tttggtaaat ttggaggtct aaaaaaaaat tttaaaagtt ttttcctatg      840
taattttttc caaaattttt agaggtctaa gcctaatatt tcgttaggct ttaagcagga      900
ccggccctgg ttaccatatg tataatacat acacaaaaca caattgtgtt gtcgttttta      960
gtactttgtg tccgtttcat tgtatatgac gtacgtaacc attcaaaacc taattaaata     1020
tggtgatccc ctaattgatc acattctaag ctctggtaaa cttctcatgg catactcttt     1080
tgatttcgta aacccttttct caaaaagcta ttttcgtatt aatttggtaa gaattatttt     1140
cctggtccat gtaggttttg tatgtttttt ttttgataa ctctggtatc tgggcagcca      1200
cattcccaac tatccattcg aaagggggtcc agcgccccgg gatgttaaat cctgttgtgg     1260
ccaaggctcg aacccgggta gcggcagtac aaccatacct cctttaccac caagttacga     1320
gtgtttggtt aagttttgta tgttgatgca gcgtgtgagt atcttagact cttagtgtct     1380
ccagccccat attcttttaa aacatggagg actgatcact atccataact cttttaacaa     1440
aactacacac aagaaataca cattttttcat ctcacacaca gttttaggta tactaatatt     1500
taatgtaatt aaaggttttc ttagttatca tattttggga tataataaaa actgtatagg     1560
ttgaactttt tatagtgact gggctcactc cgaagggtca ccttgccaga aatctccgta     1620
gggatttttt agctaaccca gtaccacccc gctgtccctg agtatcgaac tggcgacctc     1680
gggtaatcgt gtgtgagaaa cgttcagtac tgccgctagg cacctgacgt tctcaaaaaa     1740
actgtatagg ttgaactttt tttaataact aggctcaccc cggagatcac ctcgccagaa     1800
atccccgtag atataataac catatagcct ccaaaagtgg agcaatttct ttgaaacgca     1860
tctcatccat atagagacca acattaacca ttatcaccaa ttcactcttt atttccacct     1920
aaccatttaa aagtctatat atatatatat atatatatat atatatgtta aaggagctaa     1980
attaatcaaa aatgataaac atctaatata tcctattctc ctatatatag acactcccac     2040
taactctcac agacccacaa cactcacacc atcatggctt tctccactag atcaagactc     2100
ttcctcttgt tcttaacact tcttcctttc tccactcaaa tcaatgcaag agagagctat     2160
tcctttggaa agttccagag agaataccc aaagatcaaa accctaataa tctccaaacc      2220
aacgagacga gcgagcaaga cgaccagaac cctcccttta tgccccagtc cggaaacggg     2280
tacggcttgt atggtcaaga aacaacctac aacaacaatg aagagcagtt gaataacaaa     2340
aaatacgacg agaacgttaa ctacgacgac tctttctcaa ccccaagcct aagccaaacc     2400
caagaatctt acaagacata tggagacagc tatcctaaga cgaccgagag ttacaacgag     2460
aacaacaagg acacaagcta ctacgaaaac tccaatggct acgggccaga gaatagagag     2520
gaggatgcgt acaaggggtta tggcaacaac gtggagagac aaaggatgag cgataagagc     2580
tactacgaaa actccaatgg ttacgagccg gagaagagag agaaggaggc gtacaagggc     2640
tacaggaaca atgtggagag acaagggatg agcgatacga ggttcatggc caatggtaag     2700
tactactatg accttgatga cgacagaaac cacggccgtt tctaccagaa gcattactac     2760
```

```
agctacaacc ccaccagtta caatgaggac tcgaggggat ccggtaccca attccgcaaa      2820
aatccgtcaa aaatggagtc caaaacaggt gaaaatcaag atcgtccgt tttattggga       2880 ggttgggaag atcgcgatcc aaaggatgaa gaaatcctgg aactattgcc aagcatattg     2940
atgaaagtaa atgaacaatc aaacgatgaa tatcatttga tgccgatcaa attactgaag    3000
gtttcatctc aagttgtcgc tggtgtgaaa tacaagatgg atgtgcaggt tgctcgatcg    3060
caatgtaaaa aaagttcgaa tgaaaaagtt gatctaacaa agtgcaaaaa attagaagga   3120
catcctgaaa aggttatgac tttggaagtt tgggagaaac catgggagaa ttttatgcgc   3180
gtcgaaattc tgggaacaaa agaagtatga                                     3210

<210> SEQ ID NO 10
<211> LENGTH: 27
<212> TYPE: DNA
<213> ORGANISM: artificial
<220> FEATURE:
<223> OTHER INFORMATION: oligonucleotide sequence SLG26 (7)

<400> SEQUENCE: 10
atagagctcc gatgaaaggc ataagaa                                          27

<210> SEQ ID NO 11
<211> LENGTH: 28
<212> TYPE: DNA
<213> ORGANISM: artificial
<220> FEATURE:
<223> OTHER INFORMATION: oligonucleotide sequence SLG 26 (8)

<400> SEQUENCE: 11
tatggtacct tcttcagaag acaaagtg                                         28

<210> SEQ ID NO 12
<211> LENGTH: 1334
<212> TYPE: DNA
<213> ORGANISM: artificial
<220> FEATURE:
<223> OTHER INFORMATION: nucleotide sequence of the translational fusion
      in plasmid SPOV-1 (see Example 7, Figure 9)

<400> SEQUENCE: 12
gtcaacatgg tggagcacga cactctcgtc tactccaaga atatcaaaga tacagtctca      60
gaagaccaaa gggctattga acttttcaa caaagggtaa tatcgggaaa cctcctcgga     120
ttccattgcc cagctatctg tcacttcatc aaaaggacag tagaaaagga aggtggcacc    180
tacaaatgcc atcattgcga taaggaaag gctatcgttc aagatgcctc tgccgacagt     240
ggtcccaaag atggaccccc acccacgagg agcatcgtgg aaaaagaaga cgttccaacc    300
acgtcttcaa agcaagtgga ttgatgtgat aacatggtgg agcacgacac tctcgtctac    360
tccaagaata tcaaagatac agtctcgaaa gaccaaaggg ctattgagac ttttcaacaa    420
agggtaatat cgggaaacct cctcggattc cattgcccag ctatctgtca cttcatcaaa   480
aggacagtag aaaaggaagg tgcacctac aaatgccatc attgcgataa ggaaaggct     540 atcgttcaag atgcctctgc cgacagtggt cccaaagatg gaccccace acgaggagc    600 atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggaca cgctgaaatc accagtctct ctctacaaat    780
ctatctctct cgagctttcg cgagctccga tgaaaggcat aagaaaaaac tacgaaaatt    840
```

-continued

```
cttacacctt atccttttg cttgtctttt tcgtcttgat tctacttcct cctgcctttt      900
cgattaacac tttgtcttct gaagaaggta cccaattccg caaaaatccg tcaaaaatgg      960
agtccaaaac aggtgaaaat caagatcgtc ccgttttatt gggaggttgg gaagatcgcg     1020
atccaaagga tgaagaaatc ctggaactat tgccaagcat attgatgaaa gtaaatgaac     1080
aatcaaacga tgaatatcat ttgatgccga tcaaattact gaaggtttca tctcaagttg     1140
tcgctggtgt gaaatacaag atggatgtgc aggttgctcg atcgcaatgt aaaaaaagtt     1200
cgaatgaaaa agttgatcta acaaagtgca aaaattaga aggacatcct gaaaaggtta     1260
tgactttgga agtttgggag aaaccatggg agaattttat gcgcgtcgaa attctgggaa     1320
caaaagaagt atga                                                      1334
```

<210> SEQ ID NO 13
<211> LENGTH: 24
<212> TYPE: DNA
<213> ORGANISM: artificial
<220> FEATURE:
<223> OTHER INFORMATION: oligonucleotide sequence (EXK-1)

<400> SEQUENCE: 13

```
cgaattctct agaggtaccg catg                                              24
```

<210> SEQ ID NO 14
<211> LENGTH: 24
<212> TYPE: DNA
<213> ORGANISM: artificial
<220> FEATURE:
<223> OTHER INFORMATION: oligonucleotide sequence (EXK-2)

<400> SEQUENCE: 14

```
cggtacctct agagaattcg catg                                              24
```

<210> SEQ ID NO 15
<211> LENGTH: 1346
<212> TYPE: DNA
<213> ORGANISM: artificial
<220> FEATURE:
<223> OTHER INFORMATION: nucleotide sequence of the translational fusion
      in plasmid POV-1 (see Example 8a)

<400> SEQUENCE: 15

```
agacagtata cataatttag agagagtatt ttcaaggttt taatccaatt aaacataatg       60
atgttttgat agtctttaaa aagtattttc acgttttcaa gataagataa aactttgaa       120 ttttttaat tcttgtgtag gctcacgttg acatagtact tccaaagatt ttacacatcg       180
acaacataaa aaaaaacact ggtatatata tatatatata tatatatata tatatagatg      240
tttttaatat tgtgtccccc attaaaaact tttcaaaatc tgcctctgct tctctctgag      300
ctatatacat tatagccttc atatgttggt ttacgataaa tccgtccaac cgtatgtttt      360
aaacataatg tctcttcttc actcatgtca atttcataag ttggctaaca attaacctga      420
aaaatgtacg tatcataaaa atgctataaa cgtgcacgag tagaacaagt ctttcgtcta      480
ataataaacc gctagtttct caaaattaaa ttagcctagt aattccttga taattggcca      540
aacaatctaa aaaacgagac gttgagagaa aaatgggtta acatatctc cattaagggc      600 actatataaa gcagcagagg catagctaaa ctctcataaa acaaaacaaa taacaataaa      660
aaacaaataa aaaataaata aataatgggt tcatatttag gaatttatac aattttggtt      720
ctatgtttgc tgggatattc agccaatgct gaggtgttca ccgttggtgg tcctccaggt      780
```

-continued

| | |
|---|---|
| tctgatatta ctgcggttag tatctatact attttctaat tatttcatcc agagaaatct | 840 |
| ataactgttt ttttactttt tttttggcta acgtactcgt tggggttttg ttgaaggctc | 900 |
| ttcttaaagc gttcacatca gcatgcgaat tctctagagg tacccaattc cgcaaaaatc | 960 |
| cgtcaaaaat ggagtccaaa acaggtgaaa atcaagatcg tcccgtttta ttgggaggtt | 1020 |
| gggaagatcg cgatccaaag gatgaagaaa tcctggaact attgccaagc atattgatga | 1080 |
| aagtaaatga acaatcaaac gatgaatatc atttgatgcc gatcaaatta ctgaaggttt | 1140 |
| catctcaagt tgtcgctggt gtgaaataca agatggatgt gcaggttgct cgatcgcaat | 1200 |
| gtaaaaaaag ttcgaatgaa aaagttgatc taacaaagtg caaaaaatta gaaggacatc | 1260 |
| ctgaaaaggt tatgactttg gaagtttggg agaaaccatg ggagaatttt atgcgcgtcg | 1320 |
| aaattctggg aacaaaagaa gtatga | 1346 |

<210> SEQ ID NO 16
<211> LENGTH: 24
<212> TYPE: DNA
<213> ORGANISM: artificial
<220> FEATURE:
<223> OTHER INFORMATION: forward primer (GUSsense-1)

<400> SEQUENCE: 16
ggaattcacc gcgtctttga tcgc        24

<210> SEQ ID NO 17
<211> LENGTH: 18
<212> TYPE: DNA
<213> ORGANISM: artificial
<220> FEATURE:
<223> OTHER INFORMATION: reverse primer (nos #2)

<400> SEQUENCE: 17
gcgcgcgata atttatcc        18

<210> SEQ ID NO 18
<211> LENGTH: 18
<212> TYPE: DNA
<213> ORGANISM: artificial
<220> FEATURE:
<223> OTHER INFORMATION: primer (NptII-121)

<400> SEQUENCE: 18
gggcgcccgg ttcttttt        18

<210> SEQ ID NO 19
<211> LENGTH: 25
<212> TYPE: DNA
<213> ORGANISM: artificial
<220> FEATURE:
<223> OTHER INFORMATION: primer (NptII-B)

<400> SEQUENCE: 19
cagcaatatc acgggtagcc aacgc        25

<210> SEQ ID NO 20
<211> LENGTH: 28
<212> TYPE: DNA
<213> ORGANISM: artificial
<220> FEATURE:
<223> OTHER INFORMATION: forward primer (P1)

<400> SEQUENCE: 20
gcgcggatcc ttgcctgata ctgttgac        28

<210> SEQ ID NO 21
<211> LENGTH: 37
<212> TYPE: DNA
<213> ORGANISM: artificial
<220> FEATURE:
<223> OTHER INFORMATION: reverse primer (P2)

<400> SEQUENCE: 21
gcgcgaattc aagcttctaa accaaaggat aactagc                              37

<210> SEQ ID NO 22
<211> LENGTH: 18
<212> TYPE: DNA
<213> ORGANISM: artificial
<220> FEATURE:
<223> OTHER INFORMATION: primer (XK+)

<400> SEQUENCE: 22
gatcctctag aggtaccg                                                   18

<210> SEQ ID NO 23
<211> LENGTH: 18
<212> TYPE: DNA
<213> ORGANISM: artificial
<220> FEATURE:
<223> OTHER INFORMATION: primer (KX-)

<400> SEQUENCE: 23
gatccggtac ctctagag                                                   18

<210> SEQ ID NO 24
<211> LENGTH: 20
<212> TYPE: PRT
<213> ORGANISM: artificial
<220> FEATURE:
<223> OTHER INFORMATION: 20 amino acid residues of the C-terminal domain
      of BnOlnB;4 (Sta 41-9)

<400> SEQUENCE: 24

Leu Gly Ile Pro Glu Ser Ile Lys Pro Ser Asn Ile Ile Pro Glu Ser
1               5                   10                  15

Ile Lys Pro Ser
            20

<210> SEQ ID NO 25
<211> LENGTH: 1601
<212> TYPE: DNA
<213> ORGANISM: artificial
<220> FEATURE:
<223> OTHER INFORMATION: nucleotide sequence of the translational fusion
      in plasmid POP-1 (see Example 8; Figure 10)

<400> SEQUENCE: 25
agacagtata cataatttag agagagtatt ttcaaggttt taatccaatt aaacataatg      60
atgttttgat agtctttaaa aagtattttc acgttttcaa gataagataa taactttgaa    120
tttttttaat tcttgtgtag gctcacgttg acatagtact tccaaagatt ttacacatcg    180
acaacataaa aaaaaacact ggtatatata tatatatata tatatatata tatatagatg    240
tttttaatat tgtgtccccc attaaaaact tttcaaaatc tgcctctgct tctctctgag    300
ctatatacat tatagccttc atatgttggt ttacgataaa tccgtccaac cgtatgtttt    360
aaacataatg tctcttcttc actcatgtca atttcataag ttggctaaca attaacctga    420

```
aaaatgtacg tatcataaaa atgctataaa cgtgcacgag tagaacaagt ctttcgtcta      480
ataataaacc gctagtttct caaaattaaa ttagcctagt aattccttga taattggcca      540
aacaatctaa aaaacgagac gttgagagaa aaatgggtta acatatctc cattaagggc       600 actatataaa gcagcagagg catagctaaa ctctcataaa acaaaacaaa taacaataaa      660
aaacaaataa aaaataaata aataatgggt tcatatttag gaatttatac aattttggtt      720
ctatgtttgc tgggatattc agccaatgct gaggtgttca ccgttggtgg tcctccaggt      780
tctgatatta ctgcggttag tatctatact attttctaat tatttcatcc agagaaatct      840
ataactgttt ttttactttt tttttggcta acgtactcgt tggggttttg ttgaaggctc      900
ttcttaaagc gttcacatca gcatgcgaat tctctagagg atccttgcct gatactgttg      960
actggaggga caaaggagct gtcactgaag tcaaagacca aggtcactgc gggtcgtgtt     1020
ggagtttcag tgctactggt tcactcgaag gtcagcactt ccgtaaaacc ggcaaactag     1080
tgtcccttag cgaacaaaac ttggtagatt gttcaggaag atacggcaac aacggctgca     1140
acggcggtct catggacaac gccttccgtt acatcaaaga caacggcggt atcgacacgg     1200
aaaagtccta cccctaccta gccgaggacg agaaatgcca ctacaaagcc agaacagcg      1260 gcgcaaccga caagggcttt gtagacatcg aagaagccaa cgaagatgac cttaaggctg     1320
cagtggccac cgtaggcccc gtttctattg ccattgatgc cagccacgaa accttccaac     1380
tgtactcgga tggagtctac agtgatcctg aatgtagctc acaagaacta gaccatgggg     1440
tgttggtagt gggatacggt accagcgacg atggtcagga ctactggttg gtgaaaaatt     1500
cgtggggacc cagctgggga ttgaacggat acatcaagat ggccaggaat caagataaca     1560
tgtgcggagt tgcatctcag gctagttatc ctttggttta g                        1601

<210> SEQ ID NO 26
<211> LENGTH: 27
<212> TYPE: DNA
<213> ORGANISM: artificial
<220> FEATURE:
<223> OTHER INFORMATION: primer (Sta 41 ATG)

<400> SEQUENCE: 26
ctaggatcca gaccacacaa ctccttc                                            27

<210> SEQ ID NO 27
<211> LENGTH: 29
<212> TYPE: DNA
<213> ORGANISM: artificial
<220> FEATURE:
<223> OTHER INFORMATION: primer (Sta 41-13R)

<400> SEQUENCE: 27
gagaggattc caacagagat agggatggc                                          29

<210> SEQ ID NO 28
<211> LENGTH: 4129
<212> TYPE: DNA
<213> ORGANISM: artificial
<220> FEATURE:
<223> OTHER INFORMATION: nucleotide sequence of the translational fusion
      in plasmid TOG-3 (see Example 22; Figure 5d)

<400> SEQUENCE: 28
gagctccacc cacagaagca gataaaccag ctgaaggaac aacagaaaaa ccaaaagata        60
attcgactgg aggagcagcc gataaaccag aagataaacc agttggagga gcagccgata      120
```

```
aaccagaagg taaaccggat ggaggagcaa caaataagcc agaaagtaaa ccagctggag      180
gaccatcaaa taaaccaaaa gataaacccg ctggaggacc aacggataaa ccagaaagta      240
agccagcaga taaacccgct ggaggaccaa cagataagcc aggaagtaaa ccggttgata      300
aacccgctgg aggaccaaca gataagacag aaagtaaact ggttggagag gcatcaaata      360
aaccaaaaga taaacccgct ggtggatcaa cagatatgcc agaagctgga gagacatcaa      420
ataaaccaaa agataaatcc gttggaggac caacaaataa gccagaaagt aaaccagctg      480
gagaaacatc acataaacca aaagataaac ccgctggtgg accaacagat aagccagaaa      540
gtaaaccggc tggagaaaca tcacataaac caaaagataa actcgctggt ggaccaacag      600
ataagccaga aagtaaacca gctggagagg catcaaataa accaaaagat aaacccgctg      660
gtggaccaac agataaacca gctggaggat cagtagataa accaaaagat aaacctgccg      720
gaggaccaac agataaacca acaaataaac cgactggagg ggctgcaaat aaaccggctg      780
gagaggcagc aaacaaaccg actggaaaac cgaaaaataa accggctgga gagaataaac      840
caccgggatg gtataggtga atggagtagt atgaaattaa agtattgggt tccacaaatt      900
attcctaatt tatcctacac tacatgtttc ataatcattt ctataaatgt acgacttgtt      960
acaaagaaat gataaacagt gtacagaatt ttctttgtaa atttattaaa ttgatgtgga     1020
tatcattata actgacgtta gcgtatatcg accaatgcga taaccaaatc atcggtatat     1080
acctaagact tccttttttaa aaatgaatct gatactaatt taatgtacga cttccaataa     1140
ccaatcttct tgcattttc attgccattt accttgaacg cctctctttc tagtatgaga     1200
cattaacatt gcgctcttgt cacaatgaag ccatggaaaa cttcggctct ttaatcacac     1260
atgtgacaat ccagttggtt taagggaaag tattttatat tttatatagc tcgttctcag     1320
aacaaaaaaa ccaaattctt tagcaaaaat ggtccttaag gcccattccg tttcttctta     1380
taatgttctg ggctagccca tttgaattta aacctttcct ttcaatttct gcattaatat     1440
aattcagttg ttcaaaaaaa aaatagcgct tattgaaata atagagagaa agataatgag     1500
aagggagaaa atgaaaagcg tatttcatat gagagattgt caacaaaaat tgagtgactt     1560
ttatgatatt tgttcaaaga atagtctaat aacctttctt atttaaattt taattatgtt     1620
atatatcaat aatactaaaa taattagtta ctcacagttc gtgacaaaaa aaaaagcaaa     1680
tagatgaaat gaaatgaaag aaagatcttt cttcacgcgt tgatattcat aaaacaatgg     1740
aatgaaagaa aacagttaag attctacaag aaagaaaaga aagtcccaaa acatgacaa     1800 atagatgaag aagcaaatgt gacttgacgt aacgtagaac tccatatata ctcccatcgt     1860
tttgcatgga gcatgcatgt gtaccgtgca cgtcgtagac cacacaactc cttcataaaa     1920
agccctctct cttcccatca ccaaaccatc agaaaatatg agaaacgaaa ttcaaaacga     1980
aacagctcag actgatcaga cccagggaag tatgttttct tttttcaatt tgttcccttt     2040
cctcctccca atgtttgagg ttatcaagat ggttgttgct tccgttgcgt ccgtagtata     2100
tttaggcttc gccggtgtaa cactcagtgg ttcagccgtg gcattagccg tatccacccc     2160
tcttttcatc atattcagtc cgattctctt acctgctatt gcagccacta ctgtcctagc     2220
cgccgggctc ggaggtaaaa aagtggcggc ggctccggaa gcttctccgg cagcttcgcc     2280
atccctatct ctgttgggat ccccgggtgg tcagtccctt atgttacgtc tgtagaaac     2340 cccaacccgt gaaatcaaaa aactcgacgg cctgtgggca ttcagtctgg atcgcgaaaa     2400
ctgtggaatt gatcagcgtt ggtgggaaag cgcgttacaa gaaagccggg caattgctgt     2460
gccaggcagt tttaacgatc agttcgccga tgcagatatt cgtaattatg cgggcaacgt     2520
```

```
ctggtatcag cgcgaagtct ttataccgaa aggttgggca ggccagcgta tcgtgctgcg    2580
tttcgatgcg gtcactcatt acggcaaagt gtgggtcaat aatcaggaag tgatggagca    2640
tcagggcggc tatacgccat ttgaagccga tgtcacgccg tatgttattg ccgggaaaag    2700
tgtacgtatc accgtttgtg tgaacaacga actgaactgg cagactatcc cgccgggaat    2760
ggtgattacc gacgaaaacg gcaagaaaaa gcagtcttac ttccatgatt tctttaacta    2820
tgccgggatc catcgcagcg taatgctcta caccacgccg aacacctggg tggacgatat    2880
caccgtggtg acgcatgtcg cgcaagactg taaccacgcg tctgttgact ggcaggtggt    2940
ggccaatggt gatgtcagcg ttgaactgcg tgatgcggat caacaggtgg ttgcaactgg    3000
acaaggcact agcgggactt tgcaagtggt gaatccgcac ctctggcaac cgggtgaagg    3060
ttatctctat gaactgtgcg tcacagccaa agccagaca gagtgtgata tctacccgct    3120
tcgcgtcggc atccggtcag tggcagtgaa gggccaacag ttcctgatta ccacaaaacc    3180
gttctacttt actggctttg gtcgtcatga agatgcggac ttacgtggca aaggattcga    3240
taacgtgctg atggtgcacg accacgcatt aatggactgg attggggcca actcctaccg    3300
tacctcgcat taccettacg ctgaagagat gctcgactgg gcagatgaac atggcatcgt    3360
ggtgattgat gaaactgctg ctgtcggctt taacctctct ttaggcattg gtttcgaagc    3420
gggcaacaag ccgaaagaac tgtacagcga agaggcagtc aacggggaaa ctcagcaagc    3480
gcacttacag gcgattaaag agctgatagc gcgtgacaaa aaccacccaa gcgtggtgat    3540
gtggagtatt gccaacgaac cggatacccg tccgcaagtg cacgggaata tttcgccact    3600
ggcggaagca acgcgtaaac tcgacccgac gcgtccgatc acctgcgtca atgtaatgtt    3660
ctgcgacgct cacaccgata ccatcagcga tctctttgat gtgctgtgcc tgaaccgtta    3720
ttacggatgg tatgtccaaa gcggcgattt ggaaacggca gagaaggtac tggaaaaaga    3780
acttctggcc tggcaggaga aactgcatca gccgattatc atcaccgaat acggcgtgga    3840
tacgttagcc gggctgcact caatgtacac cgacatgtgg agtgaagagt atcagtgtgc    3900
atggctggat atgtatcacc gcgtctttga tcgcgtcagc gccgtcgtcg gtgaacaggt    3960
atggaatttc gccgattttg cgacctcgca aggcatattg cgcgttggcg gtaacaagaa    4020
agggatcttc actcgcgacc gcaaaccgaa gtcggcggct tttctgctgc aaaaacgctg    4080
gactggcatg aacttcggtg aaaaaccgca gcagggaggc aaacaatga             4129
```

<210> SEQ ID NO 29
<211> LENGTH: 24
<212> TYPE: DNA
<213> ORGANISM: artificial
<220> FEATURE:
<223> OTHER INFORMATION: primer (GUS-6F)

<400> SEQUENCE: 29
tagaggatcc ccgggtggtc agtc                                            24

<210> SEQ ID NO 30
<211> LENGTH: 38
<212> TYPE: DNA
<213> ORGANISM: artificial
<220> FEATURE:
<223> OTHER INFORMATION: primer (GUS-7R)

<400> SEQUENCE: 30
gagagagctc agatctttgt ttgcctccct gctgcggt                             38

<210> SEQ ID NO 31
<211> LENGTH: 36
<212> TYPE: DNA
<213> ORGANISM: artificial
<220> FEATURE:
<223> OTHER INFORMATION: primer (STA 41- 14)

<400> SEQUENCE: 31
gagaagatct atgagaaacg aaattcaaaa cgaaac          36

<210> SEQ ID NO 32
<211> LENGTH: 33
<212> TYPE: DNA
<213> ORGANISM: artificial
<220> FEATURE:
<223> OTHER INFORMATION: primer (STA 41- 15R)

<400> SEQUENCE: 32
gagagagctc atatgtgttt accaccactc cca             33

<210> SEQ ID NO 33
<211> LENGTH: 4921
<212> TYPE: DNA
<213> ORGANISM: artificial
<220> FEATURE:
<223> OTHER INFORMATION: nucleotide sequence of translational fusion in
      plasmid TOG-4 (see Example 22; Figure 5E)

<400> SEQUENCE: 33

| | | |
|---|---|---|
| gagctccacc cacagaagca gataaaccag ctgaaggaac aacagaaaaa ccaaaagata | 60 |
| attcgactgg aggagcagcc gataaaccag aagataaacc agttggagga gcagccgata | 120 |
| aaccagaagg taaaccggat ggaggagcaa caaataagcc agaaagtaaa ccagctggag | 180 |
| gaccatcaaa taaccaaaa gataaacccg ctggaggacc aacggataaa ccagaaagta | 240 |
| agccagcaga taaacccgct ggaggaccaa cagataagcc aggaagtaaa ccggttgata | 300 |
| aacccgctgg aggaccaaca gataagacag aaagtaaact ggttggagag catcaaata | 360 |
| aaccaaaaga taaacccgct ggtggatcaa cagatatgcc agaagctgga gagacatcaa | 420 |
| ataaaccaaa agataaatcc gttggaggac caacaaataa gccagaaagt aaaccagctg | 480 |
| gagaaacatc acataaacca aaagataaac ccgctggtgg accaacagat aagccagaaa | 540 |
| gtaaaccggc tggagaaaca tcacataaac caaaagataa actcgctggt ggaccaacag | 600 |
| ataagccaga aagtaaacca gctggagagg catcaaataa accaaaagat aaacccgctg | 660 |
| gtggaccaac agataaacca gctggaggat cagtagataa accaaaagat aaacctgccg | 720 |
| gaggaccaac agataaacca acaaataaac gactggaggg gctgcaaat aaaccggctg | 780 |
| gagaggcagc aaacaaaccg actggaaaac cgaaaaataa accggctgga gagaataaac | 840 |
| caccgggatg gtataggtga atggagtagt atgaaattaa agtattgggt tccacaaatt | 900 |
| attcctaatt tatcctacac tacatgtttc ataatcattt ctataaatgt acgacttgtt | 960 |
| acaaagaaat gataaacagt gtacagaatt tctttgtaa atttattaaa ttgatgtgga | 1020 |
| tatcattata actgacgtta gcgtatatcg accaatgcga taaccaaatc atcggtatat | 1080 |
| acctaagact tccttttaa aaatgaatct gatactaatt taatgtacga cttccaataa | 1140 |
| ccaatcttct tgcatttttc attgccattt accttgaacg cctctctttc tagtatgaga | 1200 |
| cattaacatt gcgctcttgt cacaatgaag ccatgcaaaa cttcggctct ttaatcacac | 1260 |
| atgtgacaat ccagttggtt taagggaaag tattttatat tttatatagc tcgttctcag | 1320 |

```
aacaaaaaaa ccaaattctt tagcaaaaat ggtccttaag gcccattccg tttcttctta    1380
taatgttctg ggctagccca tttgaattta aacctttcct ttcaatttct gcattaatat    1440
aattcagttg ttcaaaaaaa aaatagcgct tattgaaata atagagagaa agataatgag    1500
aagggagaaa atgaaaagcg tatttcatat gagagattgt caacaaaaat tgagtgactt    1560
ttatgatatt tgttcaaaga atagtctaat aacctttctt atttaaattt taattatgtt    1620
atatatcaat aatactaaaa taattagtta ctcacagttc gtgacaaaaa aaaaagcaaa    1680
tagatgaaat gaaatgaaag aaagatcttt cttcacgcgt tgatattcat aaaacaatgg    1740
aatgaaagaa aacagttaag attctacaag aaagaaaaga aagtcccaaa acatgacaa     1800 atagatgaag aagcaaatgt gacttgacgt aacgtagaac tccatatata ctcccatcgt    1860
tttgcatgga gcatgcatgt gtaccgtgca cgtcgtagac cacacaactc cttcataaaa    1920
agccctctct cttcccatca ccaaaccatc aggatccccg ggtggtcagt cccttatgtt    1980
acgtcctgta gaaccccaa cccgtgaaat caaaaaactc gacggcctgt gggcattcag     2040
tctggatcgc gaaaactgtg gaattgatca gcgttggtgg gaaagcgcgt tacaagaaag    2100
ccgggcaatt gctgtgccag gcagttttaa cgatcagttc gccgatgcag atattcgtaa    2160
ttatgcgggc aacgtctggt atcagcgcga agtctttata ccgaaaggtt gggcaggcca    2220
gcgtatcgtc ctgcgtttcg atgcggtcac tcattacggc aaagtgtggg tcaataatca    2280
ggaagtgatg gagcatcagg gcggctatac gccatttgaa gccgatgtca cgccgtatgt    2340
tattgccggg aaaagtgtac gtatcaccgt ttgtgtgaac aacgaactga actggcagac    2400
tatcccgccg ggaatggtga ttaccgacga aaacggcaag aaaaagcagt cttacttcca    2460
tgatttcttt aactatgccg ggatccatcg cagcgtaatg ctctacacca cgccgaacac    2520
ctgggtggac gatatcaccg tggtgacgca tgtcgcgcaa gactgtaacc acgcgtctgt    2580
tgactggcag gtggtggcca atggtgatgt cagcgttgaa ctgcgtgatg cggatcaaca    2640
ggtggttgca actggacaag gcactagcgg gactttgcaa gtggtgaatc gcacctctg     2700 gcaaccgggt gaaggttatc tctatgaact gtgcgtcaca gccaaaagcc agacagagtg    2760
tgatatctac ccgcttcgcg tcggcatccg gtcagtggca gtgaagggcc aacagttcct    2820
gattaaccac aaaccgttct actttactgg ctttggtcgt catgaagatg cggacttacg    2880
tggcaaagga ttcgataacg tgctgatggt gcacgaccac gcattaatgg actggattgg    2940
ggccaactcc taccgtacct cgcattaccc ttacgctgaa gagatgctcg actgggcaga    3000
tgaacatggc atcgtggtga ttgatgaaac tgctgctgtc ggctttaacc tctctttagg    3060
cattggtttc gaagcgggca acaagccgaa agaactgtac agcgaagagg cagtcaacgg    3120
ggaaactcag caagcgcact acaggcgat taaagagctg atagcgcgtg acaaaaacca     3180
cccaagcgtg gtgatgtgga gtattgccaa cgaaccggat accgtccgc aagtgcacgg     3240 gaatatttcg ccactggcgg aagcaacgcg taaactcgac ccgacgcgtc cgatcacctg    3300
cgtcaatgta atgttctgcg acgctcacac cgataccatc agcgatctct ttgatgtgct    3360
gtgcctgaac cgttattacg gatggtatgt ccaaagcggc gatttggaaa cggcagagaa    3420
ggtactggaa aaagaacttc tggcctggca ggagaaactg catcagccga ttatcatcac    3480
cgaatacggc gtggatacgt tagccgggct gcactcaatg tacaccgaca tgtggagtga    3540
agagtatcag tgtgcatggc tggatatgta tcaccgcgtc tttgatcgcg tcagcgccgt    3600
cgtcggtgaa caggtatgga atttcgccga ttttgcgacc tcgcaaggca tattgcgcgt    3660
tggcggtaac aagaaaggga tcttcactcg cgaccgcaaa ccgaagtcgg cggcttttct    3720
```

```
gctgcaaaaa cgctggactg gcatgaactt cggtgaaaaa ccgcagcagg gaggcaaaca      3780
aagatctatg agaaacgaaa ttcaaaacga aacagctcag actgatcaga cccagggaag      3840
tatgttttct tttttcaatt tgttcccttt cctcctccca atgtttgagg ttatcaagat      3900
ggttgttgct tccgttgcgt ccgtagtata tttaggcttc gccggtgtaa cactcagtgg      3960
ttcagccgtg gcattagccg tatccacccc tcttttcatc atattcagtc cgattctctt      4020
acctgctatt gcagccacta ctgtcctagc cgccgggctc ggaggtaaaa aagtggcggc      4080
ggctccggaa gcttctccgg cagcttcgcc atccctatct ctgttgggca taccggagag      4140
cattaaacca agtaatatta taccggagag tattaaacca agtaatatta taccggaggg      4200
tattaaacca agtaatatta aggacaaaat taaggatacg ataggcaaag ttaagaataa      4260
gatcaaagct aaaaggaag aaaaatccaa aggtaaaagt gaagattctt ccaagggtaa      4320
aggtaaatca aagggtgaag atacgactac ggatgacgat acgactacgg atgaagacaa      4380
acacggaagt ggagctaaac acggaaaggg agagagtaaa cacggaaaag gtgagagtac      4440
acacggaaag ggaggtaaac atggaagtga aggtaagcat ggaagtggag ttcgtctat       4500 gggtggaggt aaacacggaa gcggaggtaa acatgaaact ggaggtaaac acggaagcgg      4560
aggtaaacat gaaagtggag ttcgcctat gggtggaggt aaacatggaa gtgaaggtaa       4620
gcatggaagt ggaggtgcgt ctatggtgg aggtaaacac ggaagcggag gtaaacatga       4680
aagtggaggt tcggctatgg gtggaggtaa gcacggaagt ggaggcaaac acggaagtga      4740
aggtaaacac gggggtgaag gctcttctat gggtaaaaat agtctatcca agaagaaaaa      4800
ggaattccat tatagaggtc aagctatgga tgcaagtagt acaagtgaaa gttcagatgg      4860
aagttcagat ggcagcagtt cagatggaag ttcacatggg agtggtggta aacacatatg      4920
a                                                                     4921
```

<210> SEQ ID NO 34
<211> LENGTH: 39
<212> TYPE: DNA
<213> ORGANISM: artificial
<220> FEATURE:
<223> OTHER INFORMATION: primer (GAGA T18-2)

<400> SEQUENCE: 34
gagagagaga gactcgagtt tttttttttt tttttacg                             39

<210> SEQ ID NO 35
<211> LENGTH: 30
<212> TYPE: DNA
<213> ORGANISM: artificial
<220> FEATURE:
<223> OTHER INFORMATION: primer (SCR13-3F)

<400> SEQUENCE: 35
aacaagaatt tgctgcgagt aaaagagaat                                      30

<210> SEQ ID NO 36
<211> LENGTH: 30
<212> TYPE: DNA
<213> ORGANISM: artificial
<220> FEATURE:
<223> OTHER INFORMATION: primer (SCR13-4R)

<400> SEQUENCE: 36
attttgacta agacgaattt tggaatgatt                                      30

-continued

<210> SEQ ID NO 37
<211> LENGTH: 31
<212> TYPE: DNA
<213> ORGANISM: artificial
<220> FEATURE:
<223> OTHER INFORMATION: primer (SCR13-7F)

<400> SEQUENCE: 37
gagaattaat aaatctgatg atgccttgtg g                          31

<210> SEQ ID NO 38
<211> LENGTH: 48
<212> TYPE: DNA
<213> ORGANISM: artificial
<220> FEATURE:
<223> OTHER INFORMATION: primer (SCR13-8R)

<400> SEQUENCE: 38
ctgcagaacc aacgcgttgg agctcctaac acaatttaca atcacaag        48

<210> SEQ ID NO 39
<211> LENGTH: 3253
<212> TYPE: DNA
<213> ORGANISM: artificial
<220> FEATURE:
<223> OTHER INFORMATION: TOS13-1 (Example 23, Figure 29)

<400> SEQUENCE: 39
gagctccacc cacagaagca gataaaccag ctgaaggaac aacagaaaaa ccaaaagata    60
attcgactgg aggagcagcc gataaaccag aagataaacc agttggagga gcagccgata   120
aaccagaagg taaaccggat ggaggagcaa caaataagcc agaaagtaaa ccagctggag   180
gaccatcaaa taaccaaaaa gataaacccg ctggaggacc aacggataaa ccagaaagta   240
agccagcaga taaacccgct ggaggaccaa cagataagcc aggaagtaaa ccggttgata   300
aacccgctgg aggaccaaca gataagacag aaagtaaact ggttggagag gcatcaaata   360
aaccaaaaga taaacccgct ggtggatcaa cagatatgcc agaagctgga gagacatcaa   420
ataaaccaaa agataaatcc gttggaggac caacaaataa gccagaaagt aaaccagctg   480
gagaaacatc acataaacca aaagataaac ccgctggtgg accaacagat aagccagaaa   540
gtaaaccggc tggagaaaca tcacataaac caaaagataa actcgctggt ggaccaacag   600
ataagccaga aagtaaacca gctggagagg catcaaataa accaaaagat aaacccgctg   660
gtggaccaac agataaacca gctggaggat cagtagataa accaaaagat aaacctgccg   720
gaggaccaac agataaacca acaaataaac cgactggagg ggctgcaaat aaaccggctg   780
gagaggcagc aaacaaaccg actggaaaac cgaaaaataa accggctgga gagaataaac   840
caccgggatg gtataggtga atggagtagt atgaaattaa agtattgggt tccacaaatt   900
attcctaatt tatcctacac tacatgtttc ataatcattt ctataaatgt acgacttgtt   960
acaaagaaat gataaacagt gtacagaatt ttctttgtaa atttattaaa ttgatgtgga  1020
tatcattata actgacgtta gcgtatatcg accaatgcga taaccaaatc atcggtatat  1080
acctaagact tcctttttaa aaatgaatct gatactaatt taatgtacga cttccaataa  1140
ccaatcttct tgcattttc attgccattt accttgaacg cctctctttc tagtatgaga  1200
cattaacatt gcgctcttgt cacaatgaag ccatggaaaa cttcggctct taatcacac   1260 atgtgacaat ccagttggtt taagggaaag tattttatat tttatatagc tcgttctcag  1320
aacaaaaaaa ccaaattctt tagcaaaaat ggtccttaag gcccattccg tttcttctta  1380

-continued

```
taatgttctg ggctagccca tttgaattta aacctttcct ttcaatttct gcattaatat    1440
aattcagttg ttcaaaaaaa aaatagcgct tattgaaata atagagagaa agataatgag    1500
aagggagaaa atgaaaagcg tatttcatat gagagattgt caacaaaaat tgagtgactt    1560
ttatgatatt tgttcaaaga atagtctaat aacctttctt atttaaattt taattatgtt    1620
atatatcaat aatactaaaa taattagtta ctcacagttc gtgacaaaaa aaaaagcaaa    1680
tagatgaaat gaaatgaaag aaagatcttt cttcacgcgt tgatattcat aaaacaatgg    1740
aatgaaagaa aacagttaag attctacaag aaagaaaaga aagtcccaaa acatgacaa     1800 atagatgaag aagcaaatgt gacttgacgt aacgtagaac tccatatata ctcccatcgt    1860
tttgcatgga gcatgcatgt gtaccgtgca cgtcgtagac cacacaactc cttcataaaa    1920
agccctctct cttcccatca ccaaaccatc agaaaatatg agaaacgaaa ttcaaaacga    1980
aacagctcag actgatcaga cccagggaag tatgttttct tttttcaatt tgttcccttt    2040
cctcctccca atgtttgagg ttatcaagat ggttgttgct tccgttgcgt ccgtagtata    2100
tttaggcttc gccggtgtaa cactcagtgg ttcagccgtg gcattagccg tatccacccc    2160
tcttttcatc atattcagtc cgattctctt acctgctatt gcagccacta ctgtcctagc    2220
cgccgggctc ggaggtaaaa aagtggcggc ggctccggaa gcttctccgg cagcttcgcc    2280
atccctatct ctgttgggca taccggagag cattaaacca agtaatatta taccggagag    2340 tattaaaccca agtaatatta taccggaggg tattaaaccca agtaatatta aggacaaaat   2400
taaggatacg ataggcaaag ttaagaataa gatcaaagct aaaaaggaag aaaaatccaa    2460
aggtaaaagt gaagattctt ccaagggtaa aggtaaatca aagggtgaag atacgactac    2520
ggatgacgat acgactacgg atgaagacaa acacggaagt ggagctaaac acggaaaggg    2580
agagagtaaa cacggaaaag gtgagagtac acacggaaag ggaggtaaac atggaagtga    2640
aggtaagcat ggaagtggag gttcgtctat gggtggaggt aaacacggaa gcggaggtaa    2700
acatgaaact ggaggtaaac acggaagcgg agcggtaaacat gaaagtggag gttcgcctat   2760
gggtggaggt aaacatggaa gtgaaggtaa gcatggaagt ggaggtgcgt ctatgggtgg    2820
aggtaaacac ggaagcggag gtaaacatga agtgcaggt tcggctatgg gtggaggtaa    2880
gcacggaagt ggaggcaaac acggaagtga aggtaaacac ggggtgaag gctcttctat    2940 gggtaaaaat agtctatcca agaagaaaaa ggaattccat tatagaggtc aagctatgga    3000
tgcaagtagt acaagtgaaa gttcagatgg aagttcagat ggcagcagtt cagatggaag    3060
ttcacatggg agtggtggta acacataat  aaatctgatg atgccttgtg gctctttat    3120 gtttggaaac tgtcgcaata taggagccag ggaatgcgaa aaattaaatt cgccgggtaa    3180
gcgcaagcct tcacattgca aatgtacaga tactcaaatg ggtacttatt cttgtgattg    3240
taaattgtgt tag                                                         3253
```

<210> SEQ ID NO 40
<211> LENGTH: 33
<212> TYPE: DNA
<213> ORGANISM: artificial
<220> FEATURE:
<223> OTHER INFORMATION: primer (Atgrp19-F1)

<400> SEQUENCE: 40
aatggtaccg aataagtgag tcttgcacac tgg                            33

<210> SEQ ID NO 41

```
<211> LENGTH: 32
<212> TYPE: DNA
<213> ORGANISM: artificial
<220> FEATURE:
<223> OTHER INFORMATION: primer (Atgrp19-R1)

<400> SEQUENCE: 41
tatggatccg acgccggaac ctgctgggtt ag                                     32

<210> SEQ ID NO 42
<211> LENGTH: 37
<212> TYPE: DNA
<213> ORGANISM: artificial
<220> FEATURE:
<223> OTHER INFORMATION: primer (Atgrp19-R2)

<400> SEQUENCE: 42
tatagatcta ccatgacgcc ggaacctgct gggttag                                37

<210> SEQ ID NO 43
<211> LENGTH: 4927
<212> TYPE: DNA
<213> ORGANISM: artificial
<220> FEATURE:
<223> OTHER INFORMATION: nucleotide sequence of the translational fusion
      in plasmid TOG-2 (see Example 17; Figure 5b)

<400> SEQUENCE: 43
gagctccacc cacagaagca gataaaccag ctgaaggaac aacagaaaaa ccaaaagata        60
attcgactgg aggagcagcc gataaaccag aagataaacc agttggagga gcagccgata      120
aaccagaagg taaaccggat ggaggagcaa caaataagcc agaaagtaaa ccagctggag      180
gaccatcaaa taaccaaaaa gataaacccg ctggaggacc aacggataaa ccagaaagta      240
agccagcaga taaacccgct ggaggaccaa cagataagcc aggaagtaaa ccggttgata      300
aacccgctgg aggaccaaca gataagcaga aagtaaact ggttggagag gcatcaaata       360
aaccaaaaga taaacccgct ggtggatcaa cagatatgcc agaagctgga gagacatcaa      420
ataaaccaaa agataaatcc gttggaggac caacaaataa gccagaaagt aaaccagctg      480
gagaaacatc acataaacca aaagataaac ccgctggtgg accaacagat aagccagaaa      540
gtaaaccggc tggagaaaca tcacataaac caaaagataa actcgctggt ggaccaacag      600
ataagccaga aagtaaacca gctggagagg catcaaataa accaaaagat aaacccgctg      660
gtggaccaac agataaacca gctggaggat cagtagataa accaaaagat aaacctgccg      720
gaggaccaac agataaacca acaaataaac cgactggagg ggctgcaaat aaaccggctg      780
gagaggcagc aaacaaaccg actggaaaac cgaaaaataa accggctgga gagaataaac      840
caccgggatg gtataggtga atggagtagt atgaaattaa agtattgggt tccacaaatt      900
attcctaatt tatcctacac tacatgtttc ataatcattt ctataaatgt acgacttgtt      960
acaaagaaat gataaacagt gtacagaatt tctttgtaa atttattaaa ttgatgtgga       1020
tatcattata actgacgtta gcgtatatcg accaatgcga taaccaaatc atcggtatat     1080
acctaagact tccttttaa aaatgaatct gatactaatt taatgtacga cttccaataa      1140
ccaatcttct tgcattttc attgccattt accttgaacg cctctctttc tagtatgaga      1200
cattaacatt gcgctcttgt cacaatgaag ccatggaaaa cttcggctct ttaatcacac     1260
atgtgacaat ccagttggtt taagggaaag tattttatat tttatatagc tcgttctcag     1320
aacaaaaaaa ccaaattctt tagcaaaaat ggtccttaag gcccattccg tttcttctta    1380
```

```
taatgttctg ggctagccca tttgaattta aacctttcct ttcaatttct gcattaatat    1440
aattcagttg ttcaaaaaaa aaatagcgct tattgaaata atagagagaa agataatgag    1500
aagggagaaa atgaaaagcg tatttcatat gagagattgt caacaaaaat tgagtgactt    1560
ttatgatatt tgttcaaaga atagtctaat aacctttctt atttaaattt taattatgtt    1620
atatatcaat aatactaaaa taattagtta ctcacagttc gtgacaaaaa aaaaagcaaa    1680
tagatgaaat gaaatgaaag aaagatcttt cttcacgcgt tgatattcat aaaacaatgg    1740
aatgaaagaa aacagttaag attctacaag aaagaaaaga aagtcccaaa acatgacaa     1800 atagatgaag aagcaaatgt gacttgacgt aacgtagaac tccatatata ctcccatcgt    1860
tttgcatgga gcatgcatgt gtaccgtgca cgtcgtagac cacacaactc cttcataaaa    1920
agccctctct cttcccatca ccaaaccatc agaaaatatg agaaacgaaa ttcaaaacga    1980
aacagctcag actgatcaga cccagggaag tatgttttct tttttcaatt tgttcccttt    2040
cctcctccca atgtttgagg ttatcaagat ggttgttgct tccgttgcgt ccgtagtata    2100
tttaggcttc gccggtgtaa cactcagtgg ttcagccgtg gcattagccg tatccacccc    2160
tcttttcatc atattcagtc cgattctctt acctgctatt gcagccacta ctgtcctagc    2220
cgccgggctc ggaggtaaaa aagtggcggc ggctccggaa gcttctccgg cagcttcgcc    2280
atccctatct ctgttgggca taccggagag cattaaacca agtaatatta taccggagag    2340
tattaaacca agtaatatta taccggaggg tattaaacca agtaatatta aggacaaaat    2400
taaggatacg ataggcaaag ttaagaataa gatcaaagct aaaaggaag aaaaatccaa     2460 aggtaaaagt gaagattctt ccaagggtaa aggtaaatca aagggtgaag atacgactac    2520
ggatgacgat acgactacgg atgaagacaa acacggaagt ggagctaaac acggaaaggg    2580
agagagtaaa cacggaaaag gtgagagtac acacggaaag ggaggtaaac atggaagtga    2640
aggtaagcat ggaagtggag gttcgtctat gggtggaggt aaaacacgaa gcggaggtaa    2700
acatgaaact ggaggtaaac acggaagcgg aggtaaacat gaaagtggag gttcgcctat    2760
gggtggaggt aaacatggaa gtgaaggtaa gcatggaagt ggaggtgcgt ctatgggtgg    2820
aggtaaacac ggaagcggag gtaaacatga agtggaggt tcggctatgg gtggaggtaa     2880
gcacggaagt ggaggcaaac acggaagtga aggtaaacac ggggggtgaag gctcttctat    2940 gggtaaaaat agtctatcca agaagaaaaa ggaattccat tatagaggtc aagctatgga    3000
tgcaagtagt acaagtgaaa gttcagatgg aagttcagat ggcagcagtt cagatggaag    3060
ttcacatggg agtggtggta aacacatagg taccggatcc ccgggtggtc agtcccttat    3120
gttacgtcct gtagaaaccc caacccgtga aatcaaaaaa ctcgacgcc tgtgggcatt     3180 cagtctggat cgcgaaaact gtggaattga tcagcgttgg tgggaaagcg cgttacaaga    3240
aagccgggca attgctgtgc caggcagttt taacgatcag ttcgccgatg cagatattcg    3300
taattatgcg ggcaacgtct ggtatcagcg cgaagtcttt ataccgaaag ttgggcagg     3360 ccagcgtatc gtgctgcgtt tcgatgcggt cactcattac ggcaaagtgt gggtcaataa    3420
tcaggaagtg atggagcatc agggcggcta tacgccattt gaagccgatg tcacgccgta    3480
tgttattgcc gggaaaagtg tacgtatcac cgtttgtgtg aacaacgaac tgaactggca    3540
gactatcccg ccgggaatgg tgattaccga cgaaaacggc aagaaaaagc agtcttactt    3600
ccatgatttc tttaactatg ccgggatcca tcgcagcgta atgctctaca ccacgccgaa    3660
cacctgggtg gacgatatca ccgtggtgac gcatgtcgcg caagactgta accacgcgtc    3720
tgttgactgg caggtggtgg ccaatggtga tgtcagcgtt gaactgcgtg atgcggatca    3780
```

```
acaggtggtt gcaactggac aaggcactag cgggactttg caagtggtga atccgcacct    3840
ctggcaaccg ggtgaaggtt atctctatga actgtgcgtc acagccaaaa gccagacaga    3900
gtgtgatatc tacccgcttc gcgtcggcat ccggtcagtg gcagtgaagg ccaacagtt     3960 cctgattaac cacaaaccgt tctactttac tggctttggt cgtcatgaag atgcggactt    4020
acgtggcaaa ggattcgata acgtgctgat ggtgcacgac cacgcattaa tggactggat    4080
tggggccaac tcctaccgta cctcgcatta cccttacgct gaagagatgc tcgactgggc    4140
agatgaacat ggcatcgtgg tgattgatga aactgctgct gtcggcttta acctctcttt    4200
aggcattggt ttcgaagcgg gcaacaagcc gaaagaactg tacagcgaag aggcagtcaa    4260
cggggaaact cagcaagcgc acttacaggc gattaaagag ctgatagcgc gtgacaaaaa    4320
ccacccaagc gtggtgatgt ggagtattgc caacgaaccg ataccgtc cgcaagtgca     4380 cgggaatatt tcgccactgg cggaagcaac gcgtaaactc gacccgacgc gtccgatcac    4440
ctgcgtcaat gtaatgttct gcgacgctca caccgatacc atcagcgatc tctttgatgt    4500
gctgtgcctg aaccgttatt acggatggta tgtccaaagc ggcgatttgg aaacggcaga    4560
gaaggtactg gaaaaagaac ttctggcctg gcaggagaaa ctgcatcagc cgattatcat    4620
caccgaatac ggcgtggata cgttagccgg gctgcactca atgtacaccg acatgtggag    4680
tgaagagtat cagtgtgcat ggctggatat gtatcaccgc gtctttgatc gcgtcagcgc    4740
cgtcgtcggt gaacaggtat ggaatttcgc cgattttgcg acctcgcaag gcatattgcg    4800
cgttggcggt aacaagaaag ggatcttcac tcgcgaccgc aaaccgaagt cggcggcttt    4860
tctgctgcaa aaacgctgga ctggcatgaa cttcggtgaa aaaccgcagc agggaggcaa    4920
acaatga                                                              4927
```

<210> SEQ ID NO 44
<211> LENGTH: 3431
<212> TYPE: DNA
<213> ORGANISM: artificial
<220> FEATURE:
<223> OTHER INFORMATION: nucleotide sequence of the translational fusion
      in plasmid ATOG-3 (see Example 24; Figure 5c-2)

<400> SEQUENCE: 44

```
ggtaccgaat aagtgagtct tgcacactgg aattcttgtt tcgaccatcg taactggttt    60
ccaattagaa agccaaacct aatttttttt tcctcaaagt acttacaaat ttattcgaaa    120
caaattaatc ataaattcct gtatataaat ataaataaaa ggagtaaagg acaataaatc    180
agtgagacaa tgcatgctct tgcagctccg ccaagggtca aatggaaaat taaatacaat    240
ttaaaatagt caaagctttg accattactg accattgcgc aaaggaacaa ccgaacaatt    300
agtccatggc taataataag cccttaacat attcgattca tcattttatc tttcaatcaa    360
gtactttaaa tcgaaattaa ttagaatcag ttgcaaaaat tggtcatgta ttcggacatc    420
gatcggttat atacttaata ttctatggtc acagacgtgc tgataaagag ccacaatcat    480
aaactaaaat taatattacg attcagtaga tcaaaaaaaa aaaaaaaat tggtcgaatc     540 ttagcttttt tagattttc tttattatac taagcgatat ggctatccaa tttttttctcg   600 tttatcgaac tctaaattct tgttaccatt gttaaaggta ttttttgtta caattttct     660 taggaaaatg tgatagtcac gaactcaaat ctgtattttc ttcttttaaaa acagaaattt   720 agggatacga aatcagatc ataacacata ttaaaacaag gaaaaggcca aaaaccgtga     780
caatccacag aaaaaccaaag agagacaatg acgtgacgta acacatatct ccattttcat   840
```

```
tcagatcgtt ttgcatggag catgaatgtg tagcgtagcg ttcacgtaga cttccactag      900
ttcttgataa aaccccactt cttcccacca ctaaatcata aaccattcga tcagaccaaa      960
tcccagccgt ttaacttgat catcccaaag atgtttgaga ttattcaggc ggtcttctcc     1020
gccggggttg cactagctct tttgacattc gccggtataa ccctcggcgg ctcagtggtc     1080
gcatgtatca taagcacacc acttttttgtc attttcagtc ccgttctcgt gccagcgact     1140
atagccacta cattgctagc ttcaggtttc acagcctccg gttcctttgg tgccacggct     1200
ttcaccatcc tttcgtggct ctacaagtaa attattgcaa tttggtttac ttttattgaa     1260
atgtagtttt aggcatatgc atctacatgg gaacttattt atatgcatga ttagacatat     1320
aatatacatt tcaagggatg aacattcggt tatatatggt atagttaata gttattgatt     1380
ttgagaatgt ataaccttac taaactttat catgtttggt ttaaacctgg ttcatgttcg     1440
attcataatc tttagtttat acaaacacaa atcaacgaat ttaatttagt aatcagaagt     1500
atgtgattgt atgtaggaaa cgtacaggga gggacctacc aaaaattcca ggattgacgc     1560
caccggctcc ggcgtctaac ccagcaggtt ccggcgtcgg atcccgggt ggtcagtccc     1620
ttatgttacg tcctgtagaa accccaaccc gtgaaatcaa aaaactcgac ggcctgtggg     1680
cattcagtct ggatcgcgaa aactgtggaa ttgatcagcg ttggtgggaa agcgcgttac     1740
aagaaagccg ggcaattgct gtgccaggca gttttaacga tcgttcgcc gatgcagata      1800
ttcgtaatta tgcgggcaac gtctggtatc agcgcgaagt ctttataccg aaaggttggg     1860
caggccagcg tatcgtgctg cgtttcgatg cggtcactca ttacgcaaa gtgtgggtca     1920
ataatcagga agtgatggag catcagggcg gctatacgcc atttgaagcc gatgtcacgc     1980
cgtatgttat tgccgggaaa agtgtacgta tcaccgtttg tgtgaacaac gaactgaact     2040
ggcagactat cccgccggga atggtgatta ccgacgaaaa cggcaagaaa aagcagtctt     2100
acttccatga tttcttaac tatgccggga tccatcgcag cgtaatgctc tacaccacgc      2160
cgaacacctg ggtggacgat atcaccgtgg tgacgcatgt cgcgcaagac tgtaaccacg     2220
cgtctgttga ctggcaggtg gtggccaatg gtgatgtcag cgttgaactg cgtgatgcgg     2280
atcaacaggt ggttgcaact ggacaaggca ctagcgggac tttgcaagtg gtgaatccgc     2340
acctctggca accgggtgaa ggttatctct atgaactgtg cgtcacagcc aaaagccaga     2400
cagagtgtga tatctacccg cttcgcgtcg gcatccggtc agtggcagtg aagggccaac     2460
agttcctgat taaccacaaa ccgttctact ttactggctt tggtcgtcat gaagatgcgg     2520
acttacgtgg caaaggattc gataacgtgc tgatggtgca cgaccacgca ttaatggact     2580
ggattggggc caactcctac cgtacctcgc attacccta cgctgaagag atgctcgact     2640
gggcagatga acatggcatc gtggtgattg atgaaactgc tgctgtcggc tttaacctct     2700
ctttaggcat tggtttcgaa gcgggcaaca gccgaaaga actgtacagc gaagaggcag     2760
tcaacgggga aactcagcaa gcgcacttac aggcgattaa agagctgata gcgcgtgaca     2820
aaaaccaccc aagcgtggtg atgtggagta ttgccaacga accggatacc cgtccgcaag     2880
tgcacgggaa tatttcgcca ctggcggaag caacgcgtaa actcgacccg acgcgtccga     2940
tcacctgcgt caatgtaatg ttctgcgacg ctcacaccga taccatcagc gatctctttg     3000
atgtgctgtg cctgaaccgt tattacggat ggtatgtcca aagcggcgat ttggaaacgg     3060
cagagaaggt actggaaaaa gaacttctgg cctggcagga gaaactgcat cagccgatta     3120
tcatcaccga atacggcgtg gatacgttag ccgggctgca ctcaatgtac accgacatgt     3180
```

-continued

```
ggagtgaaga gtatcagtgt gcatggctgg atatgtatca ccgcgtcttt gatcgcgtca    3240
gcgccgtcgt cggtgaacag gtatggaatt tcgccgattt tgcgacctcg caaggcatat    3300
tgcgcgttgg cggtaacaag aaagggatct tcactcgcga ccgcaaaccg aagtcggcgg    3360
cttttctgct gcaaaaacgc tggactggca tgaacttcgg tgaaaaaccg cagcagggag    3420
gcaaacaatg a                                                        3431
```

<210> SEQ ID NO 45
<211> LENGTH: 3651
<212> TYPE: DNA
<213> ORGANISM: artificial
<220> FEATURE:
<223> OTHER INFORMATION: nucleotide sequence of the translational fusion
      in plasmid ATOG-4+ (see Example 24; Figure 5F)

<400> SEQUENCE: 45

```
ggtaccgaat aagtgagtct tgcacactgg aattcttgtt tcgaccatcg taactggttt      60
ccaattagaa agccaaacct aattttttt tcctcaaagt acttacaaat ttattcgaaa     120
caaattaatc ataaattcct gtatataaat ataaataaaa ggagtaaagg acaataaatc     180
agtgagacaa tgcatgctct tgcagctccg ccaagggtca aatggaaaat taaatacaat     240
ttaaaatagt caaagctttg accattactg accattgcgc aaaggaacaa ccgaacaatt     300
agtccatggc taataataag cccttaacat attcgattca tcattttatc tttcaatcaa     360
gtactttaaa tcgaaattaa ttagaatcag ttgcaaaaat tggtcatgta ttcggacatc     420
gatcggttat atacttaata ttctatggtc acagacgtgc tgataaagag ccacaatcat     480
aaactaaaat taatattacg attcagtaga tcaaaaaaaa aaaaaaaaat tggtcgaatc     540
ttagcttttt tagattttc tttattatac taagcgatat ggctatccaa ttttttctcg     600
tttatcgaac tctaaattct tgttaccatt gttaaggta ttttttgtta caattttct     660 taggaaaatg tgatagtcac gaactcaaat ctgtatttc ttctttaaaa acagaaattt     720
agggatacga aatcaagatc ataacacata ttaaaacaag gaaaaggcca aaaaccgtga     780
caatccacag aaaaccaaag agagacaatg acgtgacgta acacatatct ccattttcat     840
tcagatcgtt ttgcatggag catgaatgtg tagcgtagcg ttcacgtaga cttccactag     900
ttcttgataa acccccactt cttcccacca ctaaatcata aaccattcga tcagaccaaa     960
tcccagccgt ttaacttgat catcccaaag atgtttgaga ttattcaggc ggtcttctcc    1020 gccgggttg cactagctct tttgacattc gccggtataa ccctcggcgg ctcagtggtc    1080
gcatgtatca taagcacacc actttttgtc attttcagtc ccgttctcgt gccagcgact    1140
atagccacta cattgctagc ttcaggtttc acagcctccg gttcctttgg tgccacggct    1200
ttcaccatcc tttcgtggct ctacaagtaa attattgcaa tttggtttac ttttattgaa    1260
atgtagtttt aggcatatgc atctacatgg gaacttattt atatgcatga ttagacatat    1320
aatatacatt tcaagggatg aacattcggt tatatatggt atagttaata gttattgatt    1380
ttgagaatgt ataaccttac taaactttat catgtttggt ttaaacctgg ttcatgttcg    1440
attcataatc tttagtttat acaaacacaa atcaacgaat ttaatttagt aatcagaagt    1500
atgtgattgt atgtaggaaa cgtacaggga gggacctacc aaaaattcca ggattgacgc    1560
caccggctcc ggcgtctaac ccagcaggtt ccggcgtcat ggtagatctg agggtaaatt    1620
tctagttttt ctccttcatt ttcttggtta ggacccttt ctcttttat tttttgagc     1680 tttgatcttt ctttaaactg atctattttt taattgattg gttatggtgt aaatattaca    1740
```

```
tagctttaac tgataatctg attactttat ttcgtgtgtc tatgatgatg atgatagtta      1800
cagaaccgac gaactagtct gtacccgatc aacaccgaga cccgtggcgt cttcgacctc      1860
aatggcgtct ggaacttcaa gctggactac gggaaaggac tggaagagaa gtggtacgaa      1920
agcaagctga ccgacactat tagtatggcc gtcccaagca gttacaatga cattggcgtg      1980
accaaggaaa tccgcaacca tatcggatat gtctggtacg aacgtgagtt cacggtgccg      2040
gcctatctga aggatcagcg tatcgtgctc cgcttcggct ctgcaactca caaagcaatt      2100
gtctatgtca atggtgagct ggtcgtggag cacaagggcg gattcctgcc attcgaagcg      2160
gaaatcaaca actcgctgcg tgatggcatg aatcgcgtca ccgtcgccgt ggacaacatc      2220
ctcgacgata gcaccctccc ggtggggctg tacagcgagc gccacgaaga gggcctcgga      2280
aaagtcattc gtaacaagcc gaacttcgac ttcttcaact atgcaggcct gcaccgtccg      2340
gtgaaaatct acacgacccc gtttacgtac gtcgaggaca tctcggttgt gaccgacttc      2400
aatggcccaa ccgggactgt gacctatacg gtggactttc aaggcaaagc cgagaccgtg      2460
aaagtgtcgg tcgtggatga ggaaggcaaa gtggtcgcaa gcaccgaggg cctgagcggt      2520
aacgtggaga ttccgaatgt catcctctgg gaaccactga acacgtatct ctaccagatc      2580
aaagtggaac tggtgaacga cggactgacc atcgatgtct atgaagagcc gttcggcgtg      2640
cggaccgtgg aagtcaacga cggcaagttc ctcatcaaca caaaccgtt ctacttcaag       2700
ggctttggca acatgagga cactcctatc aacggccgtg gctttaacga agcgagcaat       2760
gtgatggatt tcaatatcct caaatggatc ggcgccaaca gcttccggac cgcacactat      2820
ccgtactctg aagagttgat gcgtcttgcg gatcgcgagg gtctggtcgt gatcgacgag      2880
actccggcag ttggcgtgca cctcaacttc atggccacca cgggactcgg cgaaggcagc      2940
gagcgcgtca gtacctggga gaagattcgg acgtttgagc accatcaaga cgttctccgt      3000
gaactggtgt ctcgtgacaa gaaccatcca agcgtcgtga tgtggagcat cgccaacgag      3060
gcggcgactg aggaagaggg cgcgtacgag tacttcaagc cgttggtgga gctgaccaag      3120
gaactcgacc cacagaagcg tccggtcacg atcgtgctgt ttgtgatggc taccccggag      3180
acggacaaag tcgccgaact gattgacgtc atcgcgctca atcgctataa cggatggtac      3240
ttcgatggcg gtgatctcga agcggccaaa gtccatctcc gccaggaatt tcacgcgtgg      3300
aacaagcgtt gcccaggaaa gccgatcatg atcactgagt acggcgcaga caccgttgcg      3360
ggctttcacg acattgatcc agtgatgttc accgaggaat atcaagtcga gtactaccag      3420
gcgaaccacg tcgtgttcga tgagtttgag aacttcgtgg gtgagcaagc gtggaacttc      3480
gcggacttcg cgacctctca gggcgtgatg cgcgtccaag gaaacaagaa gggcgtgttc      3540
actcgtgacc gcaagccgaa gctcgccgcg cacgtctttc gcgagcgctg gaccaacatt      3600
ccagatttcg gctacaagaa cgctagccat caccatcacc atcacgtgtg a               3651
```

<210> SEQ ID NO 46
<211> LENGTH: 31
<212> TYPE: DNA
<213> ORGANISM: artificial
<220> FEATURE:
<223> OTHER INFORMATION: primer (Atexl 4-F1)

<400> SEQUENCE: 46
ataggtacct taacattctt gtagttaggg c     31

<210> SEQ ID NO 47
<211> LENGTH: 32

<210> SEQ ID NO 48
<211> LENGTH: 4084
<212> TYPE: DNA
<213> ORGANISM: artificial
<220> FEATURE:
<223> OTHER INFORMATION: primer (Atexl 4-R1)

<400> SEQUENCE: 47
tatccatggc aaggccattc ttgatatcct gg                                        32

<210> SEQ ID NO 48
<211> LENGTH: 4084
<212> TYPE: DNA
<213> ORGANISM: artificial
<220> FEATURE:
<223> OTHER INFORMATION: nucleotide sequence of the tranlsational fusion
      in plasmid EXLG-1+ (Example 25, Figure 30)

<400> SEQUENCE: 48
ggtaccttaa cattcttgta gttagggcct cttcgagtac atggatgaat gtgaatctac    60
atgacgaaac cattgacgtt tacaaaacaa atcatcatat atatcattca ttctaaagtc   120
ttgttttctt ttcttttttgt ttggtgtaaa gcggctacat attctttatt tttttatttt   180
gtctacattt cgtcagattt gatttatgga gttaattatt atcttcctag ctaaaacatg   240
ctgacattca tcctgtgtgt acccaccact ttcatgcatt tttggcttcc ttagacaaca   300
aagactagac gtctaaaaat acttagaaaa tcacttgtat atatttacta ctgacatgag   360
cttagaagca ccactaatta aattctctat aaaacataag agagtctaaa cactgtggta   420
gaaaaaaata tagactttta gatatgtgta gtaaaataac attagtgtta actttatttt   480
ccagttattt catatcaaca gatgctgtga atggatcatt tcctgcgctt ttggcttttg   540
gagattcaat tctcgatact ggcaacaaca attttctcct gacttttatg aaaggaaata   600
tctggccata tggaaggagt ttcagcatga aagggcgac aggaagattt ggaaatggaa   660
gagttttctc tgatatagtt ggtatattat cattttttttt acaatgcttc tttgtatttc   720
ctaattttc tcatattgca tagcttagaa aatcatatgg tatgaataat attattctga   780
tatagtaagt ttattattac tacagctgaa ggtttaggga tcaagaagat tttaccagct   840
tatcgtaagt tgttcaattc tccaagtgac cttagaactg gtgtttgctt cgcatcaggt   900
ggtgcaggag ttgaccctgt tacatccaaa ttgctggtga aaataataat tataaatttg   960
ttatttcttt aaaaaaatat attatatgtc ttaactaaat atacattttc taataaatat  1020
tgtaatttat tttgggtggt gatttggtca gagagttta acgccaaagg atcaagtaaa  1080
cgatttcaaa gggtacataa gaaagctaaa ggccacagca ggtccttcaa gagcaagtag  1140
tatagtttca aatgcagtga ttcttgtttc tcaaggaaat aatgatattg gaatctcata  1200
ttttggaact ccaactgctg ctttccgagg attaactccc aatagatata ccactaaact  1260
agctggttgg aacaaacagt ttatgaaagt aatacataaa atcattttct tatcaagcat  1320
ccatatatat atatgaagta tatatattcg ttcacgtttt ttttgttcta tgtatgaagg  1380
aattatacga tcaaggagcg agaaaattcg cggtaatggg agtgataccg ttgggatgtt  1440
tgcctatgac aagaatcttc cttggtgggt tcgtcatcac gtgtaacttc ttcgcgaata  1500
gagtcgcaga acagtacaac ggaaaattga ggagcggaac taaaagttgg ggacgtgaag  1560
caggttttag gggtgcaaaa tttgtctatg tcgacatgta caacactctt atggatgtta  1620
ttaaaaatta tagaagatac ggtaagtaaa tacccaccac catttttccct tgttttttt  1680
tgctaacaac atgaattata ttggatttga attagatggg gatataatta taatgacgaa  1740
aactattgat tttatgtcac atttaactgt tcctcattct taaagatctt gtttaccgaa  1800

```
tttgttctat cgcttgataa tttatgtata tagttactaa gtatcatgta cttgtatggt    1860
tgcaggattt tctaatgaga aaaatgggtg ttgttgtatg attacggcta taataccatg    1920
ccccaaccca gataaatacg tcttctacga cttcgttcat ccatccgaga aagcttacag    1980
aacaatttct aaaaagcttg tccaggatat caagaatggc cttgccttgc catggtagat    2040
ctgagggtaa atttctagtt tttctccttc attttcttgg ttaggaccct tttctctttt    2100
tatttttttg agctttgatc tttctttaaa ctgatctatt ttttaattga ttggttatgg    2160
tgtaaatatt acatagcttt aactgataat ctgattactt tatttcgtgt gtctatgatg    2220
atgatgatag ttacagaacc gacgaactag tctgtacccg atcaacaccg agacccgtgg    2280
cgtcttcgac ctcaatggcg tctgaacttc aagctggact acgggaaag gactggaaga    2340
gaagtggtac gaaagcaagc tgaccgacac tattagtatg gccgtcccaa gcagttacaa    2400
tgacattggc gtgaccaagg aaatccgcaa ccatatcgga tatgtctggt acgaacgtga    2460
gttcacggtg ccggcctatc tgaaggatca gcgtatcgtg ctccgcttcg gctctgcaac    2520
tcacaaagca attgtctatg tcaatggtga gctggtcgtg gagcacaagg gcggattcct    2580
gccattcgaa gcggaaatca caactcgct gcgtgatggc atgaatcgcg tcaccgtcgc    2640
cgtggacaac atcctcgacg atagcaccct cccggtgggg ctgtacagcg agcgccacga    2700
agagggcctc ggaaaagtca ttcgtaacaa gccgaacttc gacttcttca actatgcagg    2760
cctgcaccgt ccggtgaaaa tctacacgac cccgtttacg tacgtcgagg acatctcggt    2820
tgtgaccgac ttcaatggcc caaccgggac tgtgacctat acggtggact ttcaaggcaa    2880
agccgagacc gtgaaagtgt cggtcgtgga tgaggaaggc aaagtggtcg caagcaccga    2940
gggcctgagc ggtaacgtgg agattccgaa tgtcatcctc tgggaaccac tgaacacgta    3000
tctctaccag atcaaagtgg aactggtgaa cgacggactg accatcgatg tctatgaaga    3060
gccgttcggc gtgcggaccg tggaagtcaa cgacggcaag ttcctcatca acaacaaacc    3120
gttctacttc aagggctttg gcaaacatga ggacactcct atcaacggcc gtggctttaa    3180
cgaagcgagc aatgtgatgg atttcaatat cctcaaatgg atcggcgcca acagcttccg    3240
gaccgcacac tatccgtact ctgaagagtt gatgcgtctt gcggatcgcg agggtctggt    3300
cgtgatcgac gagactccgg cagttggcgt gcacctcaac ttcatggcca ccacgggact    3360
cggcgaaggc agcgagcgcg tcagtacctg ggagaagatt cggacgtttg agcaccatca    3420
agacgttctc cgtgaactgg tgtctcgtga caagaaccat ccaagcgtcg tgatgtggag    3480
catcgccaac gaggcggcga ctgaggaaga gggcgcgtac gagtacttca gccgttggt    3540
ggagctgacc aaggaactcg acccacagaa gcgtccggtc acgatcgtgc tgtttgtgat    3600
ggctaccccg gagacggaca aagtcgccga actgattgac gtcatcgcgc tcaatcgcta    3660
taacggatgg tacttcgatg gcggtgatct cgaagcggcc aaagtccatc tccgccagga    3720
atttcacgcg tggaacaagc gttgcccagg aaagccgatc atgatcactg agtacggcgc    3780
agacaccgtt gcgggcttc acgacattga tccagtgatg ttcaccgagg aatatcaagt    3840
cgagtactac caggcgaacc acgtcgtgtt cgatgagttt gagaacttcg tgggtgagca    3900
agcgtggaac ttcgcggact cgcgacctc tcagggcgtg atgcgcgtcc aaggaaacaa    3960
gaagggcgtg ttcactcgtg accgcaagcc gaagctcgcc gcgcacgtct ttcgcgagcg    4020
ctggaccaac attccagatt tcggctacaa gaacgctagc catcaccatc accatcacgt    4080
gtga                                                                4084
```

-continued

```
<210> SEQ ID NO 49
<211> LENGTH: 34
<212> TYPE: DNA
<213> ORGANISM: artificial
<220> FEATURE:
<223> OTHER INFORMATION: primer (Sta44G2(2))

<400> SEQUENCE: 49
ataggtaccg acagtataca taatttagag agag                              34

<210> SEQ ID NO 50
<211> LENGTH: 33
<212> TYPE: DNA
<213> ORGANISM: artificial
<220> FEATURE:
<223> OTHER INFORMATION: primer (Sta44-4(2))

<400> SEQUENCE: 50
tatggatccc tctttgccag gagccttgac cac                               33

<210> SEQ ID NO 51
<211> LENGTH: 34
<212> TYPE: DNA
<213> ORGANISM: artificial
<220> FEATURE:
<223> OTHER INFORMATION: primer (Sta44-4(3))

<400> SEQUENCE: 51
tatccatggt ctctttgcca ggagccttga ccac                              34
```

MODIFICATION OF POLLEN COAT PROTEIN COMPOSITION

This application is a Continuation in part of U.S. application Ser. No. 09/272,204, filed Mar. 19, 1999, abandoned, which claims priority to U.S. application Ser. No. 60/078,728, filed Mar. 20, 1998, both of which are incorporated herein by reference.

The present invention relates to the expression of proteins within plant tissues. More specifically, this invention relates to the expression of proteins in floral cells including those associated with anther and pistil.

BACKGROUND OF THE INVENTION

Pollen production is essential to the sexual reproductive success of the flowering plant. Male gametogenesis is a highly regulated developmental process that occurs within the diploid sporophytic tissue of the anther. It comprises three major phases: the differentiation of the sporogenous cells and meiosis; the development of the free uninucleate microspores; and the pollen maturation following microspore mitosis and ending with the formation of mature pollen (Scott, R., Hodge, R., Paul, W., Draper, *J. Plant Sci.* 80:167-191 (1991)). Typically, pollen captured by a receptive stigma of the pistil will germinate and the pollen tube will grow extracellularly through the stigma and style until it reaches the ovule where it releases its nuclei that effect double fertilization. Similarly to a seed, the pollen accumulates reserves that enable it to germinate on a receptive stigma.

Normal pollen development is dependent upon the tapetum, a cellular layer lining the locular space of the anther. The tapetum provides the developing microspores with nutrients and other necessary products such as enzymes and structural components (Pacini, E., Franchi, G. G., Hesse, M. *Plant Syst. Evol.* 149:155-185 (1985)). In *Brassica*, the secretory tapetum is made up of cells which are metabolically very active until about microspore mitosis at which time they degenerate (Grant, I., Beversdorf, W. D., Peterson, R. L. *Can. J. Bot.* 64:1055-1068 (1986); Murgia, M., Charzynska, M., Rougier, M., Cresti, M. *Sex. Plant Reprod.* 4:28-35 (1991); Polowick, P. L., Sawhney, V. K. *Sex. Plant Reprod.* 3:263-276 (1990)). When the tapetal cells degenerate they release their cellular contents into the anther locule where they are thought to contribute to the formation of the external pollen coat (Evans, D. E., Taylor, P. E., Singh, M. B., Knox, R. B. *Planta* 186:343-354 (1992); Heslop-Harrison, *J. New Pytol.* 67:779-786 (1968)). The pollen coat (sporoderm) consists of two layers, the exine (outer wall) and the intine (inner wall). The exine can be further subdivided into the nexine and sexine layers and is often elaborately sculptured and patterned (Scott, R. J. In: *Molecular and Cellular Aspects of Plant Reproduction* (eds) Scott, R. J., Stead, M. A. 55:49-81 (1994)).

The interstices of the exine contain various substances including proteins, enzymes, lipids and allergens (Knox, R. B. In: *Embryology of Angiosperms*, (ed) Johri, B. M. pp. 197-271 (1994)) many of which are of tapetal origin. The lipidic and proteinaceous layer coating the exine is also called the tryphine. The mature pollen grain released upon anther dehiscence is dry and the drying process causes the tryphine to retract into the exine cavities. Numerous pollen enzymes have been identified (Brewbaker, J. L. In: *Pollen: Development and Physiology* (ed) Heslop-Harrison, J. pp. 156-170 (1971); Hiscock, S. J., Dewey, F. M., Coleman, J. O. D., Dickinson, H. G. *Planta* 193:377-383 (1994); Knox, R. B. In: *Pollen: Development and Physiology* (ed) Heslop-Harrison, J. pp. 171-173 (1971); Lavithis, M., Bhalla, P. L. *Sex. Plant Reprod.* 8:289-298 (1995); Travis, J., Whitworth, T., Matheson, N., Bagarozzi, D. *Acta Biochim. Pol.* 43:411-418 (1996)). Many of these enzymes are located in the pollen coat especially in the intine layer and are readily elutable from the pollen grain. Some of these enzymes such as pectate lyases and ribonucleases have been shown to correspond to pollen allergens (Knox, R. B., Suphioglu, C. *Sex. Plant Reprod.* 9:318-323 (1996)).

Recently, genes encoding some of the pollen coat proteins have been isolated. The PCP[7] gene encodes a pollen coat peptide from *Brassica oleracea* that has been shown to interact with S-locus glycoproteins (Doughty, J., Hedderson, F., McCubbin, A., Dickinson, H. *Proc. Natl. Acad. Sci. USA* 90:467-471 (1993); Hiscock, S. J., Doughty, J., Willis, A. C., Dickinson, H. G. *Planta* 194:367-374 (1995)). The PCP1 gene encodes a cysteine-rich protein which may be involved in pollen-stigma interactions in *Brassica oleracea* and which belongs to a family of 30 to 40 genes (Stanchev, B. S., Doughty, J., Scutt, C. P., Dickinson, H., Croy, R. R. D. *Plant J.* 10:303-313 (1996)). This gene was shown to be expressed gametophytically and its product is released from the pollen protoplast into the surface coating.

There have also been numerous genes isolated which show expression in the tapetum, yet the function of the proteins they encode (Schrauwen, J. A. M. *Acta Bot. Neerl.* 45:1-15 (1996)), and whether they associate with the pollen coat is largely unknown. However, genes encoding β-1,3-glucanase have been shown to be expressed in the tapetum and these enzymes are involved in breaking down the callose wall surrounding the tetrads releasing the microspores (Bucciaglia, P. A., Smith, A. G. *Plant Mol. Biol.* 24:903-914 (1994); Hird, D. L., Worrall, D., Hodge, R., Smartt, S., Paul, W., Scott, R. *Plant J.* 4:1023-1033 (1993)). There are also some examples of tapetal-specific genes (ie. expressed sporophytically) whose products were shown to be localized to the pollen coat. The related genes Satap35 and Satap44 from *Sinapis alba* are associated with the exine of the developing microspore and may be involved in sporopollenin formation and/or deposition (Staiger, D., Kappeler, S., Müller, M., Apel, K. *Planta* 192:221-231 (1994)). Recently the pollen coat localized male determinant of self-incompatibility has been identified in *B. campestris* (*B. rapa*) and *B. oleracea* as the S-locus cysteine rich protein SCR/SP11 which is expressed in the tapetum (Schopfer, C. R., Nasrallah, M. E., Nasrallah, J. B. *Science* 296:1697-1700 (1999); Takayama, S., Shiba, H., Iwano, M., Asano, K., Hara, M., Che, F. -S., Watanabe, M., Hinata, K., Isogai, A. *Proc. Natl Acad. Sci.* USA 97: 1920-1925 (2000); Kachroo, A., Schopfer, C. R., Nasrallah, M. E., Nasrallah, J. B. *Science* 293: 1824-1826 (2001); Shiba, H., Takayama, S., Iwano, M., Shimosato, H., Funato, M., Nakagawa, T., Che, F. -S., Suzuki, G., Watanabe, M., Hinata, K., Isogai, A. *Plant Physiol.* 125: 2095-2103 (2001); Shiba, H., Iwano, M., Entani, T., Ishimoto, K., Shimosato, H., Che, F. -S., Satta, Y., Ito, A., Takada, Y., Watanabe, M., Isogai, A., Takayama, S. *Plant Cell* 14: 491-504 (2002)). Similarly, the predominant protein on the surface of maize pollen is an endoxylanase synthesized by the tapetum (Bih, F. Y., Wu, S. S. H., Ratnayake, C., Walling, L. L., Nothnagel, E. A., Huang, A. H. C. *J. Biol. Chem.* 274: 22884-22894 (1999)).

The Sta 41-2 and Sta 41-9 genes from *Brassica napus* encode proteins that possess a hydrophobic domain similar to that of the seed oleosins (Robert, L. S., Gerster, J. L., Allard, S., Cass, L., Simmonds, J. *Plant J.* 6:927-933 (1994a)). Sequence similarity among the Sta 41-2 and Sta 41-9 genes, and seed oleosin genes from *Brassica napus* (Murphy, D. J., *Prog. Lipid Res*. 32:247-280 (1993)) are limited to the relatively small hydrophobic domain and show levels of 30-36% identity. These tapetally expressed genes have now been demonstrated to belong a large family of related anther oleosin-like genes in *Brassica* (Ross, J. H. E., Murphy, D. J. *Plant J*. 9:625-637 (1996); Ruiter, R. K., Van Eldik, G. J., Van Herpen, R. M. A., Schrauwen J. A. M., Wullems, G. J. *Plant Cell* 9:1621-1631 (1997)). Unlike the other tapetally expressed pollen coat localized proteins mentioned above, the oleosin-like proteins do not possess a signal peptide and are thought to be released passively into the anther locule upon tapetum degeneration by association with lipids released from the tapetum or found as part of the tryphine of the pollen coat. Without wishing to be bound by theory, the hydrophobic region of the tapetal oleosin-like protein may be required for localization upon the pollen coat by association with lipids. The tapetal oleosin-like proteins constitute the major protein of the *Brassica* pollen tryphine and they occur as post-translationally cleaved protein products (Ross, J. H. E., Murphy, D. J. *Plant J*. 9:625-637 (1996)). The function of the tapetal oleosin-like proteins is unknown but they may play a role in the interaction between the pollen and the stigma the specialized part of the pistil that receives the pollen.

The stigma is responsible for capturing and selecting compatible pollen grains and for facilitating their germination. Angiosperm stigmas have been classified morphologically as 'dry' stigmas having an extracuticular proteinaceous pellicle but no free-flowing secretion or 'wet' stigmas which are covered by a secretion at the receptive stage (Heslop-Harrison, Y., Shivanna, K. R. *Ann. Bot*. 41:1233-1258 (1977)). In *Brassica*, the dry stigma is the site of the sporophytic self-incompatibility (SI) response with incompatible pollen being unable to grow through the stigmatic papillar cells or failing to germinate altogether.

A number of genes have been shown to be preferentially expressed in the *Brassica* stigma and most of these genes correspond to genes associated with SI: SLG (S-locus glycoprotein), SRK (S receptor kinase; U.S. Pat. No. 5,484, 905) or SLR (S-locus-related; WO94/25613) genes (for review: Nasrallah, J. B., Nasrallah, M. E. *Plant Cell* 5:1325-1335 (1993)). The products of the SLG and SRK genes are believed to be involved in a signal pathway modulating the SI reaction in response to a ligand carried by the pollen grain. WO94/25613 is directed to pistil-, and anther-specific gene expression. It discloses the cloning of several SLG's genes and the isolation of the $SLG_1$ promoter region, and the preparation of transcriptional fusion products using the promoters from the SLG genes. Furthermore, U.S. Pat. No. 5,585,543 discloses several genes related to the S-locus.

Another example of a gene highly expressed in the *Brassica* stigma is Pis 63 (Robert, L. S., Allard, S., Gerster, J. L., Cass, L., Simmonds, J. *Plant Mol. Biol*. 26:1217-1222 (1994b)). The promoter obtained from the genomic clone PISG 363, which contains gene Pis 63-2 was shown to direct the expression of the marker gene β-glucuronidase transiently in *B. napus* stigmas and stably in the stigmas of transformed tobacco plants (Robert, L. S., Lévesque-Lemay, M., Gerster, J. L., Hong, H. P., Keller, W. *Plant Cell Rep*. 18:357-362 (1999)).

The SI response in *Brassica* provides an example that a molecular based interaction between the pollen grain and the stigmatic papillae exists and that such an interaction can be modified or mimicked by targeting polypeptides to the appropriate part of the pollen and/or stigma. It is thought that localization of the SLG proteins arrises as a result of the appropriate signal peptide directing the protein extracellularly, following expression.

The preparation of plants with female sterility based on a style-stigma specific "STMG" gene and derived constructs using PSTMG promoter cassettes is disclosed in U.S. Pat. No. 5,633,441. These constructs include transcriptional fusions comprising barnase, papain or RNAse. In U.S. Pat. No. 5,652,354, the use of stamen-selective promoters useful in driving expression in anther, pollen, or filament cells, especially in the tapetum or anther epidermal cells is disclosed. U.S. Pat. No. 5,571,904 is directed to male flower specific gene sequences. Genomic clones of pMS10, 14 and 18 were obtained and promoter cassettes were constructed using MS10. There is also evidence presented where pMS14 expression has been localized within the tapetal cell layer. Other publications also disclose floral-specific genes and associated regulatory elements. For example, U.S. Pat. No. 5,633,438 discloses microspore-specific regulatory element, Bnm1; U.S. Pat. No. 5,545,546 discloses the cloning of W2247, a pollen specific promoter obtained from maize (inbred maize line W22); U.S. Pat. No. 5,659,124 teaches use of existing anther specific promoters to produce male sterile plants; WO92/13957 is directed to the cloning of CA444 which is a stamen/anther specific gene; WO97/13401 discloses the cloning of a rice tapetal specific gene RTS2; WO93/25695, is directed to the preparation of male sterile plants using tapetal specific promoters such as those from the TA29 gene or PT72; CA 2,099,482, teaches the disruption of the formation of viable pollen resulting in male sterile plants using an anther specific promoter; CA 2,106, 718 is directed to the disruption of normal pollen development using anther specific promoters driving chimeric constructs that disrupt pollen development; Worrall, D., Hird, D. L., Hodge, R., Paul, W., Draper, J., Scott, R. *Plant Cell* 4:759-771 (1992)) teaches the use of a tapetal specific promoter to drive the expression of callase which prematurely degrades the callose wall surrounding the developing tetrad of microspores thereby releasing the microspores into the anther locule. This premature release of microspores leads to male sterility. CA 2,165,934 discloses the use of a polygalacturonase promoter to drive a chimeric construct within microspores of *Brassica napus* plants. However, there is no teaching of modifying the extracellular domain of a free microspore or pollen grain.

Based upon the review of the prior art, there are two known mechanisms that exist for the targeting of a protein onto the pollen coat, either by deposition following tapetal degradation, or as a result of extracellular targeting either from the tapetal cells or microspore cells via a signal peptide. Similarly, extracellular targeting of pistil-derived gene products, for example the SLG gene product, appears to involve the use of a signal peptide. However, none of the prior art publications disclose modifying the protein composition of the microspore/pollen coat or the interactions of these proteins with the stigma or pistil. Rather, most of the published literature is directed to producing sterile plants through the disruption of pollen development, although this disruption does not occur by modifying the extracellular compartment. Nor does the prior art teach a similar modification of the stigma cells using chimeric gene constructs that would affect the interaction between these cells and a modified pollen grain, while all of these cell types could remain viable. The approach described herein is primarily directed at modifying pollen or stigma function, and in some instances affects the interaction between pollen and stigma.

There is no teaching of the preparation of transcriptional or translational fusion proteins specifically designed to localize on the exterior of a pollen or stigma cell. For example, but not limited to, comprising hydrophobic domains of pollen coat proteins and the like, to direct the translocation of the fusion product to the exterior surface of the pollen. Furthermore, beyond uses that are directed to pollen disruption for the production of sterile plants, the prior art does not disclose methods that provide for peptide display, antibody production, altering the food value of pollen for human consumption, the use of treating insects, or alleviating allergenic responses by specifically targeting protein products to the surface of the appropriate floral cell.

This invention relates to a method of modifying the extracellular compartment of floral cells, including targeting proteins, protein fusions, fragments thereof, or peptides to this extracellular domain. Methods using chimeric gene constructs that allow targeting of proteins, fusion proteins or peptides of interest to cells of the pistil, microspore, or to the pollen coat to modify floral functions or interactions are disclosed and exemplified.

SUMMARY OF THE INVENTION

The present invention relates to the expression of proteins within plant tissues. More specifically, this invention relates to the expression of proteins within the extracellular compartment of floral cells including those associated with anther and pistil.

According to the present invention there is provided a method for modifying the extracellular compartment of a floral cell of a plant, the method comprising, expressing a construct comprising a gene of interest within an anther or stigma cell, the gene of interest encoding a protein, fusion protein or peptide, or a fragment of said protein, fusion protein or peptide; the protein, fusion protein or peptide, or a fragment of the protein, fusion protein or peptide capable of modifying the composition of the extracellular compartment of the floral cell and altering either the function, use or development of the floral cell, or modifying the interaction of the floral cell with other cells. This invention relates to the above method wherein the gene of interest is native, or non-native, to the plant, or wherein the construct is a chimeric gene construct.

This invention relates to the method as defined above wherein the floral cell is a pollen grain, and the protein, fusion protein or peptide, or a fragment of the protein, fusion protein or peptide is released into a locule of an anther thereby associating with the extracellular compartment of the pollen grain. This invention also embraces the above method, wherein the floral cell is either a pollen grain or a stigma cell, and the construct comprises a translated sequence capable of directing the extracellular localization of said protein, fusion protein or peptide, or a fragment of the protein, fusion protein or peptide on the floral cell. Preferably the translated sequence is selected from the group consisting of a signal peptide, a hydrophobic domain, or a combination thereof, or the translated sequence is a protein, or fragment thereof, known to be targeted to the extracellular compartment of a floral cell, for example but not limited to a oleosin-like sequence, an extracellular lipase sequence, and a pollen polygalacturonase sequence.

The present invention also provides a method (A) for modifying the extracellular compartment of a pollen grain or an anther cell of a plant, the method comprising, a) introducing into a plant a construct comprising
 i) a nucleotide sequence encoding a first amino acid sequence that directs a protein of interest, fusion protein or peptide, or a fragment of the protein, fusion protein or peptide to the extracellular compartment of the pollen grain or anther cell, the first amino acid sequence fused to a second amino acid sequence encoding the protein of interest, or ii) an alternate nucleotide sequence encoding a heterologous protein of interest, the alternate nucleotide sequence comprising a sequence that encodes an amino acid sequence that directs the heterologous protein to the extracellular compartment of the pollen grain or anther cell, the nucleotide sequence or the alternate nucleotide sequence operatively linked to a promoter sequence and a terminator sequence;

and b) expressing the construct in a plant.

The invention also includes the method (A) as described above, wherein the first amino acid sequence, encoded by the nucleotide sequence, or the amino acid sequence encoded by the alternated nucleotide sequence, is selected from the group consisting of an oleosin-like sequence, an extracellular lipase sequence, and a pollen polygalacturonase sequence. Furthermore, the oleosin-like sequence can be a tapetal oleosin-like sequence. The tapetal oleosin-like sequence may be selected from the group consisting of BnOlnB;1, BnOlnB;2, BnOlnB;3 BnOlnB;4, BnOlnB;5, BnOlnB;6, BnOlnB;7, BnOlnB;8, BnOlnB;9, BnOlnB;10, BnOlnB;11 and BnOlnB;12; AtOlnB;1, AtOlnB;2, AtOlnB;3 AtOlnB;4; BoOlnB;1 and BrOlnB;1, BrOlnB;2, BrOlnB;3 BrOlnB;4, and BrOlnB;5.

The present invention is directed to the method (A) as defined above wherin the plant is selected from the group consisting of *Brassica, Raphanu., Arabidopsis, Triticum, Hordeum, Avena, Niciotiana, Glycine, Pisum, Acer, Agropyron, Medicago, Malus, Aster, Phaseolus, Beta, Betula, Vicia, Bromus, Daucus, Cedrus, Citrus, Gossypium, Populus, Cucurbita, Helianthus, Lactuca, Lilium, Lycopersicon, Allium, Prunus, Capsicum, Pinus, Picea, Ambrosia, Secale, Tsuga, Zea, Oryz* and *Solanum*.

The present invention pertains to a microspore or a pollen, or combination thereof, prepared using the method (A) as decribed above.

According to the present invention there is provided a method (B) for localizing a protein, fusion protein, or peptide of interest, or a fragment of the protein, fusion protein, or peptide, on the extracellular compartment of a a pollen grain or an anther cell of a plant, comprising:

a) introducing into a plant a construct comprising
 i) a nucleotide sequence encoding a first amino acid sequence that directs a protein of interest, fusion protein or peptide, or a fragment of the protein, fusion protein or peptide to the extracellular compartment of the pollen grain or anther cell, the first amino acid sequence fused to a second amino acid sequence encoding the protein of interest, or ii) an alternate nucleotide sequence encoding a heterologous protein of interest, the alternate nucleotide sequence comprising a sequence that encodes an amino acid sequence that directs the heterologous protein to the extracellular compartment of the pollen grain or anther cell, the nucleotide sequence or the alternate nucleotide sequence operatively linked to a promoter sequence and a terminator sequence;

and b) expressing the construct in a plant.

Also included is a method for localizing a protein, fusion protein, or peptide of interest, or a fragment of the protein, fusion protein, or peptide, within the extracellular compartment of a floral cell, comprising:
  i) preparing a gene construct comprising:
    a) a promoter sequence capable of expressing a gene encoding the protein, fusion protein, or peptide of interest, or a fragment of the protein, fusion protein, or peptide, within the floral cell;
    b) a gene that encodes the protein, fusion protein, or peptide of interest, or a fragment of the protein, fusion protein, or peptide; and
    c) a translated sequence capable of directing the extracellular localization of the protein, fusion protein, or peptide of interest, or a fragment of the protein, fusion protein, or peptide, on the floral cell;
    d) a terminator sequence; and
  ii) transforming a plant with the gene construct; wherein the floral cell, is selected from the group consisting of pollen, anther or pistil cells.

Furthermore, this invention includes the method as just described, wherein the translated sequence of step c) is selected from the group consisting of a signal peptide, a hydrophobic domain, or a combination thereof.

This invention is also directed to a method (C) of chemically linking a protein or peptide of interest to the pollen coat comprising:
  a) activating pollen grains with a desired reagent for conjugation;
  b) adding the protein of interest This invention embraces a pollen grain prepared by the method (C) as described above.

Furthermore, this invention includes a microspore or pollen, or a combination thereof, prepared using the method (B) as described above. This invention is also directed to a transgenic plant cell, a transgenic plant comprising the microspore or pollen, or combination thereof prepared using the method (B) as described above, and to seeds obtained from the transgenic plant.

This invention also embraces a method (D) of modifying pollen-pistil interaction or function comprising, producing a microspore, pollen, or pistil cell, or combination thereof, within a plant using the method (B) as described above, so that the microspore, pollen, or pistil, or combination thereof comprise an extracellular protein, fusion protein, or peptide of interest, or a fragment of the protein, fusion protein, or peptide, that modifies pollen and pistil interaction or function. This invention also embraces a method (D), wherein the extracellular protein, fusion protein, or peptide of interest, or a fragment of the protein, fusion protein, is localized to the microspore, or pollen, or to the pistil cell, or combination thereof.

This invention also provides for a method (D) wherein the pollen-pistil interaction or function produces, mediates, or prevents self-compatibility, self-incompatibility, out-crossing, in-crossing or a combination thereof.

This invention also relates to the method (D) as described above, wherein the protein, fusion protein, or peptide of interest, or a fragment of the protein, fusion protein, or peptide, is selected from the group consisting of protease, glucosidase, glycanase, nuclease, lipase, hydrolyase, toxin and antibody, or an active portion thereof.

This invention also embraces a vector comprising:
  a) a promoter sequence capable of expressing a gene encoding a protein, fusion protein, or peptide of interest, or a fragment of the protein, fusion protein, or peptide, within a floral cell;
  b) a gene that encodes the protein, fusion protein, or peptide of interest, or a fragment of the protein, fusion protein, or peptide;
  c) a translated sequence capable of directing the extracellular localization of the protein, fusion protein, or peptide of interest, or a fragment of the protein, fusion protein, or peptide, on the floral cell; and
  d) a terminator sequence, and to a transgenic plant cell, transgenic plant, or seed obtained from the transgenic plant, comprising the vector defined above.

This invention also embraces a vector comprising a construct, the construct comprising either:
  i) a nucleotide sequence encoding a first amino acid sequence that directs a protein of interest, fusion protein or peptide, or a fragment of the protein, fusion protein or peptide to the extracellular compartment of the pollen grain or anther cell, the first amino acid sequence fused to a second amino acid sequence encoding the protein of interest, or ii) an alternate nucleotide sequence encoding a heterologous protein of interest, the alternate nucleotide sequence comprising a sequence that encodes an amino acid sequence that directs the heterologous protein to the extracellular compartment of the pollen grain or anther cell, the nucleotide sequence or the alternate nucleotide sequence operatively linked to a promoter sequence and a terminator sequence.

The present invention includes the vector as just defined, wherein the first amino acid sequence encoded by the nucleotide sequence, or the amino acid sequence encoded by the alternate nucleotide sequence, is selected from the group consisting of an oleosin-like sequence, an extracellular lipase sequence, and a pollen polygalacturonase sequence. The oleosin-like sequence may be a tapetal oleosin-like sequence. The tapetal oleosin-like sequence can be selected from the group consisting of BnOlnB;1, BnOlnB;2, BnOlnB;3 BnOlnB;4, BnOlnB;5, BnOlnB;6, BnOlnB;7, BnOlnB;8, BnOlnB;9, BnOlnB;10, BnOlnB;11 and BnOlnB;12; AtOlnB;1, AtOlnB;2, AtOlnB;3 AtOlnB;4; BoOlnB;1 and BrOlnB;1, BrOlnB;2, BrOlnB;3 BrOlnB;4, and BrOlnB;5.

The present invention provides a method (E) for modifying pollen-pistil interaction in a plant, comprising:
  i) expressing a construct comprising a coding region of interest within a stigma cell, the coding region of interest encoding a protein, fusion protein or peptide, or a fragment of the protein, fusion protein or peptide, where, the protein, fusion protein or peptide, or a fragment of the protein, fusion protein or peptide comprises a sequence that directs the protein, fusion protein or peptide, or a fragment of the protein, fusion protein or peptide to the extracellular compartment of the stigma cell,
  ii) obtaining a plant comprising a modified pollen grain produced by expressing a construct comprising a coding region of interest within a pollen grain, the coding region of interest encoding a protein, fusion protein or peptide, or a fragment of the protein, fusion protein or peptide, the protein, fusion protein or peptide, or a fragment of the protein, fusion protein or peptide comprising a sequence that directs the protein, fusion protein or peptide, or a fragment of the protein, fusion protein or peptide to the extracellular compartment of the pollen grain; and iii) exposing the modified stigma cell produced in the step of expressing (step i)), with the modified pollen grain produced in the step of obtaining (step ii)); thereby modifying pollen-pistil interation.

Furthermore, the preent invention provides a method for modifying pollen-pistil interaction in a plant, comprising:

i) expressing a construct comprising a coding region of interest within a stigma cell, the coding region of interest encoding a protein, fusion protein or peptide, or a fragment of the protein, fusion protein or peptide, where, the protein, fusion protein or peptide, or a fragment of the protein, fusion protein or peptide comprises a sequence that directs the protein, fusion protein or peptide, or a fragment of the protein, fusion protein or peptide to the extracellular compartment of the stigma cell, ii) obtaining a plant comprising the pollen grain produced using the method of claim 1; and iii) exposing the modified stigma cell produced in the step of expressing (step i)), to the pollen grain produced in the step of obtaining (step ii)); thereby modifying pollen-pistil interation.

This invention also embraces the method (B) as described above, wherein the protein, fusion protein, or peptide of interest, or a fragment of the protein, fusion protein, or peptide, is localized on the surface of a pollen grain for the purpose of peptide display.

Also included within the present invention is a method (B) defined above, wherein the protein, fusion protein, or peptide of interest, or a fragment of the protein, fusion protein, or peptide, is localized on the surface of pollen and it is an antibody or antigen, or it exhibits properties beneficial to human or animal nutrition, or health, or it is effective in controlling insect growth, behaviour, feeding, development, or reproduction, or a combination thereof, or it is capable of alleviating allergenic responses within a human.

The present invention also pertains to a method for modifying a pollen coat of a plant, comprising:

a) introducing into a plant a construct comprising i) a nucleotide sequence encoding a first amino acid sequence that directs a protein of interest, fusion protein or peptide, or a fragment of the protein, fusion protein or peptide to the pollen coat, the first amino acid sequence fused to a second amino acid sequence encoding the protein of interest, or ii) an alternate nucleotide sequence encoding a heterologous protein of interest, the alternate nucleotide sequence comprising a sequence that encodes an amino acid sequence that directs the heterologous protein to the pollen coat, the nucleotide sequence or the alternate nucleotide sequence operatively linked to a promoter sequence and a terminator sequence;

and b) expressing the construct in a plant.

Also included in the present invention is the method as just definedwherein the first amino acid sequence, encoded by the nucleotide sequence, or the amino acid sequence encoded by the alternated nucleotide sequence, is selected from the group consisting of an oleosin-like sequence, an extracellular lipase sequence, and a pollen polygalacturonase sequence. The oleosin-like sequence can be a tapetal oleosin-like sequence. The tapetal oleosin-like sequence can be selected from the group consisting of BnOlnB;1, BnOlnB;2, BnOlnB;3 BnOlnB;4, BnOlnB;5, BnOlnB;6, BnOlnB;7, BnOlnB;8, BnOlnB;9, BnOlnB;10, BnOlnB;11 and BnOlnB;12; AtOlnB;1, AtOlnB;2, AtOlnB;3 AtOlnB;4; BoOlnB;1 and BrOlnB;1, BrOlnB;2, BrOlnB;3 BrOlnB;4, and BrOlnB;5.

This invention is directed to modifying the protein composition of the extracellular domain of a microspore, or pollen coat, or the interactions of these proteins with the stigma, pistil, or other cells of interest, while possibly maintaining the pollen, and the cells of the stigma, in a viable state. Furthermore, this invention relates to modifying the protein composition of the extracellular domain of stigma cells in order to affect the interaction between these cells and either unaltered or modified pollen grains, wherein each of these cell types could remain in a viable state. The prior art is directed to producing sterile plants through the disruption of pollen development. However, this disruption does not occur by modifying the extracellular domain of the pollen. The approach described herein is primarily directed at modifying pollen or stigma cell function, and in some instances affects the interaction between pollen and stigma. However, the methods disclosed within this invention are not necessarily disruptive to pollen development as is the case within the prior art, nor are they necessarily disruptive to pistil development.

BRIEF DESCRIPTION OF THE DRAWINGS

These and other features of the invention will become more apparent from the following description in which reference is made to the appended drawings wherein:

FIG. 1 shows a drawing of anthers at two different stages of flower development and illustrates early and late pollen development. FIG. 1A shows early flower development with an intact tapetal layer and tetrad of microspores. FIG. 1B shows late flower development, with mature pollen grains having pollen coats (tryphine) containing tapetal debris.

FIG. 3 shows a schematic representation of three different translational fusions possible with the Brassica napus tapetal oleosin-like Sta 41-9 protein. FIG. 3A shows a C-terminal translational fusion with a full-length tapetal oleosin. FIG. 3B shows a C-terminal translational fusion at a proteolytic cleavage site. FIG. 3C shows an internal translational fusion at a proteolytic cleavage site. The fused protein is indicated by a hatched box.

FIG. 4 shows a schematic representation of the construction of the Brassica napus tapetal oleosin-like Sta 41-9 translational fusion cassette OFC-1.

FIG. 5 shows a schematic representation of the construction of plant transformation vectors TOG-1 and TOG-2.

FIGS. 5c-1 shows a schematic representation of the construction of plasmid pGEMTOG-2 (Example 22) comprising the TOG-2 translational fusion in a standard cloning plasmid, FIGS. 5c-2 shows a schematic representation of the construction of plant transformation vector ATOG-3 (SEQ ID NO:44; Example 24), the *Arabidopsis thaliana* tapetal oleosin-like Atgrp 19/*E. coli* GUS translational fusion.

FIG. 20A shows Western blot analysis of anther protein extracts from 4 mm flower buds of different transgenic lines separated by SDS-PAGE (sodium dodecyl sulfate-polyacrylamide gel electrophoresis) and cross-reacted with anti-CPI (cysteine protease inhibitor, unpublished results from Gleddie et al.) antibody. Lanes 1 to 13 represent 35 µg of proteins from transgenic lines No. 1 to 5, 7 to 12, 14 and 15; lane 14 contains 35 µg of proteins from a non-transformed *B. carinata* plant and lane 15 contains 30 ng of OV7/GST (cysteine protease inhibitor OV7 conjugated to GST). The OV7/GST fusion protein has a predicted molecular weight of 42 kDa. The anti-CPI antibody cross-reacted with two bands in most transgenic plants. The higher molecular weight band corresponds to the full-length fusion protein with a predicted molecular weight of 57 kDa, whereas the lower band has a molecular weight of approximately 47 kDa, which is the expected size of the processed fusion protein where the N-terminal end of the oleosin-like protein has been cleaved off. FIG. 20B shows a Coomassie blue-stained SDS-PAGE gel of anther extracts from 4 mm flower buds. The sample lanes correspond to those described in FIG. 20A. The cross-reacting bands are not evident following Coomassie blue staining.

FIG. 21A shows a Western blot analysis of anther protein extracts from developing flower buds of transgenic line No. 1 separated by SDS-PAGE and cross-reacted with anti-CPI (cysteine protease inhibitor) antibody. Lanes 1 to 6 represent 30 µg of anther proteins from 2 mm, 3 mm, 4 mm, 5 mm, 6 mm and 7 mm flower buds respectively, lane 7 contains 30 µg of anther proteins from a non-transformed *B. carinata* plant and lane 8 contains 30 ng of OV7/GST (predicted molecular weight of 42 kDa). The full-length 57 kDa fusion protein was detected in anther protein extracts from 3 mm buds and was undetectable in the older 7 mm buds. However, the 47 kDa band corresponding to the cleaved protein was evident in the anther protein extracts from 4 mm buds anthers and persisted through to the late stages of bud development. FIG. 21B shows a Coomassie blue-stained SDS-PAGE gel of anther extracts from developing flower buds from transgenic *B. carinata* line No. 1 containing TOPI-1. The sample lanes correspond to those described in FIG. 21A. The cross-reacting bands are not evident following Coomassie blue staining.

FIG. 23 shows expression of the TOG-2 translational fusion in transgenic *B. carinata* during anther development in 2 mm to 8 mm flower buds (see FIG. 5B for TOG-2 construct).

FIG. 24 shows localization of RNA, protein expression and GUS activity in anthers, pollen grains and pollen coats from plants transformed with the TOG-2 translational fusion (see FIG. 5b for TOG-2 construct) or the transcriptional fusions BnOlnB;4-GUS (corresponds to Sta 41-GUS) and Sta 44-GUS.

FIGS. 25i to k show GUS histochemical staining of pollen from TOG-2 and Sta 44-GUS transgenic plants. GUS histochemical staining of pollen from 5 mm (FIG. 25i) and 8 mm (FIG. 25j) buds of transgenic *B. carinata* containing the TOG-2 translational fusion and from 7 mm (FIG. 25k) buds of T1 progeny of a self-pollinated *B. napus* transgenic line containing a single copy of the Sta 44-GUS transcriptional fusion construct. Scale bars equal 1.6 (FIGS. 25a, b), 1.1 (FIGS. 25c-h) and 20 (FIGS. 25i-k) μm.

FIG. 26 shows the detection of TOP-1 (SEQ ID NO:4; *Brassica napus* tapetal oleosin-like STA 41-9/*Sitophilus zeamais* protease SCPc1 translational fusion protein; see FIG. 6, and Example 3) and TOPI-1 (during flower development in a transgenic *Brassica carinata*.

FIG. 27 shows a Western analysis of SPOV-1 (*Brassica napus* SLG$_{WS1}$ signal peptide/*Onchocerca volvulus* protease inhibitor OV7 translational fusion; see FIG. 9 and Example 7 for construct) in the stigmas of different transgenic *Brassica carinata* and *Nicotiana tabacum* plants (using an anti-OV7 antibody). Lanes 1 and 2: stigma protein extracts of *B. carinata* transformants; Lane 3: stigma proteins from non-transformed *B. carinata*; Lanes 4 and 5: stigma protein extracts of *N. tabacum* transformants; Lane 6: stigma proteins from non-transformed tobacco.

FIG. 31 shows schematic representations of POG-2 and POG-3.

DESCRIPTION OF PREFERRED EMBODIMENT

Figure 2:
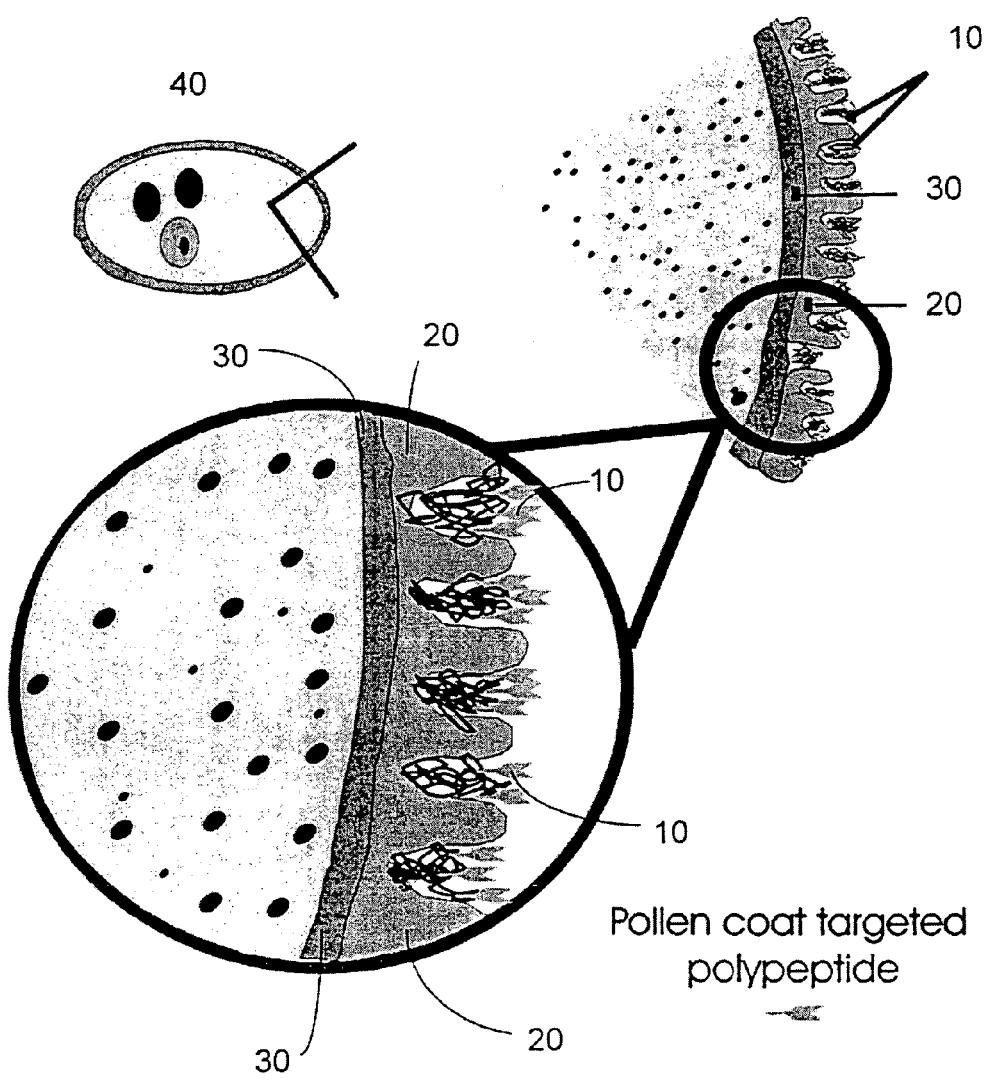
FIG. 2 shows a drawing of a pollen grain. Details of the components of the pollen coat are illustrated and an example of polypeptides targeted to the pollen coat is indicated.

The present invention relates to the expression of proteins within plant tissues. More specifically, this invention relates to the expression and localization of proteins within the extracellular compartment of floral cells including those associated with pollen, anther and pistil.

The following description is of a preferred embodiment by way of example only and without limitation to the combination of features necessary for carrying the invention into effect.

Methods and compositions are provided for the targeting of proteins or peptides to the extracellular domain of a microspore, or pollen or pistil cells. The methods include preparing chimeric DNA constructs encoding a polypeptide, or a fusion polypeptide consisting of a microspore, pollen coat or pistil protein and a coding sequence for a polypeptide of interest. Inserting this DNA construct in a plant genome, and regenerating transgenic plants that produce pollen, stigmas, or both, with the polypeptide or fusion polypeptide.

For example, the present invention provides a method for modifying the extracellular compartment of a pollen grain or an anther cell of a plant, the method comprising,
a) introducing into a plant a construct comprising
i) a nucleotide sequence encoding a first amino acid sequence that directs a protein of interest, fusion protein or peptide, or a fragment of the protein, fusion protein or peptide to the extracellular compartment of the pollen grain or anther cell, the first amino acid sequence fused to a second amino acid sequence encoding the protein of interest, or ii) an alternate nucleotide sequence encoding a heterologous protein of interest, the alternate nucleotide sequence comprising a sequence that encodes an amino acid sequence that directs the heterologous protein to the extracellular compartment of the pollen grain or anther cell, the nucleotide sequence or the alternate nucleotide sequence operatively linked to a promoter sequence and a terminator sequence;

and b) expressing the construct in a plant.

Furthermore, the present invention provides a construct comprising:
i) a nucleotide sequence encoding a first amino acid sequence that directs a protein of interest, fusion protein or peptide, or a fragment of the protein, fusion protein or peptide to the extracellular compartment of the pollen grain or anther cell, the first amino acid sequence fused to a second amino acid sequence encoding the protein of interest, or ii) an alternate nucleotide sequence encoding a heterologous protein of interest, the alternate nucleotide sequence comprising a sequence that encodes an amino acid sequence that directs the heterologous protein to the extracellular compartment of the pollen grain or anther cell, the nucleotide sequence or the alternate nucleotide sequence operatively linked to a promoter sequence and a terminator sequence.

Also included in the present invention are plant cells, plants, and seeds comprising the construct as just defeined.

As used herein "pollen function" includes processes associated with development of pollen, dispersal of the pollen, recognition, interaction and adhesion of the pollen to any cell, for example, but not limited to a stigma cell, natural or artificial substrates, pollen tube germination and pollen tube growth, and fertilization.

By "pistil function" it is meant processes associated with development of the pistil, interactions with pollen, including pollen capture, permitting or preventing pollen germination, pollen tube growth, fertilization, or a combination thereof, and nurturing zygote development.

By "extracellular compartment" or "extracellular domain" it is meant the region of the cell that includes, and lies outside, the plasmalemma. However, the extracellular compartment, or domain, may be associated with the cell in some manner. This compartment may comprise proteins that are anchored within the plasmalemma and that are displayed toward the outside of the cell, or proteins that are localized, via excretion or deposition, within the apoplast, cell wall or outer regions of the cell wall such as the surface of the cell, or that are released within the locule. For example, in the case of pollen (40; see FIGS. 1 and 2), this compartment includes the anther locule (5), tryphine (10), and the pollen coat exine (20) comprising the nexine and sexine, and intine (30), as well as the pollen tube and compounds that are synthesised and excreted from within the pollen or pollen tube, or compounds that are deposited onto the outer wall during development of pollen, the pollen tube or locule. In the case of the pistil, this compartment includes the ovary and the style, including the transmitting tract and compounds that are synthesised and excreted from cells of this tract, or compounds that are deposited onto the outer cell walls during development of the tract. In the case of the stigma, this compartment includes the cuticle, and compounds that are synthesised and excreted outside the cuticle, such as compounds that are deposited onto the outer surface of the papillar cells including, but not limited to, the proteinaceous pellicle of *Brassica* stigmas, or secretions of tobacco stigmas.

By "directing extracellular localization" it is meant using a chimeric gene construct comprising motifs capable of targeting a protein or protein fusion or peptide of interest passively or actively to the extracellular compartment. For example, which is not to be considered limiting in any manner, such motifs responsible for actively directing extracellular localization may include sequences encoding signal peptides, or hydrophobic domains, for example fragments obtained from the tapetal oleosin-like protein, or a hydrophobic domain obtained from a seed oleosin or tapetal oleosin-like protein. Motifs responsible for passively targeting extracellular localization upon tapetal degradation may include, but are not limited to, protein primary structure or protein modifications affecting affinity to the extracellular domain. This localization may also comprise a transient association between the protein, fusion protein, or peptide of interest and the extracellular domain, such as enzyme substrate interactions, for example glycosidase-carbohydrate or protease-protein reactions.

By "oleosin-like protein" it is meant a protein, or a fragment thereof comprising a hydrophobic domain (see Huang, A. H. C. (1996) Plant Physiol. 110: 1055-1061; WO 96/21029, both of which are incorporated herein by refrence, for examples of oleosin-like proteins), and characterized as having a conserved region known as a Proline Knot Motif (PKM; Abell, B. M., Holbrook, L. A., Abenes, M., Murphy, D. J., Hills, M. J., Moloney, M. M. (1997) Plant Cell 9: 1481-1493, which is incorporated herein by reference). This group includes but is not limited to seed oleosin proteins and tapetal-oleosin-like proteins. An oleosin like protein or a fragement thereof comprising the PKM and neighbouring amino acids as known in the art, is capable of directing of the protein, or a translational fusion of the oleosin-like protein with a protein of interest, to the pollen coat using the methods described herein.

By "tapetal oleosin-like protein" it is meant a protein, or a fragment of a protein comprising a hydrophobic domain, a PKM, or both a hydrophobic domain and a PKM, or other sequence, that directs targeting of the protein, or a translational fusion of the protein with a protein of interest, to the pollen coat. Non-limiting examples of tapetal oleosin-like proteins include STA 41-2 and STA 41-9 (renamed BnOlnB;3 and BnOlnB;4 respectively, Robert, L. S., Gerster, J., Allard, S., Cass, L., Simmonds, J. *Plant J.* 6:927-933 (1994a)), PUTG1, ATGRP-6, -7, and -8 (renamed AtOln;B1, AtOln;B2, AtOln;B3, AtOln;B4 de Oliveira, D. E., Franco, L. O., Simoens, C., Seurinck, J., Coppieters, J., Botterman, J., Van Montagu, M. *Plant J* 3:495-507 (1993)), 13 (renamed BnOlnB;1 Roberts, M. R., Robson, F., Foster, G. D., Draper, J., Scott, R. J. *Plant Mol. Biol.* 17:295-299 (1991)), C98 (renamed BnOlnB;2, Hodge, R., Paul, W., Draper, J., Scott, R. *Plant J* 2:257-260 (1992)), POL3 (renamed BnOlnB;5, Roberts, M. R., Hodge, R., Scott, R. *Planta* 195:469-470 (1995)), BOPC4 (renamed BoOlnB;1, Ruiter, R. K., Van eldik, G. J., Van Herpen, R. M. A., Wullems, G. J, Schrauwen, J. A. M. *Plant Cell* 9:1621-1631 (1997)), BrOlnB1, 2,3,4 and 5 (Lim et al. (1994) EMBL Acc. No. L33510, L33543, L33564, L33603, L33618), BnOlnB;6, 7, 8, 9, 10, 11 and 12 (Ross, J. H. E., Murphy, D. J. *Plant J.* 9:625-637 (1996)). These OlNB proteins comprise conserved hydrophobic domains, and any of these proteins, or a fragment of any of these proteins may be used for targeting a protein of interest to the pollen coat, using the methods as described herein.

By "gene of interest" or "coding region of interest" it is meant a nucleic acid sequence that encodes a protein. The gene of interest, or coding region of interest may be of native origin, in that it is obtained from the same species of plant within which it is to be reintroduced, or it may be of non-native origin, i.e. it is obtained from a plant that is different from the plant to which it is to be introduced, or it is obtained from another source, i.e. bacterial, viral, animal etc. A coding region of interest may further be operatively linked to regulatory regions such as promoters, enhancers, terminator sequences and the like that are endogenous to the coding region of interest with which they are isolated. By "operatively linked" it is meant that the particular sequences interact either directly or indirectly to carry out an intended function, such as mediation or modulation of gene expression. The interaction of operatively linked sequences may, for example, be mediated by proteins that interact with the operatively linked sequences. A coding region of interest may also be introduced within a vector along with other sequences, typically heterologous, to produce a chimeric construct.

By "chimeric DNA construct" or "chimeric construct" it is meant a nucleic acid molecule comprising-regions of DNA sequences not normally associated with the gene of interest. These regions may be homologous or heterologous with respect to the gene of interest, and may be obtained from native or non-native sources. For example, a chimeric construct that results in a translational fusion product may include a native or heterologous enhancer region, a native or heterologous promoter region, followed by regions comprising a portion of a native or heterologous 5' coding region including such motifs as signal peptides, or hydrophobic domains as required, a native or heterologous DNA sequence capable of encoding a protein or peptide of interest, followed by 3' motifs that may also be involved in extracellular targeting or regulatory functions, or both, and a terminator region. It is to be understood that a range of 5' or 3' regions of the chimeric construct may be used in order to optimize synthesis of the final gene construct, expression of the gene product, and localization of the gene product within the extracellular compartment. Furthermore, a chimeric construct that results in a transcriptional fusion product may comprise a native or non-native enhancer and promoter region operationally fused with an optional signal peptide and the protein or peptide of interest, followed by a 3' regulatory, or terminator region, or a region comprising both a regulatory and terminating function as defined above.

By "modified gene" or "modifed coding region" it is meant a gene or coding region whose sequence has been altered using methods known in the art such as but not limited to site-directed, or random mutagenesis, deletions, rearrangements, or fusions and the like.

By "fusion protein" it is meant proteins synthesized from chimeric DNA constructs. These proteins may comprise a portion of a native protein along with a heterologous protein comprising the protein of interest. Such a fusion protein may comprise a signal peptide, or hydrophobic domain, or other motif that permits targeting of the protein of interest to the extracellular compartment, for example, but not limited to, motifs obtained from an oleosin-like protein, STA 41-2 or STA 41-9, STA 44, $SLG_{WS1}$ or PIS 63. It is to be understood that increases in protein expression levels may also be obtained by protein modification that affects protein stability or by multimeric constructs involving multiple copies of the protein or peptide of interest.

By "expression cassette" it is meant a chimeric DNA molecule that includes transcriptional and translational regulatory sequences of DNA capable of expressing a chimeric gene whose product is subsequently targeted to the extracellular compartment of a floral cell. For example, an expression cassette may comprise promoter and regulatory sequences controlling the expression of genes, and the targeting of the encoded products within the tapetum or the pollen. However, this is not to be considered limiting in any manner as other constructs may also be directed to other extracellular compartments as previously defined. In the case of tapetal expression, the gene product may be expressed in the tapetum and subsequently translocated to the pollen or developing microspores, for example callase or oleosin-like proteins, or the protein may be expressed within the pollen and re-located to the microspore or pollen coat during development or germination, for example, pectate lyase or PCP1.

By "promoter" or "regulatory region", it is meant a region typically within a genomic sequence that has the property of controlling the expression of a DNA sequence that is operably linked with the regulatory region. Such regulatory regions may include promoter or enhancer regions, and other regulatory elements recognized by one of skill in the art. Typically this region comprises nucleotide sequences at the 5' end of a coding region, or fragment thereof that contain all the signals essential for the initiation of transcription and for the regulation of the rate of transcription. The promoters used to exemplify the present invention may be selected to ensure expression of a desired gene within the tissue of interest, or during appropriate stages of development, for example, but not limited to the organ-specific promoters regulating the following genes:

tapetal—for example, but not limited to, Sta 41-2 and Sta 41-9 (renamed BnOlnB;3 and BnOlnB;4 respectively, Hong, H. P., Ross, J. H. E., Gerster, J. L., Rigas, S., Datla, R. S. S., Hatzopoulos, P., Scoles, G., Keller, W., Murphy, D., Robert, L. S. *Plant Mol. Biol.* 34:549-555 (1997b)), putG1, atgrp-6, -7, and-8 (renamed AtOlnB; 1,2,3 and 4, de Oliveira, D. E., Franco, L. O., Simoens, C., Seurinck, J., Coppieters, J., Botterman, J., Van Montagu, M. *Plant J* 3:495-507 (1993)), I3 (renamed BnOlnB;1 Roberts, M. R., Robson, F., Foster, G. D., Draper, J., Scott, R. J. *Plant Mol. Biol.* 17:295-299 (1991)), C98 (renamed BnOlnB;2, Hodge, R., Paul, W., Draper, J., Scott, R. *Plant J* 2:257-260 (1992)), Pol3 (renamed BnOlnB;5, Roberts, M. R., Hodge, R., Scott, R. *Planta* 195:469-470 (1995)), bopc4 (renamed BoOlnB;1, Ruiter, R. K., Van eldik, G. J., Van Herpen, R. M. A., Wullems, G. J, Schrauwen, J. A. M. *Plant Cell* 9:1621-1631 (1997)), BrOlnB1, 2,3,4 and 5 (Lim et al. (1994) EMBL Acc. No. L33510, L33543, L33564, L33603, L33618), BnOlnB;6, 7, 8, 9, 10, 11 and 12 (Ross, J. H. E., Murphy, D. J. *Plant J.* 9:625-637 (1996)).

pollen—for example but not limited to Sta 44 (Hong, H. P., Gerster, J. L., Datla, R. S. S., Albani, D., Scoles, G., Keller, W., Robert, L. S. *Plant Cell Rep.* 16:373-378 (1997a)); Sta 39 (Gerster et al. *Plant Physiol.* 110: 1231-1237 (1996)).

pistil—for example but not limited to Pis 63 (Robert, L. S., Lévesque-Lemay, M., Gerster, J. L., Hong, H. -P., Keller, W. *Plant Cell Rep.* 18: 357-362 (1999)).

These and other promoters are, or would be, known to those of skill in the art. If desired, constitutive promoters may also be used such as, but not limited to, the CaMV 35S (Timmermans, M. C. P., Maliga, P., Vieira, J., Messing, J. *J. Biotechnol.* 14: 333-344 (1990)), ubiquitin (Holtorf, S., Apel, K., Bohlmann, H. *Plant Mol. Biol.* 29: 637-646 (1995)), actin (An, Y. Q., McDowell, J. M., Huang, S., McKinney, E. C., Chamblis, S., Meagher, R. B. *Plant J.* 10:107-121(1996)), rice actin 1 (Zhang, W., McElroy, D., Wu, R. *Plant Cell*, 3:1155-1165 (1991)), triosephosphate isomerase 1 (Xu, Y., Yu, H., Hall, T. C. *Plant Physiol.* 106:459-467 (1994)), the maize ubiquitin 1 (Cornejo, M. J., Luth, D., Blankenship, K. M., Anderson, O. D., Blechl, A. E. *Plant Mol. Biol.* 29:637-646 (1993)), tobacco t-CUP (WO/99/67389; U.S. Pat. No. 5,824,872), the HPL (WO 02/50291), and the tobacco translational initiation factor 4A (Mandel, T., Fleming, A. J., Krahenbuhl, R., Kuhlemeier, C. *Plant Mol. Biol.* 29:995-1004 (1995)) promoter.

Also included are inducible promoters which may also be used in order to regulate the expression of the gene following the induction of expression by providing the appropriate stimulus for inducing expression. The inducer can be a chemical agent such as a protein, metabolite, growth regulator, herbicide or phenolic compound, or a physiological stress imposed directly by heat, cold, salt, or toxic elements or indirectly through the action of a pathogen or disease agent such as a virus. For example, a plant or plant cell containing an inducible regulatory element may be exposed to an inducer by externally applying the inducer to the cell or plant such as by spraying, watering, heating or similar methods. Inducible elements may be derived from either plant or non-plant genes (e.g. Gatz, C. and Lenk, I. R. P. *Trends Plant Sci.* 3:352-358 (1998); which is incorporated by reference). Examples, of potential inducible promoters include, but are not limited to, tetracycline-inducible promoter (Gatz, C. *Ann. Rev. Plant Physiol. Plant Mol. Biol.* 48:89-108 (1997); which is incorporated by reference), steroid inducible promoter (Aoyama, T. and Chua, N. H. *Plant J.* 2:397-404 (1997); which is incorporated by reference) and ethanol-inducible promoter (Salter, M. G., et al. *Plant J.* 16:127-132 (1998); Caddick, M. X., Greenland, A. J., Jepson, I., Krause, K. P., Qu, N., Riddel,1 K. V., Salter, M, G., Schuch, W., Sonnewald, U., Tomsett, A. B. *Nature Biotech.* 16:177-180 (1998), which are incorporated by reference), cytokinin inducible IB6 and CK11 genes (Brandstatter, I. and Kieber, J. J. *Plant Cell* 10:1009-1019 (1998); Kakimoto, T. *Science* 274:982-985 (1996), which are incorporated by reference) and the auxin inducible element, DR5 (Ulmasov, T., Murfett, J., Hagen, G., Guilfoyle, T. J. *Plant Cell* 9:1963-1971 (1997), which is incorporated by reference).

The chimeric gene constructs of the present invention can farther comprise a 3' untranslated region. A 3' untranslated region refers to that portion of a gene comprising a DNA segment that contains a polyadenylation signal and any other regulatory signals capable of effecting mRNA processing, mRNA stability, or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Examples of suitable 3' regions are the 3' transcribed non-translated regions containing a polyadenylation signal of *Agrobacterium* tumour inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The 3' untranslated region from the structural gene of the present construct can therefore be used to construct chimeric genes for expression in plants.

The gene constructs of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

To aid in identification of transformed plant cells, the constructs of this invention may be further manipulated to include plant selectable markers. Useful selectable markers include enzymes that provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

By "transformation" it is meant the stable transfer of genetic information. The constructs of the present invention can be introduced into plant cells using Ti plasmids, Ri plasmids, plant virus vectors, direct DNA transformation, micro-injection, electroporation, etc as would be known to those of skill in the art. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki, B. and Iyer, V. *Fundamentals of Gene Transfer in Plants*. In *Plant Metabolism*, 2d Ed. Dennis, D. T., Turpin, D. H., Lefebrve, D. D., Layzell, D. B. (eds), Addison Wesly, Langmans Ltd. London, pp. 561-579 (1997). For transformation of Arabidopsis see Clough, S. J. and Bent, A. F. *Plant J.* 16: 735-743 (1998)). Also reference is made to the Examples of the present application for additional transformation protocols.

Also considered as part of the present invention are transgenic plants containing the chimeric gene construct as described herein. Plants include, but are not limited to members of the *Brassica*-family, for example, which is not to be considered limiting, canola, *Brasica napus, B. carinata, B. nigra, B. oleracea, B. chinensis, B. cretica, B. incana, B. insularis, B. japonica, B. atlantica, B. bourgeaui, B. narinosa, B. juncea, B. rapa, Raphanus* species, *Arabidopsis* species however, other plants may also be modifed using the methods described herein for example but not limited to, *Zea* species, *Oryza* species, *Triticum* species, *Hordeum* species, *Avena* species, *Niciotiana* species, *Glycine* species, *Pisum* species, *Acer* species, *Agropyron* species, *Medicago* species, *Malus* species, *Aster* species, *Phaseolus* species, *Beta* species, *Betula* species, *Vicia* species, *Bromus* species, *Daucus* species, *Cedrus* species, *Citrus* species, *Gossypium* species, *Populus* species, *Cucurbita* species, *Helianthus* species, *Lactuca* species, *Lilium* species, *Lycopersicon* species, *Allium* species, *Prunus* species, *Capsicum* species, *Pinus* species, *Picea* species, *Ambrosia* species, *Secale* species, *Tsuga* species, and *Solanum* species. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

By "sporophytically expressed pollen coat protein" it is meant a protein synthesised within sporophytic tissue, and via subsequent processing and translocation, is deposited upon the outer surface of the pollen coat. For example, the Sta 41-2 and Sta 41-9 gene products are expressed within tapetal tissue, and, even though not comprising a signal peptide, these gene products are deposited on the exterior of the pollen coat during development. Furthermore, other gene products comprising signal peptides that are tapetally expressed can be targeted to the pollen coat, e.g. SCR, SATAP35 and SATAP44.

By "gametophytically expressed pollen coat proteins" it is meant, proteins that are synthesised within gametophytic tissue, such as microspore, pollen, or ovary cells, and are translocated to the extracellular compartment of these cells. For example, the PCP1 pollen coat protein is synthesized in the pollen cell and relocated to the pollen coat.

The methods of this invention allow for the localization of a protein or peptide of interest within the extracellular compartment of pollen or stigma cells, including enzymes, receptors, antigens, antibodies, ligands, substrates, inhibitors and peptides which may modify normal male or female reproductive tissues (including but not limited to pollen, microspore, pollen tube, stigma, ovary, or egg) interaction, function, or both. When expressed on the surface of pollen or pistil, the fusion peptides or proteins can be used:

- for the production of either self-incompatible, self-compatible, or self-only-compatible flowers thus providing a novel method for hybrid seed production, plant maintenance, or to prevent outcrossing;
- as sources of immobilized enzymes;
- as sources of antigens for direct immunization or vaccination;
- as sources of value-added products for feed and food use;
- as novel methods of controlling pests and pathogens; and
- to modify allergenic properties of pollen.
- as novel methods of treating insects.

These applications will be described in more detail below.

Furthermore, it is contemplated that the linkage of peptides to the pollen coat may also be achieved chemically. This may be achieved by a variety of ways known to those of skill in the art, for example, using lectin concavalin A to covalently link the proteins to sugar residues on the pollen exine, or using tannic acid to covalently link proteins of interest to naturally occurring proteins expressed on the pollen coat. Such methods may either be used to prepare modified coat walls of pollen for the purposes disclosed within this invention, or for evaluating the feasibility, or function of desired proteins of interest located to the extracellular compartment of pollen, prior to designing, preparing and transforming plants with appropriate constructs and vectors leading to the expression of the desired protein.

In accordance with the subject invention, the method for modifying the protein composition of the extracellular compartment of a floral cell of a plant comprises expressing a construct comprising a gene of interest within an anther or pistil cell. The gene of interest encodes a protein, fusion protein or peptide, or a fragment thereof, and this protein or fragment thereof is capable of modifying the composition of the extracellular compartment of the floral cell. By altering the composition of the extracellular compartment of the floral cell, the function, development or use of the floral cell, or the interaction of said floral cell with other cells is modified while possibly maintaining the pollen, and the cells of the pistil or stigma, in a viable state. However, it is not necessary that these cells remain viable. For example, expression of a protease on the surface of a stigma cell may or may not kill the stigma cell depending upon the protease selected and the concentration of protease expressed. If the stigma cell is killed by the protease, pollen (especially if expressing protease inhibitor) may still germinate on the surface of the stigma, however, a female sterile plant may be obtained if germination is prevented as a result of protease expression or disruption of the stigma cells. Similarly, pollen may or may not remain viable following the modification of the extracellular compartment as described herein.

This invention also relates to a method for expressing a protein of interest on the surface of a pollen or pistil cell which includes preparing an expression cassette containing a construct comprising one or more regulatory sequences and a gene of interest which encodes a polypeptide or derivatives thereof, along with motifs that ultimately direct the expression of the protein extracellularly, so that when produced in a transgenic plant the protein is localized extracellularly, that is that the protein is located on the surface of the pollen or pistil cell. The peptide of interest may be a novel protein not normally found on the pollen or pistil cell surface, however, it is also contemplated that it may be desired to modify the composition of the extracellular domain or the abundance or the properties of a native protein within the extracellular compartment using the method of this invention. For example a protein from the following list, which is not to be considered limiting, may be used for the preparation of chimeric constructs:

cysteine protease from *Sitophilus*, (Matsumoto, I., Emori, Y., Abe, K, Arai, S. *J. Biochem*. 121: 464-476 (1997)).

cysteine protease inhibitor from *Onchocerca* (Lustigman, S., Brotman, B., Huima, T., Prince, A. M. *Mol. Biochem. Parasitol*. 45: 65-76 (1991)).

oxidases (Kato, N. and Esaka, M. *Plant Mol. Biol*. 30: 833-837 (1996));

chitinases (Bork C., and Hell. R. *Plant Physiol*. 115: 864 (1997));

invertase (Lorenz, K., Lienhard, S., Sturm. A. *Plant Mol. Biol*. 28:189-194 (1995));

endo-β-1,4-xylanase (Millward-Sadler, S., Davidson, K., Hazelwood, G., Black, G., Gilbert, H., Clarke, J. *Biochem. J*. 312: 39-48 (1985));

callase from *Arabidopsis thaliana* (Patent WO 9302197-A);

lipases, for example triacylglycerol lipase (EC.3.1.1.3) from *Magnaporthe grisea* (Wu, Bernstein, Darvill, Albersheim Genebank Accession No. AA415091 (1997);

phytase from *Aspergillus fumigatus* (Pasamontes, L., Haiker, M., Wyss, M., Tessier, M., VanLoon, A. *Appl. Environ. Microbiol*. 63: 1696-1700 (1997));

glucosidases, for example, glucan 1,3β-glucosidase cDNA from *Schizosaccharomyces pombe* (Yoshioka, S., Kato, K., Okayama, H. Genebank Accession No. AB000539 (1997));

endo 1,3-1,4β-glycanase cDNA from *Sinorhizobium meliloti* (York, G., Walker, G. *Mol. Microbiol*. 25: 117-134 (1997));

N-glycosidase F from *Flavobacterium menigosepticum* (EC. 3.5.1.5.2) (Lemp, D., Haselbeck, A., Klebl, F., *J. Biol. Chem*. 265: 1506-15610 (1990));

trypsin inhibitor from *Brassica oleracea* (Williams, D., Kain, W., Broadway, R. *Plant Physiol*. 114: 747(1997));

caspase eg. ICE cysteine proteases (Thornberry, N. A., Bull, H. G., Calaycay, J. R., Chapman, K. T., Howard, A. D., Kostura, M. J., Miller, D. K., Molineaux, S. M., Weidner, J. R., Aunins, J., et al. *Nature* 356: 768-774 (1992));

aspartic protease from *Brassica napus* (D'Hondt, K., Bosch, D., VanDAmme, J., Goethals, M., Vanderkerckhove, J., Krebbers E. *J. Biol. Chem*. 268: 20884-20891 (1993));

lactase (intestinal) (Freund, J. N., Jost, B., Lorentz, O., Duluc, I. *Biochem. J*. 322: 491-498 (1997));

cellulases and xylanases (Li, X., Chen, H., Ljungdahl, L. *Appl. Environ. Microbiol*. 63: 628-635 (1997));

fructosyl amino acid oxidases (Yoshida, N., Sakai, Y., Isogai, A., Fukuya, H., Yagi, M., Tani, Y., Kato, N. *Eur. J. Biochem*. 242:499-505 (1996));

polygalacturonidase (Ruttkowski, E., Ngugen, Q., Gottshalk, M., Jany, K., Loeffler, F., Piepersberg, W., Schuster, E., Gassen, H. (Patent EP 0388593-A));

pectate lyase from *Zea mays* (Turcich, M. P., Hamilton, D. A., Mascarenhas, J. P. *Plant Mol. Biol*. 23: 1061-1065 (1993));

pectin methylesterase (Turner, L., Kausch, K., Hand. A. *Plant Physiol*. 111: 652. (1996));

chalcone synthase (Itoh, M., Ichinose, Y., Kato, H., Shiraishi, T., Yamada, T. *Mol. Gen. Genet*. 255: 28-37 (1997));

alginate lyase (Chavagnat, F., Duez, C., Guinand, M., Potin, P., Barbeyron, T., Henrissat, B., Wallach, J., Ghuysen, J. *Biochem. J*. 319: 575-583 (1996));

D-amino acid oxidase (Konno, R. *Biochem. Biophys. Acta* 1335: 173-181 (1997));

β-glucuronidase (Jefferson, R., Kavanagh, T., Bevan, M. *EMBO J.* 6: 3901-3907 (1987));

lectins such as avidin (Gope, M., Keinanen, R., Kristo, P., Connely, O., Beattie, W., Zanucki-Schulz, T., O'Malley, B., Kulomaa M. *Nucleic Acids Res.* 15:3595-3606. (1987));

arabinogalactans (Gerster, J., Allard, S., Robert, L. S. *Plant Physiol.* 110: 1231-1237. (1996));

canine parvovirus coat protein (Dalsgaard, K., Uttenthal, A., Jones, T., Xu, F., Merryweather, A., Hamilton, W., Langeveld, J., Boshuizen, R., Kamstrup, S., Lomonossoff, G., Porta, C., Vela, C., Casal, I., Meloen, R., Rodgers, P. *Nature Biotech.* 15: 248-252 (1997));

nuclease (Hartley, R. W. *Biochem.* 32:5978-5984 (1993));

calpan (Karcz, S., Podesta, R., Siddiqui, R., Dekaban, G., Strejan, G., Clarke, M. *Molec. Biochem. Parasitology* 49:333-336 (1991));

thaumatin (Ruiz-Medrano, R., Jimenez-Moraila, B., Herrera-Estrella, L., Rivera-Bustamante, R. *Plant Mol. Biol .* 20:1199-1202 (1992));

Pin-I and Pin-II, protease inhibitors (Johnson, R., Narvaez, J., An, G., Ryan C., *Proc. Nat. Acad. Sci.* USA 86: 9871-9875 (1989));

calmodulin (Heo, W. D., Lee, S. H., Kim, M. C., Kim, J. C., Chung, W. S., Chun, H. J., Lee, K. J., Park, C. Y., Park, H. C., Choi, J. Y., Cho, M. J. *Proc. Nat. Acad. Sci.* USA 96: 766-771 (1999));

aquaporin (Ikeda, S., Nasrallah, J. B., Dixit, R., Preiss, S., Nasrallah, M. E. *Science* 276: 1564-1566 (1997));

phosphatases (Rodriguez, P. L. *Plant Mol. Biol.* 38: 919-927 (1998));

proteins involved in wax synthesis (Aarts, M. G. M., Keijzer, C. J., Stiekema, W. J., Pereira, A. *Plant Cell* 7: 2115-2127 (1995));

elicitins (Bonnet, P., Bourdon, E., Ponchet, M., Blein, J. -P., Ricci, P. *Europ. J. Plant Pathol.* 102: 181-192 (1996); Gómez-Gómez, L., Bauer, Z., Boller, T. *Plant Cell* 13: 1155-1163 (2001));

avirulence proteins (Van Kan, J. A. L., van den Ackerveken, G. F., de Wit, P. J. *Mol. Plant-Microbe Interact.* 4: 52-59 (1991); Joosten, M. H. A. J., Cozijnsen, T. J., De Wit, P. J. *Nature* 367: 384-386 (1994));

pollen coat proteins (Doughty, J., Dixon, S., Hiscock, S. J., Willis, A. C., Parkin, I. A. P., Dickinson, H. G. *Plant Cell* 10: 1333-1347 (1998); Stanchev, B. S., Doughty. J., Scutt, C. P., Dickinson, H., Croy, R. R. *Plant J.* 10: 303-313 (1996); Bih, F. Y., Wu, S. S. H., Ratnayake, C., Walling, L. L., Nothnagel, E. A., Huang, A. H. C. *J. Biol. Chem.* 274: 22884-22894 (1999); Schopfer, C. R., Nasrallah, M. E., Nasrallah, J. B. *Science* 296:1697-1700 (1999); Takayama, S., Shiba, H., Iwano, M., Asano, K., Hara, M., Che, F. -S., Watanabe, M., Hinata, K., Isogai, A. *Proc. Natl Acad. Sci.* USA 97: 1920-1925 (2000); Kachroo, A., Schopfer, C. R., Nasrallah, M. E., Nasrallah, J. B. *Science* 293: 1824-1826 (2001); Shiba, H., Takayama, S., Iwano, M., Shimosato, H., Funato, M., Nakagawa, T., Che, F. -S., Suzuki, G., Watanabe, M., Hinata, K., Isogai, A. *Plant Physiol.* 125: 2095-2103 (2001); Vanoosthuyse, V., Miege, C., Dumas, C., Cock, J. M. *Plant Mol. Biol.* 16: 17-34 (2001); Shiba, H., Iwano, M., Entani, T., Ishimoto, K., Shimosato, H., Che, F. -S., Satta, Y., Ito, A., Takada, Y., Watanabe, M., Isogai, A., Takayama, S. *Plant Cell* 14: 491-504 (2002)).

Proteins localized extracellularly can be used to modulate pollen function and for example prevent normal fertilization. The pollen from the genetically modified plant can also be used as a carrier for various polypeptides. This provides a novel protein expression, production and purification system.

Example 17 describes the results of the translational fusion of a coding region of interest, for example but not limited to, the *E. coli* β-glucuronidase reporter gene, at the C-terminus of the full-length sequence of the tapetal oleosin-like gene Sta 41-9 (including the N-terminal, central hydrophobic and C-terminal domains). The N-terminal domain of the tapetal oleosin-like proteins are highly variable in length (ranging from 6 to 67 amino acid residues) and sequence, and the central hydrophobic domain is variable in sequence and slightly variable in length (Ross, J. H. E. and Murphy, D. J. *Plant J.* 9: 625-637 (1996)). The C-terminal domain is variable in length and sequence; the different types of sequence found in the C-terminal domains consist of varying classes of repeated domains which are rich in various amino acids, such as glycine, lysine and glycine, or proline and, alanine (Ross, J. H. E. and Murphy, D. J. *Plant J.* 9: 625-637 (1996)). Both the N- and C-terminal domains contain sequences that differ considerably among the varying classes of tapetal oleosin-like genes (Ross, J. H. E. and Murphy, D. J. *Plant J.* 9: 625-637 (1996)). In *B. napus* and Arabidopsis, a common characteristic of the tapetal oleosin-like proteins is their localization to the pollen coat, despite their sequence variability (Murphy, D. J. and Ross, J. H. E. *Plant J.* 13: 1-16 (1998); Mayfield, J. A., Fiebig, A., Johnstone, S. E., Preuss, D. *Science* 292:2482-2485 (2001)).

Figure 5A:
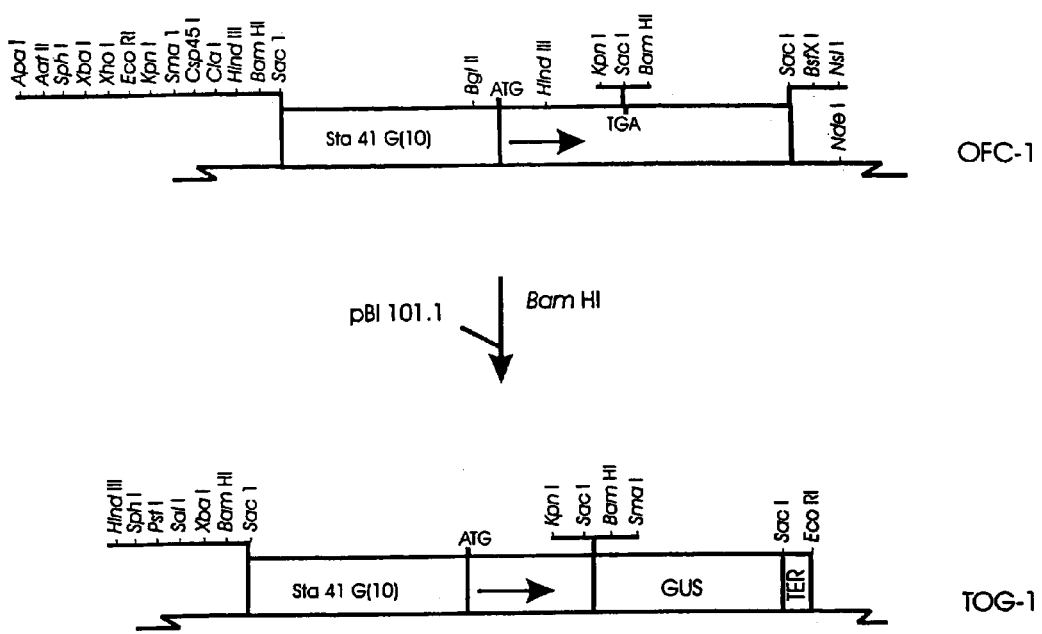
FIG. 5a shows construction of TOG-1 (SEQ ID NO:3; Example 17), the *Brassica napus* tapetal oleosin-like Sta 41-9/*E. coli* β-glucuronidase translational fusion.
Figure 5B:
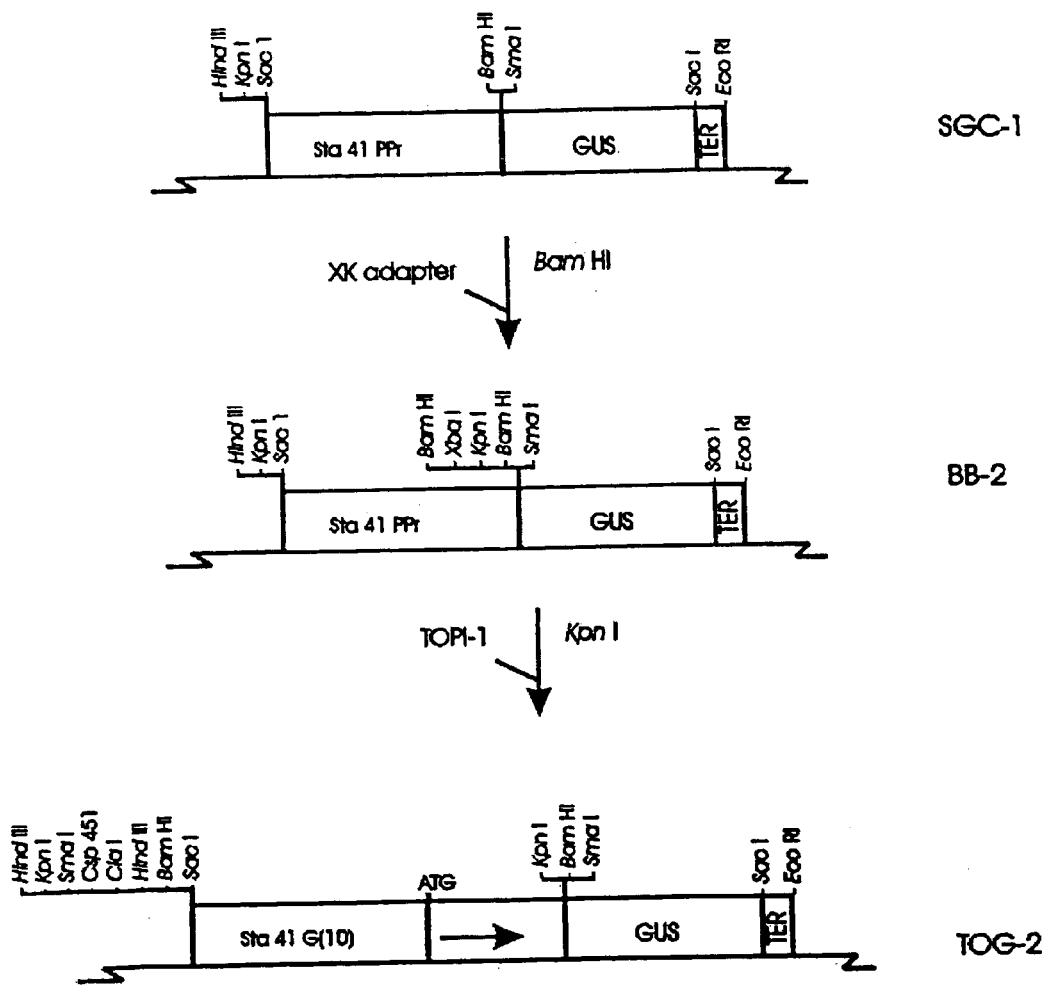
FIG. 5b shows an alternate method for construction of a tapetal oleosin-like/GUS (TOG-2; Example 17, SEQ ID NO:43) translational fusion construct comprising *B. napus* OlnB;4 (also known as Sta 41-9) promoter and coding regions fused to the uidA sequence encoding β-glucuronidase (GUS) and the nopaline synthase terminator (TER).

Therefore, strategies for the construction of translational fusions of targeting proteins such as, but not limited to, STA 41-9, to target proteins of interest to the pollen coat include, (also see FIG. 3):

1) modifying the C-terminal domain by altering the length, or nucleotide or amino acid sequence of, or eliminating the C-terminal domain;
2) modifying the N-terminal domain by altering the length, or nucleotide or amino acid sequence of, or eliminating the N-terminal domain;
3) altering the length, or nucleotide or amino acid sequence of the central hydrophobic domain;
4) creating C-terminal, N-terminal, or both N-terminal and C-terminal translational fusions of the protein of interest with the targeting protein;
5) varying the position of the protein of interest within the C-terminal or N-terminal domain, for example, fusing the protein of interest at the beginning, at the end, or at variable positions within a full-length or modified domain of the targeting protein; or
6) any combination of the above.

In order to obtain a sporophytically expressed pollen coat protein, the tapetal oleosin-like proteins can be fused translationally to a polypeptide of interest. For example, which is not to be considered limiting, the nucleotide and deduced amino acid sequences of a tapetum-expressed oleosin-like gene Sta 41-9 (Robert, L. S., Gerster, J., Allard, S., Cass, L., Simmonds, J. *Plant J.* 6:927-933 (1994a); also termed BnOlnB;4) is used for the preparation of a number of possible translational fusions. The polypeptide of interest can be fused to the C-terminal end of the protein Sta 41-9 (FIG. 3A, see Example 2), or the polypeptide of interest can also be fused internally next to the proteolytic cleavage site observed in the pollen-targeted protein. In this latter fusion, the native C-terminal region can be deleted or preserved (FIGS. 3B and 3C, respectively). It is to be understood that the constructs exemplified in FIGS. 3A-3C are to be considered examples of a range of possible protein fusions that could be prepared using the Sta 41-9 gene, and are not intended to limit the scope of this invention in any manner. For example, fusion of a protein of interest with STA 41-9, where the C-terminal domain is eleiminated, is shown in FIG. 5*d* (TOG-3; see Example 22), while N-terminal fusion of GUS to fall length STA 41-9 is shown in FIG. 5*e* (TOG-4, Example 22). Other expressed proteins as shown in the examples, or as disclosed within the prior art (e.g. U.S. Pat. No. 5,652,354; U.S. Pat. No. 5,571,904; U.S. Pat. No. 5,633,438; U.S. Pat. No. 5,545,546; U.S. Pat. No. 5,659,124; WO92/13957; WO97/13401; WO93/25695; CA 2,099,482; CA 2,106,718; CA 2,165,934, which are incorporated herein by reference) may also be used for translational fusions, and are considered within the scope of the present invention.

Also considered within the scope of this invention is the expression of a gene in the tapetum whose product could modify a protein that is subsequently targeted to the extracellular domain of pollen. Similarly, the expression of a gene encoding a protein that is targeted to the extracellular domain of a floral cell, for example, but not limited to, an oleosin-like protein, may be inhibited using methods known within the art, for example but not limited to, antisense RNA, ribozymes, RNA interference or co-suppression. In this manner a reduction of a protein within the extracellular domain of a pollen grain results and modifies pollen stigma interaction.

Gametophytically expressed pollen coat proteins are also used in translational fusions with the polypeptide of interest or this polypeptide is directed to the microspore or pollen coat by transcriptional or translational fusion to a promoter directing pollen expression. These can be part of the coat of the pollen grain or can be released extracellularly. As an example, which is not to be considered limiting in any manner, a translational fusion is made to the cysteine rich *B. oleracea* PCP1 pollen coat protein (Stanchev, B. S., Doughty, J., Scutt, C. P., Dickinson, H., Croy, R. R. D. *Plant J.* 10:303-313 (1996)) that is synthesized in the pollen cell and relocated to the pollen coat.

It is also contemplated that a chimeric DNA construct encoding a polypeptide of interest can be prepared so that the polypeptide is synthesised within gametophytic tissue, and released at a later time, for example within pollen, and released upon pollen germination. In this case, the protein of interest is either fused translationally to *B. napus* pollen polygalacturonase STA 44 (Robert, L. S., Allard, S., Gerster, J. L., Cass, L., Simmonds, *J. Plant Mol. Biol*. 23:1273-1278 (1993)), or fused transcriptionally to the promoter of Sta 44G(2) (Hong, H. P., Gerster, J. L., Datla, R. S. S., Albani, D., Scoles, G., Keller, W., Robert, L. S. *Plant Cell Rep.* 16:373-378 (1997a); U.S. patent application Ser. No. 08/577,463). These fusion proteins are then produced within the pollen grain and released upon germination.

Figure 7:
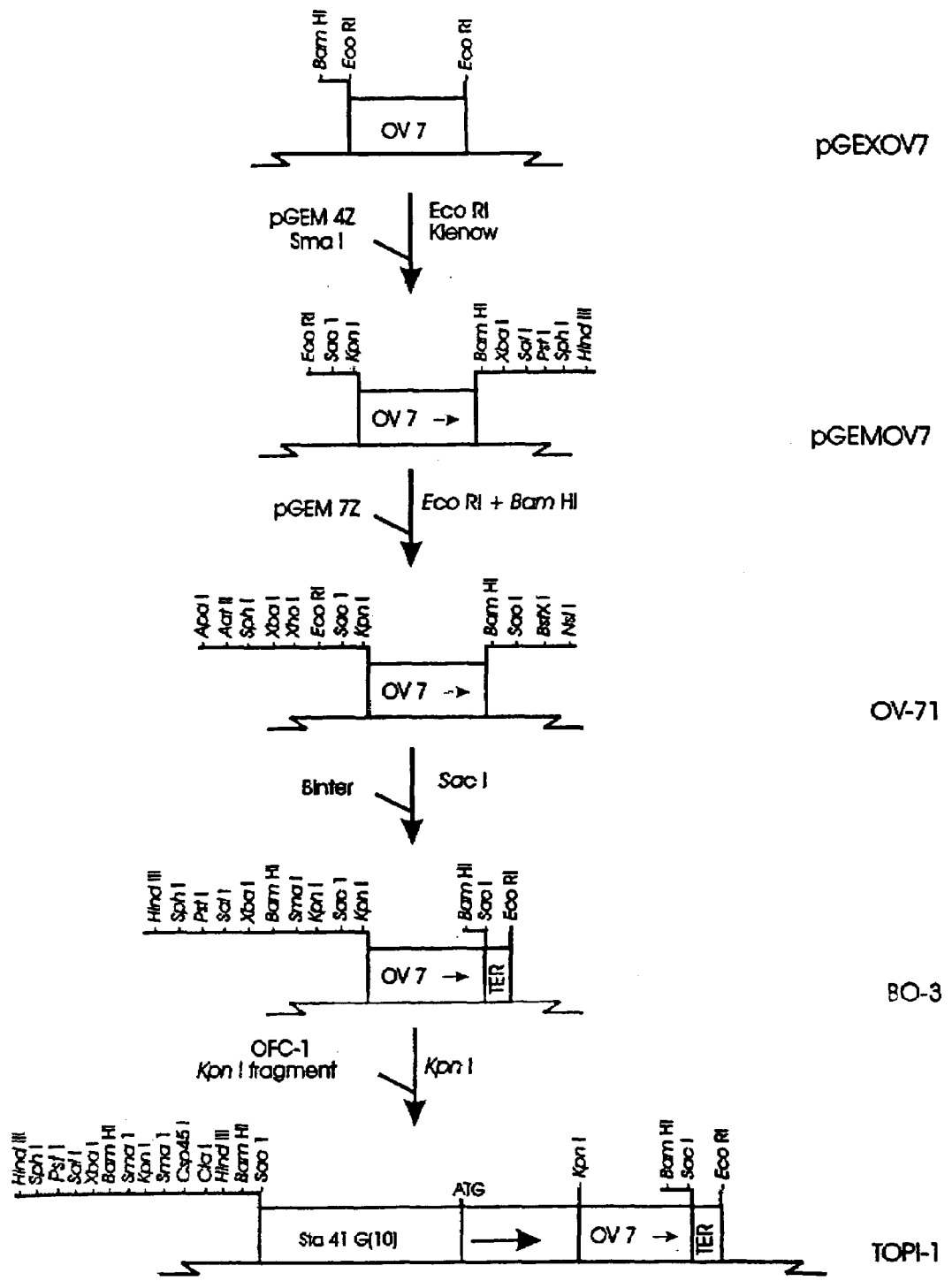
FIG. 7 shows a schematic representation of the construction of the plant transformation vector TOPI-1, the *Brassica napus* tapetal oleosin-like Sta 41-9/*Onchocerca volvulus* protease inhibitor OV7 translational fusion.
Figure 20:
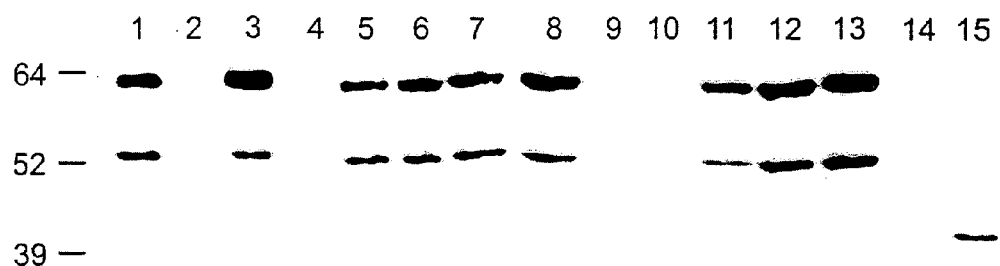
FIG. 20 shows the detection of the *Brassica napus* tapetal oleosin-like STA 41-9/*Onchocerca volvulus* protease inhibitor OV7 fusion protein in transgenic *Brassica carinata* containing TOPI-1 (SEQ ID NO:5).
Figure 20:
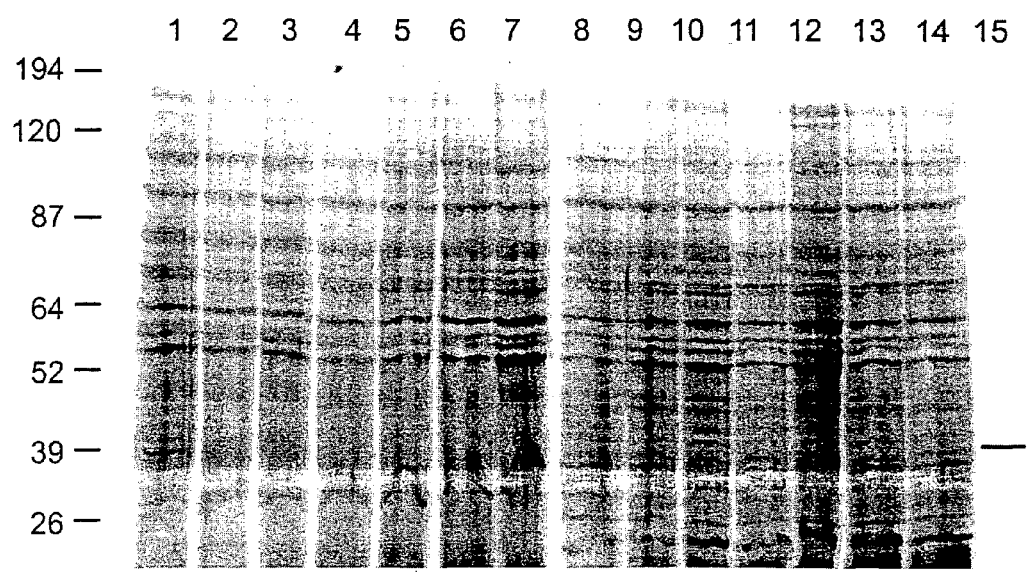
Figure 21:
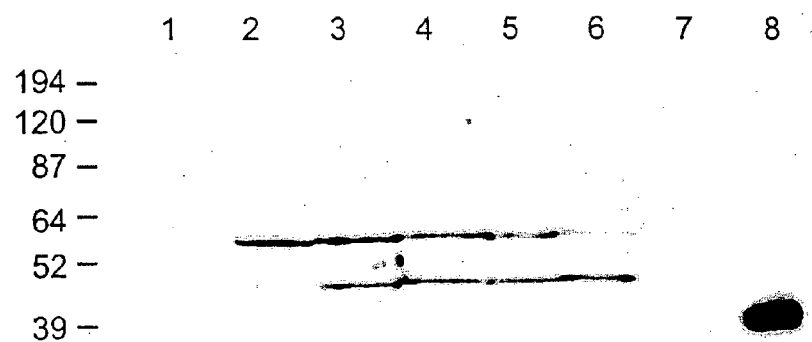
FIG. 21 shows the detection of the *Brassica napus* tapetal oleosin-like STA 41-9/*Onchocerca volvulus* protease inhibitor OV7 fusion protein during the flower development of a transgenic *Brassica carinata* plant containing TOPI-1 (SEQ ID NO:5).
Figure 21:
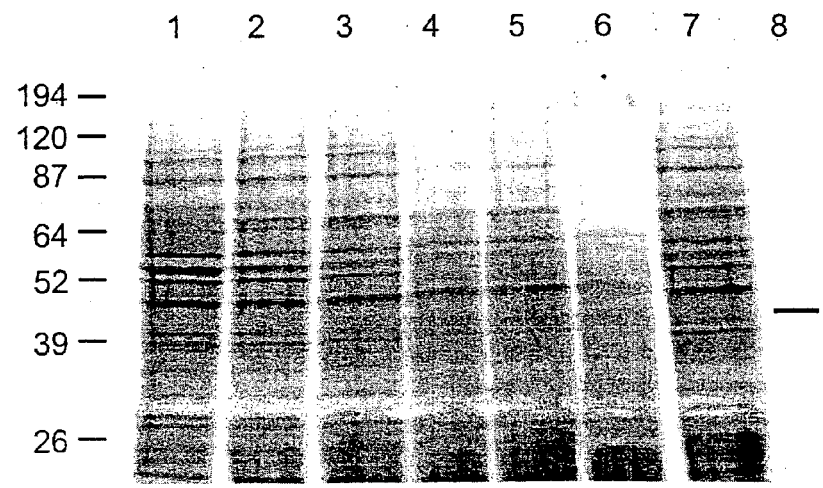
Figure 21C:
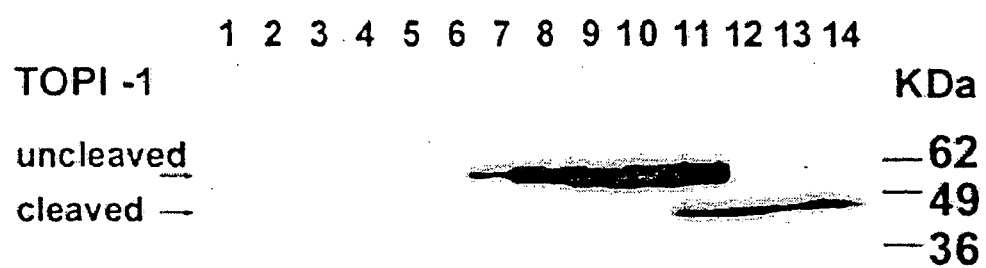
FIG. 21C shows a Western blot analysis of TOPI-1 protein during flower development in transgenic *B. carinata*, using an anti-CPI (cysteine protease inhibitor) antibody. Lanes 1 to 3: anther protein extracts from 3 mm, 5 mm and 8 mm buds of non-transformed *B. carinata*, respectively. Lanes 4 and 5: anther and pollen protein extracts, respectively, from non-transformed *B. carinata* open flowers. Lanes 6 to 12: anther protein extracts from 2 mm, 3 mm, 4 mm, 5 mm, 6 mm, 7 mm and 8 mm buds, respectively, from transgenic *B. carinata*. Lanes 13 and 14: anther and pollen protein extracts, respectively, from open flowers of transgenic *B. carinata*.

Translational fusions comprising a tapetal oleosin-like protein, for example, but not limited to, Sta 41-91/*Onchocerca volvulus* protease inhibitor OV7 fusion (TOPI-1; FIG. 7 and Example 4), were detected in anther protein extracts from 3, 4 or 7 mm flower buds (FIGS. 20A and 21A; see Example 16). These results demonstrate tapetal expression, processing (cleaving) of the fusion product, and targeting to the pollen coat by the native tapetal oleosin-like proteins. Further characteization of TOPI-1 during flower development in a transgenic *Brassica carinata* is shown in FIGS. 21C and 26B. The full-length fusion protein was detected in anther, pollen and pollen coat protein extracts of the transgenic plant and was cleaved later in flower development. These results demonstrate that the oleosin-like Sta 41-9/*Onchocerca volvulus* protease inhibitor fusion protein while expressed specifically in the tapetum re-locates to the pollen.

Similar results are also observed during flower development in transgenic *Nicotiana tabacum* (FIG. 21D), using the tapetal oleosin-like *Brassica napus* Sta 41-9/*Onchocerca volvulus* protease inhibitor fusion protein (TOPI-1). These results indicate that the oleosin-like STA 41-9/*Onchocerca* volvulus protease inhibitor OV7 fusion protein localizes to the pollen grain in the Solanaceae (tobacco) family as well.

With reference to FIG. 26 there is shown another non-limiting example of the targeting of a *Brassica napus* tapetal oleosin-like Sta 41-9/*Sitophilus zeamais* protease SCPc1 translational fusion protein (TOP-1; FIG. 6, and Example 3) to pollen during flower development in *Brassica carinata.*

To further demonstrate the targeting of a protein of interest to the pollen coat, a tapetal oleosin-like gene was translationally fused to the protein of interest and expressed within developing anthers. In this example, which is not to be considered limiting in any manner, the tapetal oleosin-like gene BnOlnB;4 (also known as Sta 41-9; including the promoter and the entire coding region with the exception of the TGA stop codon), isolated from *B. napus* anthers (Robert, L. S., Gerster, J. L., Allard, S., Cass, L., Simmonds, J., *Plant J.* 6:927-933 (1994a)), was translationally fused to GUS to produce TOG (see FIGS. 5A, B, D and E for TOG-1, TOG-2, TOG-3 and TOG-4, and examples 2, 17, and 22 for their preparation) and introduced into *B. carinata* (see Example 17 for further details).

Figure 24A:
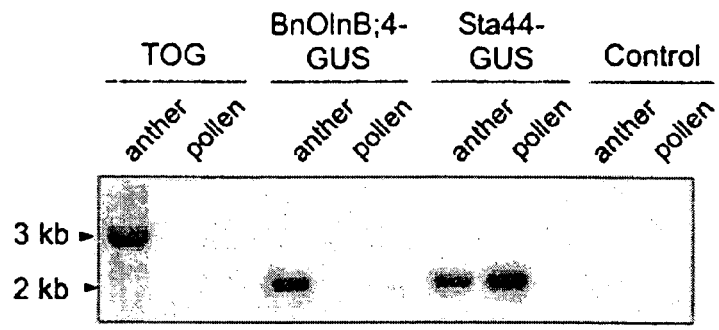
FIG. 24a shows a Northern blot analysis using the GUS probe at high stringency. Molecular weights of the TOG-2 or GUS mRNAs are indicated on the left.

Northern analysis (using either a GUS or BnOlnB;4 probe) revealed that TOG-2 mRNA was detectable during anther development, first in anthers isolated from about 3 mm flower buds, reaching its maximum level in anthers from 5 mm buds, and decreasing in anthers from buds 6-7 mm in length, correlating with the onset of tapetal degeneration. By the late pollen maturation stage (8 mm buds), TOG-2 mRNA was no longer detectable in anthers (FIGS. 23A, and 24A, TOG-2). The pattern of TOG-2 mRNA accumulation in anthers is similar to that previously described for the BnOlnB;4 gene (Robert, L. S., Gerster, J. L., Allard, S., Cass, L., Simmonds, J., *Plant J.* 6:927-933 (1994a)). Western blot analysis (using either an anti-GUS, or an anti-BnOlnB;4 antibody) demonstrates that the full-length TOG-2 fusion protein was first detected in anthers from 4 mm flower buds prior to tapetal degeneration, peaked in 6 mm buds and was no longer observed in 8 mm buds (FIGS. 23B, 24B, TOG-2). As shown in FIG. 24B (TOG-2). Western analysis also demonstrates that TOG-2 is present on pollen coats isolated from mature pollen. Processing of the TOG-2 protein in pollen and pollen coats is evident. GUS enzymatic activity (FIGS. 23C and 24C, TOG-2) indicates that GUS activity, initially detected in anthers from 3 mm flower buds, persists throughout anther development. Thus, GUS activity was detected before, during and after tapetal degeneration indicating that both the full-length and the processed forms of the TOG-2 fusion protein are enzymatically active.

To determine whether a translational fusion is necessary to target proteins from the tapetum to pollen grains, expression of a GUS transcriptional fusion to the tapetum-specific BnOlnB;4 promoter (BnOlnB;4-GUS (also called Sta 41-9-GUS) which lacks the coding region of BnOlnB;4) was analyzed in transgenic *B. napus*. GUS expression directed by the BnOlnB;4 promoter was previously shown to be specific to the tapetum in anthers isolated from 3-5 mm flower buds of *B. napus* (Hong, H. P., Ross, J. H. E., Gerster, J. L., Rigas, S., Datla, R. S. S., Hatzopoulos, P., Scoles, G., Keller, W., Murphy, D., Robert, L. S. *Plant Mol. Biol.* 34:549-555 (1997b)). The approximately 2 kb BnOlnB;4 promoter is the same as that used to direct expression of the TOG-2 translational fusion. GUS mRNA from the BnOlnB; 4-GUS construct was detected in transgenic *B. napus* prior to tapetal degradation in 4-5 mm flower buds (anther; consistent with earlier reports, Hong, H. P., Ross, J. H. E., Gerster, J. L., Rigas, S., Datla, R. S. S., Hatzopoulos, P., Scoles, G., Keller, W., Murphy, D., Robert, L. S. *Plant Mol. Biol.* 34:549-555 (1997b)) and undetectable in pollen isolated from 6-7 mm buds (pollen) after the tapetum had degenerated just prior to floral opening (BnOlnB;4-GUS; FIG. 24A).

Figure 24B:
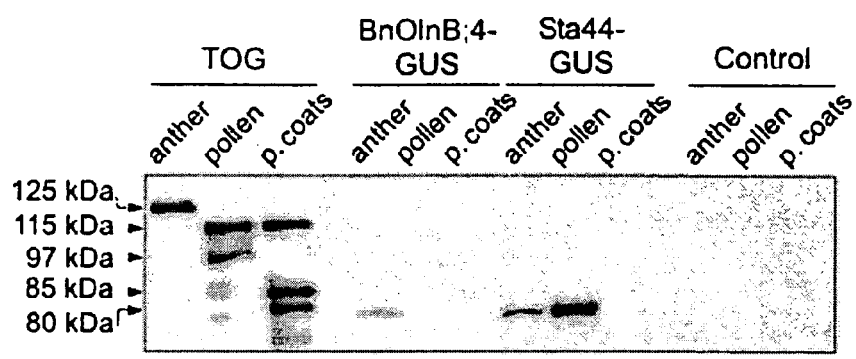
FIG. 24b shows a Western blot analysis using an anti-GUS antibody. The molecular weights of the TOG-2 proteins are indicated on the left. Pollen coat samples (p.coats) were purified from anthers harvested prior to anthesis from recently opened flowers.
Figure 24C:
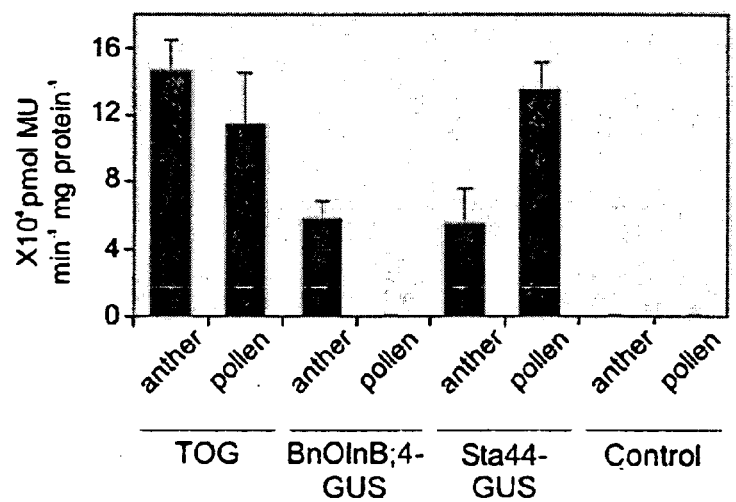
FIG. 24c shows a fluorogenic analysis of GUS enzymatic activity expressed in $10^4$ pmol MU min$^{-1}$ mg protein- ± standard error with n=3. Samples were obtained from anthers of 5 mm *B. carinata* flower buds (TOG-2 transgenic and non-transformed control) or 4-5 mm *B. napus* buds (BnOlnB;4-GUS and Sta 44-GUS) and from pollen of 8 mm *B. carinata* buds (TOG-2 transgenic and non-transformed control) or 6-7 mm *B. napus* buds (BnOlnB;4-GUS and Sta 44-GUS).

Western blot analyses with an anti-GUS antibody detected the GUS protein, of BnOlnB;4-GUS, in anthers from 4-5 mm buds (anther; FIG. 24B), however, no cross-reacting proteins encoded by BnOlnB;4-GUS were observed in pollen grains isolated from 6-7 mm buds (pollen). GUS activity was also present in anthers isolated from 4-5 mm buds but not in pollen isolated from 6-7 mm buds (BnOlnB;4-GUS; FIG. 24C).

A GUS transcriptional fusion to a *B. napus* polygalacturonase promoter (Sta 44-GUS) that directs high levels of expression within pollen late in development (Hong, H. P., Gerster, J. L., Datla, R. S. S., Albani, D., Scoles, G., Keller, W., Robert, L. S. *Plant Cell Rep.* 16: 373-378) was also examined (FIG. 24, Sta 44-GUS). GUS mRNA was present in 4-5 mm buds (anther) and 6-7 mm buds (pollen FIG. 24A). Western blot analysis (using anti-GUS antibody) demonstrates GUS protein in anthers and pollen, but not pollen coats (FIG. 24B). GUS assays showed GUS activity (FIG. 24C) in anthers (isolated from 4-5 mm buds) and isolated mature pollen (6-7 mm buds), as the Sta 44-GUS construct drives expression within the pollen grain itself.

Collectively, these data indicate that a protein of interest, for example but not limited to GUS, relocates to the pollen coat upon tapetal degeneration if fused translationally to a tapetal oleosin-like protein, for example but not limited to, BnOlnB;4 (also known as STA 41-9). Furthermore, the coding region of interest is active when associated with pollen. Transcriptional fusion of the GUS gene to promoters driving its expression in either the tapetum or the pollen grain is not sufficient for pollen coat targeting.

Figure 25:
FIG. 25 shows immunogold localization of tapetal oleosin-like, TOG-2 and GUS proteins during anther development (see FIG. 5b for TOG-2 construct). Anthers from non-transformed *B. carinata* 5 mm (FIG. 25a) and 8 mm (FIG. 25b) flower buds reacted with the anti-BnOlnB;4 antibody in tapetosome lipid bodies and pollen coats, respectively. Anthers from 5 mm (FIG. 25c) and 8 mm (FIG. 25d) buds of transgenic *B. carinata* containing the TOG-2 translational fusion reacted with the anti-GUS antibody in tapetosomes and pollen coats, respectively. Examples of elaioplast (e) and tapetosome (t) lipid bodies and the exine (ex), intine (in) and pollen coat (pc) layers are indicated in FIGS. 25a to d. The anti-GUS antibody reacted with the tapetum in anthers from the 4 mm bud stage (FIG. 25e) but not with the 7 mm bud stage (f) of transgenic *B. napus* containing the BnOlnB;4-GUS transcriptional fusion, and within pollen grains at the 5 mm (FIG. 25g) and 7 mm (FIG. 25h) bud stage of transgenic *B. napus* containing the Sta 44-GUS transcriptional fusion.

Subcellular localization of native tapetal oleosin-like proteins (FIGS. 25*a* and *b*) and TOG-2-derived proteins (FIGS. 25*c* and *d*) in anthers during development was carried out using in situ immunogold localization. In non-transformed *B. carinata*, the anti-BnOlnB;4 antibody cross-reacts with the tapetosome lipid bodies of anthers from 5 mm flower buds (FIG. 25*a*). In anthers isolated from 8 mm buds, lacking a tapetum and where the tapetosomes have disintegrated, gold particles are localized to the pollen coat. (FIG. 25*b*). In transgenic TOG-2 plants, anti-GUS antibody cross-reacted with the tapetosomes within the tapetum of anthers isolated from 5 mm flower buds (FIG. 25*c*), and with the pollen coat, in anthers isolated from 8 mm buds (FIG. 25*d*), demonstrating that the TOG-2 translational fusion is initially present within the tapetum, associated with the tapetosomes, and ultimately becomes localized to the pollen coat. Immunogold localization of transgenic plants containing the tapetal-expressed BnOlnB;4-GUS that lacks the coding region of BnOlnB;4 (FIGS. 25*e* and *f*) or the pollen-expressed Sta 44-GUS, that is expressed within the pollen grain (FIGS. 25*g* and *h*) demonstrates that no pollen coat localization is observed.

GUS histochemical staining with pollen from 5 mm bud anthers obtained from TOG-2 plants is negligible (FIG. 25*i*), but pronounced with pollen from 8 mm bud anthers (FIG. 25*j*), indicating that GUS enzymatic activity is localized to the pollen after the disappearance of the tapetum late in anther development. GUS activity also persists following the release of pollen from the anther, as pollen grains continued to exhibit GUS histochemical staining for more than two months after collection and storage under ambient conditions (data not shown).

To indicate whether the GUS activity localized to pollen of TOG-2 transgenic plants was indeed the result of sporophytic expression rather than gametophytic expression, GUS histochemical analysis was performed on TOG-2 lines containing single copy insertions. In 9 GUS-positive progeny of each of two self-pollinated T0 plants, GUS histochemical staining of pollen from 8 mm flower buds typically revealed about 98±0.2% GUS positive pollen grains. In comparison, a mix of stained and unstained pollen grains are observed by GUS histochemical staining of T1 progeny of a self-pollinated *B. napus* transgenic line containing a single copy of the pollen-expressed Sta 44-GUS construct (FIG. 25*k*). The frequency of GUS staining of pollen from the TOG-2 plants reflects the enzymatic activity transferred to the pollen from the sporophytic tapetum, rather than from gametophytic expression.

Therefore, as demonstrated herein (Example 17), the composition of the pollen coat protein can be altered by targeting a protein of interest synthesized in the tapetum to the pollen coat. Targeting to the pollen coat can be achieved with a translational fusion between a tapetal oleosin-like protein gene, for example but not limited to, BnOlnB;4, and a protein of interest, for example but not limited to the uidA gene encoding GUS (TOG-2, see FIG. 5B).

Tapetal oleosin-like proteins, which lack a signal peptide, use a unique targeting pathway to move from the tapetum into the locule and ultimately to the pollen. The TOG-2 proteins are localized to tapetosomes within the tapetum, remain associated with the tapetosomes following tapetal degradation and then become localized to the pollen coat of mature pollen (e.g. see FIG. 25 and Example 17 for supporting text). Without wishing to be bound by theory, the association of proteins with lipid bodies, which occurs with tapetal oleosin-like proteins, may protect proteins during tapetal degeneration. This is further supported by the observation that in transgenic *B. napus* plants containing a transcriptional fusion between a BnOlnB;4 tapetal promoter (no tapetal oleosin-like coding region) and GUS, the GUS protein disappears from anthers after tapetal degradation (results not shown). This suggests that the persistence of GUS after tapetal degeneration in the TOG-2 plants may be a result of protection of the protein due to its association with the tapetosomes.

Furthermore, as demonstrated, for example in Example 17, targeting of a protein of interest to the pollen coat is not affected by the addition of a lengthy translational fusion of the protein of interest, at the C-terminus of a tapetal oleosin-like protein.

Figures 1, 5C:
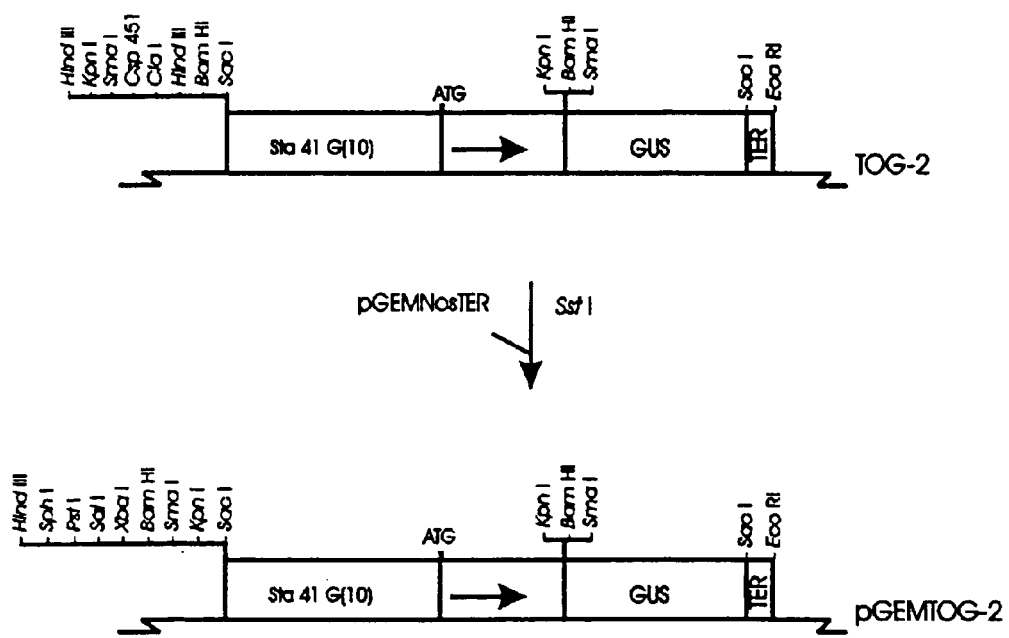
Figures 2, 5C:
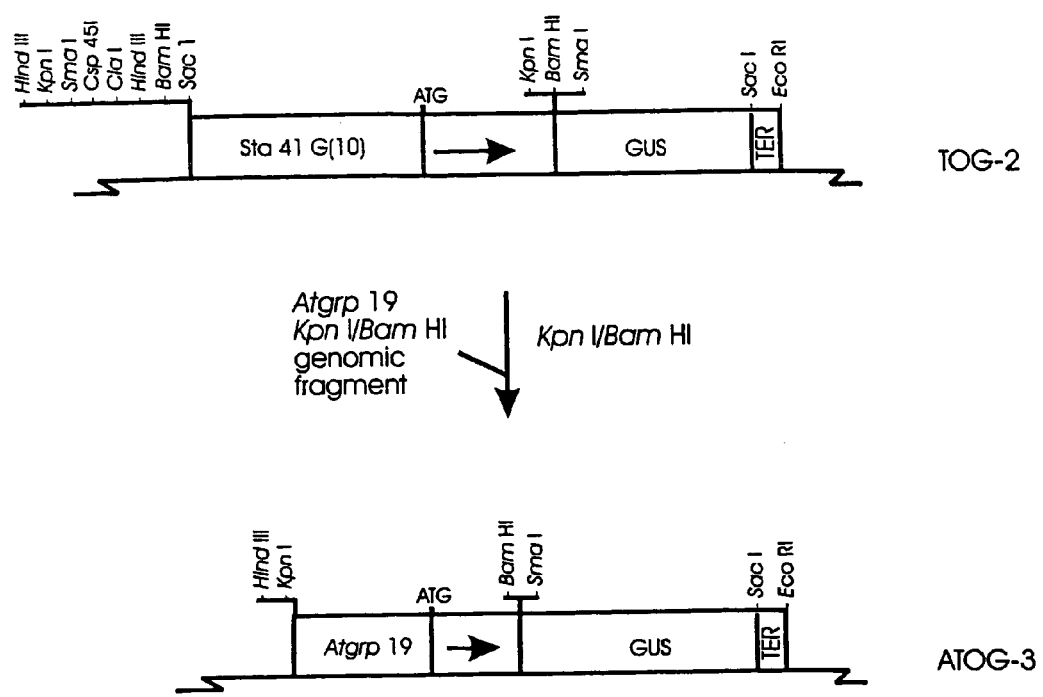
Figure 5D:
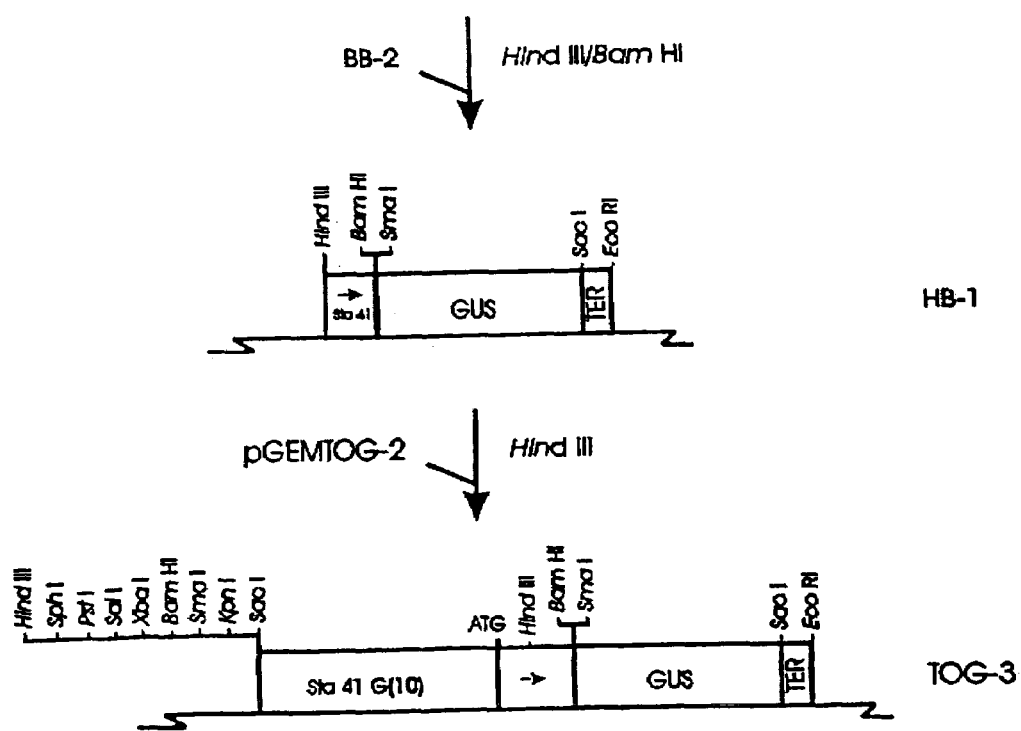
FIG. 5d shows a schematic representation of the construction of plant transformation vector TOG-3, a *Brassica napus* tapetal oleosin-like Sta 41-9/*E. coli* β-glucuronidase translational fusion (Example 22; SEQ ID NO:28). The GUS gene in TOG-3 is positioned adjacent to the C-terminal end of the STA 41-9 hydrophobic domain and replaces the C-terminal domain.
Figure 5E:
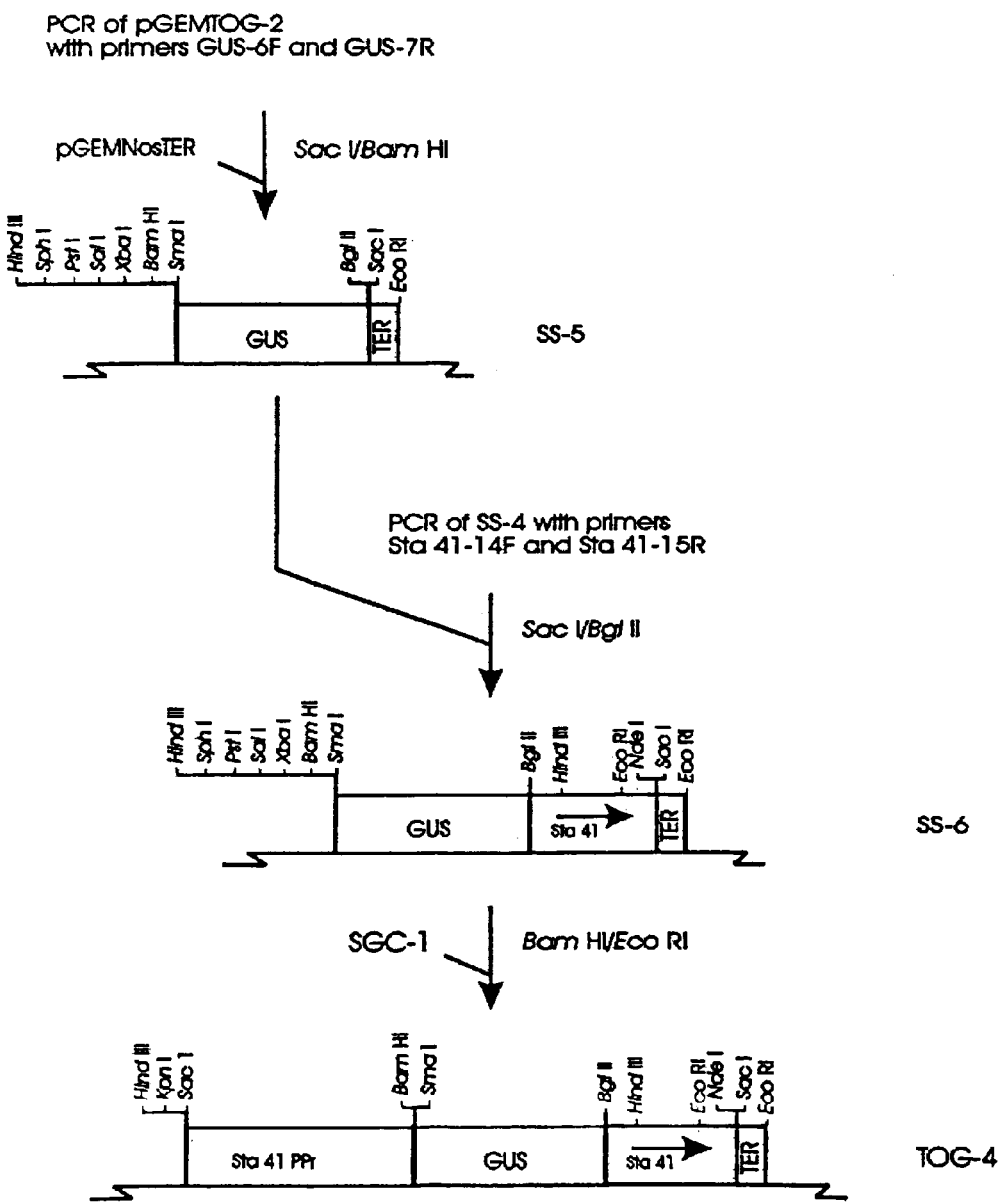
FIG. 5e shows a schematic representation of the construction of plant transformation vector TOG-4, a *Brassica napus* tapetal oleosin-like Sta 41-9/*E. coli* β-glucuronidase translational fusion (Example 22; SEQ ID NO:33). The GUS gene in TOG-4 is positioned adjacent to the N terminus of the full length STA 41-9 protein.
Figure 5F:
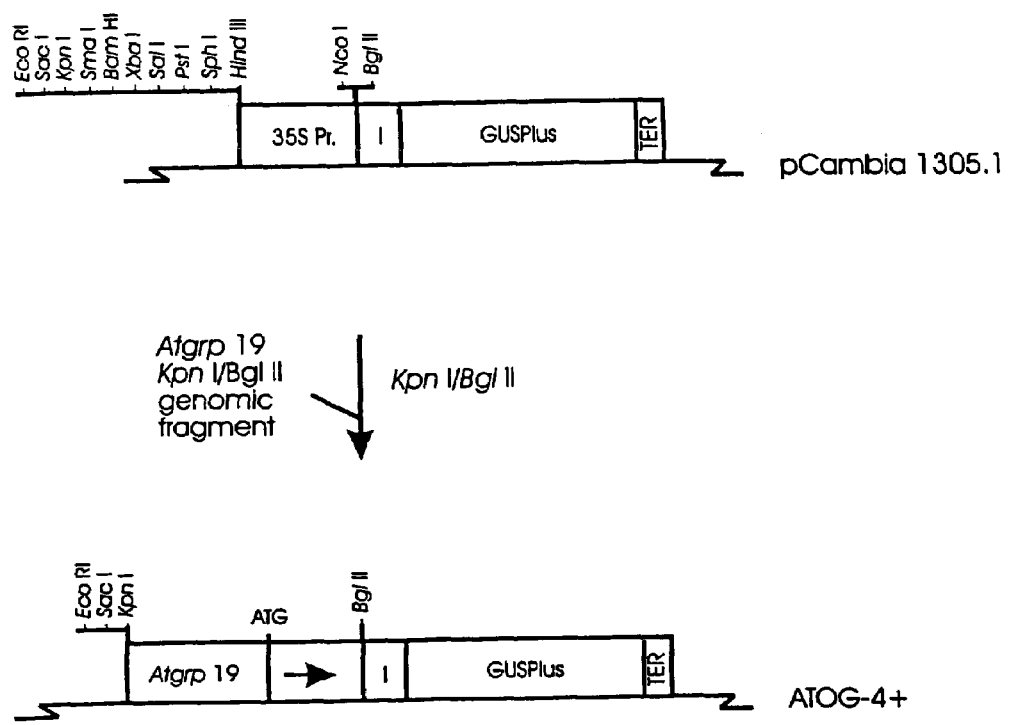
FIG. 5f shows a schematic representation of the construction of the plant transformation vector ATOG-4+, the *Arabidopsis thaliana* oleosin-like Atgrp19/*Staphylococcus* GUSPlus™ translational fusion.

An alternate example of an oleosin-like sequence that may be used to target a coding region of interest to the pollen coat, in a manner as demonstrated above using Sta 41-9 (BnOlnB;4, as exemplified with TOG-2), includes an oleosin-like sequence, Atgrp 19 (see FIGS. 5C-2 and 5F, and Example 24 for the preparation of ATOG-3 and ATOG-4+; SEQ ID NOs:44 and 45, respectively), obtained from *Arabidopsis thaliana*.

Similar targeting may also be effected using other proteins, or portions thereof, for example extracellular lipase. A non-limiting example of such a protein is an *A. thaliana* exl 4 extracellular lipase, as shown in Example 25, used in the preparation of EXLG-1+ (see FIG. 30, SEQ ID NO:48).

Figure 28A:
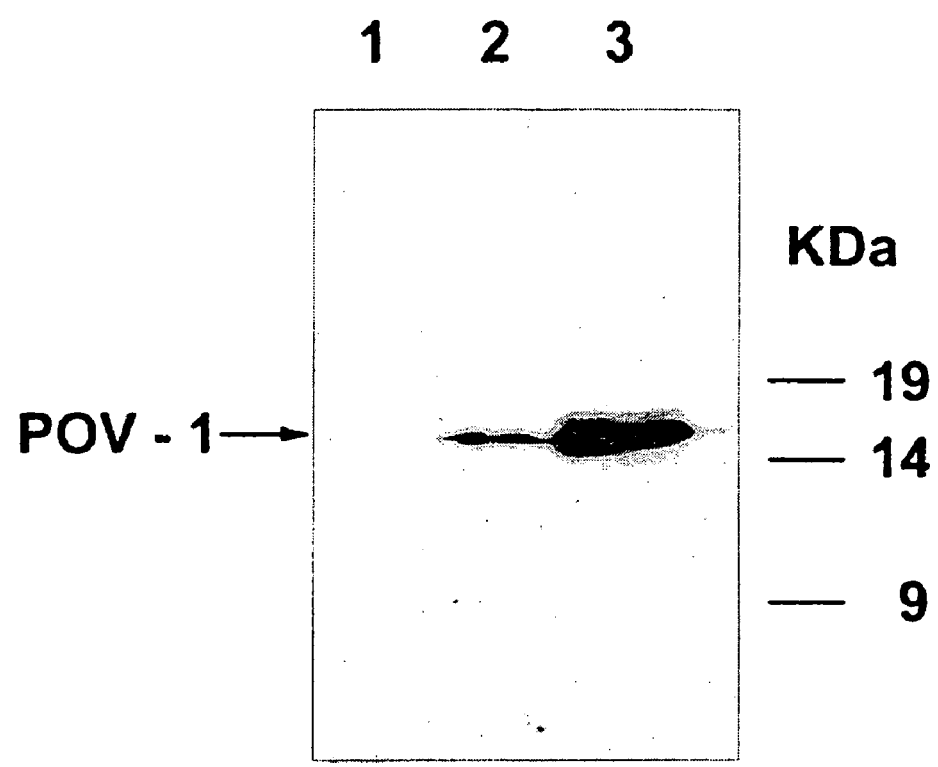
FIG. 28 shows a Western analysis of POV-1 (*Brassica napus* STA 44G(2)/*Onchocerca volvulus* protease inhibitor OV7 translational fusion; see FIG. 10 and Example 8) in the pollen of different transgenic *Brassica carinata* plants (using an anti-OV7 antibody). Lane 1 corresponds to pollen proteins extracted from 8 mm buds of non-transformed *B. carinata* and Lanes 2 and 3 correspond to pollen proteins extracted from 8 mm buds of transformed *B. carinata* lines No. 3 and No. 20 respectively.
FIG. 28B shows a chart depicting the results of protease inhibition assays on transgenic *B. carinata* plants containing the POV-1 construct. The protease inhibition assay was performed for 2 to 3 h in a microtiter plate with 5 µg of protein extract from mature pollen, 20 ng of purified papain and the substrate Pyr-Phe-Leu-pNA, and the readings were recorded at 410 nm. Results were calculated as the percentage of papain protease activity present in the mature pollen protein extract of the non-transformed control plant±standard deviation.
Figure 28B:
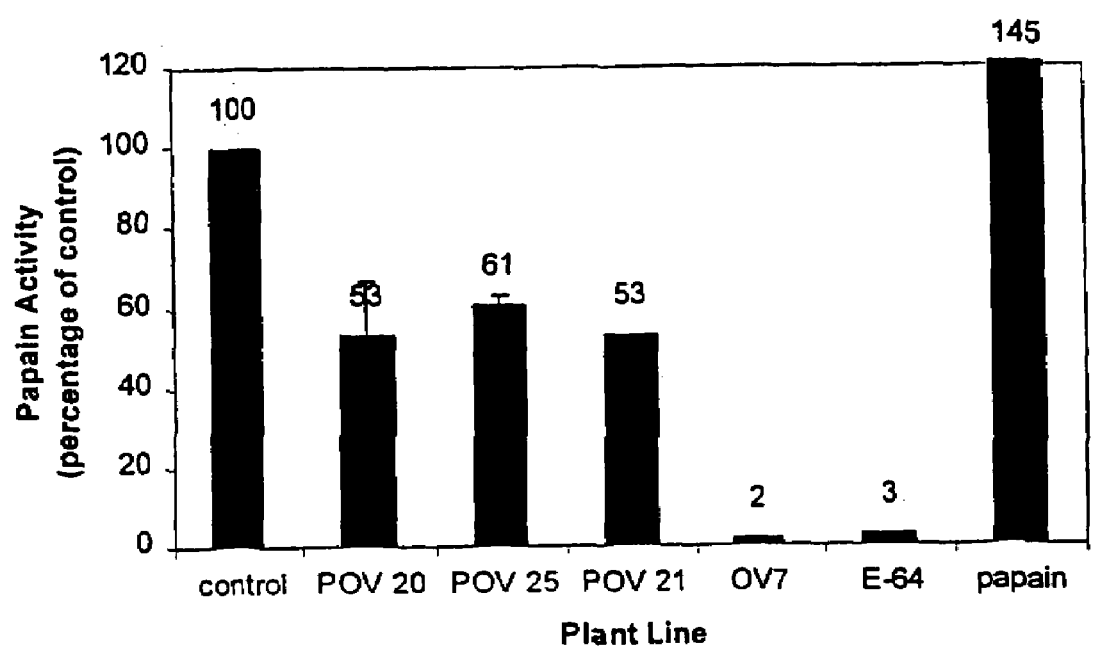

Further evidence that chimeric constructs of the present invention, for example comprising POV-1 (see FIG. 10, and Example 8), are active following expression in plants may be found in Example 19 and FIGS. 28A and B. Western analysis, using anti-OV-7 antibody, of pollen obtained from transformed plants indicates the occurence of the protease inhibitor in pollen grains. This result demonstrates that the use of a signal sequence from Sta 44G(2), fused to a coding region of interest is localized to the pollen grain. Analysis of the activity of the protease inhibitor OV7 in pollen grains is provided in Example 19 where inhibition of protease activity was determined using mature pollen grains isolated from a POV-1 expressing plant (FIG. 28B).

Co-expression of POP-1 (protease) and POV-1 (protease inhibitor) in pollen demonstrated that loss of pollen viability observed in pollen obtained from plants expressing POP-1 (e.g. see Example 21, Table 4) may be overcome in the presence of POV-1 (see Table 5, Example 21). In this example, plants expressing POV-1, that were shown to exhibit protease inhibitior activity (FIG. 28B), were crossed with plants expressing POP-1, that exhibited reduced pollen viability due to expression of protease (Table 4). In progeny of the cross, where POV-1 is expressed at sufficient levels, increased pollen viability is observed (Table 5).

An alternate example of a construct comprising a polygalacturonase fusion, includes POG-2 (FIG. 31A) and POG-3+ (FIG. 31B), comprising the coding region of Sta 44 and GUS and GUSPlus™ respectively (see Example 26).

Therefore, the present invention provides a method for modifying the extracellular compartment of a pollen grain or an anther cell of a plant comprising, expressing a construct comprising a coding region of interest within the pollen grain or the anther cell, where the coding region of interest encodes a protein, a fusion protein, a peptide, or a fragment of the protein, fusion protein or peptide. Furthermore, the protein, fusion protein or peptide, or a fragment of the protein, fusion protein or peptide comprises a tapetal oleosin-like sequence that directs the protein, fusion protein or peptide, or a fragment of the protein, fusion protein or peptide to the extracellular compartment of the pollen grain or anther cell.

The method of this invention can be used for the purposes of altering pollen function; preventing self-pollination, allowing self-pollination; preventing cross-pollination; peptide display, antigen delivery, altering nutritional value of pollen; treatment or control of insect populations; or alleviating allergenic responses. These are discussed in more detail below:

1. Alter Pollen or Pistil Function.

Normal pollen function necessitates specific inter- and intra-molecular interactions with constituents of the stigma, style and ovary. Modifying pollen or pistil function, or these interactions could result in the failure or allowance of pollen germination, pollen tube growth and/or fertilization of the egg. Modification can be achieved by specific catalytic enzymes (eg. proteases, glucosidases, glycanases, nucleases, lipases, hydrolases etc.), toxins (eg. *Diphteria* toxin A chain), antibodies, lectins etc. localized on the surface of the pollen or pistil cell, or released from the pollen, or pollen tube.

As an example of this embodiment, which is not to be considered limiting in any manner, the tapetally expressed STA 41-9 protein or the gametophytically expressed STA 44 is fused to a cysteine protease from *Sitophilus*, (Matsumoto, I., Emori, Y., Abe, K, Arai, S. *J. Biochem*. 121: 464-476 (1997)). It is also contemplated that transcriptional fusions may also be used for protease expression. Once targeted to the microspore/pollen coat, these enzymes digest proteins important to pollen germination or pollen-stigma interactions and therefore prevent pollen germination or pollen tube growth (see FIG. 11). It is to be understood that other proteases such as trypsin, chymotrypsin, caspases, sulfhydryl proteases, aspartic proteases or metallo-proteases and the like may also be used. Furthermore, other tapetum- or pollen-expressed proteins may also be used as the basis for protein fusions as would be evident to one of skill in the art. Similarly, as an example of passively targeting extracellular localization, pollen coat composition could be modified by tapetal proteins, encoded by chimeric gene constructs, which are secreted or released in the anther locule. Other modifying polypeptides such as those mentioned above could also be used in a similar way to affect pollen function (e.g. see FIG. 17). For example, which is not to be considered limiting, these chimeric gene constructs may also comprise sequences encoding proteins such as the protease inhibitor from *Onchocerca* (see FIG. 15).

As further examples of this embodiment, chimeric gene constructs could comprise the stigma-expressed gene encoding the PIS 63 protein fused to the Sitophilus protease (see FIG. 14) or *Onchocerca* protease inhibitor (see FIG. 12). These proteins could be used to modify pollen-stigma interactions or functions. Other proteins, for example glycanase, may also be localized on the surface of the stigma to affect pollen-stigma interactions or functions (see FIG. 18).

2 Permitting Hybrid Seed Production by Preventing Self-Pollination.

Heterosis (hybrid vigour) corresponds to the increase in productivity and vigour that results from the genetic differences in parental lines. The advantage of growing hybrid crop varieties becomes evident when the benefits from the yield increase due to heterosis significantly outweigh the cost of seed production. Values reported for heterosis in *Brassica napus* seed yield have been greater than 50% (Grant I. and Beversdorf W. D., *Can. J Genet. Cytol*. 27: 472-478 (1985)). Although heterosis is observed in nearly every crop, the use of hybrids is mostly limited to crops for which there is an economically viable and effective means of pollination control. Many major crops, such as Canola, have small bisexual flowers that render manual emasculation impractical and thus hybrids cannot be produced commercially without using methods of interfering with pollen development and causing male sterility (Williams M. E., *TIBTECH* 13: 344-349 (1995)). Cytoplasmic male sterility (CMS) has been used for this purpose in oilseed rape, but this approach suffers from the breakdown of sterility in certain environments and from undesirable agronomic traits linked to the restorer genes (Feistritzer, W. P. and Kelly, A. F., (eds) *Hybrid Seed Production of Selected Cereal Oil and Vegetable Crops*, FAO (1987)). Genetically engineered nuclear-encoded male sterility may represent a viable alternative approach for pollination control in crops such as Canola (Stefansson, B. R. and Downey, R. K. in: Harvest of Gold: *The History of Field Crop Breeding in Canada*, Slinkard, A. E. and Knott, D. R. (Eds) Saskatoon: University Extension Press (1995)).

Several stages of plant reproduction including gamete development, pollination and fertilization depend on both gametophytic and sporophytic gene expression. Male or female sterility can result from mutations disrupting normal gene expression in haploid (eg. pollen) or diploid cells (eg.

tapeturm) throughout these developmental stages. Examples of molecular approaches used successfully to generate transgenic male sterile plants have been reported. Such approaches can involve the use of cytotoxic genes (Mariani, C., De Beuckeleer, M., Truettner, J. Leemans, J., Goldberg, R. B. *Nature* 347: 737-741 (1990); Koltunow, A. M., Truettner, J., Cox, K. H., Wallroth, M., Goldberg, R. B. *Plant Cell* 2: 1201-1224 (1990)), antisense versions of essential pollen genes (Muschietti, J., Dircks, L., Vancanney, G., McCormick, S. *Plant J* 6: 321-338 (1994); Xu, H., Knox, R. B., Taylor, P. E., Singh, M. B. *Proc. Natl. Acad. Sci.* USA 92: 2106-2110 (1995)) or genes encoding enzymes involved in pollen development (Worrall, D., Hird, D. L., Hodge, R., Paul, W., Draper, J., Scott, R. *Plant Cell* 4: 759-771 (1992)). These approaches have been the subject of patent applications such as WO 90/08828 and WO 92/18625. However, none of these approaches are aimed at modifying the protein composition of the microspore/pollen coat or the interactions of these proteins.

Figure 13:
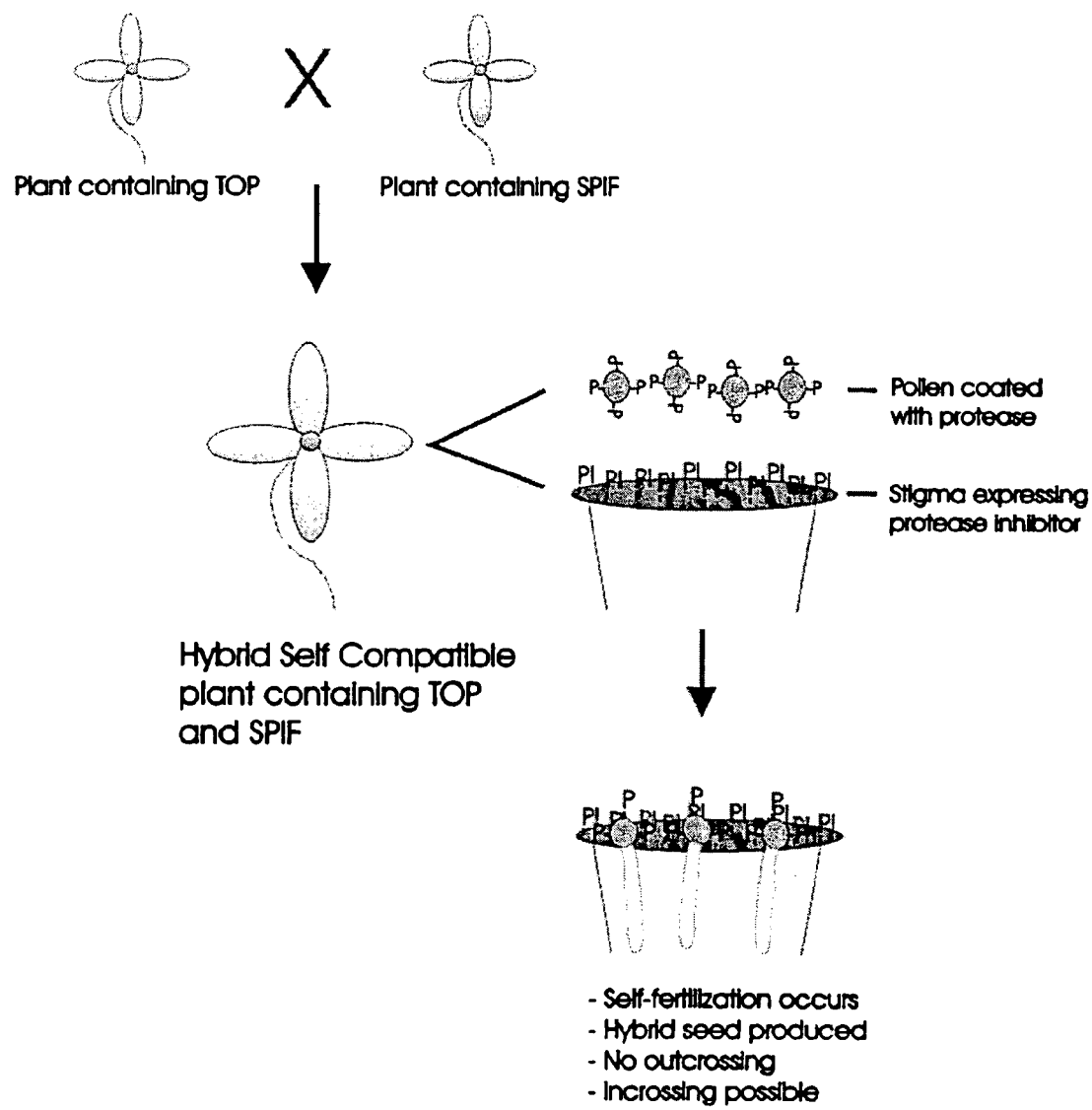
FIG. 13 shows a schematic representation illustrating an example of the pollen, stigma and their interaction in a hybrid self-compatible plant containing TOP, a tapetal oleosin-like/protease fusion and SPIF, a stigma protein/protease inhibitor fusion.
Figure 14:
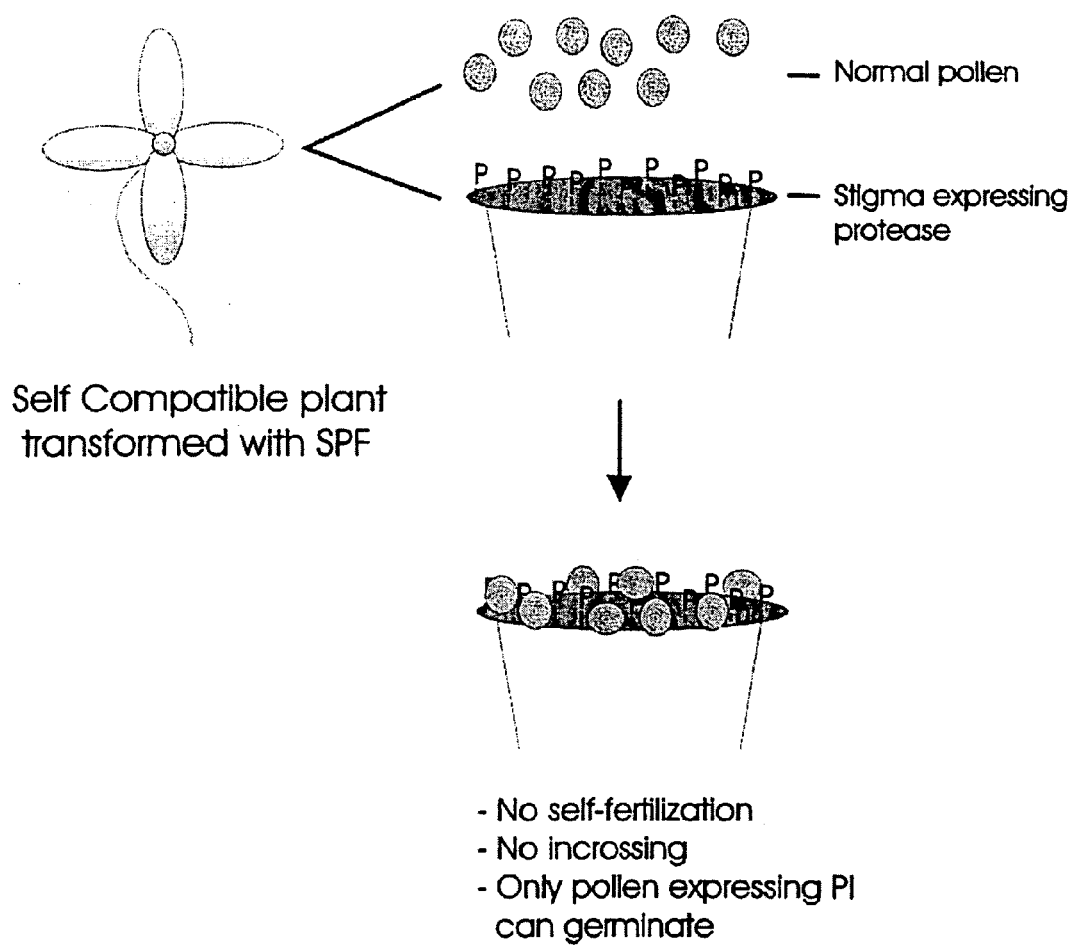
FIG. 14 shows a schematic representation illustrating an example of the pollen, stigma and their interaction in a self-compatible plant expressing SPF, a stigma protein/protease fusion.
Figure 15:
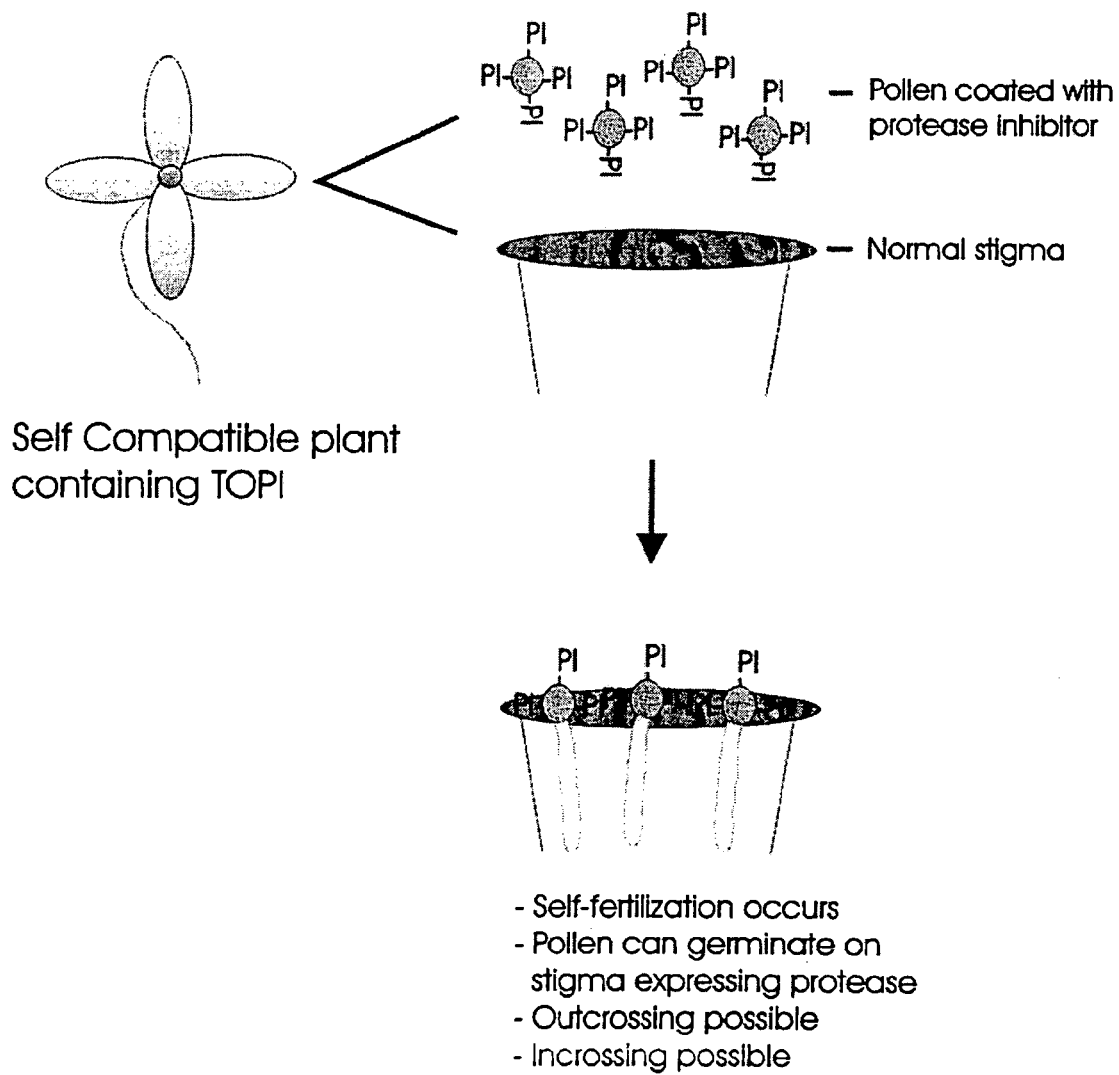
FIG. 15 shows a schematic representation illustrating an example of the pollen, stigma and their interaction in a self-compatible plant expressing TOPI, a tapetal oleosin-like/protease inhibitor fusion.
Figure 16:
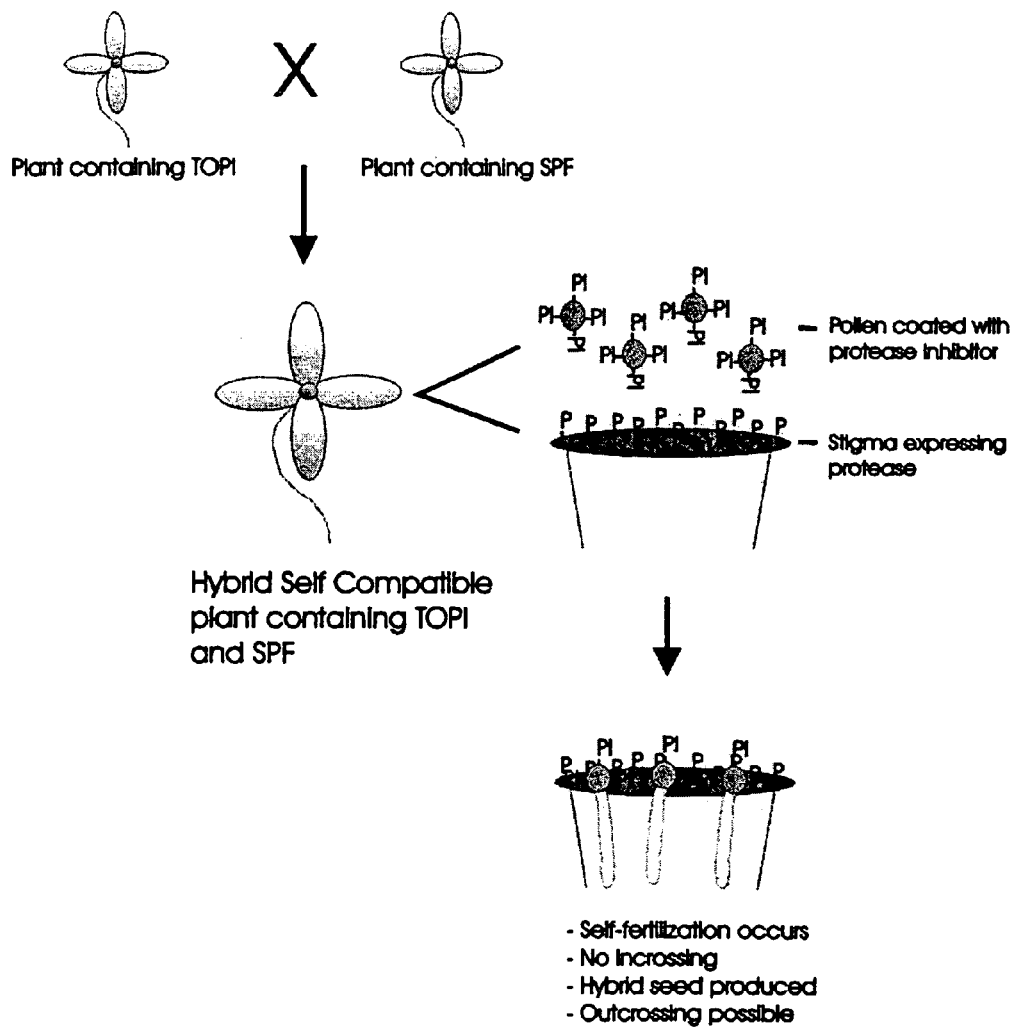
FIG. 16 shows a schematic representation illustrating an example of the pollen, stigma and their interaction in a hybrid self-compatible plant containing TOPI, a tapetal oleosin-like/protease inhibitor fusion and SPF, a stigma protein/protease fusion.
Figure 17:
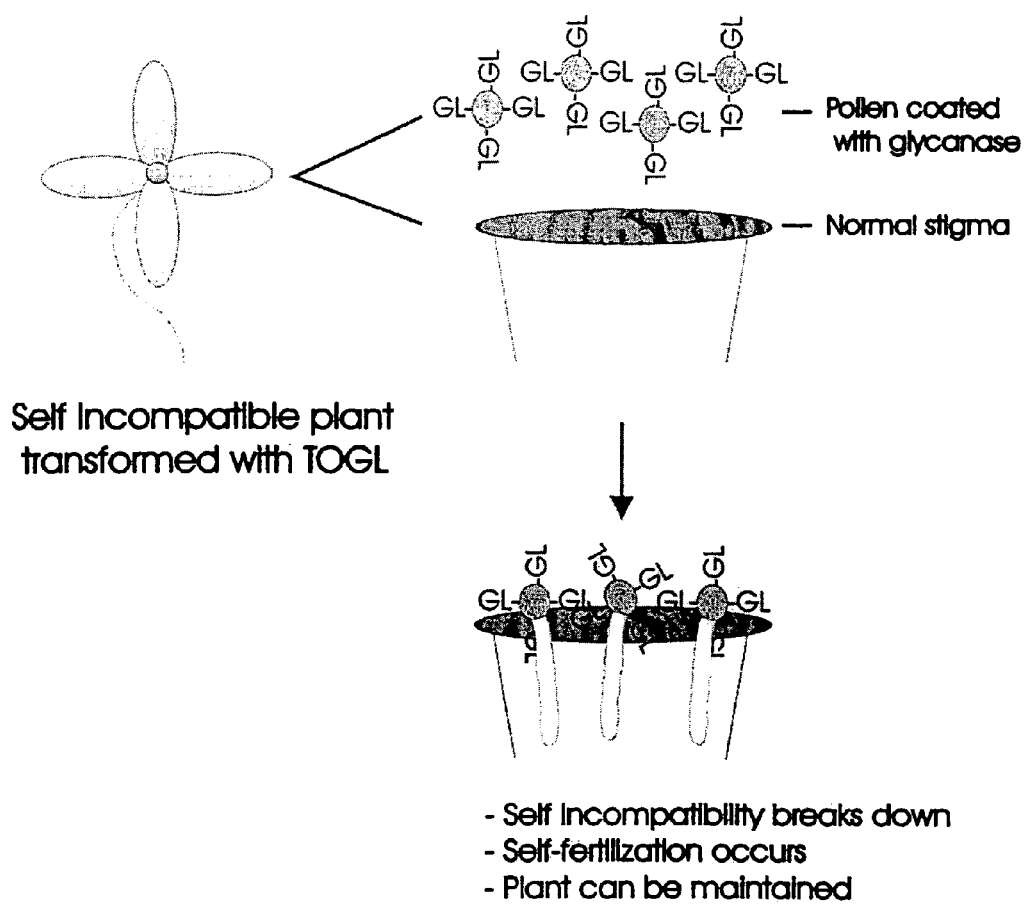
FIG. 17 shows a schematic representation illustrating an example of the pollen, stigma and their interaction in a self-incompatible plant expressing TOGL, a tapetal oleosin-like/glycanase fusion.
Figure 18:
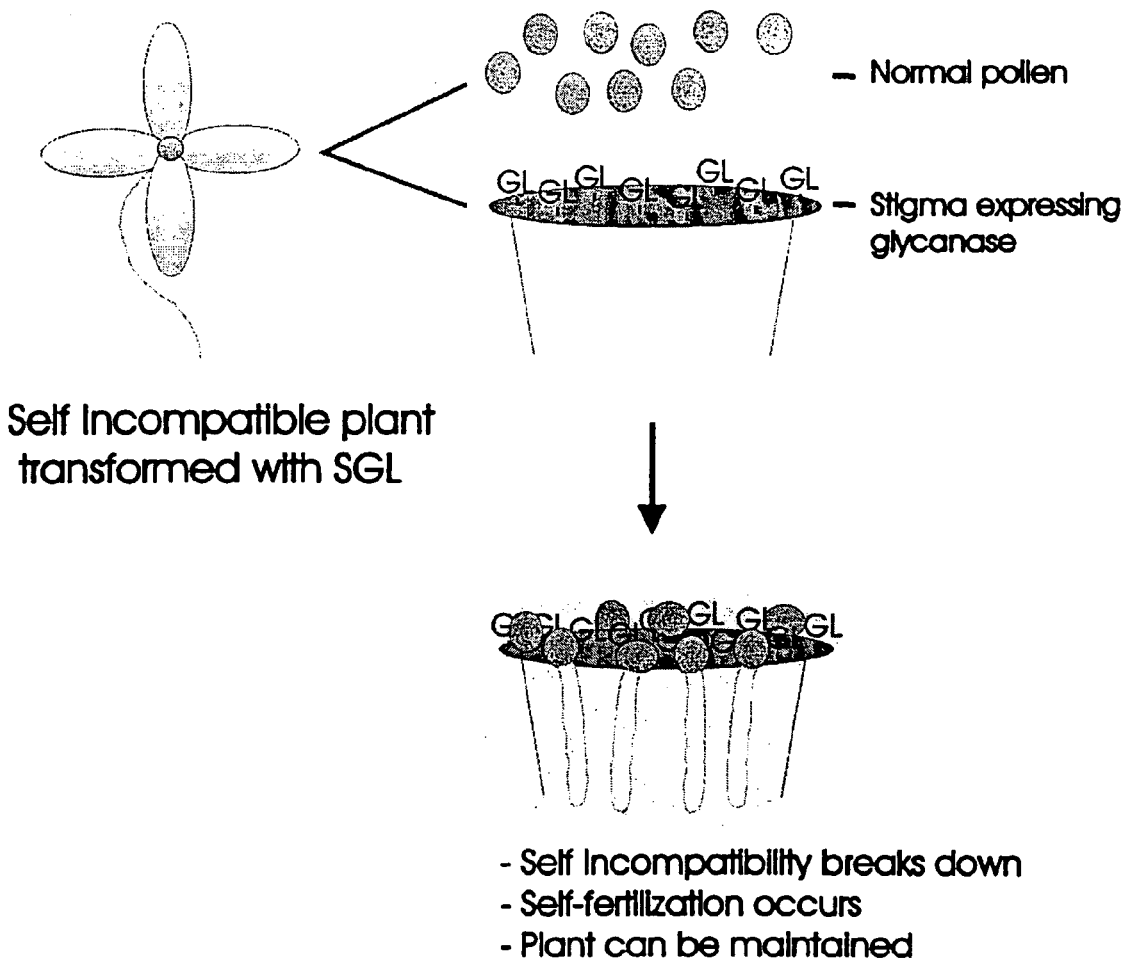
FIG. 18 shows a schematic representation illustrating an example of the pollen, stigma and their interaction in a self-incompatible plant expressing SGL, a stigma protein/glycanase fusion.
Figure 19A:
FIG. 19 shows in vitro germination of tobacco pollen after 3 h incubation in either casein, FIG. 19A, papain FIG. 19B or cycloheximide FIG. 19C.
Figure 19B:
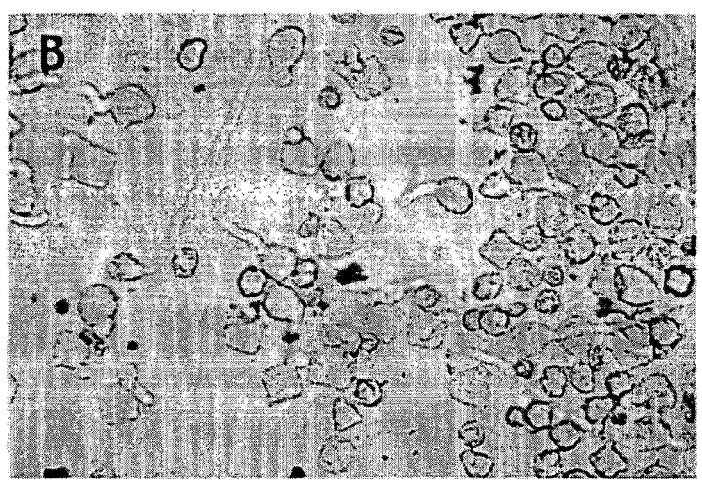
Figure 19C:
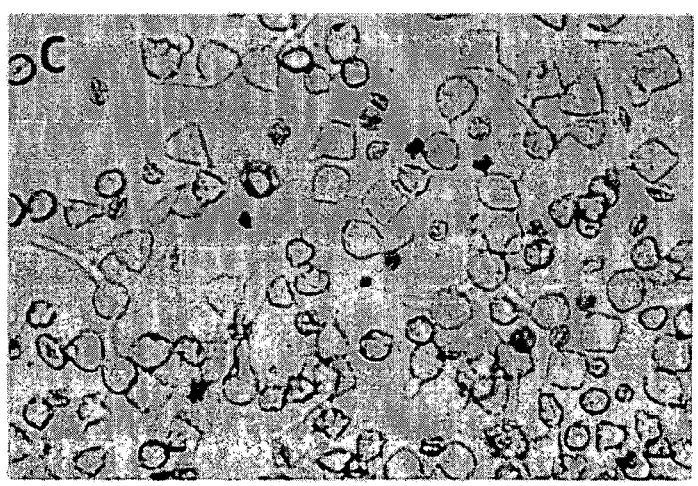

The targeting to the microspore/pollen coat of proteases, antigens, enzymes, inhibitors, ligands, or peptide(s) which interact with endogenous or supplemented stigma constituents (eg. stigma-expressed protease inhibitors, antibodies, receptors, protein binding polypeptides, proteolytic enzymes) modulate the activity of the microspore/pollen coat or'stigma (see FIGS. 13 and 16). This approach modifies self-compatibility or self-incompatibility, or prevents out-crossing (cross-pollination) and results in a "lock and key mechanism" for controlling pollination since only specific pollen germinate on specific stigmas. This lock and key mechanism may function either within the same plant or on separate plants. For example, which is not to be considered limiting, a male plant transformed with the Sta 41-9/cysteine protease from Sitophilus, (Matsumoto, I., Emori, Y., Abe, K, Arai, S. *J. Biochem.* 121: 464-476 (1997)) fusion construct will not self-pollinate, however, the pollen will germinate on a female plant that has been transformed so that the stigma expresses a specific inhibitor, the *Onchocerca* cysteine protease inhibitor gene (Lustigman, S., Brotman, B., Huima, T., Prince, A. M. *Mol. Biochem. Parasitol.* 45: 65-76 (1991)). The resulting seed of such a cross is hybrid and this represents a novel molecular approach to hybrid seed production. However, as would be evident to one of skill in the art, other protein/protein or protein/substrate interactions such as, but not limited to, protease/inhibitor, or activator/repressor, or receptor/ligand, or nuclease/inhibitor combinations may be used in this application. Maintaining either parental line is possible through the use of exogenously applied moderators, such as protease inhibitor solutions as required.

This approach can also be used to prevent out-crossing (cross-pollination). In this example, the same plant has both the pollen coat protease and a stigmatic inhibitor of the protease thereby allowing self-fertilization (FIG. 13). Pollen grains with the protease will be unable to germinate on any other plant. Furthermore, the reverse approach is feasible, plants could be generated that express the protease in the stigmna thus allowing only pollen with the specific protease inhibitor to germinate (FIG. 16). The utility of these approaches is the control of pollen flow among transgenic cultivars in plant species prone to outcrossing for eg. Canola. This may help diminish environmental concerns with respect to the release of transgenic plants, and may serve to reduce the risk of outcrossing among different transgenic lines, or cultivars.

Figure 29:
FIG. 29 shows a schematic representation of the construction of plant transformation vector TOS13-1 (Example 23; SEQ ID NO:39), a *Brassica napus* tapetal oleosin-like STA 41-9/*B. oleracea* SCR13 translational fusion.

This approach can also be used to modify self-compatibility or self-incompatibility for example when a self-incompatible plant contains an introduced S-locus cysteine rich (SCR) protein fused translationally to STA 41-9 (FIG. 29). If the endogenous S-haplotype is recessive to that of the introduced SCR, then self-incompatibility will be reduced or eliminated. If the endogenous S-haplotype is co-dominant to that of the introduced SCR, then a new S-haplotype specificity will be conferred on the pollen grain.

It is also contemplated that localization of a tapetal oleosin-like/anti-S-locus glycoprotein antibody fusion to the pollen coat could be used to disrupt normal pollen or pistil development. For example, an antibody to a S-locus glycoprotein could be raised and the immunoglobulin heavy chain and light chain variable regions fused into a single chain antibody fragment (ScFv). This fragment could be cloned and expressed on the pollen coat as described in Examples 1-3. When expressed on the pollen coat of a self-incompatible *Brassica* species for example, this antibody could interfere with the normal interactions with the stigma and abolish self-incompatibility. Other examples of polypeptides that could also disrupt or improve normal pollen or pistil development include: lectins such as avidin, inhibitor peptides obtained by affinity screening and arabinogalactan proteins (Gerster, J., Allard, S., Robert, L. S. *Plant Physiol.* 110: 1231-1237 (1996)).

3. Targeting Proteins or Peptides to the Pollen Coat for the Purposes of Peptide Display, for Protein Production and Utilization.

The display of a protein on the surface of a pollen grain would permit a ready source of the protein for further purification or for utilization, for example as an immobilized enzyme. It is conceived that the construct employed for protein production further comprises a site that permits cleavage of the protein from the rest of the fusion protein. Such a site may be a proteolytic site and susceptible to cleavage using a protease, or a site susceptible to chemical cleavage. Proteins or peptides produced in plants have the advantage of being properly glycosylated as opposed to prokaryotic expression systems. Any peptide that could be produced by this method may be selected for use in this application, including therapeutic, or nutritive peptides such as leptin or any other useful polypeptide such as avidin, interleukin, interferon etc.

Immobilized enzymes may also be prepared using the method of this invention. For example, the enzyme β-glucuronidase (GUS) when targeted to the pollen coat could be utilized as an immobilized enzyme. Other examples of enzymes which could be attached to the pollen coat include invertase, xylanase, β-1,3-glucanase, cysteine protease (*Sitophilus*), cysteine protease inhibitor (*Onchocerca*), oxidases, chitinases, invertases, endo-β-1,4-xylanases, callases, triacylglycerol lipases, phytases, glucan 1,3 β-glucosidases, endo 1,3-1,4β-glycanases, N-glycosidases, trypsin inhibitors, caspases (e.g. ICE cysteine proteases), aspartic protease lactases (intestinal), cellulases, xylanases, fructosyl amino acid oxidases, polygalacturonidases, pectate lyases, pectin methylesterases, chalcone synthases, alginate lyases, D-amino acid oxidases, β-glucuronidase.

Tapetal oleosin-like protein fusions may be used to produce, utilize or purify recombinant polypeptides. For example, the peptide tripticin can be produced on the surface of pollen and used directly as a bacteriostatic agent. Alternatively, the recombinant peptide can be proteolytically cleaved by introducing a cleavage site, such as the one used by thrombin, between the tapetal oleosin-like protein and the peptide of interest. Other peptides which could be produced in this way include, for example, leptin fragment, lectin (e.g.

avidin), arabinogalactans, canine parvovirus coat protein, thaumatin, Pin-I and Pin-II, protease inhibitors.

4. Antigen Delivery for Antibody Production.

To generate anti-peptide or anti-protein antibodies, the peptides are often prepared by chemical synthesis using solid phase techniques (Merrifield, R. *Science* 85: 2149-2154 (1963)) and coupled to a carrier. Since many small peptides (haptens) are not highly immunogenic, they require a means of increasing their antigenicity such as chemical coupling to keyhole limpet haemocyanin (KLH), or bovine serum albumin (BSA). By expressing a peptide on the surface of, or within pollen grains, these peptides can be released or presented directly to the animal immune system. The benefits include multiple copies of the antigen displayed on the surface of each pollen grain, the elimination of chemical coupling to carrier molecules, the production of large quantities of pollen and therefore antigen, and the possibility to administer the immunogen orally or. nasally, and therefore stimulate the mucosal immune system. The large size of the pollen grain may also alleviate the need for adjuvants and therefore be useful in immunization.

This approach is also an economical means of producing and presenting oral vaccines and therapeutic agents, since plants are not known to be contaminated with any animal viruses or pathogens. Recombinant proteins and therapeutics may be expressed in transgenic plants and packaged on intact pollen grains with little processing or purification in some cases. Irradiation of pollen grains prior to administration or use could eliminate the possibility of pollen escape.

Antigens for antibody or vaccine production may also be prepared using the method of this invention. For example, the antigen or vaccine could be fused to the tapetal oleosin-like protein and pollen coated with this fusion protein could be administered for example: intradermally, intramuscularly, intraperitoneally, intravenously, subcutaneously and nasally (nasal spray). Any protein or peptide now used for the production of vaccines could be utilized in this way, for example canine parvovirus (Dalsgaard, K., Uttenthal, A., Jones, T., Xu, F., Merryweather, A., Hamilton, W., Langeveld, J., Boshuizen, R., Kamstrup, S., Lomonossoff, G., Porta, C., Vela, C., Casal, I., Meloen, R., Rodgers, P. *Nature Biotech.* 15: 248-252 (1997)).

This approach can also be used to raise antibodies to poorly immunogenic antigens such as small peptides due to the method of presentation on the pollen grain.

5. Pollen Coat of Protein(s) or Peptide(s) for Animal Consumption.

Pollen is consumed by humans for its potential health benefits. Pollen is also consumed as a component of certain foods such as broccoli. Targeting novel proteins and/or peptides to the pollen coat could enhance these health benefits or add value to food. For example, value-added components that can be expressed on the surface of pollen grains include sweeteners (eg. thaumatin, brazzein, monellin) to increase palatability, peptides beneficial to human health (eg. antibiotics, hormones such as endorphins, enzymes such as lactase, peptides high in essential amino acids). Transgenic plants producing pollen with these novel characteristics can be planted in a greenhouse or similarly confined growth environments where pollen can be collected manually or by using bees and hive pollen traps.

6. Treatment or Control of Insect Populations.

Beneficial insects such as honeybees can be beneficially treated by providing transgenic pollen comprising antibiotics or food supplements (eg. synthetic proteins or peptides rich in insect-essential amino acids, especially the aromatic amino acids). The treatment of harmful, destructive or phytophagous insects such as pollen beetles with antifeedants or antibiotics (protease inhibitors, Bt toxins, lectins) represents a novel and efficient control method of these insects. Examples of protease inhibitors that may be used in this manner include the serine class of protease inhibitors, Pin-I and Pin-II, (Johnson, R., Narvaez, J., An, G., Ryan C. *Proc. Nat. Acad. Sci.* USA 86: 9871-9875 (1989)) and cysteine protease inhibitors such as onchocystatin (OV7; Lustigman, S., Brotman, B., Huima, T., Prince, A. M. *Mol. Biochem. Parasitol.* 45: 65-76 (1991)). The effects of the inhibitors can be measured by monitoring weight loss of insects feeding on modified pollen. An alternative strategy is to employ pollen coated with protease inhibitor inducing factors (PIIF) that induce the systemic induction of protease inhibitors and defensive compounds in distal organs of plants (McGurl, B. F., Pearce, G., Orozco-Cardenas, M., Ryan, C. A. *Science* 255: 1570-1573 (1992)). In a similar manner, pollen coat targeting of insecticidal toxins from *Bacillus thuringiensis* (Bt toxins) in plants such as maize (*Zea mays*) which sheds high quantities of pollen over foliar, silk, and floral surfaces represents a novel method to deliver insecticidal proteins. This method of delivery is also useful for the dissemination of antifungal, antiviral, and antibacterial peptides and proteins over the vegetative and floral surfaces of plants. Such proteins could consist of pectinases, oxidases and chitinases.

7. Alleviation of Allergenic Responses.

Many pollen coat proteins have been implicated as potential allergens for eg. pathogenesis-related proteins, cysteine-rich proteins of unknown function and cell wall associated enzymes (Knox, R. B. and Suphogliu, C. *Sex. Plant Reprod.* 9: 318-323 (1996)). Therefore, targeting proteins that bind, interact, inactivate or mask these allergenic proteins of the pollen coat could potentially alleviate allergic reactions. Examples of proteins that could be used to interfere with the allergenic proteins include antibodies specific to an allergenic protein, binding proteins (for eg. selected by phage display), protease inhibitors, endopolygalacturonase-inhibiting protein (PGIP; Toubart, P., Desiderio, A., Salvi, G., Cervone, F., Daroda, L., De Lorenzo, G. *Plant J.* 2: 367-373 (1992)) or enzymes that would interfere or destroy the pollen allergen (eg. proteases). Such pollen could be used to de-sensitize allergic responses by repeated exposure to pollen grains with attenuated allergenicity. Pollen or fractions thereof could be collected from transgenic plants and administered directly as mentioned in example 4 above. Furthermore, transgenic plants producing pollen with reduced or non-allergenic properties could be made available, for example, for nursery stocks of cedars or birch.

The above description is not intended to limit the claimed invention in any manner, furthermore, the discussed combination of features might not be absolutely necessary for the inventive solution.

The present invention will be further illustrated in the following examples. These examples are for illustrative purposes only, and should not be used to limit the scope of the present invention in any manner.

EXAMPLES

The following sequences are used in order to exemplify the present invention:

SEQ ID NO's: 1 and 2 are oligonucleotide sequence (KSB-3): TAG GTA CCG AGC TCG GGG GAT CC; (SEQ ID NO:1) corresponding to the plus strand of the KSB adapter, and oligonucleotide sequence (KSB-4): TAG GAT CCC CCG AGC TCG GTA CC (SEQ ID NO:2) corresponding to the minus strand of the KSB adapter (see Example 2).

SEQ ID NO:3 is the nucleotide sequence of the translational fusion in plasmid TOG-1 (see Example 2; FIG. 5A). This fusion consists of the 5' upstream and coding sequence from the *Brassica napus* genomic clone Sta 41 G(10) which encodes the Sta 41-9 tapetal oleosin-like protein fused to the *E. coli* β-glucuronidase coding region from plasmid pBI 101.1 (Clontech). The upstream region was shown to regulate tapetal-specific expression in transgenic *Brassica napus* plants (Hong, H. P., Ross, J. H. E., Gerster, J. L., Rigas, S., Datla, R. S. S., Hatzopoulos, P., Scoles, G., Keller, W., Murphy, D. J., Robert, L. S. *Plant Mol. Biol.* 34: 549-555 (1997b); U.S. patent application Ser. No. 08/595,937).

Figure 6:
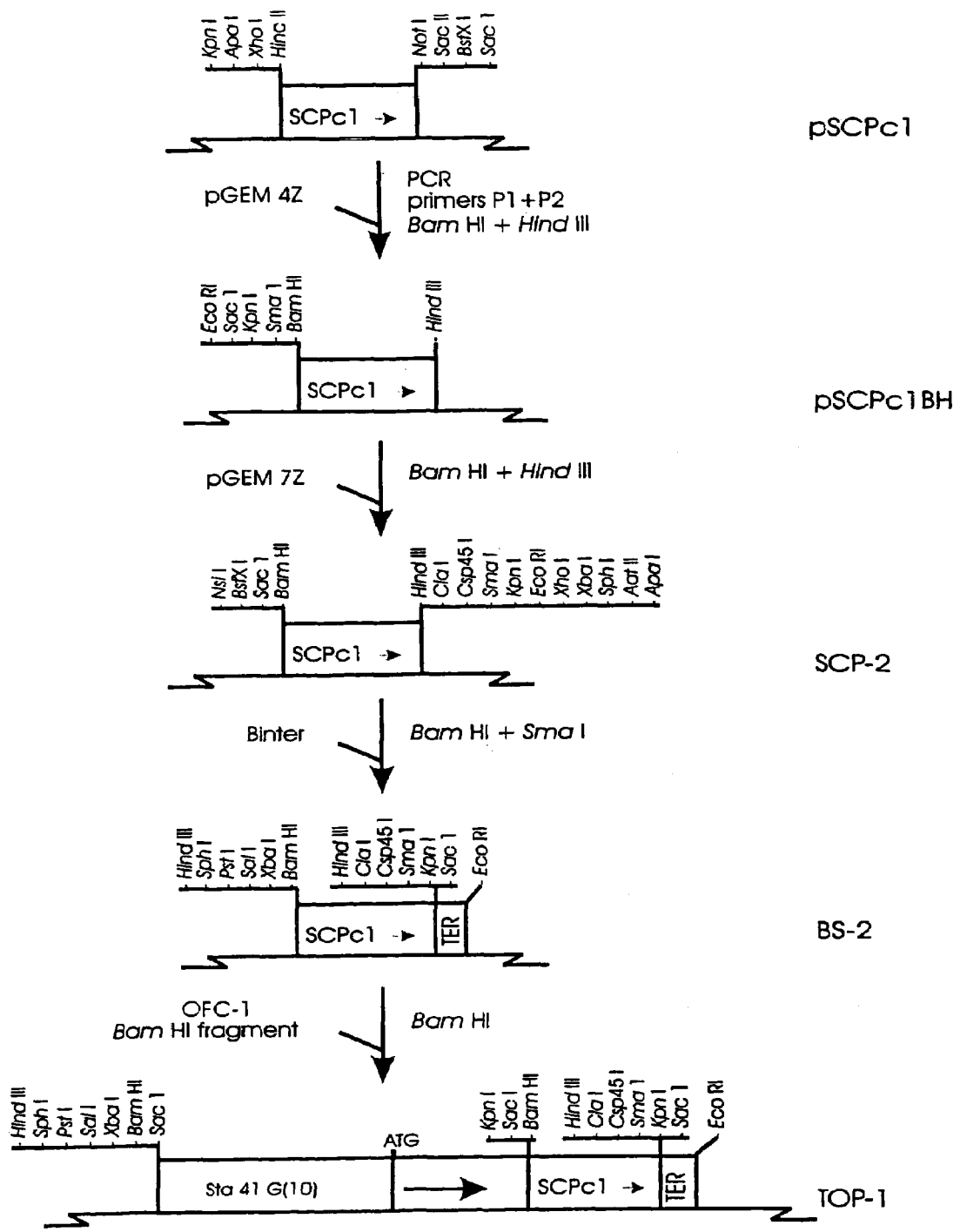
FIG. 6 shows a schematic representation of the construction of the plant transformation vector TOP-1, the *Brassica napus* tapetal oleosin-like Sta 41-9/*Sitophilus zeamais* SCPc1 protease translational fusion.

SEQ ID NO:4 is the nucleotide sequence of the translational fusion in plasmid TOP-1 (see Example 3, FIG. 6). This fusion consists of the 5' upstream and coding sequence from the *Brassica napus* genomic clone Sta 41 G(10) which encodes the Sta 41-9 tapetal oleosin-like protein fused to the *Sitophilus zeamais* SCPc1 protease coding region (Matsumoto, I., Emori, Y., Abe, K., Arai, S. *J. Biochem.* 121: 464-476 (1997)).

SEQ ID NO:5 is the nucleotide sequence of the translational fusion in plasmid TOPI-1 (see example 4; FIG. 7). This fusion consists of the 5' upstream and coding sequence from the *Brassica napus* genomic clone Sta 41 G(10) which encodes the Sta 41-9 tapetal oleosin-like protein fused to the *Onchocerca volvulus* protease inhibitor OV7 coding region (Lustigman, S., Brotman, B., Huima, T., Prince, A. M. *Mol. Biochem. Parasitol.* 45: 65-76 (1991)).

SEQ ID NO's: 6 and 7 are oligonucleotide sequence (BKX-1): TCG AGG GGA TCC GGT ACC TCT AGA (SEQ ID NO:6); corresponding to the plus strand of the BKX 12 adapter, and oligonucleotide sequence (BKX-2): TCG ATC TAG AGG TAC CGG ATC CCC (SEQ ID NO:7) corresponding to the minus strand of the BKX 12 adapter (see Example 5).

Figure 8:
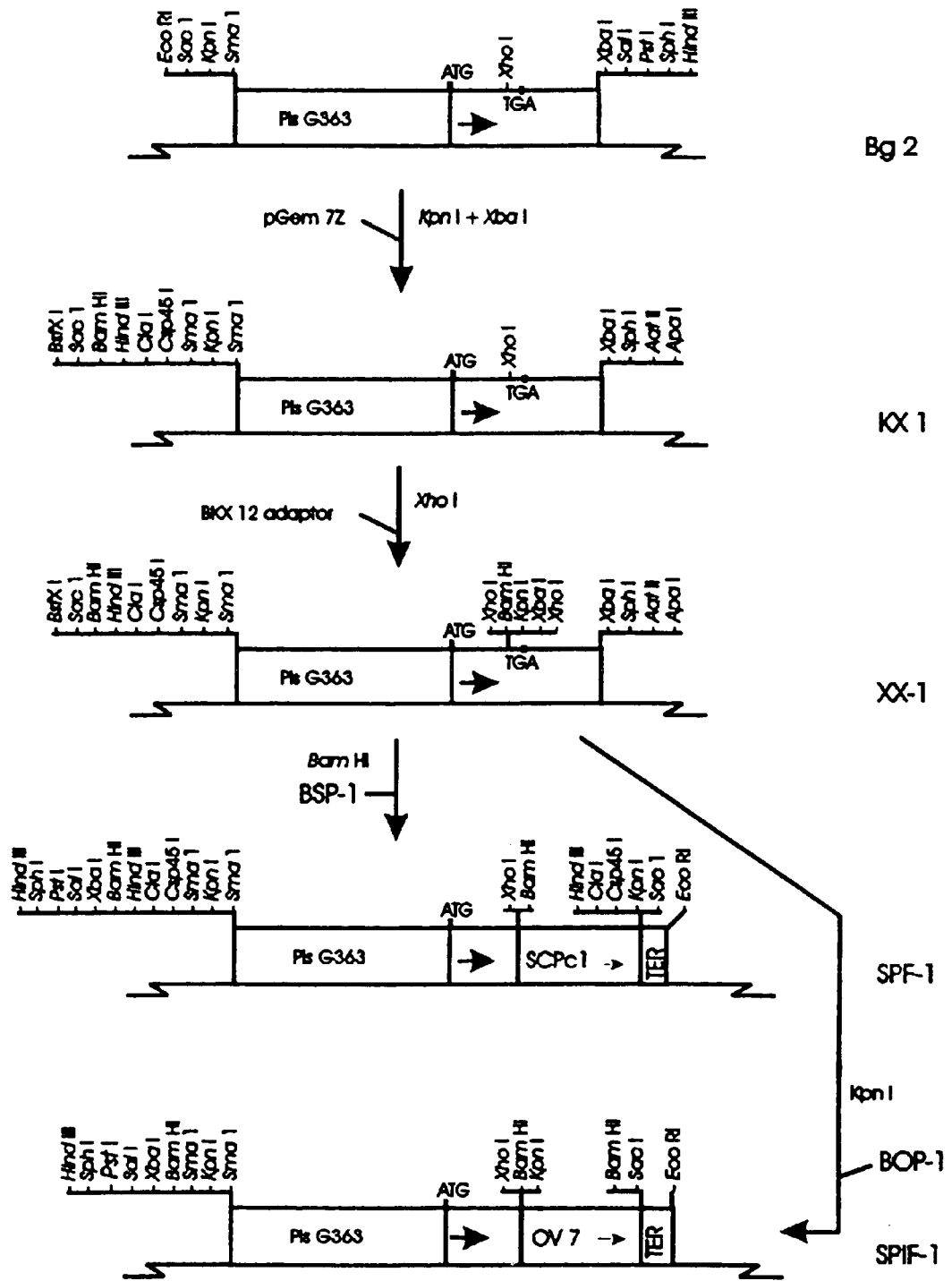
FIG. 8 shows schematic representation of the construction of plant transformation vectors SPF-1 containing the *Brassica napus* Pis G363/*Sitophilus zeamais* protease SCPc1 translational fusion and SPIF-1 containing the *Brassica napus* Pis G363/*Onchocerca volvulus* protease inhibitor OV7 translational fusion.

SEQ ID NO:8 is the nucleotide sequence of the translational fusion in plasmid SPF-1 (see Example 5, FIG. 8). This fusion consists of the 5' upstream and coding sequence from the *Brassica napus* genomic clone Pis G363 that encodes a gene highly expressed in the stigma fused to the *Sitophilus zeamais* protease SCPc1 coding region.

SEQ ID NO:9 is the nucleotide sequence of the translational fusion in plasmid SPIF-1 (see Example 6, FIG. 8). This fusion consists of the 5' upstream and coding sequence from the *Brassica napus* genomic clone Pis G363 that encodes a gene highly expressed in the stigma fused to the *Onchocerca volvulus* protease inhibitor OV7 coding region.

SEQ ID NO's: 10 and 11 are oligonucleotide sequence SLG26 (7): ATA GAG CTC CGA TGA AAG GCA TAA GAA (SEQ ID NO:10), and oligonucleotide sequence SLG 26 (8): TAT GGT ACC TTC TTC AGA AGA CAA AGT G (SEQ ID NO:11), see Example 7.

Figure 9:
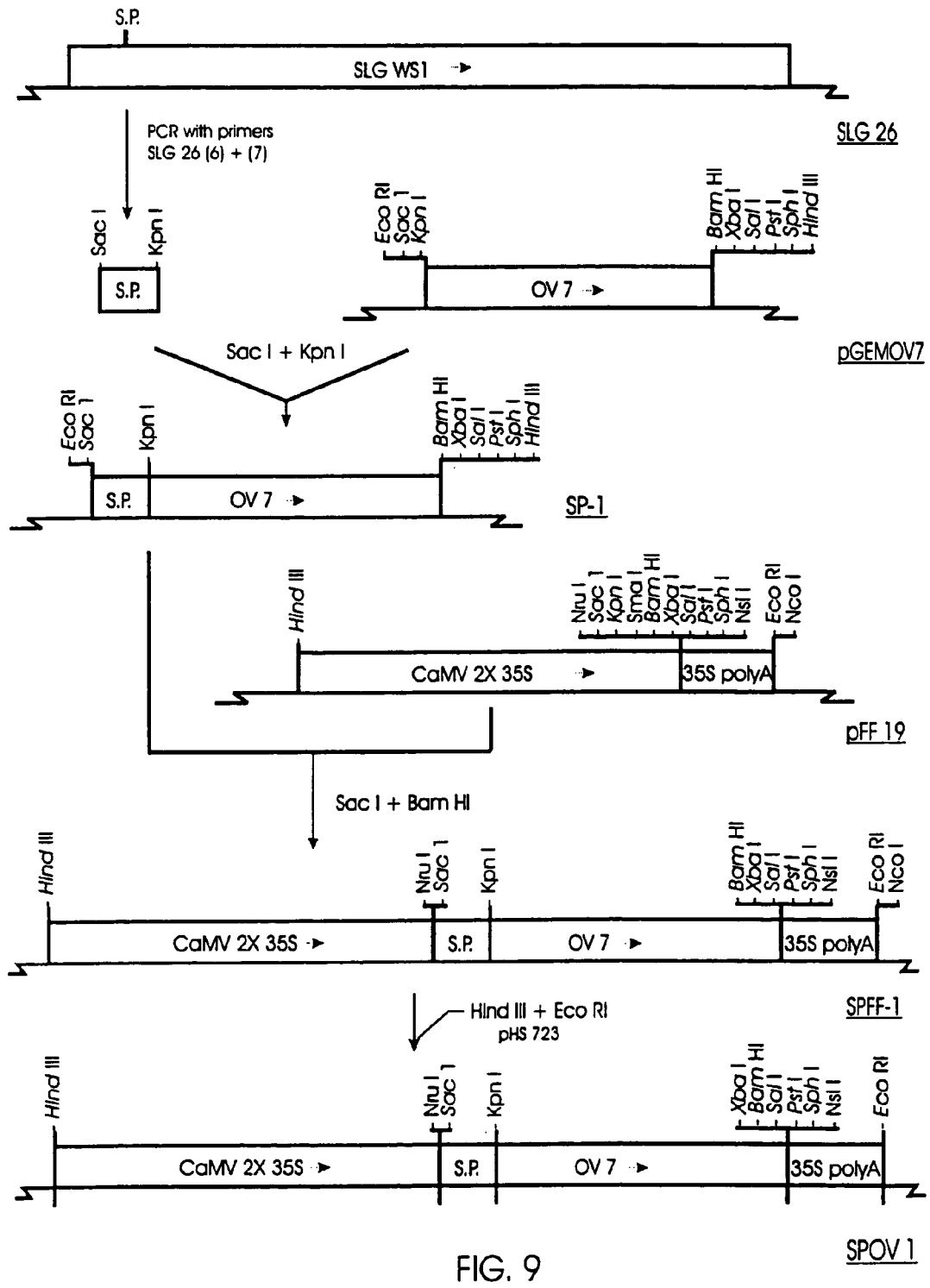
FIG. 9 shows a schematic representation of the construction of plant transformation vector SPOV-1 containing an enhanced CaMV35S promoter directing the expression of the *Brassica napus* SLG$_{WS1}$ signal peptide/*Onchocerca volvulus* protease inhibitor OV7 translational fusion.

SEQ ID NO:12 is the nucleotide sequence of the translational fusion in plasmid SPOV-1 (see Example 7, FIG. 9). This fusion consists of the CaMV double enhancer promoter fused to the partial coding region of *Brassica napus* cDNA clone SLC$_{WS1}$ including the signal peptide fused to the *Onchocerca volvulus* protease inhibitor OV7 coding region.

SEQ ID NO's: 13 and 14 are oligonucleotide sequence (EXK-1): CGA ATT CTC TAG AGG TAC CGC ATG (SEQ ID NO:13); corresponding to the plus strand of the EXK 12 adapter, and oligonucleotide sequence (EXK-2): CGG TAC CTC TAG AGA ATT CGC ATG (SEQ ID NO:14); corresponding to the minus strand of the EXK 12 adapter (see Example 8).

SEQ ID NO:15 is the nucleotide sequence of the translational fusion in plasmid POV-1 (see Example 8a). This fusion consists of the 5' upstream and the partial coding region including the signal peptide of *Brassica napus* genomic clone Sta 44G(2) which encodes a pollen-expressed polygalacturonase gene (Robert, L. S., Allard, S., Gerster, J. L., Cass, L., Simmonds, J. *Plant Mol. Biol.* 23: 1273-1278 (1993); Hong, H. P., Gerster, J. L., Datla, R. S. S., Albani, D., Scoles, G., Keller, W., Robert, L. S. *Plant Cell Rep.* 16: 373-378 (1997a); U.S. patent application Ser. No. 08/577,463) fused to the *Onchocerca volvulus* protease inhibitor OV7 coding region.

SEQ ID NO's: 16 and 17 are a forward primer (GUS-sense-1): GGA ATT CAC CGC GTC TTT GAT CGC (SEQ ID NO:16), and reverse primer (nos #2): GCG CGC GAT AAT TTA TCC (SEQ ID NO:17) that anneal to the GUS gene and nopaline synthase terminator, respectively (see Example 13).

SEQ ID NO's: 18 and 19 are primer (NptII-121): GGG CGC CCG GTT CTT TTT (SEQ ID NO:18) and primer (NptII-B): CAG CAA TAT CAC GGG TAG CCA ACG C (SEQ ID NO:19), see Example 13.

SEQ ID NO's: 20 and 21 are primers used for detection of the Sitophilus protease gene (see Example 3): forward primer (P1): GCG CGG ATC CTT GCC TGA TAC TGT TGA C: (SEQ ID NO:20) and reverse primer (P2): GCG CGA ATT CAA GCT TCT AAA CCA AAG GAT AAC TAG C (SEQ ID NO:21).

SEQ ID NO's: 22 and 23 are primers used for TOG-2 construction (see Example 17): (XK+): GAT CCT CTA GAG GTA CCG (SEQ ID NO:22) and (KX−): GAT CCG GTA CCT CTA GAG (SEQ ID NO:23).

SEQ ID NO:24 comprises the first 20 amino acid residues of the C-terminal domain of BnOlnB;4 (Sta 41-9), LGIPESIKPS NIIPESIKPS.

Figure 10:
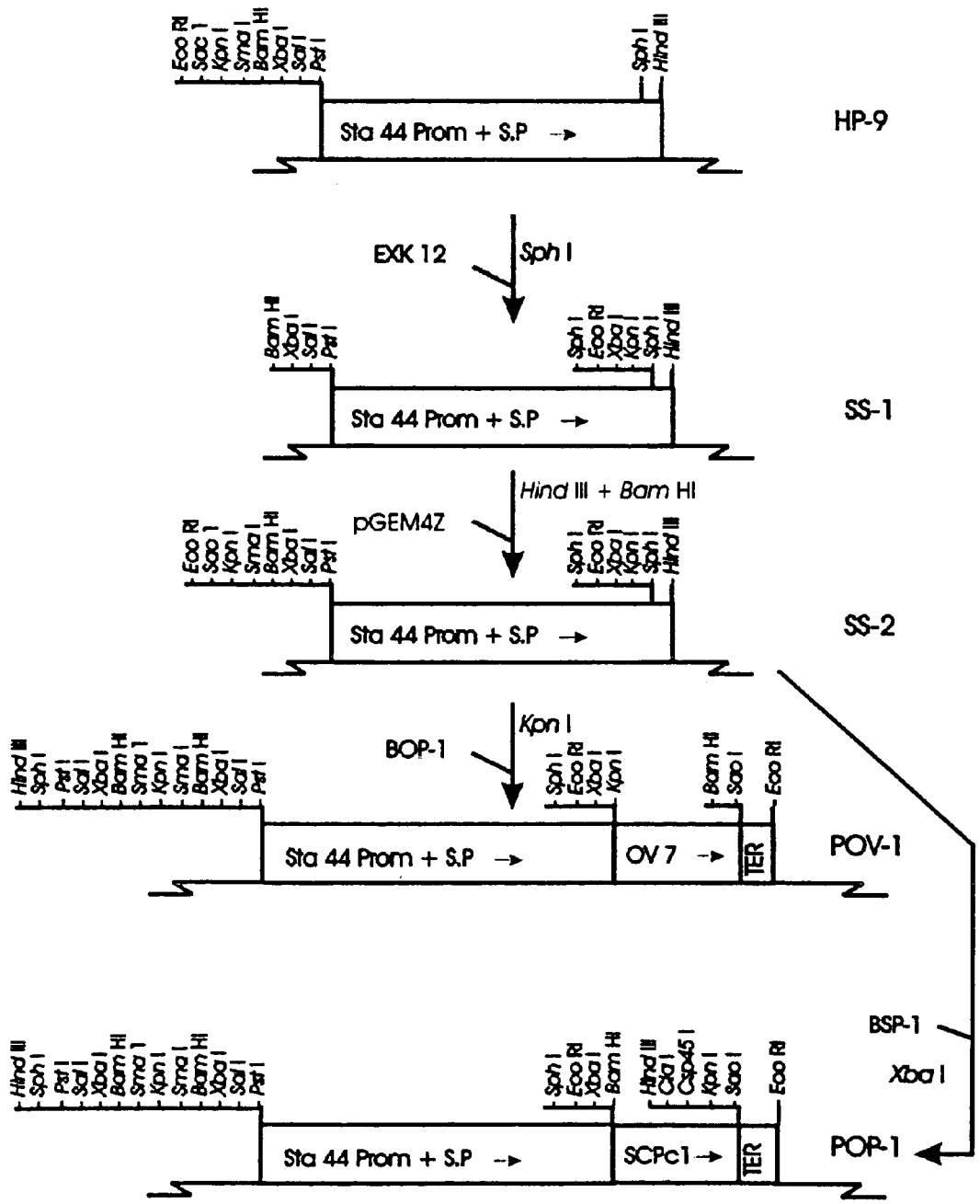
FIG. 10 shows a schematic representation of the construction of plant transformation vectors POV-1 containing the *Brassica napus* Sta44G(2)/*Onchocerca volvulus* protease inhibitor OV7 translational fusion, and POP-1 containing the *Brassica napus* Sta44G(2)/*Sitophilus zeamais* SCPc1 protease translational fusion.
Figure 11:
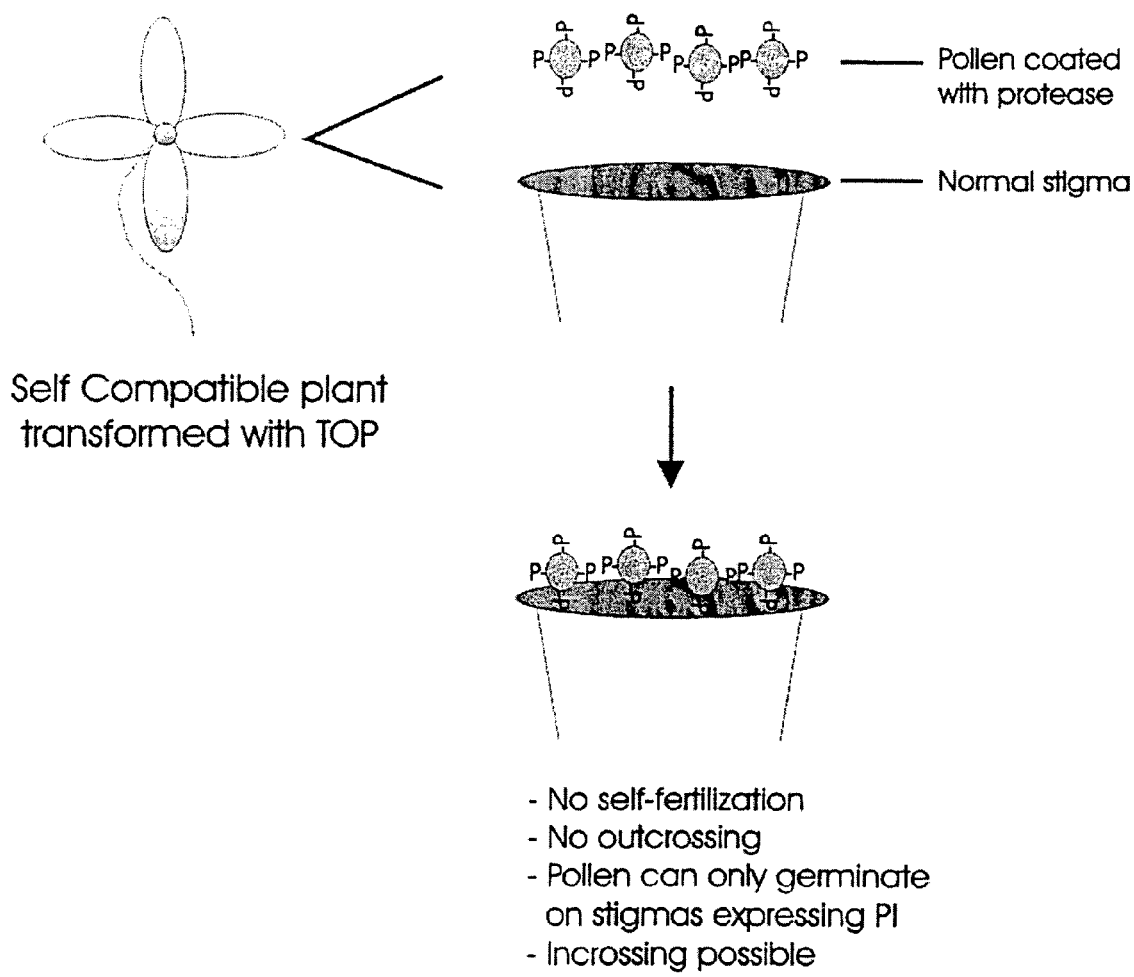
FIG. 11 shows a schematic representation illustrating an example of the pollen, stigma and their interaction in a self-compatible plant expressing TOP, a tapetal oleosin-like/protease fusion.
Figure 12:
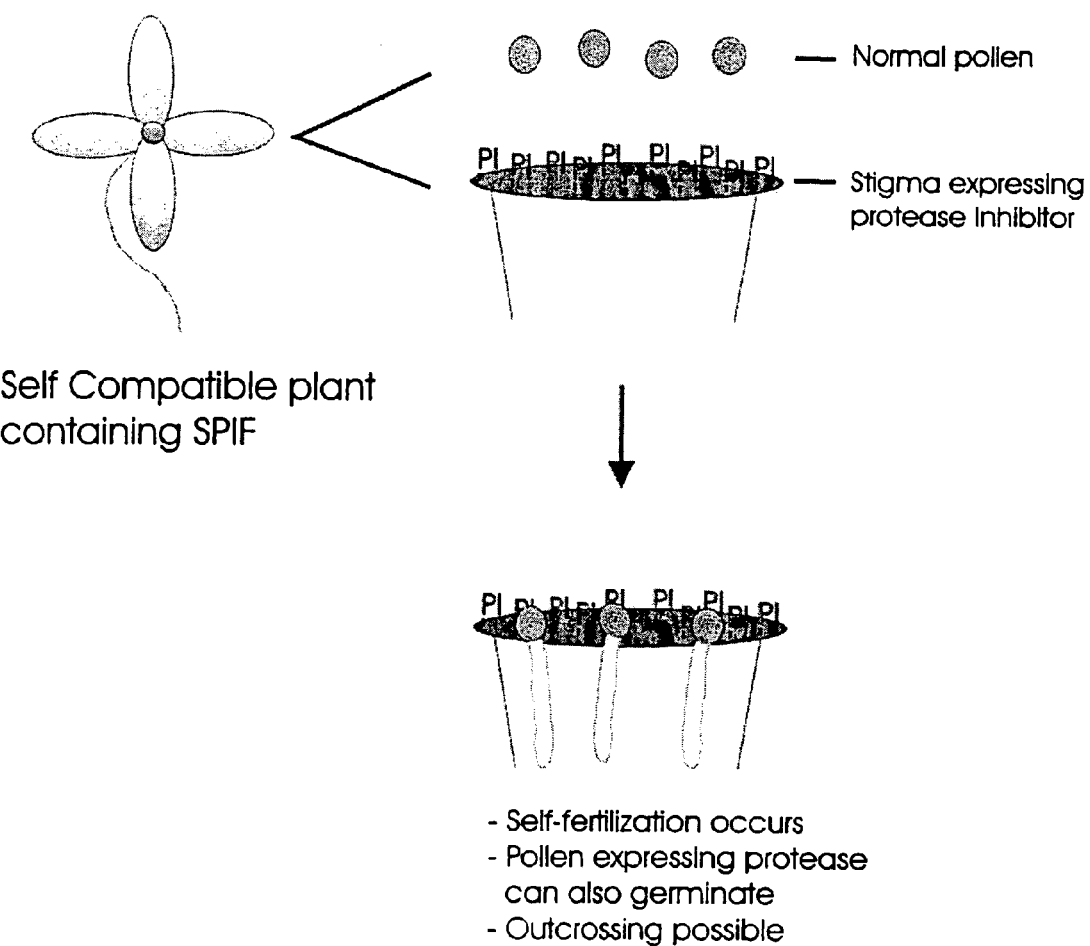
FIG. 12 shows a schematic representation illustrating an example of the pollen, stigma and their interaction in a self-compatible plant expressing SPIF, a stigma protein/protease inhibitor fusion.

SEQ ID NO:25: is the nucleotide sequence of the translational fusion in plasmid POP-1 (see Example 8; FIG. 10). This fusion consists of the 5' upstream and the partial coding region including the signal peptide of *Brassica napus* genomic clone Sta 44G(2) which encodes a pollen-expressed polygalacturonase gene (Robert, L. S., Allard, S., Gerster, J. L., Cass, L., Simmonds, J. *Plant Mol. Biol.* 23: 1273-1278 (1993); Hong, H. P., Gerster, J. L., Datla, R. S. S., Albani, D., Scoles, G., Keller, W., Robert, L. S. *Plant Cell Rep.* 16: 373-378 (1997a); U.S. patent application Ser. No. 08/577,463) fused to the *Sitophilus zeamais* protease SCPc1 coding region.

SEQ ID NO's: 26 and 27 are primer pairs for TOG-3 construction (see Example 22): (Sta 41 ATG): CTA GGA TCC AGA CCA CAC AAC TCC TTC (SEQ ID NO:26) and (Sta 41-13R): GAGA GGATTC CAA CAG AGA TAG GGA TGG C (SEQ ID NO:27).

SEQ ID NO:28 is the nucleotide sequence of the translational fusion in plasmid TOG-3 (see Example 22; FIG. 5d). This fusion consists of the 5' upstream and a partial coding sequence from the *Brassica napus* genomic clone Sta 41 G(10) which encodes the Sta 41-9 tapetal oleosin-like protein fused to the *E. coli* β-glucuronidase coding region.

SEQ ID NO's29 and 30: primer pairs for GUS amplification (Example 22): primers (GUS-6F): TAG AGG ATC CCC GGG TGG TCA GTC (SEQ ID NO:29) and (GUS-7R): GAG AGA GCT CAG ATC TTT GTT TGC CTC CCT GCT GCG GT (SEQ ID NO:30).

SEQ ID NO's: 31 and 32: primer pairs for amplifying Sta 41-9 (Example 22): primers (STA 41-14): GAG AAG ATC TAT GAG AAA CGA AAT TCA AAA CGA AAC (SEQ ID NO:31) and (STA 41-15R): GAG AGA GCT CAT ATG TGT TTA CCA CCA CTC CCA (SEQ ID NO:32).

SEQ ID NO:33: TOG-4 (see Example 22; FIG. 5E). This fusion consists of the 5' upstream sequence from the *Brassica napus* genomic clone Sta 41 G(10) which encodes the STA 41-9 tapetal oleosin-like protein to regulate the expression of the *E. coli* β-glucuronidase coding region fused upstream of the Sta 41-9 coding region.

SEQ ID NO's: 34-36: primers for SCR 13 isolation (see Example 23): primers (GAGA T18-2): GAG AGA GAG AGA CTC GAG TTT TTT TTT TTT TTT TTT A/C/G (SEQ ID NO:34), (SCR13-3F): AAC AAG AAT TTG CTG CGA GTA AAA GAG AAT (SEQ ID NO:35) and (SCR13-4R): ATT TTG ACT AAG ACG AAT TTT GGA ATG ATT (SEQ ID NO:36).

SEQ ID NO's: 37 and 38: primers to amplify the coding region corresponding to the mature SCR protein (see Example 23): primers (SCR13-7F): GAG AAT TAA TAA ATC TGA TGA TGC CTT GTG G (SEQ ID NO:37) and (SCR13-8R): CTG CAG AAC CAA CGC GTT GGA GCT CCT AAC ACA ATT TAC AAT CAC AAG (SEQ ID NO:38).

SEQ ID NO:39: TOS13-1 (Example 23, FIG. 29). This fusion consists of the 5' upstream and coding sequence from the *Brassica napus* genomic clone Sta 41 G(10) which encodes the Sta 41-9 tapetal oleosin-like protein fused to the coding region of SCR 13.

SEQ ID NO's: 40-42: primers for amplifying the *A. thaliana* Atgrp 19 gene (Example 24, FIG. 5C-2): primers (Atgrp19-F1): AAT GGT ACC GAA TAA GTG AGT CTT GCA CAC TGG (SEQ ID NO:40), (Atgrp19-R1): TAT GGA TCC GAC GCC GGA ACC TGC TGG GTT AG (SEQ ID NO:41) and (Atgrp19-R2): TAT AGA TCT ACC ATG ACG CCG GAA CCT GCT GGG TTA G (SEQ ID NO:42).

SEQ ID NO:43: is the nucleotide sequence of the translational fusion in plasmid TOG-2 (see Example 17; FIG. 5b). This fusion consists of the 5' upstream and coding sequence from the *Brassica napus* genomic clone Sta 41 G(10) which encodes the Sta 41-9 tapetal oleosin-like protein fused to the *E. coli* β-glucuronidase coding region from plasmid pBI 101.1 (Clontech).

SEQ ID NO:44: is the nucleotide sequence of the translational fusion in plasmid ATOG-3 (see Example 24; FIG. 5c-2). This translational fusion consists of the 5' upstream and coding sequence of the *Arabidopsis thaliana* Atgrp 19 oleosin-like gene fused to the *E. coli* β-glucuronidase coding sequence.

SEQ ID NO:45: is the nucleotide sequence of the translational fusion in plasmid ATOG-4+ (see Example 24; FIG. 5F). This fusion consists of the 5' upstream and coding sequence of the *Arabidopsis thaliana* Atgrp 19 oleosin-like gene fused to the *Staphylococcus* GUSPlus™ coding sequence.

SEQ ID NO's:46 and 47: primers for amplifying the *A. thaliana* exl 4 gene (Example 25, FIG. 30): primers: (Atexl 4-F1): ATA GGT ACC TTA ACA TTC TTG TAG TTA GGG C (SEQ ID NO:46) and (Atexl 4-R1): TAT CCA TGG CAA GGC CAT TCT TGA TAT CAT GG (SEQ ID NO:47).

Figure 30:
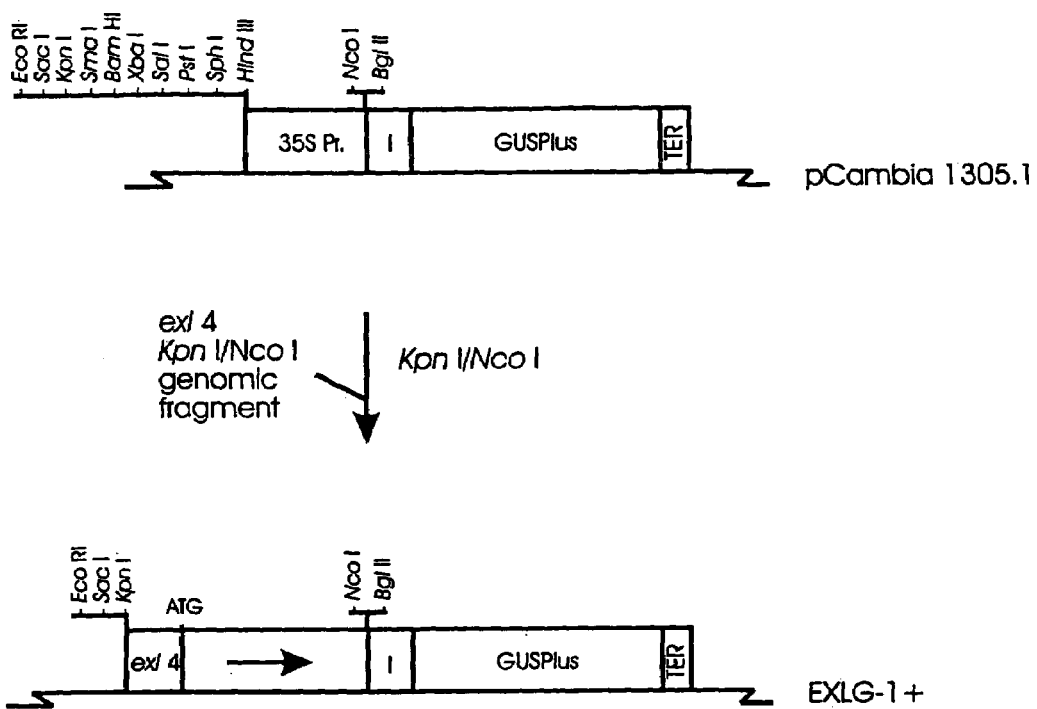
FIG. 30 shows a schematic representation of the construction of the plant transformation vector EXLG-1$^+$ (Example 25; SEQ ID NO:48), comprising an *Arabidopsis thaliana* oleosin-like EXL 4/*Staphylococcus* GUSPlus™ translational fusion.

SEQ ID NO:48: is the nucleotide sequence of the translational fusion in plasmid EXLG-1+ (Example 25, FIG. 30). This fusion consists of the 5' upstream and coding sequence of the *Arabidopsis thaliana* exl 4 extracellular lipase gene fused to the *Staphylococcus* GUSPlus™ coding sequence.

SEQ ID NO's:49-51: Primers for amplifying the *Brassica napus* Sta 44 gene (Example 26, FIGS. 31A and 31B): primers: (Sta44G2(2)): ATA GGT ACC GAC AGT ATA CAT AAT TTA GAG AGA G (SEQ ID NO:49). (Sta44-4 (2)): TAT GGA TCC CTC TTT GCC AGG AGC CTT GAC CAC (SEQ ID NO:50) and (Sta44-4(3)): TAT CCA TGG TCT CTT TGC CAG GAG CCT TGA CCA C (SEQ ID NO:51).

Example 1

Isolation of *Brassica napus* Tapetal Oleosin-Like Gene

The cDNA clones Sta 41-2 and Sta 41-9 encoding tapetal oleosin-like proteins were isolated by differential screening of a flower cDNA library from *Brassica napus* (Robert, L. S., Gerster, J. L., Allard, S., Cass, L., Simmonds, J., *Plant J.* 6:927-933 (1994a)). The genomic clone Sta 41G(10) corresponding to cDNA clone Sta 41-9 was also isolated and the region upstream of the coding region shown to direct expression of a marker gene to the tapetum of transgenic *Brassica napus* plants (Hong, H. P., Ross, J. H. E., Gerster, J. L., Rigas, S., Datla, R. S. S., Hatzopoulos, P., Scoles, G., Keller, W., Murphy, D., Robert, L. S. *Plant Mol Biol.* 34:549-555 (1997b); U.S. patent application Ser. No. 08/595,937).

The genomic clone Sta 41G(10) was used for the construction of translational fusions to polypeptides of interest for targeting to the pollen coat. Other tapetal oleosin-like genes are also known (Ross, J. H. E., Murphy, D. J. *Plant J.* 9:625-637 (1996); Ruiter, R. K., Van Eldik, G. J., Van Herpen, R. M. A., Schrauwen, J. A. M., Wullems, G. J. *Plant Cell* 9:1621-1631 (1997); de Oliveira, D. E., Franco, L. O., Simoens, C., Seurinck, J., Coppieters, J., Botterman, J., Van Montagu, M. *Plant J* 3:495-507 (1993); Lim et al. EMBL Acc. No. L33510, L33543, L33564, L33603, L33618 (1994)) and can be used for gene fusions aimed at targeting polypeptides to the pollen coat.

Example 2

Fusion of a *Brassica napus* Tapetal Oleosin-Like Gene to the *E. coli* β-*Glucuronidase Gene (TOG*-1)

Figure 4A:
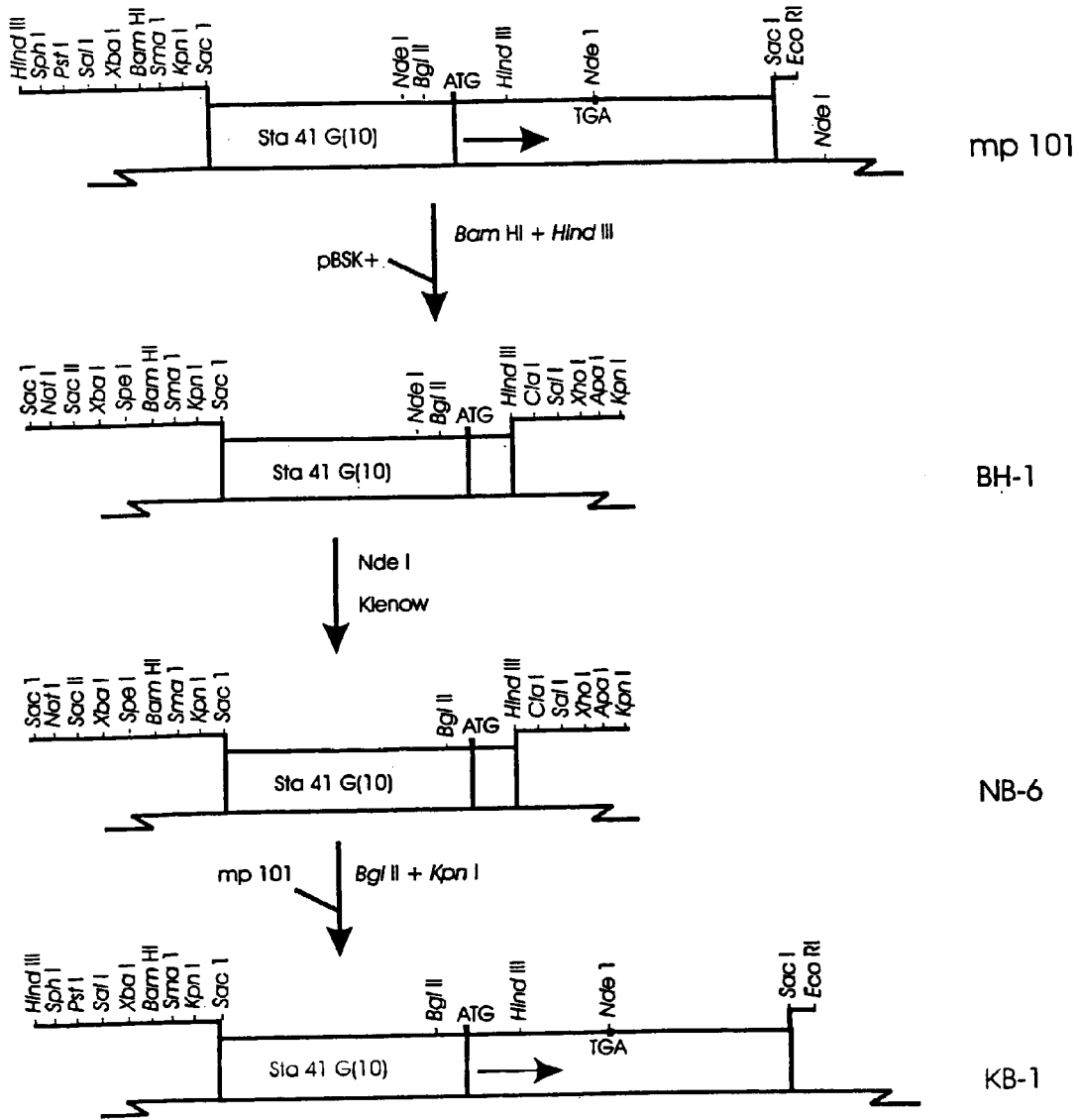
FIG. 4A shows the removal of the Nde I site in the promoter of Sta 41G(10) and the preparation of BH-1, NB-6 and KB-1 from mp 101.

The Sta 41 G(10) Sac I subclone mp 101 is digested with Bam HI and Hind III releasing a fragment containing the 5' upstream region of the tapetal oleosin-like gene and cloned into the Bam HI and Hind III sites of pBSK+ (Stratagene) to generate plasmid BH-1. Plasmid BH-1 is digested with Nde I, blunt ended with the Klenow fragment of DNA polymerase I and religated, effectively destroying the Nde I site and generating plasmid NB-6. Plasmid NB-6 is digested with Bgl II and Kpn 1 and used to replace the Bgl II and Kpn 1 fragment of mp 101. This effectively reconstructs the Sta 41 G(10) Sac I subclone (without the Nde I site within the promoter while preserving the Nde I site just upstream of the stop codon) and generates plasmid KB-1 (FIG. 4A). The Sta 41G(10) Sac I subclone is then cloned into pGEM7Z (Promega) to give plasmid SS-4. Plasmid SS-4 is digested with Nde I and ligated to the adaptors:

KSB-3: TAG GTA CCG AGC TCG GGG GAT CC (SEQ ID NO:1) and

Figure 4B:
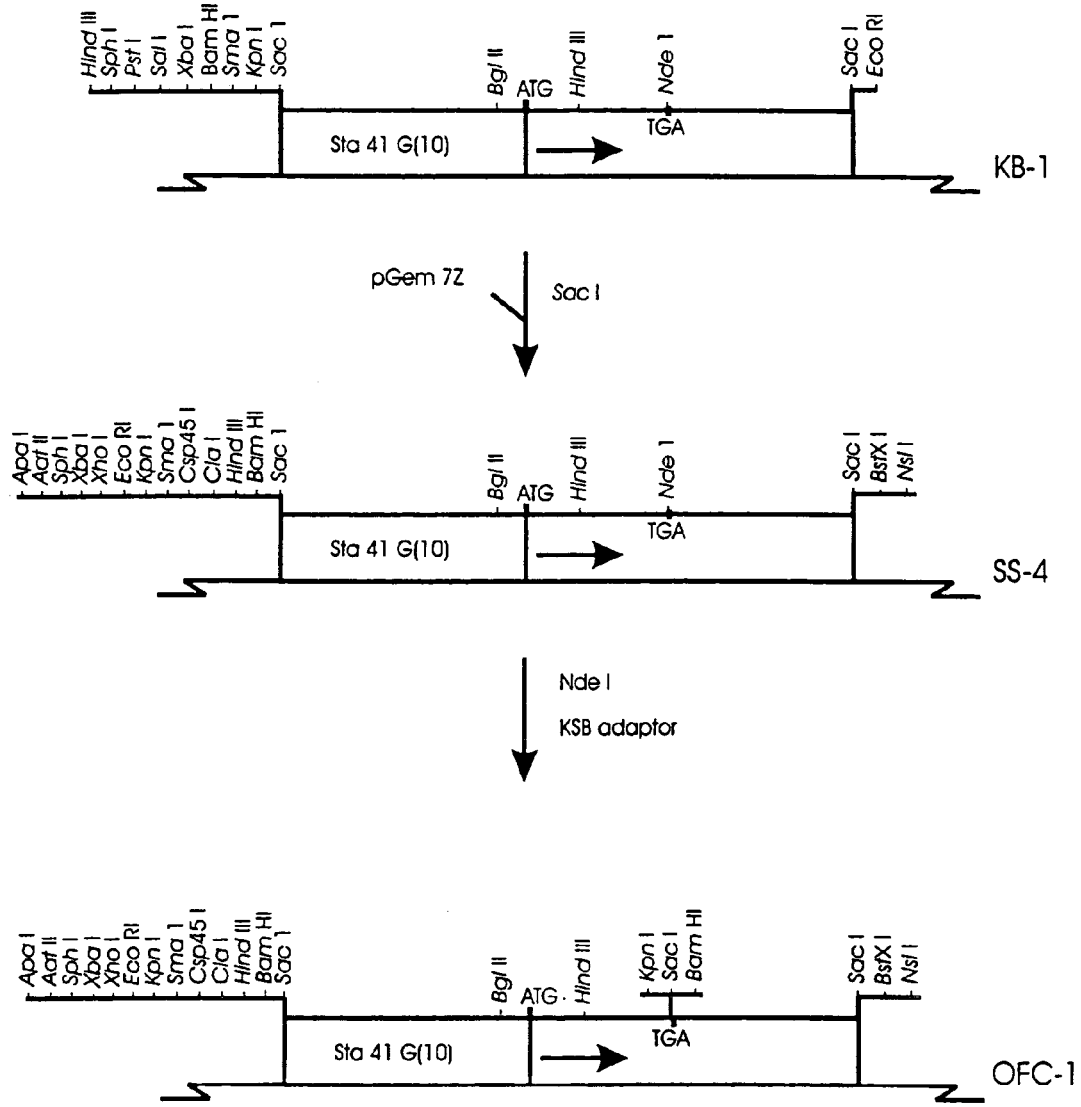
FIG. 4B shows the preparation of SS-4 and OFC-1 from KB-1.

KSB-4: TAG GAT CCC CCG AGC TCG GTA CC (SEQ ID NO:2)

generating plasmid OFC-1 (FIG. 4B). This double stranded adaptor possesses Nde I overhangs and encodes the restriction sites Kpn I, Sac I and Bam HI. The Bam HI fragment of OFC-1 containing the tapetal oleosin-like gene (promoter and coding sequence) is translationally fused to the GUS coding region (followed by the Nos terminator) of pBI 101.1 (Clontech) to produce plasmid TOG-1 (FIG. 5A; SEQ ID NO:3).

Example 3

Fusion of the Brassica napus Tapetal Oleosin-Like Gene to the Sitophilus SCPc 1 Protease Gene (TOP-1)

A fragment of a cysteine protease from Sitophilus, from plasmid pSCPc1, was amplified by PCR (polymerase chain reaction). This fragment corresponds to the SCPc1 cDNA fragment cloned into pBSK-(Matsumoto, I., Emori, Y., Abe, K, Arai, S. J Biochem. 121: 464-476 (1997)). The oligonucleotide primers used in the PCR reaction are:

forward primer: P1: GCGCGGATCCTTGCCTGATACT-GTTGAC (SEQ ID NO:20)

and reverse primer: P2: GCGCGAATTCAAGCT-TCTAAACCAAAGGATAACTAGC (SEQ ID NO:21).

These primers permit the amplification of the mature cysteine protease coding sequence and introduce a Bam HI site (bold) at the 5' end of the amplified DNA fragment and Eco RI and Hind III sites (bold) at the 3' end.

The PCR fragment is digested with Bam HI and Hind III, and subcloned into the Bam HI and Hind III sites of pGEM 4Z (Promega) generating plasmid pSCPc1BH. Plasmid pSCPc1BH is digested with Bam HI and Hind III and ligated into the Bam HI and Hind III sites of pGEM 7Z generating plasmid SCP-2. Plasmid SCP-2 is digested with Bam HI and Sma I and the fragment containing the protease coding sequence ligated into the Bam HI and Sma I of Binter (this corresponds to the binary vector Bin 19 (Bevan, M. Nucleic Acids Res. 12:8711-8721 (1984)) into which the nopaline synthase terminator polyadenylation signal is subcloned as a Sac I and Eco RI fragment) generating plasmid BS-2. The Bam HI fragment of OFC-1 containing the tapetal oleosin promoter and coding sequence referred to in Example 2 is ligated into the Bam HI site of BS-2 generating a translational fusion between the tapetal oleosin-like gene and the Sitophilus protease gene in plasmid TOP-1 (FIG. 6; SEQ ID NO:4). The Eco RI/Bam HI fragment containing the Sitophilus protease/nopaline synthase polyadenylation signal of plasmid BS-2 was also cloned into plasmid pHS 723 to generate binary vector BSP-1 (data not shown) with the GUS/NPTII fusion (Datla, R. S. S., Hammerlindl, J. K., Pelcher, L. E., Crosby, W. L., Selvaraj, G. Gene 101: 239-246 (1991)).

Example 4

Fusion of a Brassica napus Tapetal Oleosin-Like Gene to the Onchocerca OV 7 Cysteine Protease Inhibitor Gene (TOPI-1)

Plasmid pGEXOV7 (Lustigman, S., Brotman, B., Huima, T., Prince, A. M. Mol. Biochem. Parasitol. 45: 65-76 (1991)) containing the cDNA clone coding for the Onchocerca protease inhibitor (PI) is digested with Eco RI releasing a 582 bp fragment which is blunt ended by filling in with the Klenow DNA polymerase I fragment and subcloned into the Sma I site of pGEM 4Z generating plasmid pGEMOV7. This fragment contains the coding sequence for the mature Onchocerca PI. Plasmid pGEMOV7 is digested with Bam HI and Eco RI, and ligated into the Bam HI and Eco RI sites of pGEM 7Z to generate plasmid OV-71. Plasmid OV-71 is digested with Sac I and ligated into the Sac I of Binter generating plasmid BO-3. The Kpn I fragment of OFC-1 containing the tapetal oleosin promoter and coding sequence referred to in Example 2 is ligated into the Kpn I site of BO-3 generating a translational fusion between the tapetal oleosin-like gene and the Onchocerca OV7 gene of plasmid TOPI-1 (FIG. 7; SEQ ID NO:5). The Eco RI/Hind III fragment of plasmid BO-3 containing the Onchocerca protease inhibitor/nopaline synthase polyadenylation signal was also cloned into pHS 723 to generate binary vector BOP-1 (data not shown) with the GUS/NPTII fusion.

Example 5

Fusion of the Brassica napus Pis G363 Gene to the Sitophilus SCPc 1 Protease Gene (SPF-1)

A fragment of genomic clone Pis G363 containing the promoter and the Pis 63 coding region was cloned into pGEM 4Z resulting in plasmid Bg2. Plasmid Bg2 was digested with Kpn I and Xba I, and the insert cloned into the corresponding sites of pGEM 7Z to yield plasmid KX-1 (FIG. 8). Plasmid KX-1 was digested with Xho I and ligated to the BKX 12 adaptors:

BKX-1: TCG AGG GGA TCC GGT ACC TCT AGA (SEQ ID NO:6) and

BKX-2: TCG ATC TAG AGG TAC CGG ATC CCC (SEQ. ID NO:7)

introducing additional Bam HI, Kpn I and Xba I sites within the 3' coding region and resulting in plasmid XX-1. The Bam HI fragment of plasmid XX-1 containing the Pis G363 promoter and partial coding region was cloned into the Bam HI site of BSP-1 (Example 3) resulting in a translational fusion to the SCPc 1 protease in plasmid SPF-1 (FIG. 8; SEQ ID NO:8).

Example 6

Fusion of the Brassica napus Pis G363 Gene to the Onchocerca OV7 Protease Inhibitor (SPIF-1)

The Kpn I fragment of plasmid XX-1 described above containing the Pis G363 promoter and partial coding region was cloned into the Kpn I site of BOP-1 (Example 4) resulting in a translational fusion to the OV7 protease inhibitor in plasmid SPIF-I (FIG. 8; SEQ ID NO:9).

Example 7

Fusion of the Cauliflower Mosaic Virus (CaMV) 35S Promoter to the Brassica napus SLG$_{WS1}$ Signal Peptide and the Onchocerca OV7 Protease Inhibitor (SPOV-1)

The region coding for the signal peptide of the Brassica napus SLG$_{WS1}$ gene was obtained by PCR amplification from plasmid SLG 26 using oligonucleotide primers SLG 26(7) and SLG 26(8) (SEQ ID NO's:10 and 11). These primers introduced respectively Sac I and Kpn I sites flanking the signal peptide. The signal peptide was digested with Sac I and Kpn I, and introduced into the Sac I and Kpn I sites of pGEMOV7 to yield plasmid SP-1 (FIG. 9). The translational fusion between the $SLG_{WS1}$ signal peptide and the *Onchocerca* protease inhibitor OV7 was then cloned into the Sac I and Bam HI sites between the CaMV 35S promoter and polyadenylation signal of vector pFF19 (Timmermans, M. C. P., Maliga, P., Vieira, J., Messing, J. *J. Biotechnol.* 14:333-344 (1990) to yield plasmid SPFF-1. The construct containing the CaMV 35S double enhancer promoter/$SLG_{WS1}$ signal peptide/*Onchocerca* protease inhibitor OV7/CaMV 35S polyadenylation signal was introduced into the plant binary transformation vector pHS 723 (Datla, R. S. S. Plant Biotechnology Institute, Saskatoon Canada) as an Eco RI/Hind III fragment to generate the vector SPOV-1 (FIG. 9; SEQ ID NO:12). A similar vector called COV-1 containing the signal peptide from the OV7 protease inhibitor instead of the $SLG_{WS1}$ signal peptide was also constructed and used for plant transformation.

Example 8

Fusion of the *Brassica napus* Pollen Polygalacturonase Sta 44G(2) Promoter and Signal Peptide to a Protease Inhibitor (POV-1), or a Protease (POP-1)

a) Fusion of the *Brassica napus* Pollen Polygalacturonase Sta 44G(2) Promoter and Signal Peptide to the *Onchocerca* OV7 Protease Inhibitor (POV-1).

Plasmid HP-9 containing the Sta 44G(2) promoter and signal peptide was digested with Sph I and ligated to EXK-12 adaptor:

EXK-1: CGA ATT CTC TAG AGG TAC CGC ATG (SEQ ID NO:13) and

EXK-2: CGG TAC CTC TAG AGA ATT CGC ATG (SEQ ID NO:14)

introducing additional Sph I, Eco RI, Xba I and Kpn I sites downstream of the signal peptide and yielding plasmid SS-1 (FIG. 10). Plasmid SS-1 was digested with Bam HI and Hind III, and cloned into vector pGEM4Z (Promega) to re-introduce an upstream Kpn I site lost during cloning. Plasmid SS-2 was digested with Kpn I and the fragment containing the Sta 44G(2) promoter and signal peptide was cloned into plasmid BOP-1 described above resulting in a translational fusion to the OV7 protease inhibitor and producing plasmid POV-1 (FIG. 10; SEQ ID NO:15).

b) Fusion of the *Brassica napus* Pollen Polygalacturonase Sta 44G(2) Promoter and Signal Peptide to the Sitophilus SCPc 1 Protease (POP-1).

Plasmid SS-2 (FIG. 10) was digested with Xba I and the fragment containing the Sta 44G(2) promoter and signal peptide was cloned into plasmid BSP-1 described above resulting in a translational fusion to the *Sitophilus* SCPc 1 protease and producing plasmid POP-1 (FIG. 10; SEQ ID NO:25).

Example 9

Transcriptional Fusion of the Antisense Sta 41-2 Tapetal Oleosin-Like cDNA Clone to the Sta 41 G(10) Promoter (SAS-1)

Plasmid T28 containing the tapetal oleosin-like Sta 41 G(10) promoter fragment (Hong, H. P., Ross, J. H. E., Gerster, J. L., Rigas, S., Datla, R. S. S., Hatzopoulos, P., Scoles, G., Keller, W., Murphy, D., Robert, L. S. *Plant Mol. Biol.* 34:549-555 (1997b)) was digested with Bam HI and Hind III, and the fragment containing the promoter was cloned into Camter III a derivative of the binary vector Bin 19 (Bevan, M., *Nucleic Acids Res.* 12:8711-8721 (1984)) containing the nopaline synthase polyadenylation signal. The resulting plasmid was called T1. The tapetal oleosin-like cDNA clone Sta 41-2 was partially digested with Eco RI and cloned in the antisense orientation into the Eco RI site of T1 to generate the plant transformation vector SAS-1 (FIG. 22). SAS-1 was used to transform *Brassica napus* to reduce the levels of tapetal oleosin-like mRNA in the tapetum and consequently cause a reduction of the tapetal oleosin-like protein which is part of the pollen tryphine.

Example 10

Covalent Linkage of Enzymes and Proteins to the Pollen Coat

Pollen grains may be conjugated to a protein of interest, for example, the enzyme horseradish peroxidase, the protease papain, or the protease inhibitor potato multicystatin, through conjugation to sugar residues on the exine. However, residues of the protein may also be modified prior to conjugation.

Pollen grains from opened flowers of *Brassica napus* cv. Westar are collected and "activated" by suspension in phosphate-buffered saline (PBS) solution containing 10 mM $Ca^{+2}$, 10 mM $Mn^{+2}$, 10 mM $Mg^{+2}$, 0.5% Triton X-100, and 10 μg/ml Concanavalin A (Sigma C2010) for 1 h at room temperature. Pollen grains are washed repeatedly in PBS solution by centrifugation at 800×g in 1.5 ml centrifugation tubes for 5 min. Conjugation of purified enzymes (e.g. horseradish peroxidase, papain, or potato multicystatin, a cysteine protease inhibitor) is performed by incubating the selected protein at 50 μg/ml in PBS solution with the activated pollen grains for 1 h at room temperature. Pollen grains are then washed five times with PBS solution and centrifuged for 5 min.

Germination of pollen grains is evaluated by plating isolated pollen grains on 1 ml of filter sterile Brewbaker medium (10% (w/v) sucrose, 100 ppm $H_3BO_3$, 300 ppm $Ca(NO_3)_2.4H_2O$, 200 ppm $MgSO_4.7H_2O$, 100 ppm KNO3) in sterile petri dishes 15×60 mm diameter at 25° C. for 24 h. The percentage of germinating pollen grains is determined under an inverted microscope, in the presence or absence of proteases or protease inhibitors.

Detection of the conjugated enzymes is measured by placing the pollen grains in enzyme substrate solutions. For horseradish peroxidase, pollen grains are incubated in 50 mM sodium acetate pH 5.0 containing 0.01% $H_2O_2$, 200 ug/ml amino ethyl carbazole, and the blue pollen grains are recorded under an inverted microscope. Papain activity is recorded on conjugated pollen grains by incubating pollen grains in microtitre plates containing the chromogenic substrate Pyr-Phe-Leu-pNA at 2 mM in Tris.Cl pH 6.5 at 37° C. for 30 min and reading the absorbance of the substrate solution at 410 nm in a microtitre plate reader. Papain inhibitory activity is measured on conjugated pollen grains by incubating pollen grains in a solution containing 10 μg/ml papain in Tris.Cl at pH 6.5 for 10 min at 37° C., and then adding the chromogenic papain substrate Pyr-Phe-Leu-pNA at 2 mM for 30 min at 37° C. The reactions are quantitated by measuring the absorbance at 410 nm.

Immune response of conjugated proteins to pollen grains is quantified by washing fresh pollen grains of canola with PBS solution for 5 min and centrifugation at 800×g. Pollen grains are suspended in PBS at 5% (vol/vol) and an equal volume of freshly prepared 0.005% tannic acid solution is added and mixed. This mixture is incubated at 37° C. for 15 min with gentle agitation, before removing the tannic acid solution by centrifugation. The pollen grains are incubated in either purified papain, horseradish peroxidase, or potato multicystatin in PBS solution for 15 min at 37° C. with gentle shaking. The pollen grains are then washed in PBS by centrifugation three times prior to immunization of mice. Pollen grains coated with either antigen are used to immunize Balb/c mice. Approximately 100 µg of coated pollen grains are suspended in Freund's incomplete adjuvant (100 µL) and used to inject into the foot pads of mice. A boost is administered after 10 days with the same concentration of antigen, and the same route of injection. Trial bleeds are examined for the titre of antibodies specific for the antigen coated on the surface of pollen grains, and compared to pre-immune serum.

Example 11

Cysteine Protease Inhibitor Retains Specificity when Expressed as a Fusion Protein To demonstrate that the protease inhibitor OV7 from *Onchocera vovulus* (Lustigman, S., Brotman, B., Huima, T., Prince, A. *Mol. Biochem. Parasitol*. 45: 65-76 (1991)) is capable of normal function as a fusion protein, it is cloned into the phagemid pCantab 5E (Pharmacia Inc.) and expressed on the surface of filamentous phage as a fusion to the gene 3 phage coat protein.

A SacI and Nco I digest of the coding region of the protease inhibitor clone OV7 (Lustigman et al 1991), is ligated to the pCantab 5E vector (Pharmacia Biotech) Sac I and Nco I sites. This phagemid is transformed into *E. coli* TG1 cells by electroporation. An overnight culture of 10 μL of these cells are grown in 5 ml of SOBAG medium containing 10 μl of carbenicillin (50 mg/mL) at 28° C. The next day, 0.5 ml of this culture is used to inoculate 25 ml of 2×YT medium, containing 50 μl of carbenicillin (50 mg/ml) and 1.56 ml of 2M glucose and grown for 1.25 h at 37° C., with shaking at 250 rpm. At this point 62.5 μl of helper phage strain M13K07 (9.0×10 pfu/ml) is added and the cells were incubated at 37° C. for 30 min with shaking at 150 rpm, and for another 30 min at 250 rpm. Recombinant phage particles are harvested by centrifugation and PEG precipitation. Phage are used in an ELISA assay to determine the specificity of binding to the cysteine protease papain, the serine protease trypsin, and to rabbit polyclonal antibodies directed against a potato cysteine protease inhibitor which also recognize the native OV7 protease inhibitor (anti-OV7 antibodies). Wells of a Nunc microtitre plate (maxisorb) are coated with either papain, anti-cysteine protease inhibitor antibodies, trypsin, or anti M13 antibodies in 100 μl $Na_2CO_3$ buffer.

After incubating the phage indicated (OV7-those displaying the cysteine protease inhibitor on their surface, M13-wild type or control phage not displaying any foreign protein, and a no phage control) for 2 h, the wells are washed in PBS with 0.5% Tween-20. Phage particles that bound to the antigens are detected with a 1:5000 dilution of anti-M13 antibody/HRP conjugate (Pharmacia). Detection is with the HRP substrate ABTS solution (Pharmacia) for 30 min and absorbance was measured at 410 nm.

The results (Table 1) demonstrate that the phage displaying the OV7 protease inhibitor clearly binds specifically to the cysteine protease papain and to the anti-cysteine protease inhibitor antibodies at high levels. The O.D. values for the negative control phage binding (either M13 phage not expressing the protease inhibitor bound to papain, or the phage expressing the cysteine protease inhibitor bound to trypsin a serine protease) are very low.

TABLE 1

| Antigen coated in well | Phage Added | $O.D._{410}$* | Result |
|---|---|---|---|
| papain | OV7 | 0.788 | specific binding of OV7-papain |
| papain | M13 | 0.043 | no binding of M13-papain |
| papain | none | 0.016 | no background |
| none | OV7 | 0.125 | very little OV7-plate interaction |
| anti-OV7 antibodies | OV7 | 0.451 | specific binding of OV7-antibodies |
| anti-OV7 antibodies | M13 | 0.026 | no interaction M13-antibodies |
| anti-OV7 antibodies | none | 0.024 | no background |
| trypsin | OV7 | 0.037 | no OV7-trypsin interaction |
| trypsin | M13 | 0.026 | no M13-trypsin interaction |
| anti-M13 antibodies | M13 | 0.326 | positive control |

*Value for Phage Diluted 1 in 100

Phage display demonstrates that the cysteine protease inhibitor OV7 is capable of functioning as a fusion protein when bound to the phage coat protein 3 and phage particles. This protease inhibitor is capable of binding specifically to papain (cysteine protease) and does not bind to trypsin (serine protease).

It has also been demonstrated that proteases can be expressed on the surface of bacteriophage and that they too can function as fusion proteins (Corey, D. R., Shiau, A. K., Yang, Q., Janawski, B. A., Craik, C. S. *Gene* 128: 129-134 (1993)).

Example 12

Effect of a Cysteine Protease Papain, a Cysteine Protease Inhibitor Onchocystatin, and a Protein Synthesis Inhibitor Cycloheximide on the Germination of Tobacco Pollen in vitro Pollen from *Nicotiana tabacum* cv. Delgold was harvested by placing 5 dehiscent anthers in 1 ml of sterile Brewbaker and Kwack medium (Brewbaker, J. and Kwack, B. *Amer. J. Bot*. 50: 859-865 (1963)) containing various concentrations of cylcoheximide, or papain, or casein. The medium consisted of 10% w/v sucrose, 100 ppm $H_3BO_3$, 300 ppm $Ca(NO_3)_2.4H_2O$, 200 ppm $MgSO_4.7H_2O$, and 100 ppm $KNO_3$ with either 42 μM papain (twice crystallized, Sigma), with or without 30 μM recombinant onchocystatin, or 71 μM cycloheximide (Sigma), or 1 mg/ml casein. Anthers were vortexed in medium for 30 sec followed by centrifugation at 2,000 rpm for 2 min. Pollen was cultured in 50 μl drops in sterile 15×60 mm petri dishes at 25° C. The percentage of pollen grains germinated after 3 h of culture was measured and the average pollen tube length was recorded using an ocular micrometer on an inverted microscope. The protease papain at 42 μM inhibited the germination and stunted the growth of pollen tubes. The addition of 30 μM of the protease inhibitor onchocystatin (OV7) to the 42 μM papain treatment restored the germination and pollen tube growth. Cycloheximide at 71 μM also inhibited the germination and elongation of pollen tubes in vitro (Table 2, FIG. 19).

TABLE 2

| Treatment | Pollen Germination | Average Pollen Tube Length |
|---|---|---|
| Casein (control) | 74% | 95 μm |
| Papain | 56% | 28 μm |
| Papain + Onchocystatin | 69% | 80 μm |
| Cycloheximide | 27% | 15 μm |

These in vitro germination assays demonstrate that pollen germination can be affected by enzymes and antibiotics. Furthermore, the reduction in pollen germination caused by a protease can be restored by a protease inhibitor.

Example 13

Nicotiana tabacum Transformation

Plant transformation vectors were introduced separately into *Agrobacterium tumefaciens* strain EHA 105 following the protocol supplied with the Pharmacia *Agrobacterium* cells (product: #27-1535). To prepare the *Agrobacterium* competent cells, 5 ml of YEP medium (10 g yeast extract, 10 g peptone, 5 g sodium chloride per liter, pH 7.0) with 25 μg/ml chloramphenicol was inoculated with a loopful of a glycerol stock of *Agrobacterium tumefaciens* and cultured at 28° C. by shaking at 250 rpm approximately 15 h. Two ml of the culture was added to 50 ml of fresh YEP medium and grown at 28° C. to an O.D. of 0.5-1.0 at 600 nm. The culture was then chilled on ice for 10 min and centrifuged at 5,000 rpm. The cells were resuspended in 1 ml of cold 20 mM $CaCl_2$. These competent cells were dispensed into pre-chilled 1.5 ml Eppendorf tubes in 100 μl aliquots and frozen at −80° C.

The *Agrobacterium* EHA 105 cells were transformed as follows. One μg of uncut plasmid DNA in water was added to 100 μl of *Agrobacterium* competent cells and incubated on ice for 30 min. The cells were then frozen in liquid nitrogen and thawed quickly at 37° C. for 5 min and 1 ml of YEP medium was added to the cell/DNA mixture and incubated at 28° C. for 2 h with gentle shaking (100 rpm). Cells were then centrifuged in a microfuge for 30 s, the supernatant was poured out and the pellet resuspended in the remaining supernatant (50-100 μl). The resuspended cells were spread on a YEP plate with 25 μg/ml chloramphenicol and 50 μg/ml kanamycin, and incubated at 28° C. for 2-3 days.

Plasmid DNA from individual *Agrobacterium* colonies was digested and analyzed by agarose gel electrophoresis to verify the integrity of the vector. Individual colonies that contained the desired recombinant plasmid were selected and grown overnight in 10 ml LB medium (10 g/L bactotryptone, 5 g/L yeast extract, 10 g/L NaCl, pH 7.0) with 25 μg/ml chloramphenicol and 50 μg/ml kanamycin. One ml of overnight culture was centrifuged at 13,000 rpm for 5 min and the cells resuspended in MMO medium (4.6 g/L MMO, GIBCO BRL) to an O.D. of 0.1.

*Agrobacterium*-mediated transformation of tobacco cv. Delgold was performed as follows. Pieces of fresh young tobacco leaves were sterilized 1-2 min in 70% ethanol, 5 min in Javex and then rinsed in sterile water for 2 min 3 times. Leaf discs were obtained with a 5 mm cork borer. Leaf discs were transferred to a dish containing the *Agrobacterium* cell suspension and placed at 25° C., 16 h light/8 h dark with lights to 70-100 μE for 2-3 days. The co-cultivated discs were transferred to TTK plates (4.56 g/L MMO, 1.0 mg/L benzyl adenine (BA), 0.1 mg/L α-naphthaleneacetic acid (NAA), 3% sucrose, pH 5.8; 300 μg/ml timentin and 25 μg/ml kanamycin added after autoclaving) and incubated at 25° C., 16 h light/8 h dark with lights to 70-100 μE for 2 weeks. Regenerated shoots were transferred to Magenta GA-7 vessels containing B5 rooting medium (23.2 g/L Gamborg's B5 medium (GIBCO BRL), 7.5 g/L phytagar, pH 5.7; 300 μg/ml timentin and 100 μg/ml kanamycin added after autoclaving). Once a good root system had developed, the plantlets were removed from the vessels, most of the agar was removed from the roots and the plantlets transferred to moist potting soil.

Kanamycin resistant *Nicotiana tabacum* plants were demonstrated to be transformed by PCR analysis following transformation with TOG-1 (SEQ ID NO: 3).

Forward Primer

GUSsense-1: GGA ATT CAC CGC GTC TTT GAT CGC-3' (SEQ ID NO:16); and Reverse Primer nos #2: GCG CGC GAT AAT TTA TCC-3' (SEQ ID NO:17), that anneal in the GUS gene and nopaline synthase terminator, respectively, were used to amplify a 513 base pair fragment. Transformation of tobacco plants with plasmids TOP-1 (SEQ ID NO:4) and TOPI-1 (SEQ ID NO:5) was also confirmed by PCR using primers NptII-121: GGG CGC CCG GTT CTT TTT-3' (DNA SEQ ID:18)

and NptII-B: CAG CAA TAT CAC GGG TAG CCA ACG C-3' (SEQ ID NO:19).

Example 14

Brassica napus Transformation

Plant transformation vectors were introduced separately into *Agrobacterium tumefaciens* strain GV3101:pMP90 following the protocol supplied with the Pharmacia *Agrobacterium* cells (product: #27-1535). To prepare the *Agrobacterium* competent cells, 5 ml of YEP medium (10 g yeast extract, 10 g peptone, 5 g sodium chloride per liter, pH 7.0) with 150 μg/ml rifampicin and 100 μg/ml gentamycin was inoculated with a loopful of a glycerol stock of *Agrobacterium tumefaciens* and cultured at 28° C. by shaking at 250 rpm approximately 15 h. Two ml of the culture was added to 50 ml of fresh YEP medium and grown at 28° C. to an O.D. of 0.5-1.0 at 600 nm. The culture was then chilled on ice for 10 min and centrifuged at 5,000 rpm. The cells were resuspended in 1 ml of cold 20 mM $CaCl_2$. These competent cells were dispensed into pre-chilled 1.5 ml Eppendorf tubes in 100 μl aliquots and frozen at −80° C.

The *Agrobacterium* cells were transformed as follows. One μg of uncut plasmid DNA in water was added to 100 μl of *Agrobacterium* competent cells and incubated on ice for 30 min. The cells were then frozen in liquid nitrogen and thawed quickly at 37° C. for 5 min, and 1 ml of YEP medium was added to the cell/DNA mixture and incubated at 28° C. for 2 h with gentle shaking (100 rpm). Cells were then centrifuged in a microfuge for 30 s, the supernatant was poured out and the pellet resuspended in the remaining supernatant (50-100 μl). The resuspended cells were spread on a YEP plate with 150 μg/ml rifampicin, 100 μg/ml gentamycin and 50 μg/ml kanamycin, and incubated at 28° C. for 2-3 days.

Plasmid DNA from individual *Agrobacterium* colonies was digested and analyzed by agarose gel electrophoresis to verify the integrity of the vector. Colonies that contained the desired recombinant plasmid were selected and grown overnight in 5 ml AB minimal medium with 50 µg/ml kanamycin and 50 µg/ml gentamycin. The overnight culture was centrifuged at 4500 rpm for 15 min and the cells resuspended in 1 ml of double distilled water or 10 mM $MgSO_4$.

*Agrobacterium*-mediated transformation of *B. napus* cv. Westar was performed according to the method of Moloney M. M., Walker, J. M., Sharma, K. K. *Plant Cell Rep.* 8:238-242 (1989) with modifications. Seeds were sterilized by brief wetting in 95% ethanol then 70% commercial bleach (Javex) with a drop of detergent (Tween 20) for 15 min with occasional agitation; 0.025% mercuric chloride with a drop of Tween 20 for 10 min and finally rinsed well with sterile distilled water at least 3 times. Thirty to forty seeds were plated on ½ strength hormone-free MS medium (Sigma) with 1% sucrose in 15×60 mm petri dishes. They were then placed, with the lid removed, into sterilized Magenta GA-7 vessels and kept at 25° C., with 16 h light/8 h dark and a light intensity of 70-80 µE.

Cotyledons were excised from 4-day old seedlings by gently grasping both petioles just above the point where they join the hypocotyl. The cotyledons were soaked in BASE solution (4.3 g/L MS (GIBCO BRL), 10 ml 100×B5 Vitamins (0.1 g/L nicotinic acid, 1.0 g/L thiamine-HCl, 0.1 g/L pyridoxine-HCl, 10 g/L m-inositol), 2% sucrose, 1 mg/L 2,4-D, pH 5.8; 1% DMSO and 200 µM acetosyringone added after autoclaving) containing *Agrobacterium* cells with the recombinant plant transformation vector. Most of the BASE solution was removed and the cotyledons were incubated at 28° C. for 2 days in the dark. The dishes containing the cotyledons were then transferred to 4° C. for 3-4 days in the dark. Cotyledons were transferred to plates containing MS B5 selection medium (4.3 g/L MS, 10 ml 100×B5 Vitamins, 3% sucrose, 4 mg/L benzyl adenine (BA) ph 5.8; timentin (300 µg/ml) and kanamycin (20 µg/ml) were added after autoclaving) and left at 25° C., 16 h light/8 h dark with lighting to 70-100 µE. Shoots were transferred to Magenta GA-7 vessels containing MS B5 selection medium without BA. When shoots were sufficiently big they were transferred to Magenta GA-7 vessels containing rooting medium (4.3 g/L MS, 5.0 ml 100×B5 Vitamins, 3% sucrose, 0.1 mg/L α-naphthaleneacetic acid (NAA), pH 5.8; 300 µg/ml timentin and 20 µg/ml kanamycin were added after autoclaving). Once a good root system had developed, the plantlets were removed from the vessels, most of the agar was removed from the roots and the plantlets transferred to moist potting soil.

Example 15

*Brassica carinata* Transformation

Plant transformation vectors were introduced separately into *Agrobacterium tumefaciens* strain GV3101:pMP90 following the protocol supplied with Pharmacia *Agrobacterium* cells (product: #27-1535). To prepare the *Agrobacterium* competent cells, 5 ml of YEP medium (10 g yeast extract, 10 g peptone, 5 g sodium chloride per liter, pH 7.0) with 150 µg/ml rifampicin and 100 µg/ml gentamycin was inoculated with a loopful of a glycerol stock of *Agrobacterium tumefaciens* and cultured at 28° C. by shaking at 250 rpm approximately 15 h. Two ml of the culture was added to 50 ml of fresh YEP medium and grown at 28° C. to an O.D. of 0.5-1.0 at 600 nm. The culture was then chilled on ice for 10 min and centrifuged at 5,000 rpm. The cells were resuspended in 1 ml of cold 20 mM $CaCl_2$. These competent cells were dispensed into pre-chilled 1.5 ml Eppendorf tubes in 100 µl aliquots and frozen at −80° C.

The *Agrobacterium* cells were transformed as follows. One µg of uncut plasmid DNA in water was added to 100 µl of *Agrobacterium* competent cells and incubated on ice for 30 min. The cells were then frozen in liquid nitrogen and thawed quickly at 37° C. for 5 min and 1 ml of YEP medium was added to the cell/DNA mixture and incubated at 28° C. for 2 h with gentle shaking (100 rpm). Cells were then centrifuged in a microfuge for 30 s, the supernatant was poured out and the pellet resuspended in the remaining supernatant (50-100 µl). The resuspended cells were spread on a YEP plate with 150 µg/ml rifampicin, 100 µg/ml gentamycin and 50 µg/ml kanamycin, and incubated at 28° C. for 2-3 days.

Plasmid DNA from individual *Agrobacterium* colonies was digested and analyzed by agarose gel electrophoresis to verify the integrity of the vector. Individual colonies that contained the desired recombinant plasmid were selected and grown for 2-3 days in 5 ml of LB medium (10 g/L bacto-tryptone, 5 g/L yeast extract, 10 g/L NaCl, pH 7.0) with 50 µg/ml kanamycin with shaking at 28° C. A 50 µl aliquot of this culture was used to inoculate 5 ml of fresh LB medium containing 50 µg/ml kanamycin and incubated as above to an O.D. of 0.1 at 660 nm.

The *B. carinata* (Ethiopian mustard, *B. carinata* A. Braun, breeding line C90-1163, obtained from Dr. K. Falk, Saskatoon Research Centre, AAFC) seeds were sterilized in 2% PPM (Plant Preservative Mixture, Plant Cell Technology Inc.) for 4 h with gentle stirring and rinsed with 1L of sterilized water. Twenty seeds were plated on fresh seed germination medium (½ strength MS pH 5.6 (GIBCO BRL), 1% sucrose and 0,7% phytagar) in a 60×20 mm petri dishes fitted inside GA-7 Magenta vessels. They were incubated at 25° C. for 3-4 days under a 16 h light/8 h dark photoperiod.

*Brassica carinata* plants were transformed as described by Babic, V., Datla, R. S., Scoles, G. J., Keller, W. *Plant Cell Reports*, 17, 183-188 (1998) with modifications. Healthy green cotyledons were cut at the point where they join the hypocotyl. The petiole of each explant was dipped into the *Agrobacterium* suspension and then transferred to 100×25 mm petri dishes with Whatman No. 1 filter paper covering the regeneration medium (MS pH 5.8, 3% sucrose; 2 mg/L BA, 0.05 mg/L NAA and 0.7% phytagar). The explants were incubated at 25° C. for 2 days under a 16 h light/8 h dark photoperiod. The explants were then transferred to 100×25 mm petri dishes containing the selection medium (MS, 2% sucrose; 2 mg/L BA; 0.05 mg/L NAA; 5 mg/L $AgNO_3$; 500 mg/L soluble PVP-10; 500 mg/L MES pH 5.8 and 0.7% phytagar supplemented with 25 µg/ml kanamycin and 300 µg/ml timentin) and incubated for 2 weeks as above.

Regenerated shoots were transferred to shoot elongation medium (½ MS pH 5.8; 2% sucrose; 0.05 mg/L BA; 0.03 mg/L (gibberellic acid) GA 3; 150 mg/L phloroglucinol; 0.9% phytagar supplemented with 25 µg/ml kanamycin and 300 µg/ml timentin) in 60×20 mm petri dishes fitted in GA-7 Magenta vessels and incubated for two weeks as above. Shoots were transferred to rooting media (½ MS; 1% sucrose; 0.05 mg/L NAA and 0.7% phytagar supplemented with 25 µg/ml kanamycin and 300 µg/ml timentin) and when healthy roots appeared the plantlets were transferred to soil.

Anther Development in *B. carinata* Flowers:

The tapetum is present within anthers of flower buds from 2-6 mm in length but is absent in 7 mm buds. Flowers open and release mature pollen once the buds have reached approximately 8 mm in length. Anther development in *B. carinata* parallels that of *B. napus*, in which flower bud length can be correlated to developmental events within the anther (Scott, R., Dagless, E., Hodge, R., Paul, W., Soufleri, I., Draper, J. *Plant Mol. Biol.* 17: 195-207 (1991)). However, *B. carinata* buds tend to be somewhat larger than those of *B. napus* at similar developmental stages. In *B. napus*, tapetal degeneration occurs at about 5 mm bud length and floral opening occurs by approximately 6-7 mm bud length.

Anthers were carefully dissected from buds at different developmental stages corresponding to the length of the bud (measured in mm) from the base to the tip of the closed sepals. Anther development was determined by staining resin-embedded sections of buds at different lengths with Toluidine Blue.

Example 16

Analysis of TOPI-1 (Sta 41-9/*Onchocerca volvulus* OV7 Protease Inhibitor Fusion) and TOP-1 (Sta 41-9/*Sitophilus zeamais* SCPc 1 Protease Fusion) Expression TOPI-1 Expression in *B. carinata*

*B. carinata* plants were transformed, as described in Example 15, with TOPI-1 (SEQ ID NO:5, Example 4).

Anthers were dissected from *B. carinata* flower buds, frozen in liquid nitrogen and ground to a fine powder. Proteins were extracted from the frozen powder by mixing and sonicating at 6 µl/mm length of flower bud with 1.2× SDS-PAGE (sodium dodecyl sulfate-polyacrylamide gel electrophoresis) loading buffer (75 mM Tris-HCl pH 6.8; 2.4% SDS; 12% glycerol; 6% 2-mercaptoethanol; 0.01% bromophenol blue). The extract was centrifuged for 5 min at 13,000 rpm, the supernatant transferred to a fresh tube and heated to 50° C. before loading on the gel.

The SDS PAGE was performed according to the Laemmli, U. K. *Nature* 227: 680-685 (1970) using a 10% acrylamide gel. The gel was blotted electrophoretically (Hoeffer) to a PVDF membrane (Millipore) in 50 mM Tris-HCl, 380 mM glycine, 0.1% SDS and 20% methanol. The membrane was blocked with 5% skim milk powder, 3% bovine serum albumin (BSA) in TBS (50 mM Tris-HCl pH 7.5, 150 mM NaCl) for 1 h at 20° C. The blocked PVDF membrane was incubated with the anti-CPI (cysteine protease inhibitor) antibody diluted 1/12,500 in 0.5% blocking solution (Roche Molecular Biochemicals). The membrane was washed twice in TBST (TBS+0.1% Tween 20) for 10 min and twice more in 0.5% blocking solution. The membrane was incubated with the secondary antibody, anti-rabbit horseradish peroxidase conjugate, diluted to 1/2000 in 0.5% blocking solution for 30 min at 20° C. The membrane was then washed 4 times 15 min in TBST at 20° C. Proteins were detected using the Chemiluminescence Blotting Substrate (POD, Roche Molecular Biochemicals) and the membranes were exposed to X-ray film (Kodak, X-Omat).

Western blot analysis was performed on transgenic *Brassica carinata* plants containing TOPI-1 (SEQ ID NO:5). The full-length *Brassica napus* tapetal oleosin-like STA 41-9/*Onchocerca volvulus OV*7 protease inhibitor fusion (expected molecular weight 57 kDa) and the smaller processed version where the N-terminal end of the oleosin-like protein is cleaved (expected molecular weight 47 kDa) were both detected in anther protein extracts from 4 mm flower buds obtained from different transgenic *B. carinata* plants (FIG. 20A: lanes 1 to 13 represent transgenic lines, lane 14 is a non-transformed line and lane 15 is the purified OV7/GST fusion control; the Coomassie stained gel is shown in FIG. 20B). These proteins were not detected in anther extracts from non-transformed *B. carinata* plants.

With reference to FIG. 21C there is shown the detection of the TOPI-1 fusion protein (FIG. 7) during flower development in transgenic *Brassica carinata*. Western blot analysis of an equal amount of anther or pollen protein extracted from developing flower buds of transgenic *B. carinata* line No. 13D were separated by SDS-PAGE and cross-reacted with anti-CPI (cysteine protease inhibitor) antibody. Lanes 1 to 3 correspond to anther protein extracts from 3 mm, 5 mm and 8 mm buds of non-transformed *B. carinata*, and Lanes 4 and 5 correspond to anther and pollen protein extracts respectively, from non-transformed *B. carinata* open flowers. Lanes 6 to 12 correspond to anther protein extracts from 2 mm, 3 mm, 4 mm, 5 mm, 6 mm, 7 mm and 8 mm buds from transformant 13 D. Lanes 13 and 14 correspond to anther and pollen protein extracts respectively, from transformant 13D open flowers. The full-length fusion protein was detected in anther and pollen protein extracts of the transgenic plant and was cleaved later in flower development (arrows). These results demonstrate that the oleosin-like STA 41-9/*Onchocerca volvulus* OV7 protease inhibitor fusion protein while expressed specifically in the tapetum re-locates to the pollen.

Pollen used for pollen coat fractionation were isolated by gently squeezing anthers from open flowers just prior to anther dehiscence in an Eppendorf tube with a disposable blue pestle to release the pollen grains and suspend them in extraction buffer (100 mM HEPES pH7.5, 10 mM KCl, 1 mM $MgCl_2$, 1 mM EDTA, 1 mM DTT, 0.4 M sucrose, 0.01% Triton X-100). The pollen grains were centrifuged at 1000×g for 3 min and the pollen pellet was washed in extraction buffer. Pollen coats were prepared by drying suspended pollen by centrifugation in a glass fibre-plugged filter basket at 20,000×g for 20 sec and then extracting the pollen coats by centrifuging cyclohexane through the dried pollen on the filter into a new tube. Cyclohexane was evaporated under a stream of nitrogen gas leaving the pollen coats as a residue. Proteins were solubilized from the pollen coat residue by mixing with 0.2 µl per anther 2×SDS-PAGE loading buffer described above. The extracts were centrifuged for 1 to 5 min at 13,000 rpm, the supernatant transferred to a fresh tube and heated to 50° C. or 95° C. for 4 min before loading on the gel.

FIG. 26B shows the detection of the *Brassica napus* tapetal oleosin-like Sta 41-9/*Onchocerca volvulus* OV7 protease inhibitor fusion protein in transgenic *Brassica carinata* containing TOPI-1 (SEQ ID NO:5). Western blot analysis of anther proteins isolated from 5 mm and 8 mm flower buds, and of pollen coat proteins from anthers harvested from open flowers just prior to anther dehiscence from three TOPI-1 plant lines separated by SDS-PAGE and cross-reacted with anti-OV7 antibody (Lustigman, S., Brotman, B., Huima, P., Prince, A. M. *J. Biol. Chem*. 267: 17339-17346 (1992)). The anti-OV7 antibody cross-reacted with two bands in most transgenic plants. The higher molecular weight band corresponds to the full-length fusion protein with a predicted molecular weight of 57 kDa, whereas the lower band has a molecular weight of approximately 47 kDa, which is the expected size of the processed fusion protein where the N-terminal end of the oleosin-like protein has been cleaved off. The positions of the predicted proteins are indicated on the left. Two lower molecular weight bands are also observed in 8 mm bud anther and pollen coat lanes that may reflect spurious cleavage of the TOPI-1 translational fusion protein. TOPI-1 protein product (the 47 kDa cleaved fusion protein) was detected on pollen coats fractionated from three transgenic lines Nos. 1, 13 and 9 (FIG. 26b). This reflects the cleavage and targeting to the pollen coat of the TOPI-1 construct in a manner similar to the native tapetal oleosin-like proteins.

TOPI-1 Expression in N. tabacum

N. tabacum plants were transformed, as described in Example 13, with TOPI-1 (SEQ ID NO:5, Example 4).

Figure 21D:
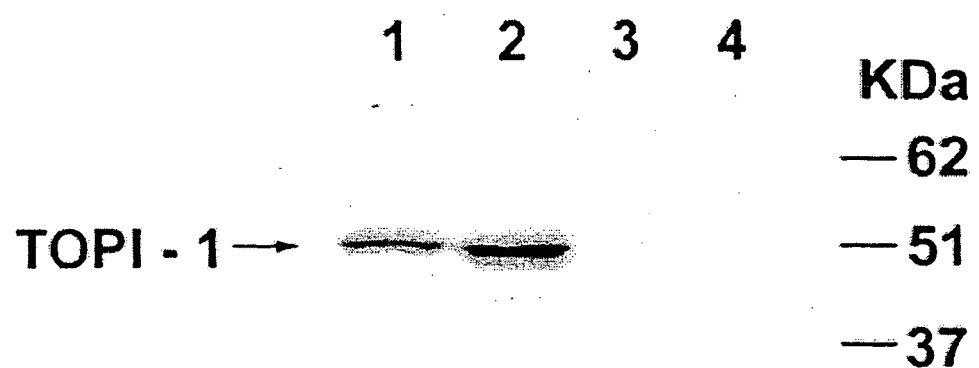
FIG. 21D shows detection of TOPI-1 (SEQ ID NO:5); the tapetal oleosin-like *Brassica napus* STA 41-9/*Onchocerca volvulus* protease inhibitor OV7 fusion protein (see FIG. 7 and Example 4) during flower development in a transgenic *Nicotiana tabacum*. Western blot analysis of equal amounts of anther or pollen protein extracted from developing flower buds of transgenic tobacco line No. 18 were separated by SDS-PAGE and cross-reacted with anti-CPI (cysteine protease inhibitor) antibody. Lane 1: protein extracted from pollen grains from stage 3; Lanes 2, 3 and 4: to proteins extracted from single anthers from stages 3, 6 and 9, respectively. The full-length fusion protein (arrow) is detected in anther and pollen protein extracts of stage 3.
Figure 22:
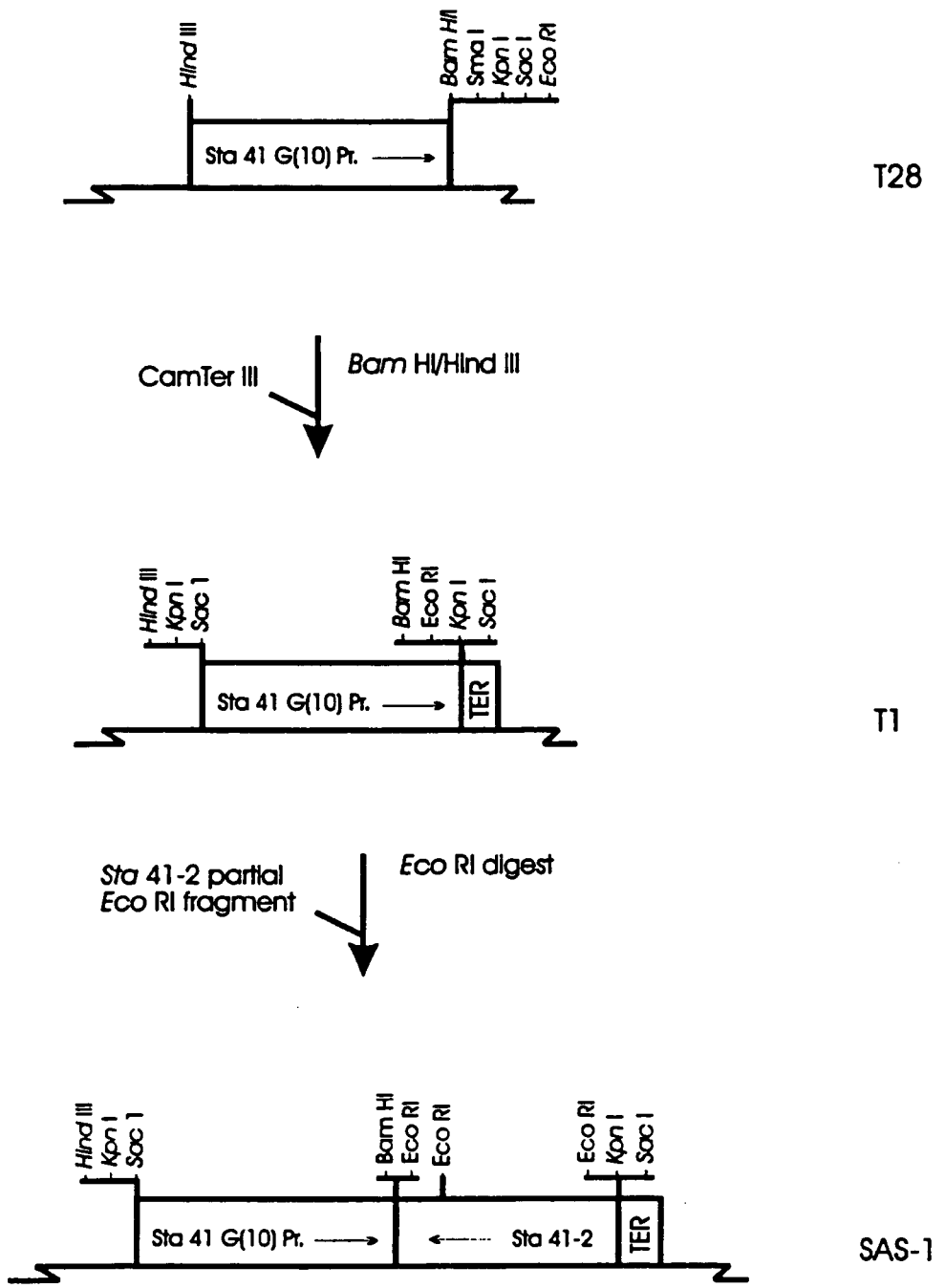
FIG. 22 is a schematic representation of the construction of plant transformation vector SAS-1 containing the *Brassica napus* tapetal oleosin-like Sta 41 G(10) promoter fragment transcriptionally fused to the *B. napus* tapetal oleosin-like Sta 41-2 cDNA in the antisense orientation.

With reference to FIG. 21D, there is shown the detection of the tapetal oleosin-like Brassica napus STA 41-9/Onchocerca volvulus OV7 protease inhibitor fusion protein during flower development in a transgenic Nicotiana tabacum plant (member of the Solanaceae family) containing TOPI-1 (SEQ ID NO:5, Example 4). Western blot analysis (FIG. 21D) of equal amounts of anther or pollen protein extracted from developing flower buds of transgenic tobacco were separated by SDS-PAGE and cross-reacted with anti-CPI (cysteine protease inhibitor) antibody. Lane 1 corresponds to protein extracted from tobacco pollen grains from stage 3 and Lanes 2, 3 and 4, correspond to proteins extracted from single anthers from stages 3, 6 and 9 (Koltunow, A. M., Truettner, J., Cox, K. H., Wallroth, M., Goldberg, R. B. *Plant Cell* 2: 1201-1224 (1990)) respectively. The full-length fusion protein (arrow) was detected in anther and pollen protein extracts of stage 3.

These results demonstrate that the oleosin-like STA 41-9/ Onchocerca volvulus OV7 protease inhibitor fusion protein while expressed specifically in the tapetum can re-locate to the pollen grain.

TOP-1 Expression in B. carinata

B. carinata plants were transformed, as described above with TOP-1 (SEQ ID NO:4, Example 3).

Figure 26A:
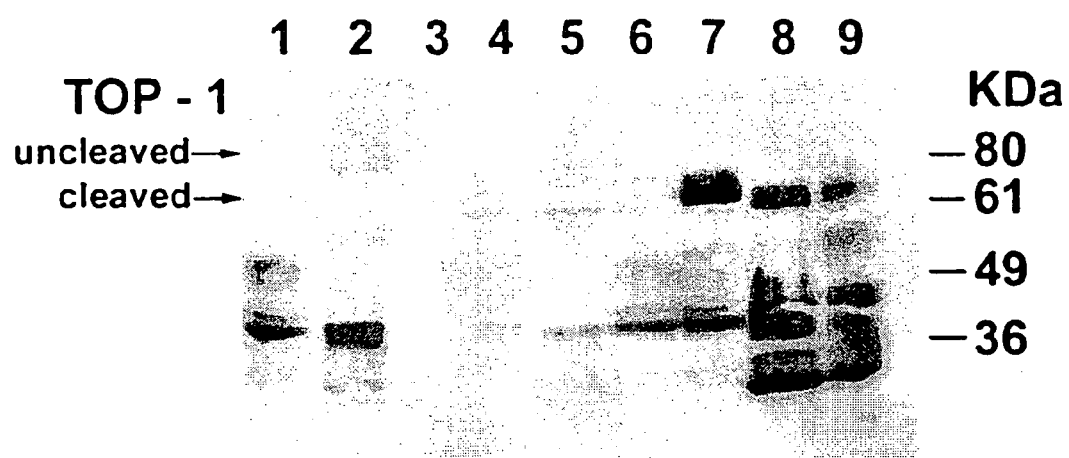
FIG. 26a shows a Western blot analysis of equal amounts of anther or pollen proteins extracted from developing flower buds separated by SDS-PAGE and cross-reacted with an antibody raised against the STA 41-9-derived peptide (LGIPESIKPS NIIPESIKPS; SEQ ID NO:24). Lane 1: anther protein extract from a 6 mm bud from a non-transformed *B. carinata* plant; Lane 2: pollen protein extract from an 8 mm bud of a non-transformed *B. carinata* plant; Lanes 3 to 8: anther protein extracts from 3 mm, 4 mm, 5 mm, 6 mm, 7 mm and 8 mm buds respectively of a *B. carinata* transformant; Lane 9: corresponds to a pollen protein extract from an 8 mm bud. As expected the fusion protein migrates at a higher molecular weight than the native oleosin-like proteins. Arrows indicate TOP-I fusion protein products before and after the predicted proteolytic cleavage in anthers and pollen extracts of the transgenic plants.
Figure 26B:
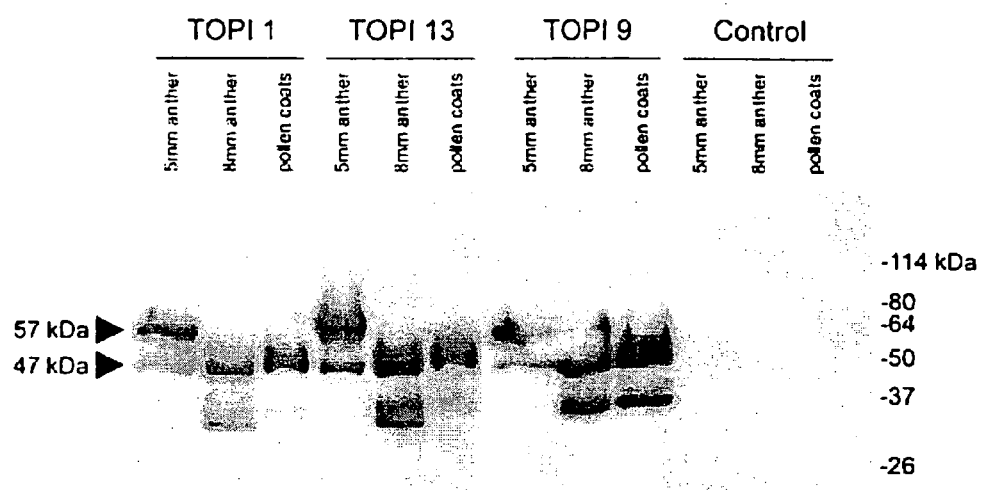
FIG. 26*b* shows detection of the *Brassica napus* tapetal oleosin-like STA 41-9/*Onchocerca volvulus* protease inhibitor OV7 fusion protein in transgenic *Brassica carinata* containing TOPI-1 (SEQ ID NO:5). Western blot analysis of anther proteins isolated from 5 mm and 8 mm flower buds, and of pollen coat proteins from anthers harvested from open flowers just prior to anther dehiscence from three TOPI-1 plant lines separated by SDS-PAGE and cross-reacted with anti-OV7 antibody. Lanes 1 to 3 represent proteins from TOPI-1 plant line No. 1, lanes 4 to 6 from plant line No. 13, lanes 7 to 9 from plant line No. 9 and lanes 10 to 12 from a non-transformed control *B. carinata* plant. Anther lanes each contain 0.5 anther's worth of protein, while pollen coat lanes each contain 10 anthers' worth of pollen coat residue. The positions of the predicted proteins are indicated on the left.

With reference to FIG. 26a there is shown the detection of the Brassica napus tapetal oleosin-like STA 41-9/Sitophilus zeamais SCPc 1 protease translational fusion protein (see FIG. 6) during flower development in transgenic Brassica carinata containing TOP-1 (SEQ ID NO:4).

Western blot analysis (FIG. 26a) of equal amounts of anther or pollen proteins were extracted from developing flower buds of a transgenic line, separated by SDS-PAGE and cross-reacted with an antibody raised against the STA 41-9-derived peptide (LGIPESIKPS NIIPESIKPS; SEQ ID NO:24). Lane 1 is an anther protein extract from a 6 mm bud from a non-transformed B. carinata plant and Lane 2 is a pollen protein extract from an 8 mm bud of a non-transformed B. carinata plant. Lanes 3 to 8 correspond to anther protein extracts from 3 mm, 4 mm, 5 mm, 6 mm, 7 mm and 8 mm buds respectively of B. carinata transformant 7B, and Lane 9 corresponds to a pollen protein extract from an 8 mm bud of transformant 7B. As expected the fusion protein migrates at a higher molecular weight than the native oleosin-like proteins. The arrows point to the TOP-1 fusion protein products before and after proteolytic cleavage in anthers and pollen extracts of the transgenic plants. These proteins are absent from the non-transformed plants. These results also demonstrate that the oleosin-like STA 41-9/ Sitophilus zeamais SCPc 1 protease translational fusion protein while regulated by a tapetal-specific promoter (Robert, L. S., Gerster, J., Allard, S., Cass, L., Simmonds, J. *Plant J.* 6:927-933 (1994a)) can re-locate to the pollen grain.

Example 17

Expression of TOG-2 in Transgenic Brassica carinata

This example provides data that demonstrates that a protein of interest, for example but not limited to the GUS protein, translationally fused to a tapetal oleosin-like protein, for example but not limited to, BnOlnB;4 (also known as Sta 41-9) is targeted to the pollen coat.

Pollen isolation: Anthers were gently squeezed in an Eppendorf tube with a disposable blue pestle (Eppendorf) to release and suspend the pollen in extraction buffer (100 mM HEPES pH 7.5, 10 mM KCl, 1 mM $MgCl_2$, 1 mM EDTA, 1 mM DTT, 0.4 M sucrose, 0.01% Triton X-100). The pollen grains were centrifuged at 1000×g for 3 min and the pollen pellet was washed in extraction buffer.

Pollen coat purification: Suspended pollen was dried by centrifugation in a glass fibre-plugged filter basket at 20,000×g for 20 sec and the pollen coats extracted by similarly centrifuging cyclohexane through the dried pollen on the filter into a new tube. Cyclohexane was evaporated under a stream of nitrogen gas leaving the pollen coats as a residue. Pollen viability was determined using a 1:1 mixture of two viability staining solutions containing malachite green, acid fuchsin and orange G (Alexander, M. P. *Stain Technol.* 44: 117-122 (1969); Alexander, M. P. *Stain Technol.* 55: 13-18 (1980)).

Northern analysis: Total RNA was isolated from anthers and pollen grains using Trizol (Gibco BRL) according to the manufacturer's instructions. Five to ten micrograms of total RNA were electrophoresed on 1-1.5% (w/v) agarose/formaldehyde gels and transferred to Hybond-N nylon membranes (Amersham Pharmacia Biotech). Membranes were hybridized in a modified Church aqueous phosphate buffer (Amersham Pharmacia Biotech) at 65° C. with random-primed $^{32}$P-labelled GUS (2 kb Bam HI/Sac I fragment of pBI121 (Clontech)) or BnOlnB;4 (0.2 and 1.1 kb Eco RI fragments of the BnOlnB;4 cDNA clone Sta 41-9; see Robert, L. S., Gerster, J. L., Allard, S., Cass, L., Simmonds, J., *Plant J.* 6: 927-933 (1994a)) probes. Blots were washed in 2×SSC, 0.1% SDS at 65° C., 3 times for 30 min, and exposed to X-ray film. Equal loading was assessed by $A_{260}$ of the sample and by ethidium bromide staining of rRNA bands.

GUS enzymatic assays: GUS fluorogenic assays of tissue samples from stem, leaf, pistil, anther and pollen were performed (Jefferson, R. A. *Plant Mol. Biol. Reporter*, 5: 387-405 (1987)). Extracts were centrifuged to remove debris and the supernatant was assayed for GUS activity and protein concentration using a modified Bradford assay (Bio-Rad). Fluorescence at timed intervals was measured with excitation at 320-390 nm and emission at 415-650 nm using a Hitachi F-2000 Fluorescent Spectrophotometer and the slope was determined. The specific activity of the GUS enzyme was calculated as pmol 4-methyl umbelliferone (MU) min-$^1$ mg-$^1$ total protein. GUS activity was estimated from the average of at least three replicate assays. GUS histochemical staining of pollen was performed using a method modified from that of Jefferson, R. A. *Plant Mol. Biol. Reporter*, 5: 387-405 (1987) in a solution of 50 mM $NaPO_4$ pH 7.0, 10 mM EDTA, 0.5 mM $K_3[Fe(CN)_6]$, 0.5 mM $K_4[Fe(CN)_6]$, 0.1% sarcosyl, 0.1% β-mercaptoethanol, 0.1% Triton X-100, 1 mg/ml X-gluc (5-bromo-4-chloro-3-indolyl-β-D-glucuronic acid) at 37° C. overnight and imaged using a Zeiss Axioplan 2 microscope. For the analysis of segregating progeny of single-copy TOG-2 lines, 400 to 800 pollen grains were counted per GUS-positive plant SDS-PAGE and western blotting: Protein samples were extracted directly in 2× loading buffer and separated by SDS-PAGE according to the methods of Laemmli, U. K. *Nature*, 227: 680-685 (1970). Protein concentrations were determined by a modified Lowry RCDC Protein assay (BioRad). Proteins were transferred to PVDF membranes (BioRad) and blocked in 3% bovine serum albumin, 5% skim milk powder in TBS (10 mM Tris pH 8.0, 150 mM NaCl). A polyclonal anti-GUS rabbit IgG (Molecular Probes) was used at a 1:4000-5000 dilution in 0.5% blocking solution (Roche Molecular Biochemicals). A polyclonal anti-BnOlnB;4 rabbit IgG was generated using a synthesized 20-mer peptide (LGIPESIKPS NIIPESIKPS; SEQ ID NO:24; Syngentia), corresponding to the first 20 residues of the C-terminal domain of BnOlnB;4, conjugated to Keyhole limpet haemocyanin (KLH). The anti-BnOlnB;4 IgG was used at a 1:3000 dilution. Proteins were detected using a 1:15000 dilution of goat anti-rabbit IgG conjugated to horseradish peroxidase (Sigma) using BM chemiluminescence blotting substrate (Roche Molecular Biochemicals)

Preparation of TOG-2

The tapetal oleosin-like BnOlnB;4 gene, isolated from *B. napus* anthers (also known as Sta 41-9; (Robert, L. S., Gerster, J. L., Allard, S., Cass, L., Simmonds, J., *Plant J.* 6: 927-933 (1994a)) was used to construct a translational fusion between the BnOlnB;4 gene, including the promoter and the entire coding region with the exception of the TGA stop codon, and the uidA gene encoding β-glucuronidase (TOG-2; FIG. 5b; SEQ ID NO:43). The junction between the coding sequences of BnOlnB;4 and uidA was verified to confirm the integrity of the open reading frame.

TOG-2 was constructed by ligating an adapter of two annealed oligos containing Kpn I sites:

XK+: GATCCTCTAGAGGTACCG (SEQ ID NO:22) and
KX-: GATCCGGTACCTCTAGAG (SEQ ID NO:23), into the Bam HI site located upstream of the GUS coding region of SGC-1 (FIG. 5b; also named BnOlnB;4-GUS (Foster, E., Schneiderman, D., Cloutier, M., Gleddie, S., Robert, L. S. *Plant J.* 31: 477-486 (2002)) creating plasmid BB-2 (FIG. 5b). The BnOlnB;4 promoter and coding region from TOPI-1 (FIG. 7) was then ligated into BB-2 replacing the Kpn I fragment consisting of the Sta 41-9 promoter region (FIG. 5b) to create the TOG-2 plasmid.

Construction of the control plasmids BnOlnB;4-GUS (pOB4G) and the *B. napus* Sta 44-GUS transcriptional fusions and *Brassica napus* transformations were described elsewhere (Hong, H. P., Gerster, J. L., Datla, R. S. S., Albani, D., Scoles, G., Keller, W., Robert, L. S. *Plant Cell Rep.* 16:373-378 (1997a); Hong, H. P., Ross, J. H. E., Gerster, J. L., Rigas, S., Datla, R. S. S., Hatzopoulos, P., Scoles, G., Keller, W., Murphy, D., Robert, L. S. *Plant Mol. Biol.* 34:549-555 (1997b)).

The TOG-2 translational fusion construct was introduced into Ethiopian mustard (*B. carinata*, A. Braun, breeding line C90-1163, obtained from Dr. K. Falk, Saskatoon Research Centre, AAFC) grown in growth cabinets or the greenhouse typically at 15° C. day/10° C. night or 20° C. day/15° C. night under natural and/or artificial light), by *Agrobacterium*-mediated transformation (*Agrobacterium* strain EHA 105) performed essentially as described by Babic, V., Datla, R. S., Scoles, G. J., Keller, W. *Plant Cell Reports*, 17, 183-188 (1998); see Example 15.

Figure 23A:
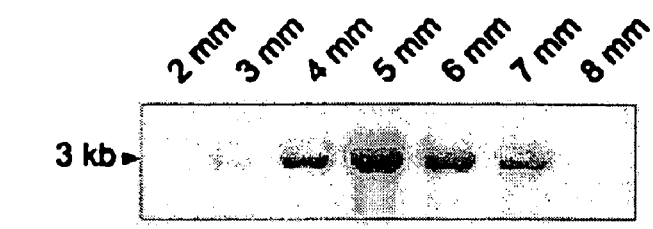
FIG. 23A shows a Northern blot analysis using total anther RNA, a GUS probe and high stringency conditions. Molecular weight of the TOG-2 mRNA is indicated on the left.
Figure 23B:
FIG. 23B shows a Western blot analysis using the anti-GUS antibody and approximately equal quantities of proteins from isolated anthers. The molecular weights of TOG-2 proteins are indicated on the left.

TOG-2 containing transgenic *B. carinata* plants were screened histochemically for GUS enzymatic activity of the fusion protein in anthers isolated from 5 mm flower buds. Nine TOG-2 lines exhibited GUS activity at various levels. GUS expression in anthers isolated from 5-mm buds was analysed in all nine GUS-positive TOG plant lines (Nos. 5, 8, 11, 15, 19, 20, 22, 24, 28) by fluorogenic analysis (FIG. 23D). GUS activity (pmol 4-methyl umbelliferone (MU) min-$^1$ mg-$^1$ total protein) was measured in all 9 plant lines as well as in control transgenic plants containing Sta 41-GUS (transcriptional fusion of the Sta 41 promoter to the GUS coding region; Hong, H. P., Ross, J. H. E., Gerster, J. L., Rigas, S., Datla, R. S. S., Hatzopoulos, P., Scoles, G., Keller, W., Murphy, D., Robert, L. S. *Plant Mol. Biol.* 34: 549-555 (1997b)) and Sta 44-GUS (transcriptional fusion of the Sta 44 promoter to the GUS coding region; Hong, H. P., Gerster, J. L., Datla, R. S. S., Albani, D., Scoles, G., Keller, W., Robert, L. S. *Plant Cell Rep.* 16: 373-378 (1997a) but not in the non-transformed control plant.

To confirm that expression of the TOG-2 construct was restricted to the tapetum, GUS fluorogenic assays were performed on various plant tissues of two high expressing TOG-2 transformants Nos. 5 and 22. GUS activity (pmol 4-methyl umbelliferone (MU) min-$^1$ mg-$^1$ total protein) was not detected in any tissue tested (leaf, stem, emasculated floral bud and pistil) except anthers (FIG. 23E). Emasculated bud, pistil and anther samples were isolated from 7-8 mm buds. These plant lines were previously determined to be high-expressing TOG-2 lines by fluorogenic analysis (FIG. 23D). GUS activity was measured as pmol 4-methyl umbelliferone (MU) min-$^1$ mg-$^1$ total protein in the tissue extracts ± standard deviation. GUS activity was not detected in the non-transformed control plant.

Transmission of the TOG-2 phenotype (the ability to target GUS enzyme activity to pollen grains) to the progeny was confirmed by GUS histochemical staining of anthers from self-progeny of TOG-2 plant line No. 22 (Table 3).

TABLE 3

| Plant Line | GUS Activity |
| --- | --- |
| TOG 22 T1 #1 | + |
| TOG 22 T1 #2 | + |
| TOG 22 T1 #3 | + |
| TOG 22 T1 #4 | Nd |
| TOG 22 T1 #5 | + |
| TOG 22 T1 #6 | + |
| TOG 22 T1 #7 | + |
| TOG 22 T1 #8 | + |
| TOG 22 T1 #9 | + |
| TOG 22 T1 #10 | + |
| control | − |
| TOG 22 T0 | + |

All self-progeny plants tested, along with the parent plant TOG-2 plant line No. 22, exhibited a positive reaction for GUS activity on the pollen grains (+), unlike the non-transformed control *B. carinata* plant which failed to exhibit any GUS activity (−). Consistent with the high frequency of transmission of the TOG-2 phenotype to progeny, TOG-2 plant line No. 22 was shown to contain approximately 5 copies of the TOG-2 transgene by Southern blot hybridization of restriction enzyme digested genomic DNA with a GUS coding region probe (results not shown).

Based on these data, TOG-2 lines were selected as described below for detailed analyses.

The TOG-2 Fusion is Expressed During Anther Development

Two transgenic TOG-2 lines showing high levels of GUS activity were selected for further analysis during anther development. Results are presented for line 22. A northern blot hybridized with a GUS probe revealed a transcript of approximately 3 kb, consistent with the predicted size of the TOG-2 construct (FIG. 23a). The TOG-2 mRNA was first detected in anthers isolated from about 3 mm flower buds and then accumulated rapidly, reaching its maximum level in anthers from 5 mm buds. Thereafter steady-state levels of the TOG-2 mRNA decreased somewhat in anthers from buds 6-7 mm in length, correlating with the onset of tapetal degeneration. By the late pollen maturation stage (8 mm buds), the TOG-2 mRNA was no longer detectable in anthers. Northern blot analysis using a BnOlnB;4 probe also detected the approximately 3 kb TOG-2 mRNA, as well as higher levels of the native BnOlnB;4 mRNA at approximately 1.6 kb (data not shown).

The pattern of TOG-2 protein accumulation differed from that of the TOG-2 transcript. Western blot analysis with an anti-GUS primary antibody revealed a protein at approximately 125 kDa, consistent with the molecular weight predicted for a full-length fusion protein between BnOlnB;4 and GUS (FIG. 23b). The full-length TOG-2 fusion protein was first detected in anthers from 4 mm flower buds prior to tapetal degeneration, peaked in 6 mm buds and was no longer observed in 8 mm buds. Another protein was detected at approximately 115 kDa in anthers from 6-8 mm buds. The molecular weight of this polypeptide is consistent with that predicted for the mature TOG-2 fusion protein following processing at or near the beginning of the BnOlnB;4 C-terminal domain (Murphy, D. J. and Ross, J. H. E. Plant J. 13: 1-16 (1998)). A second protein of approximately 97 kDa was also detected in the later stages of anther development (7-8 mm buds). Proteins cross-reacting with the anti-GUS antibody were not detected in non-transformed B. carinata anthers.

Western blot analysis with an anti-BnOlnB;4 primary antibody revealed the same proteins as described for the anti-GUS antibody (data not shown). In addition to the TOG-2 proteins, lower molecular weight native tapetal oleosin-like proteins were detected with the anti-BnOlnB;4 antibody in both transgenic TOG-2 and non-transformed B. carinata plants. Two proteins were detected of about 54 and 62 kDa in 4-7 mm flower buds and two proteins of about 38 and 46 kDa persisted during late anther development (data not shown). The multiple forms of the native tapetal oleosin-like protein detected in B. carinata with the anti-BnOlnB;4 antibody were reminiscent of the multiple forms which have been identified in B. napus with an anti-BnOlnB;3 antibody (Murphy, D. J. and Ross, J. H. E. Plant J. 13: 1-16 (1998)). The detection of multiple forms in B. napus was thought to occur due to the similarity of amino acid sequence between BnOlnB;3 and BnOlnB;4, as well as the alternative splicing of tapetal oleosin like genes (Murphy, D. J. and Ross, J. H. E. Plant J. 13: 1-16 (1998)).

Figure 23C:
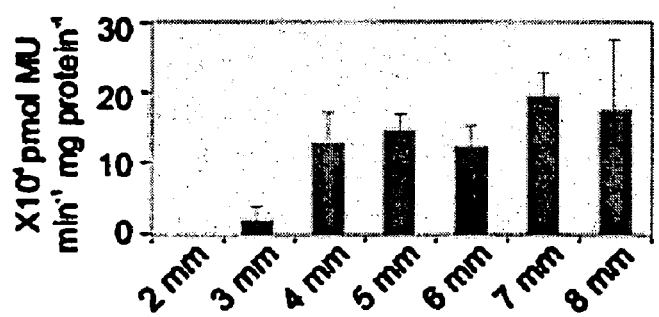
FIG. 23C shows fluorogenic analysis of GUS enzymatic activity in isolated anthers. GUS activity is expressed in $10^4$ pmol methyl umbelliferone (MU) min$^{-1}$ mg protein$^{-1}$ ± standard error with n=3. For controls, see FIG. 24.
Figure 23D:
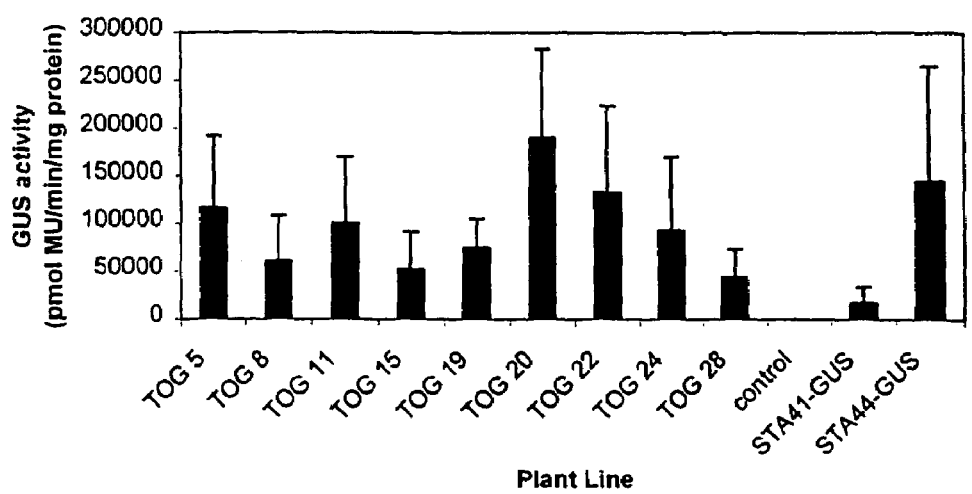
FIG. 23D shows fluorogenic analysis of GUS expression in anthers isolated from 5-mm buds from TOG-2 plant lines Nos. 5, 8, 11, 15, 19, 20, 22, 24, 28. GUS activity was measured as pmol methyl umbelliferone (MU) min$^{-1}$ mg protein$^{-1}$ in the anther extracts i standard deviation. The levels were in the same range as observed in the transcriptional fusion positive controls Sta 41-GUS and Sta 44-GUS. GUS activity was not detected in the non-transformed control plant.
Figure 23E:
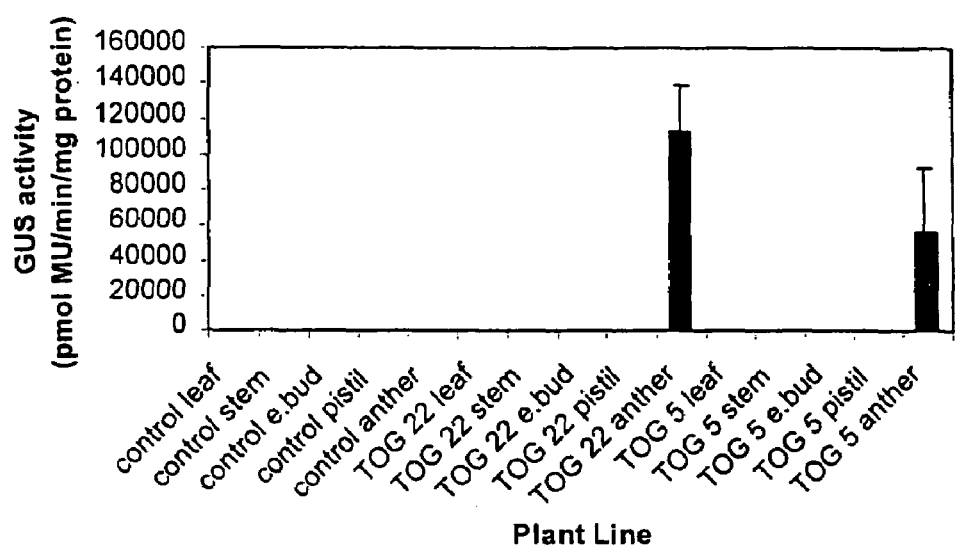
FIG. 23E shows fluorogenic analysis of β-glucuronidase (GUS) expression in leaf, stem, emasculated bud, pistil and anther tissues isolated from high expressing TOG-2 (SEQ ID NO:43) plant lines Nos. 5 and 22. Emasculated bud, pistil and anther samples were isolated from 7-8 mm buds. GUS activity was measured as pmol methyl umbelliferone (MU) min$^{-1}$ mg protein$^{-1}$ in the tissue extracts ± standard deviation.

GUS enzymatic activity was also examined throughout anther development (FIG. 23c). GUS activity was initially detected in anthers from 3 mm flower buds and persisted throughout anther development. Thus, GUS activity was detected before, during and after tapetal degeneration indicating that both the full-length and the processed forms of the TOG-2 fusion protein are enzymatically active.

The TOG-2 Fusion Protein is Targeted to the Pollen

Expression of the TOG-2 gene fusion was examined in isolated pollen grains at the late pollen maturation stage (8 mm flower buds; FIG. 24a). Northern analyses using a GUS probe, indicated that GUS-positive TOG-2 transgenic lines exhibited TOG-2 mRNA (approximately 3 kb) in anthers isolated from 5 mm buds (anther). TOG-2 RNA was not detected in pollen isolated from 8 mm buds (pollen). However, western analyses indicated that the full-length TOG-2 fusion protein (approx. 125 kDa) was detected with the anti-GUS antibody in anthers from 5 mm buds prior to tapetum degeneration, whereas the mature 115 kDa protein and the 97 kDa protein were detected in pollen isolated from 8 mm buds (FIG. 24b). TOG-2 proteins were also detected using the anti-BnOlnB;4 antibody as were the native tapetal oleosin-like proteins (data not shown). GUS enzymatic activity was also localized to pollen grains isolated from 8 mm buds, in addition to being detected in anthers isolated from 5 mm buds (FIG. 24c).

To determine whether a translational fusion is necessary to target proteins from the tapetum to pollen grains, expression of a GUS transcriptional fusion to the tapetum-specific BnOlnB;4 promoter (BnOlnB;4-GUS; lacking the coding region of BnOlnB;4) was analysed in transgenic B. napus. GUS expression directed by the BnOlnB;4 promoter was previously shown to be specific to the tapetum in anthers isolated from 3-5 mm flower buds of B. napus (Hong, H. P., Ross, J. H. E., Gerster, J. L., Rigas, S., Datla, R. S. S., Hatzopoulos, P., Scoles, G., Keller, W., Murphy, D., Robert, L. S. Plant Mol. Biol. 34:549-555 (1997b)). The approximately 2 kb BnOlnB;4 promoter is the same as that used to direct expression of the TOG-2 translational fusion.

Like the TOG-2 RNA, the GUS mRNA (approx. 2 kb) transcriptionally fused to the BnOlnB;4 tapetal oleosin-like promoter (and lacking the coding region of BnOlnB;4) was detected in transgenic B. napus prior to tapetal degradation in 4-5 mm flower buds (anther) as previously reported (Hong, H. P., Ross, J. H. E., Gerster, J. L., Rigas, S., Datla, R. S. S., Hatzopoulos, P., Scoles, G., Keller, W., Murphy, D., Robert, L. S. Plant Mol. Biol. 34:549-555 (1997b)). However, BnOlnB;4-GUS RNA was undetectable in pollen isolated from 6-7 mm buds (pollen) after the tapetum had degenerated just prior to floral opening (BnOlnB;4-GUS; FIG. 24a).

Western blot analyses with an anti-GUS antibody detected the GUS protein, of BnOlnB;4-GUS, in anthers from 4-5 mm buds (anther; FIG. 24b). However, the anti-GUS antibody did not detect cross-reacting proteins encoded by BnOlnB;4-GUS in pollen grains isolated from 6-7 mm buds (pollen). Fluorogenic analysis revealed GUS activity in anthers isolated from 4-5 mm buds but not in pollen isolated from 6-7 mm buds (BnOlnB;4-GUS; FIG. 24c).

Collectively, these data demonstrate that a coding region of interest, for example but not limited to GUS, that is produced in the tapetum associates with pollen when it is fused translationally to a tapetal oleosin-like protein, for example but not limited to, BnOlnB;4. Furthermore, the coding region of interest is active when associated with pollen.

A GUS transcriptional fusion to a B. napus polygalacturonase promoter (Sta 44-GUS) that directs high levels of expression within pollen late in development (Hong, H. P., Gerster, J. L., Datla, R. S. S., Albani, D., Scoles, G., Keller, W., Robert, L. S. Plant Cell Rep. 16: 373-378 (1997a)) was also examined. GUS mRNA was present in 4-5 mm buds of B. napus transformed with Sta 44-GUS and was also detected at high levels in pollen isolated from 6-7 mm buds (FIG. 24a). Western blot analysis with the anti-GUS antibody revealed the GUS protein (FIG. 24b) and fluorogenic analysis showed GUS activity (FIG. 24c) in anthers isolated from 4-5 mm buds as well as in isolated mature pollen from 6-7 mm buds. The persistence of GUS expression after tapetal degeneration in these transgenic B. napus plants indicates that the Sta 44-GUS construct drives expression within the pollen grain itself.

The TOG-2 Fusion Protein is Localized to the Pollen Coat

To determine whether the TOG-2 translational fusion protein was targeted to the pollen coat, pollen coats were purified by cyclohexane solubilization and western blot analyses were performed using the anti-GUS antibody.

The mature 115 kDa TOG-2 protein was found in pollen coats purified from pollen of open flowers immediately prior to anther dehiscence (FIG. 24b). Two additional proteins of about 85 and 80 kDa also appeared in mature open flower pollen, however the 97 kDa band, noted previously in anthers from about 8 mm buds, was no longer detectable. Western blot analyses of pollen coats with the anti-BnOlnB;4 antibody detected, in addition to native tapetal oleosin-like proteins, the mature 115 kDa TOG-2 protein, but not the 85 and 80 kDa proteins (data not shown) suggesting that the 85 and 80 kDa proteins, unlike the 115 kDa protein, no longer contain the 20 residues recognized by the anti-BnOlnB;4 antibody.

Pollen coats purified from open flowers of transgenic B. napus containing the transcriptional fusion constructs BnOlnB;4-GUS (comprising only the promoter region of BnOlnB;4 also known as Sta 41-9), or Sta 44-GUS (construct expressed within pollen) did not exhibit detectable proteins cross-reacting with the anti-GUS antibody (FIG. 24b).

Collectively, these data indicate that a protein of interest, for example but not limited to GUS, relocates to the pollen coat upon tapetal degeneration only if fused translationally to a tapetal oleosin-like protein, for example but not limited to, BnOlnB;4 (also known as STA 41-9).

Immunogold Localization

Anthers were fixed in 0.8% glutaraldehyde, 4% paraformaldehyde, 0.1 M NaPO$_4$ buffer pH 7.2. After washing in 0.1 M NaPO$_4$ pH 7.2, tissues were dehydrated in an ethanol series and infiltrated with LR White acrylic resin (London Resin Co., London) over several days at 25° C. Following polymerisation of the resin at 50° C. overnight, ultra-thin sections (approx. 100 nm) were cut using a Reichert ultramicrotome and collected on nickel grids. Sections were incubated in 1% glycine in PBS (0.01 M NaPO$_4$ pH 7.4, 0.85% NaCl) for 30 min to inactivate residual aldehydes and blocked in 1% ovalbumin in PBS for 10 min. Antibody incubations were carried out with anti-GUS (1:1000 dilution) or anti-BnOlnB;4 (1:100) primary antibodies in 0.01% ovalbumin in PBS followed by re-blocking in 1% ovalbumin in PBS and then with 10-15 nm-diameter gold-conjugated goat anti-rabbit secondary antibody (EY Laboratories, CA, USA) in 0.01% ovalbumin in PBS for 1 h at 25° C. Three 5 min washes in PBS were performed between each incubation or blocking step. After the procedure, residual salts were removed by washing in water. As a control, samples were incubated with pre-immune rabbit serum. Samples were observed in a Zeiss EM902A transmission electron microscope.

Immunogold localization was used to determine the subcellular localization of native tapetal oleosin-like proteins (FIGS. 25a and b) and TOG-2-derived proteins (FIGS. 25c and d) in anthers during development.

Native tapetal oleosin-like proteins were assessed in non-transformed B. carinata with the anti-BnOlnB;4 antibody, which cross-reacted with the tapetosome lipid bodies of anthers from 5 mm flower buds (FIG. 25a). Gold particles were not detected binding to another type of tapetal lipid body (elaioplasts), or elsewhere in the anther. In anthers isolated from 8 mm buds of non-transformed B. carinata, where the tapetum has disappeared and the tapetosomes have disintegrated, gold particles are localized to the pollen coat which fills the interstices of the exine indicating that oleosin-like proteins are localized to the pollen coat (FIG. 25b).

The anti-GUS antibody cross-reacted with the tapetosomes within the tapetum of anthers isolated from 5 mm flower buds, but not elsewhere within the anther obtained from transgenic TOG-2 plants (FIG. 25c). In anthers isolated from 8 mm buds, the anti-GUS antibody specifically cross-reacted with the pollen coat (FIG. 25d). These data indicate that the TOG-2 translational fusion is initially present within the tapetum, associated with the tapetosomes, and ultimately becomes localized to the pollen coat. Pre-immune serum exhibited only a background signal with anthers or pollen isolated from TOG-2 transgenic lines (data not shown). In another control, the anti-GUS antibody did not cross-react with proteins from non-transformed anthers or pollen (data not shown).

Immunogold localizations were also performed with transgenic B. napus containing the tapetal-expressed BnOlnB;4-GUS (lacking the coding region of BnOlnB;4: FIGS. 25e and f) or the pollen-expressed Sta 44-GUS (expressed within the pollen grain; FIGS. 25g and h) transcriptional fusions. In anthers isolated from 4 mm flower buds of B. napus transformed with BnOlnB;4-GUS (which correspond to the same developmental stage as 5 mm flower buds of B. carinata), the anti-GUS antibody detected GUS protein dispersed throughout the tapetum (FIG. 25e). The lack of tapetosome localization and the lower GUS expression level in the BnOlnB;4-GUS plants as compared to the TOG-2 plants (FIG. 25b) likely accounted for the lower number of gold particles observed in the BnOlnB;4-GUS sections. In 7 mm bud anthers (which correspond to the same developmental stage as 8 mm buds of B. carinata), the GUS protein was not detected in the anther, locule or pollen (FIG. 25f) consistent with its disappearance after tapetal degradation. In contrast, in B. napus transformed with Sta 44-GUS, immunogold localization revealed the GUS protein to be dispersed within the pollen cytoplasm in both 5 mm (FIG. 25g) and 7 mm bud anthers (FIG. 25h).

Collectively, these data confirm that a protein of interest, for example but not limited to the GUS protein, requires a translational fusion to a tapetal oleosin-like protein, for example but not limited to, BnOlnB;4 for localization to the tapetosomes and ultimately to the pollen coat.

In agreement with the immunolocalization of the TOG-2 protein to pollen, GUS histochemical staining was negligible with pollen from 5 mm bud anthers (FIG. 25i), but pronounced with pollen from 8 mm bud anthers (FIG. 25j) in TOG-2 plants. This indicates that GUS enzymatic activity is largely localized to the pollen after the disappearance of the tapetum late in anther development. GUS activity also persists following the release of pollen from the anther, as pollen grains continued to exhibit GUS histochemical staining for more than two months after collection and storage under ambient conditions (data not shown).

To indicate whether the GUS activity localized to pollen of TOG-2 transgenic plants was indeed the result of sporophytic expression rather than gametophytic expression, GUS histochemical analysis was performed on TOG-2 lines containing single copy insertions. In 9 GUS-positive progeny of each of two self-pollinated T0 plants, GUS histochemical staining of pollen from 8 mm flower buds typically revealed about 98±0.2% GUS positive pollen grains. In comparison, a mix of stained and unstained pollen grains could be observed by GUS histochemical staining of T1 progeny of a self-pollinated B. napus transgenic line containing a single copy of the pollen-expressed Sta 44-GUS construct (FIG. 25k). The frequency of GUS staining of pollen from the TOG-2 plants thus reflects the enzymatic activity transferred to the pollen from the sporophytic tapetum, rather than from gametophytic expression. GUS histochemical staining did not occur with pollen from non-transformed plants (data not shown).

These data demonstrate that the protein composition of the pollen coat can be modified by the targeting of a translational fusion protein from the tapetum. A tapetal oleosin-like protein, for example but not limited to BnOlnB;4 (also known as STA 41-9), provides an effective translational fusion partner to shuttle proteins from the tapetum to the pollen coat. Furthermore, a protein targeted to the pollen coat can remain active. Significantly, the activity of the GUS enzyme used in this demonstration persisted for weeks after dehiscence.

Example 18

Expression of SPOV-1 in Transgenic B. carinata and N. tabacum Plants

B. carinata and N. tabacum plants were transformed, as described above, with SPOV-1 (SEQ ID NO:12, FIG. 9, Example 7 above).

Figure 27:
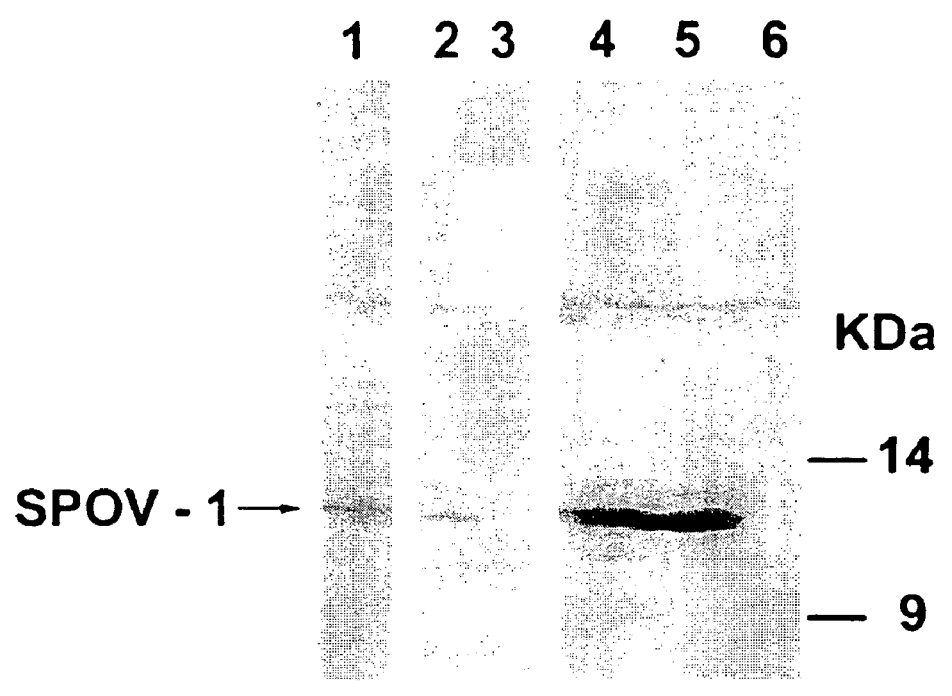

With reference to FIG. 27 there is shown the detection of the Brassica napus $SLG_{WS1}$ signal peptide/Onchocerca volvulus OV7 protease inhibitor translational fusion (SPOV-1) protein in the stigmas of different transgenic Brassica carinata and Nicotiana tabacum plants. Western blot analysis of stigma protein extracts from transgenic B. carinata and N. tabacum lines were separated by SDS-PAGE and cross-reacted with anti-OV7 (cysteine protease inhibitor) antibody. Lanes 1 and 2 correspond to stigma protein extracts of B. carinata transformants No. 2 and No. 25 respectively. Lane 3 corresponds to stigma proteins from non-transformed B. carinata. Lanes 4 and 5 correspond to stigma protein extracts of N. tabacum transformants No. 24 and No. 30 respectively. Lane 6 corresponds to stigma proteins from non-transformed tobacco. These results demonstrate that the $SLG_{WS1}$/protease inhibitor OV7 translational fusion can produce proteins in the stigmas of different species.

Example 19

Expression of POV-1 in Transgenic B. carinata Plants

B. carinata plants were transformed, as described in Example 15, with POV-1 (SEQ ID NO:15, FIG. 10, Example 8 above).

With reference to FIG. 28A there is shown the detection of the Brassica napus Sta 44G(2)/Onchocerca volvulus OV7 protease inhibitor translational fusion POV-1 in the pollen of different transgenic Brassica carinata plants. Western blot analysis of an equal amount of pollen protein extracted from developing flower buds of transgenic B. carinata lines were separated by SDS-PAGE and cross-reacted with anti-OV7 (cysteine protease inhibitor) antibody. Lane 1 corresponds to pollen proteins extracted from 8 mm buds of non-transformed B. carinata and lanes 2 and 3 correspond to pollen proteins extracted from 8 mm buds of transformed B. carinata lines No. 3 and No. 20 respectively.

These results demonstrate that the use of a signal sequence, fused to target a gene of interest, for example the protease inhibitor protein, is also targeted to the pollen grain.

Protease Inhibition Assays of Transgenic B. carinata Plants Containing the POV-1 Construct.

Mature pollen was isolated by gently squeezing anthers from open flowers just prior to anther dehiscence in a microfuge tube with a pestle to release the pollen grains and suspend them in extraction buffer (100 mM HEPES pH 7.5, 10 mM KCl, 1 mM $MgCl_2$, 1 mM EDTA, 1 mM DTT, 0.4 M sucrose, 0.01% Triton X-100). Pollen grains were filtered through 0.44 μm mesh to remove debris, pelleted by centrifugation and frozen in liquid nitrogen. Pollen grains were ground to a fine powder, mixed with 1.4 μl per anther of extraction buffer (100 mM MES pH 6.5, 1% Triton X-100) and centrifuged at 4° C. for 5 min. Protein contents of extracts were determined using the BioRad Protein Assay.

For the protease inhibition assay, 5 μg of protein extract in 50 μl of extraction buffer described above was added to a microtiter plate followed by 20 ng of papain in 50 μl of 50 mM MES pH6.5 and incubated for 15 min at room temperature. Then 100 μl of substrate solution (1 mM Pyr-Phe-Leu-pNA (BACHEM) in activation buffer (30% DMSO, 1 mM EDTA,.1 mM DTT in 50 mM MES pH 6.5)) was added and the plate incubated in the dark at room temperature. The plate was read after 2 to 3 h of incubation on a plate reader at 410 nm. Results were calculated as the percentage of papain protease activity present in the mature pollen protein extract of the non-transformed control plant±standard deviation. Inhibition controls (purified protease inhibitors E-64 and OV7-GST), protease controls (purified papain without extract), negative controls (non-transformed control plant) and background controls (plant protein extract without substrate) were included. Results are shown in FIG. 28B.

The protease inhibition controls of purified protease inhibitors E-64 and OV7-GST exhibited 3% and 2%, respectively, of the papain protease activity exhibited by the non-transformed plant, whereas the protease control of purified papain without plant extract exhibited 145% of the protease activity of the non-transformed control plant. The background absorbance of proteins extracted from mature pollen, in the absence of added substrate, were included in the assay and subtracted from the readings.

Isolated pollen grains from three transgenic B. carinata plant lines containing the POV-1 construct (Nos. 20, 25 and 21) exhibited 53% to 61% of the papain activity in the non-transformed control plant (FIG. 28B), reflecting an inhibition of papain protease activity. The protease inhibition controls consisting of purified protease inhibitors E-64 and OV7/GST exhibited 3% and 2% respectively of the papain protease activity exhibited by the non-transformed plant, whereas the protease control consisting of purified papain without plant extract exhibited 145% of the activity of the non-transformed plant. The background absorbance of proteins extracted from mature pollen, in the absence of added substrate, were included in the assay and subtracted from the readings. These data indicate that pollen grains can be modified to exhibit increased protease enzyme inhibitor activity.

Example 20

Transformation of Arabidopsis thaliana

Arabidospsis thaliana plants were transformed according to the method of Clough, S. J. and Bent, A. F. Plant J. 16: 735-743 (1998).

Arabidopsis thaliana seeds were germinated 5-6 weeks prior to transformation. The seeds were cold treated before sowing by placing 50 seeds per ml 0.1% agarose per pot in the refrigerator overnight. Three pots per construct were prepared by overfilling with moistened soil, covering with fibreglass screen and autoclaving. Pots were allowed to imbibe overnight, the tops of the pots were re-watered and 1 ml of the seeds/cold agarose was distributed onto the top of the soil. The pots were transferred to a growth cabinet set at 22° C. constant temperature, 16 h day/8 h night. Plants were thinned to a density of 10 to 12 plants per pot. The plants were grown until 5-10 plants per pot were bolting and the bolts were about 1-15 cm tall (about 4-5 weeks).

Four ml 2YT (or LB) liquid medium containing 50 mg/L kanamycin and 50 mg/L gentamycin was inoculated with Agrobacterium strain GV3 101 (containing the construct of interest) in a 50 ml Falcon tube and grown overnight at 28° C. with shaking at 250 rpm. Four ml overnight culture was used to inoculate 500 ml 2YT (or LB) containing 50 mg/L kanamycin, 30 mg/L gentamycin and 50 mg/L rifampicin, and bacteria grown overnight at 28° C. at 250 rpm until the culture reached an optical density at 600 nm of 1.2 to 1.5. (O.D. $_{600}$~8×10$^8$ cells/ml). The culture was centrifuged at 5000×g for 7-10 min, the medium decanted and the cells resuspended in 300 ml, total, of ½×MS+5% sucrose+0.05% Silwet L77.

Prior to dipping, opened *A. thaliana* flower buds and seed pods were trimmed. The plants were soaked by inverting the bolts into the *Agrobacterium* solution for 30-45 seconds. The pots were incubated on their sides, covered and without watering, for 2 nights at room temperature and then transferred to the growth cabinet (22° C.) 16 h day/8 h night for an additional 24 h. The plants were partially uncovered for another 24 h and then the lid were removed completely. The plants were wrapped with acetate sheets to keep them separate while setting seed. After about 4 weeks, the plants started to form some seed pods and turn yellow. The plants were removed from the cabinet and the seeds harvested after one week at room temperature.

T0 seeds (100 µl per pot) in Eppendorf tubes were surface sterilized by vortexing for 2 min at maximum speed at room temperature in 70% ethanol. The ethanol was discarded, 50% bleach added and the seeds vortexed for 1 min at maximum speed followed by shaking for 9 min. The bleach was removed and the seeds rinsed well with autoclaved Milli Q water by vortexing for 10-30 sec. The water was removed and the washes repeated 4 more times. One ml 0.1% agarose was added to each tube and the seeds resuspended. The seeds were then placed at 4° C. overnight before plating onto selection medium (½×MS salts, 1% sucrose, 0.8% agarose, pH 6.0 containing 250 mg/L timentin and 30-50 mg/L kanamycin). The plates were incubated at 22-23° C. for 16 h day/8 h night. Within 7-10 days, the putative transformed plants appeared bright green whereas the non-transformed plants were a lighter green and then turned white by two weeks. Two weeks after being plated on selection medium, the seedlings were transferred onto recovery medium (½× MS salts, 1% sucrose, 0.8% agarose, pH 6.0) and incubated at 22° C. for 16 h day/8 h night for two weeks. The plants were then transferred to soil.

Example 21

Expression of POP-1 in Transgenic Plants

Staining of Pollen Grains from Transgenic *B. carinata*, *A. thaliana* and *N. tabacum* Plants Transformed with the POP-1 Construct Transgenic *B. carinata* (20 plants), *A. thaliana* (54 plants) and *N. tabacum* (13 plants) containing the POP-1 construct (transformed as indicated in Examples 15, 20 and 13, respectively; see Example 8, FIG. 10 for POP-1 construct) were subjected to Alexander staining (Alexander, M. P. *Stain Technol.* 44: 117-122 (1969); Alexander, M. P. *Stain Technol.* 55: 13-18 (1980)). Dehisced anthers (containing mature pollen grains) were submerged in a 1:1 ratio of 1980 stain (20 ml 95% ethyl alcohol, 20 mg (2 ml of 1% solution in 95% ethanol) malachite green, 50 ml distilled water, 40 ml glycerol, 100 mg (10 ml of 1% aqueous solution) acid fuchsin, 5 g phenol, 3 ml of 1 M lactic acid) and 1969 stain 10 ml 95% ethanol, 10 mg (1 ml of 1% solution in 95% ethanol) malachite green, 50 ml distilled water, 25 ml glycerol, 5 g phenol, 5 g chloral hydrate, 50 ml (5 ml of 1% solution in water) acid fuchsin, 5 mg (0.5 ml of 1% solution in water) Orange G, 2 ml glacial acetic acid).

*B. carinata* POP-1 transgenic plant lines were also subjected to northern blot analysis of RNA isolated from anthers to verify the expression of POP-1. Some plants exhibited a partial loss of viability phenotype (see Table 4; *B. carinata* POP-1 plant line Nos. 2, 5, 12; *A. thaliana* POP-1 plant lines Nos. 7, 8, 10, 21, 24, 25, 27, 30, and *N. tabacum* plant lines Nos. 32, 33, 37, 40, 42, 55) indicating an alteration in the function of pollen grains as a result of expression of the POP-1 construct. However, most plant lines exhibited higher levels of steady state POP-1 mRNA than plant lines Nos. 2 and 12 (which exhibited the most severe loss of viability phenotype) indicating that expression of POP-1 also occurred in viable pollen (results not shown).

TABLE 4

Pollen viability in POP-1 expressing plants*

| Brassica carinata Plant Line | Percent Loss of Viability | Arabidopsis thaliana Plant Line | Percent Loss of Viability | Nicotiana tabacum Plant Line | Percent Loss of Viability |
|---|---|---|---|---|---|
| Bc POP 2 | ~90 | At POP 7 | ~30 | Nt POP 11 | ~5 |
| Bc POP 5 | ~40 | At POP 8 | ~15 | Nt POP 32 | ~10 |
| Bc POP 6 | <10 | At POP 10 | ~55 | Nt POP 33 | ~90 |
| Bc POP 7 | <10 | At POP 21 | ~40 | Nt POP 37 | ~15-20 |
| Bc POP 9 | <10 | At POP 24 | ~25 | Nt POP 40 | ~20 |
| Bc POP 10 | <10 | At POP 25 | ~60 | Nt POP 42 | ~30 |
| Bc POP 12 | ~60 | At POP 27 | ~10 | Nt POP 50 | <5 |
| Bc POP 13 | <10 | At POP 30 | ~50 | Nt POP 55 | ~10 |
| control | <10 | control | ~5 | control | <5 |

*not all plants are listed that exhibited a loss less than or about control activity Interaction Between POV-1 and POP-1 when Co-expressed in F1 *B. carinata* Plants.

Pollen of POV-1 primary transgenic *B. carinata* line Nos. 20 or 25, which exhibited enhanced protease inhibitor activity (FIG. 28B), were crossed separately onto the stigmas of emasculated buds of POP-1 primary transgenic *B. carinata* line Nos. 2 and 12, which exhibited an altered pollen viability phenotype (Table 4), seeds were obtained and F1 plants were grown. Genomic DNA was isolated from these F1 plants and subjected to Southern blot analysis to confirm the presence or absence of the POP-1 and POV-1 constructs (Table 5).

POP-1 and POV-1 expression in anthers was analyzed by northern blot analysis and western blot analysis as described above. Several F1 plants contained and expressed both POP-1 and POV-1 constructs (Table 5). When dehisced anthers from these F1 plants were subjected to Alexander staining as described above, they exhibited a pollen viability that was higher, than that compared to the parent POP-1 plants (see Table 5: POP-1 No. 2×POV-1 No. 20 progeny Nos. 2 and 3; and POP-1 No. 12×POV-1 No. 20 progeny Nos. 1 and 2).

There were other instances when POV-1 was expressed at a level insufficient to counteract the protease activity from the POP-1 expression found in F1 plants containing both POP-1 and POV-1 (see Table 5: POP-1 No. 12 ×POV-1 No. 20 progeny Nos. 1 and 4). In the absence of POV-1, POP-1 causes loss of viability, whereas in the absence of POP-1, POV-1 fails to affect viability as determined by Alexander staining.

TABLE 5

| Plant | Percent Loss of Viability | n = | POP DNA | POV DNA | POP mRNA | POV mRNA |
|---|---|---|---|---|---|---|
| control | 7 ± 3 | 4 | − | − | − | − |
| POP 2 parent | 93 ± 13 | 3 | + | − | + | − |
| POP 12 parent | 68 ± 25 | 3 | + | − | + | − |
| POV 20 parent | Nd | | − | + | − | + |
| POV 25 parent | Nd | | − | + | − | + |
| POP 2 X POV 20 No. 2 | 19 ± 3 | 3 | + | + | + | + |
| POP 2 X POV 20 No. 3 | 21 ± 5 | 3 | + | + | + | + |
| POP 12 X POV 25 No. 1 | 26 ± 8 | 4 | + | + | + | + |
| POP l2 X POV 25 No. 2 | 19 ± 5 | 3 | + | + | + | + |
| POP l2 X POV 20 No. 1 | 66 ± 4 | 3 | + | + | + | + |
| POP 12 X POV 20 No. 4 | 58 ± 9 | 4 | + | + | + | + |
| POP 2 X POV 25 No. 3 | 28 ± 5 | 4 | − | + | − | + |
| POP 12 X POV 20 No. 2 | 23 ± 2 | 3 | − | + | − | + |
| POP 12 x control No. 1 | 75 ± 17 | 4 | + | − | + | − |

Example 22

Modifying the Pollen Coat Protein Composition by Translational Fusion of β-glucuronidase to the Tapetal Oleosin-Like Gene Sta 41-9

Translational Fusion Eliminating the C-Terminal Domain of STA 41-9 (TOG-3)

A translation fusion between *E. coli* β-glucuronidase and the tapetal oleosin-like gene Sta 41-9 was made which eliminated the C-terminal domain of STA 41-9 and positioned the β-glucuronidase coding region at the C-terminus. Plasmid pGEMTOG-2 (FIGS. 5c-1) was used as a template for PCR with primers:

Sta 41 ATG: CTA GGA TCC AGA CCA CAC AAC TCC TTC (SEQ ID NO:26) and

Sta 41-13R: GAGA GGATTC CAA CAG AGA TAG GGA TGG C (SEQ ID NO:27)

to amplify the region corresponding to nucleotides 1 to 400 of Sta 41-9 (GenBank Acc. No. L33283). Primer Sta 41-13R includes a Bam HI restriction site to allow in frame translational fusion of GUS at the end of the STA 41-9 hydrophobic domain (Ross, J. H. E. and Murphy, D. J. *Plant J.* 9: 625-637 (1996)). The resulting PCR product was then digested with Hind III and Bam HI, and ligated to the Hind III and Bam HI fragment of BB-2 (FIG. 5b) which corresponds to the GUS coding region and nopaline synthase terminator in pRD400 (Datla, R. S., Hammerlindl, J. K., Panchuk, B., Pelcher, L. E., Keller, W. *Gene* 122: 383-384 (1992)) creating plasmid HB-1 (FIG. 5d). Plasmid HB-1 was then digested with Hind III and ligated to the Hind III fragment from pGEMTOG-2 (FIGS. 5c-1) which contains the promoter, N-terminal domain and a portion of the hydrophobic domain of Sta 41-9 creating plant transformation vector TOG-3 (FIG. 5d; SEQ ID NO:28).

Translational Fusion with Protein of Interest at the N-Terminal Domain of STA 41-9 (TOG-4)

A translation fusion between *E. coli* β-glucuronidase (GUS) and the full-length sequence of the *B. napus* tapetal oleosin-like gene Sta 41-9 was made in which the β-glucuronidase protein was positioned at the N-terminus of STA 41-9. The GUS gene was PCR amplified from pGEMTOG-2 (FIGS. 5c-1) using primers:

```
GUS-6F: TAG AGG ATC CCC GGG TGG TCA GTC and            (SEQ ID NO:29)
GUS-7R: GAG AGA GCT CAG ATC TTT GTT TGC CTC CCT GCT GCG GT. (SEQ ID NO:30)
```

GUS-6F encompasses the Bam HI and Sma I sites upstream of the GUS gene. GUS-7R removes the stop codon TGA from the 3' end of the GUS gene and adds Bgl II and Sac I restriction sites. The PCR product was digested with Bam HI and Sac I, and ligated to Bam HI and Sac I digested plasmid pGEMNosTer (FIGS. 5c-1) creating plasmid SS-5 (FIG. 5e). The Sta 41-9 coding region was PCR amplified from SS-4 (FIG. 4B) using primers:

```
Sta 41-14F: GAG AAG ATC TAT GAG AAA CGA AAT TCA AAA CGA AAC and  (SEQ ID NO:31)
Sta 41-15R: GAG AGA GCT CAT ATG TGT TTA CCA CCA CTC CCA.        (SEQ ID NO:32)
```

Sta 41-14F contains the ATG methionine translation initiation codon of Sta 41-9, includes an upstream Bgl II site and maintains the reading frame with GUS. Sta 41-15R encompasses the Nde I site and TGA stop codon of Sta 41-9 and adds a Sac I site. The PCR product was digested with Bgl II and Sac I, and ligated into Bgl II and Sac I digested plasmid SS-5 creating an N-terminal translational fusion of GUS to STA 41-9 as shown in plasmid SS-6 (FIG. 5e). Plasmid SS-6 was digested with Bam HI and partially digested with Eco RI to release a fragment containing the GUS-Sta 41 translational fusion and the nopaline synthase terminator. The desired SS-6 Bam HI and Eco RI fragment was ligated into the Bam HI and Eco RI fragment of SGC-1 (FIG. 5b) containing the binary vector pRD400 and Sta 41 PCR promoter (PPr) creating plant transformation vector TOG-4 (SEQ ID NO:33; FIG. 5e).

Example 23

Translational Fusion Between a *Brassica napus* Tapetal Oleosin-Like Protein and a *Brassica oleracea* SCR/SP11 Self-Incompatibility Male Determinant (TOS13-1)

It is well known that self-incompatibility (SI) in the Brassicaceae is sporophytically determined. Recently the male determinant of self-incompatibility has been identified in *B. campestris* (*B. rapa*) and *B. oleracea* as the S-locus cysteine rich protein SCR/SP11 (Schopfer, C. R., Nasrallah, M. E., Nasrallah, J. B. *Science* 296:1697-1700 (1999); Takayama, S., Shiba, H., Iwano, M., Asano, K., Hara, M., Che, F. -S., Watanabe, M., Hinata, K., Isogai, A. *Proc. Natl Acad. Sci. USA* 97: 1920-1925 (2000); Kachroo, A., Schopfer, C. R., Nasrallah, M. E., Nasrallah, J. B. *Science* 293: 1824-1826 (2001); Shiba, H., Takayama, S., Iwano, M., Shimosato, H., Funato, M., Nakagawa, T., Che, F. -S., Suzuki, G., Watanabe, M., Hinata, K., Isogai, A. *Plant Physiol.* 125: 2095-2103 (2001); Shiba, H., Iwano, M., Entani, T., Ishimoto, K., Shimosato, H., Che, F. -S., Satta, Y., Ito, A., Takada, Y., Watanabe, M., Isogai, A., Takayama, S. *Plant Cell* 14: 491-504 (2002)).

Similar genes have also been found in related species, for example, *B. napus* and *A. thaliana* (Acc. No. AJ250857, AJ250856; Nasrallah, M. E., Liu, P., Nasrallah, J. B. *Science* 297: 247-249 (2002)). It has also been demonstrated that expression of an SCR gene transcriptionally fused to an SCR promoter was sufficient to confer a new SI phenotype specifically on pollen grains (the stigma phenotype was unaltered) when transformed into *B. oleracea* or *B. campestris* having a different S haplotype than the introduced gene ((Schopfer, C. R., Nasrallah, M. E., Nasrallah, J. B. *Science* 296:1697-1700 (1999); Shiba, H., Takayama, S., Iwano, M., Shimosato, H., Funato, M., Nakagawa, T., Che, F. -S., Suzuki, G., Watanabe, M., Hinata, K., Isogai, A. *Plant Physiol.* 125: 2095-2103 (2001)).

A *B. oleracea* SCR13 (Acc. No. AF195626) gene was isolated by RT-PCR performed on total RNA from 2 to 4 mm length flower buds from an S13 haplotype plant line using primer:

GAGA T18-2: GAG AGA GAG AGA CTC GAG TTT TTT TTT TTT TTT TTT A/C/G (SEQ ID NO:34)

and Superscript II (Invitrogen) for the first strand cDNA synthesis, and gene specific primers:

SCR13-3F: AAC AAG AAT TTG CTG CGA GTA AAA GAG AAT (SEQ ID NO:35) and

SCR13-4R: ATT TTG ACT AAG ACG AAT TTT GGA ATG ATT (SEQ ID NO:36)

and Taq DNA polymerase (Invitrogen) for the PCR according to the manufacturer's protocols.

The amplified region corresponds to a 367 bp fragment beginning in the 5' untranslated region, contains the entire SCR13 coding region and ends in the 3' untranslated region of SCR13. The resulting PCR product was ligated into pGEM T-Easy (Promega) and transformed into *E. coli* strain DH5FT (Invitrogen) according to the manufacturer's protocols to create plasmid SCR13-1. The portion of SCR13 corresponding to the mature SCR peptide was amplified from SCR13-1 using primers:

SCR13-7F: GAG AAT TAA TAA ATC TGA TGA TGC CTT GTG G and (SEQ ID NO:37)

SCR13-8R: CTG CAG AAC CAA CGC GTT GGA GCT CCT AAC ACA ATT TAC AAT CAC AAG. (SEQ ID NO:38)

Primer SCR13-7F introduces a unique Ase I site and an additional nucleotide immediately upstream of the first nucleotide encoding the putative mature peptide of SCR13 to facilitate in frame translational fusion with the Sta 41 G(10) promoter and coding region at its Nde I restriction site. Primer SCR13-8R introduces unique Sac I and Bst XI sites immediately 3' of the stop codon of the SCR13 coding sequence. The PCR product was digested with Ase I and Bst XI, and ligated to SS-4 (FIG. 4B), which had previously been digested with Nde I and Bst XI, generating the plasmid AB-1. The plasmid AB-1 is then digested with Sac I to release the Sta 41 G(10)::SCR13 translational fusion fragment which is then ligated into TOPI-1 (FIG. 7) replacing the tapetal oleosin/protease inhibitor fragment. The resulting plant transformation vector was called TOS13-1 (FIG. 29; SEQ ID NO:39).

Example 24

Fusion of an *Arabidopsis thaliana* Oleosin-Like Gene to the *E. coli* β-glucuronidase gene (ATOG-3 and ATOG-4+)

A genomic sequence including the *A. thaliana* Atgrp 19 oleosin-like gene (Acc. No. AF362478) was PCR amplified using oligonucleotides SEQ ID NO's:40-42, all derived from the *A. thaliana* BAC clone T2I1 sequence (Acc. No. AL163912).

Atgrp19-F1: AAT GGT ACC GAA TAA GTG AGT CTT GCA CAC TGG (SEQ ID NO:40) is used to amplify the plus strand of the *Arabidopsis thaliana* genomic sequence containing the Atgrp 19 oleosin-like gene (Acc. No. AL163912). This oligonucleotide introduces a unique Kpn I site at the 5' end of the genomic fragment.

Atgrp 19-R1: TAT GGA TCC GAC GCC GGA ACC TGC TGG GTT AG (SEQ ID NO:41) is used to amplify the minus strand of the *Arabidopsis thaliana* genomic sequence containing the Atgrp 19 oleosin-like gene (Acc. No. AL163912). This oligonucleotide introduces a unique Bam HI site at the 3' end of the genomic fragment.

Atgrp19-R2: TAT AGA TCT ACC ATG ACG CCG GAA CCT GCT GGG TTA G (SEQ ID NO:42) is used to amplify the minus strand of the *Arabidopsis thaliana* genomic sequence containing the Atgrp 19 oleosin-like gene (Acc. No. AL163912). This oligonucleotide introduces a unique Bgl II site at the 3' end of the genomic fragment.

The amplified region consists of 978 bp of sequence upstream of the initiation ATG codon and the complete coding sequence (including the intron) up to, but excluding the stop codon. Oligonucleotide SEQ ID NO:40 introduces a unique Kpn I site at the 5' end of the genomic fragment, whereas oligonucleotide SEQ ID NO:41 introduces a unique Bam HI site at the 3' end of the Atgrp 19 coding region thus allowing an in-frame fusion with the GUS coding region by replacing the Kpn I/Bam HI fragment containing the Brassica oleosin-like gene in TOG-2 (FIG. 5b; SEQ ID NO:43) and creating binary vector ATOG-3 (FIGS. 5c-2; SEQ ID NO:44). Oligonucleotide SEQ ID NO:42 was also used in combination with oligonucleotide SEQ ID NO:40 to generate a similar genomic fragment but which contained a Bgl II site at the 3' end of the Atgrp 19 coding sequence to allow an in-frame fusion to the GUSPlus™ gene in the binary vector pCambia 1305.1 (see cambia.org) and generate binary vector ATOG-4+ (FIG. 5f; SEQ ID NO:45).

Example 25

Fusion of an *Arabidopsis thaliana* Extracellular Lipase Gene to the *E. coli* β-Glucuronidase Gene (EXLG-1+)

The genomic sequence including the *A. thaliana* exl 4 extracellular lipase gene (Acc. No. AY028612) was PCR amplified from genomic DNA using oligonucleotides:

Atexl 4-F1: ATA GGT ACC TTA ACA TTC TTG TAG TTA GGG C (SEQ ID NO:46)

and

Atexl 4-R1: TAT CCA TGG CAA GGC CAT TCT TGA TAT CCT GG (SEQ ID NO:47)

derived from the *A. thaliana* BAC clone T4012 (Acc. No. AC007396). Atexl 4-F1 is used to amplify the plus strand of the *Arabidopsis thaliana* genomic sequence containing the exl 4 extracellular lipase gene (Acc. No. AC007396). This oligonucleotide introduces a unique Kpn I site at the 5' end of the genomic fragment. Atexl 4-R1 is used to amplify the minus strand of the *Arabidopsis thaliana* genomic sequence containing the Atgrp 19 oleosin-like gene (Acc. No. AC007396). This oligonucleotide introduces a unique Nco I site at the 3' end of the genomic fragment.

The amplified region consists of 438 bp of sequence upstream of the initiation ATG codon and the complete coding sequence except the stop codon. Oligonucleotide SEQ ID NO:46 introduces a unique Kpn I site at the 5' end of the genomic fragment, whereas oligonucleotide SEQ ID NO:47 introduces a unique Nco I site at the 3' end of the exl 4 coding region to allow an in-frame fusion with the GUSPlus™ gene in the binary vector pCambia 1305.1 (see cambia.org) and generate binary vector EXLG-1+ (FIG. 30; SEQ ID NO:48).

Example 26

Fusion of the *Brassica napus* Pollen Polygalacturonase Gene to the *E. coli* β-Glucuronidase Gene (POG-2 and POG-3+)

The genomic sequence including the *Brassica napus* Sta 44 pollen polygalacturonase gene (Robert, L. S., Allard, S., Gerster, J. L., Cass, L., Simmonds, J. *Plant Mol. Biol.* 23: 1273-1278 (1993)) was PCR amplified from genomic clone Sta 44G(2) using oligonucleotides:

Sta44G2(2): ATA GGT ACC GAC AGT ATA CAT AAT TTA GAG AGA G (SEQ ID NO:49) and

Sta44-4(2): TAT GGA TCC CTC TTT GCC AGG AGC CTT GAC CAC (SEQ ID NO:50), or

Sta44-4(3): TAT CCA TGG TCT CTT TGC CAG GAG CCT TGA CCA C(SEQ ID NO:51).

Figure 31A:
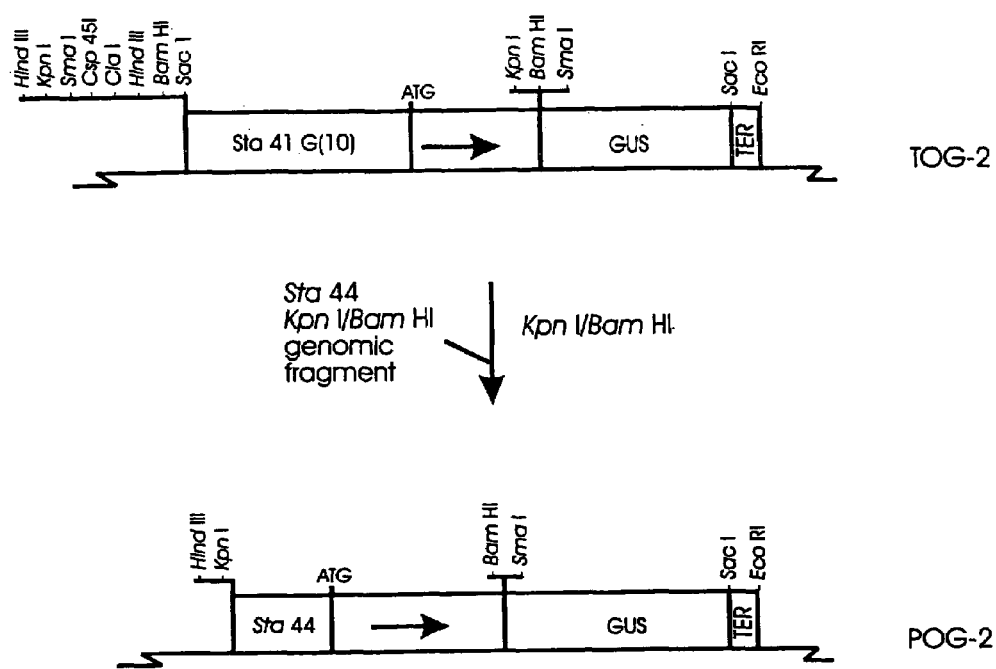
FIG. 31A shows a schematic representation of the construction of the plant transformation vector POG-2 (Example 26), the *Brassica napus* pollen polygalacturonase STA 44/*E. coli* GUS translational fusion.
Figure 31B:
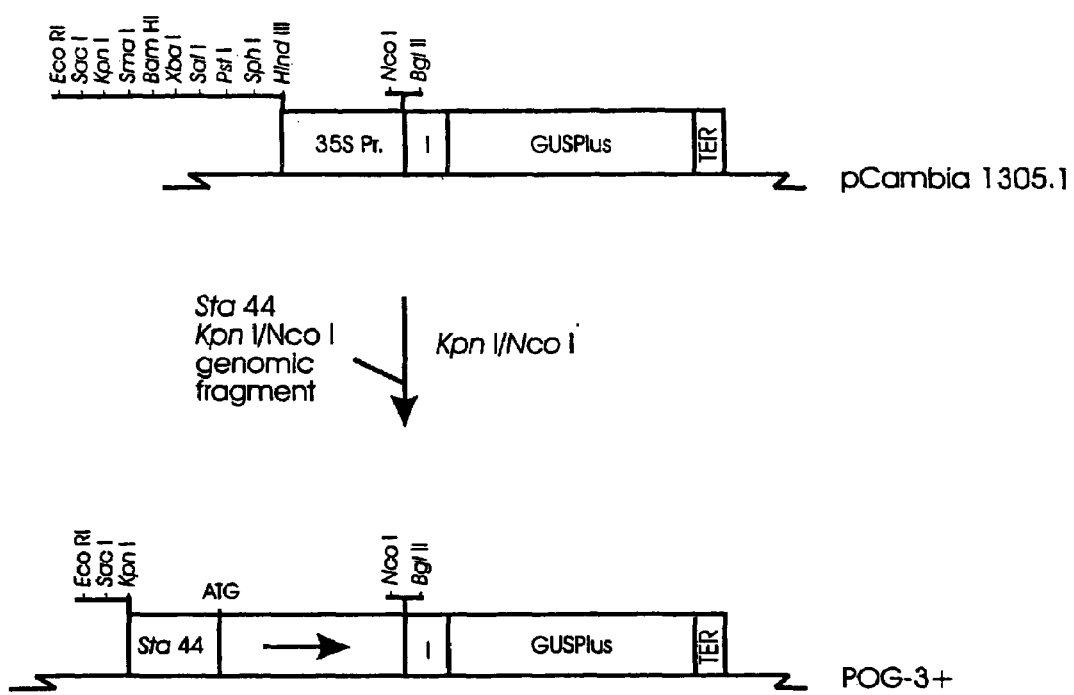
FIG. 31B shows a schematic representation of the construction of the plant transformation vector POG-3$^+$ (Example 26), the *Brassica napus* pollen polygalacturonase STA 44/*Staphylococcus* GUSPlus™ translational fusion.

Oligonucleotide SEQ ID NO:49 is derived from the Sta 44 promoter sequence (U.S. Pat. No. 5,689,053), whereas oligonucleotides SEQ ID NO:50 and SEQ ID NO:51 are derived from the Sta 44-4 cDNA clone (Acc. No. L19879). The amplified region consists of 647 bp of sequence upstream of the initiation ATG codon and the complete coding sequence except the stop codon. Oligonucleotide SEQ ID NO:49 introduces a unique Kpn I site at the 5' end of the genomic fragment, whereas oligonucleotide SEQ ID NO:50 introduces a unique Bam HI site at the 3' end of the Sta 44 coding region to allow an in-frame fusion with the GUS coding region by replacing the Kpn I/Bam HI fragment containing the Brassica oleosin-like gene in TOG-2 (FIG. 5b; SEQ ID NO:43) and creating binary vector POG-2 (FIG. 31A). Oligonucleotide SEQ ID NO:51 was also used in combination with oligonucleotide SEQ ID NO:49 to generate a similar genomic fragment but which contained a Nco I site at the 3' end of the Sta 44 coding sequence to allow an in-frame fusion to the GUSPlus™ gene in the binary vector pCambia 1305.1 (see cambia.org) and generate binary vector POG-3+ (FIG. 31B).

All citations are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A method for modifying the extracellular compartment of a pollen grain or an anther cell of a plant, the method comprising: (a) introducing into a plant a construct comprising a nucleotide sequence encoding a first amino acid sequence and a second amino acid sequence, wherein the first amino acid sequence comprises a hydrophobic domain of a tapetal oleosin-like protein of Brassicaceae family, fused to the second amino acid sequence comprising a protein of interest, the first amino acid sequence targeting the protein of interest to the extracellular compartment of the pollen grain or anther cell; and b) expressing the construct in a plant, and wherein the hydrophobic domain comprises a proline knot motif (PKM) of said tapetal oleosin-like protein.

2. The method of claim 1, wherein the tapetal oleosin-like protein is selected from the group consisting of: BnOlnB;1, BnOlnB;2, BnOlnB;3 BnOlnB;4, BnOlnB;5, BnOlnB;6, BnOlnB;7, BnOlnB;8, BnOlnB;9, BnOlnB;10, BnOlnB;11 and BnOlnB;12; AtOlnB;1, AtOlnB;2, AtOlnB;3 AtOlnB;4, Atgrp 19, BoOlnB;1 and BrOlnB;1, BrOlnB;2, BrOlnB;3, BrOlnB;4, and BrOlnB;5.

3. The method of claim 1, wherein the plant is selected from the group consisting of: Brassica, Raplzanus, Arabidopsis, Triticum, Hordeum, Avena, Niciotiana, Glycine, Pisum, Acer, Agropyron, Medicago, Malus, Aster, Phaseolus, Beta, Betula, Vicia, Bromus, Daucus, Cedrus, Citrus, Gossypium, Populus, Cucurbita, Helianthus, Lactuca, Lilium, Lycopersicon, Allium, Prunus, Capsicum, Pinus, Picea, Ambrosia, Secale, Tsuga, Solanum, Zea, and Oryza.

4. A method for modifying a pollen coat of a plant, (a) introducing into a plant a construct comprising a nucleotide sequence encoding a first amino acid sequence and a second amino acid sequence, wherein the first amino acid sequence comprises a hydrophobic domain of a tapetal oleosin-like protein of Brassicaceae family, fused to the second amino acid sequence comprising a protein of interest, to produce a fusion protein, the first amino acid sequence targeting the fusion protein to the pollen coat, wherein the nucleotide sequence is operatively linked to a promoter sequence and a terminator sequence; and b) expressing the construct in a plant, and wherein said hydrophobic domain comprises a proline knot motif (PKM) of said tapetal oleosin-like protein.

5. The method of claim 4, wherein the tapetal oleosin-like protein is selected from the group consisting of: BnOlnB;1, BnOlnB;2, BnOlnB;3 BnOlnB;4, BnOlnB;5, BnOlnB;6, BnOlnB;7, BnOlnB;8, BnOlnB;9, BnOlnB;10, BnOlnB;11 and BnOlnB;12; AtOlnB;1, AtOlnB;2, AtOlnB;3 AtOlnB;4, Atgrp 19, BoOlnB;1 and BrOlnB;1, BrOlnB;2, BrOlnB;3, BrOlnB;4, and BrOlnB;5.

6. A microspore or a pollen, or combination thereof, prepared using the method of claim 1.

7. A microspore or a pollen, or combination thereof, prepared using the method of claim 4.

8. A vector comprising a construct comprising a nucleotide sequence encoding a first amino acid sequence and a second amino acid sequence, wherein the first amino acid sequence comprises a hydrophobic domain of a tapetal oleosin-like protein of Brassicaceae family, fused to the second amino acid sequence comprising a protein of interest, the first amino acid sequence targeting the protein of interest to an extracellular compartment of a pollen grain or anther cell, wherein the nucleotide sequence is operatively linked to a promoter sequence and a terminator sequence, and wherein said hydrophobic domain comprises a proline knot motif (PKM) of said tapetal oleosin-like protein.

9. The vector of claim 8, wherein the tapetal oleosin-like protein is selected from the group consisting of: BnOlnB;1, BnOlnB;2, BnOlnB;3 BnOlnB;4, BnOlnB;5, BnOlnB;6, BnOlnB;7, BnOlnB;8, BnOlnB;9, BnOlnB;10, BnOlnB;11 and BnOlnB;12; AtOlnB;1, AtOlnB;2, AtOlnB;3 AtOlnB;4, Atgrp 19, BoOlnB;1 and BrOlnB;1, BrOlnB;2, BrOlnB;3, BrOlnB;4, and BrOlnB;5.

10. A transgenic plant cell comprising the construct defined in claim 8.

11. A transgenic plant comprising the construct defined in claim 8.

12. A seed comprising the construct defined in claim 8.

13. A pollen having a pollen coat comprising the fusion protein made according to the method of claim 4.

14. A transgenic plant comprising the pollen of claim 13.

15. A seed obtained from the transgenic plant of claim 14, and comprising a nucleotide sequence encoding the fusion protein.

16. The method of claim 1, wherein the extracellular compartment comprises the tryphine, exine, nexine, sexine, intine, or a combination thereof.

17. The method of claim 16, wherein the extracellular compartment is the exine.

18. The method of claim 2, wherein the tapetal oleosin-like protein is BnOlnB;4 or Atgrp 19.

19. The method of claim 3, wherein the plant is a member of the Brassicaceae family.

20. The method of claim 5, wherein the tapetal oleosin-like protein is BnOlnB;4 or Atgrp 19.

21. The method of claim 9, wherein the tapetal oleosin-like protein is BnOlnB;4 or Atgrp 19.

22. The method of claim 4, wherein the plant is selected from the group consisting of: *Brassica, Raphanus, Arabidopsis, Triticum, Hordeum, Avena, Niciotiana, Glycine, Pisum, Acer, Agropyron, Medicago, Malus, Aster, Phaseolus, Beta, Betula, Vicia, Bromus, Daucus, Cedrus, Citrus, Gossypium, Populus, Cucurbita, Helianthus, Lactuca, Lilium, Lycopersicon, Allium, Prunus, Capsicum, Pinus, Picea, Ambrosia, Secale, Tsuga, Solanum, Zea,* and *Oryza.*

23. The transgenic plant cell of claim 10, wherein the plant cell is selected from the group consisting of: *Brassica, Raplianus, Arabidopsis, Triticum, Hordeum, Avena, Niciotiana, Glycine, Pisum, Acer, Agropyron, Medicago, Malus, Aster, Phaseolus, Beta, Betula, Vicia, Bromus, Daucus, Cedrus, Citrus, Gossypium, Populus, Cucurbita, Helianthus, Lactuca, Lilium, Lycopersicon, Allium, Prunus, Capsicum, Pinus, Picea, Ambrosia, Secale, Tsuga, Solanum, Zea,* and *Oryza.*

24. The transgenic plant of claim 11, wherein the plant is selected from the group consisting of: *Brassica, Raphanus, Arabidopsis, Triticum, Hordeum, Avena, Niciotiana, Glycine, Pisum, Acer, Agropyron, Medicago, Malus, Aster, Phaseolus, Beta, Betula, Vicia, Bromus, Daucus, Cedrus, Citrus, Gossypium, Populus, Cucurbita, Helianthus, Lactuca, Lilium, Lycopersicon, Allium, Prunus, Capsicum, Pinus, Picea, Ambrosia, Secale, Tsuga, Solanum, Zea,* and *Oryza.*

25. The seed of claim 12, wherein the seed is selected from the group consisting of: *Brassica, Raphanus, Arabidopsis, Triticum, Hordeum, Avena, Niciotiana, Glycine, Pisum, Acer, Agropyron, Medicago, Malus, Aster, Phaseolus, Beta, Betula, Vicia, Bromus, Daucus, Cedrus, Citrus, Gossypium, Populus, Cucurbita, Helianthus, Lactuca, Lilium, Lycopersicon, Allium, Prunus, Capsicum, Pinus, Picea, Ambrosia, Secale, Tsuga, Solanum, Zea,* and *Oryza.*

\* \* \* \* \*